(12) United States Patent
Stagliano et al.

(10) Patent No.: US 8,563,269 B2
(45) Date of Patent: Oct. 22, 2013

(54) MODIFIED ANTIBODY COMPOSITIONS, METHODS OF MAKING AND USING THEREOF

(75) Inventors: Nancy E. Stagliano, Santa Barbara, CA (US); James W. West, Santa Barbara, CA (US); Kathryn Kamath, Santa Barbara, CA (US); Paul H. Bessette, Camarillo, CA (US); Frederick W. Gluck, Santa Barbara, CA (US); Jason Sagert, Santa Barbara, CA (US); Patrick Daugherty, Santa Barbara, CA (US)

(73) Assignee: CytomX Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 13/315,623

(22) Filed: Dec. 9, 2011

(65) Prior Publication Data

US 2012/0149061 A1    Jun. 14, 2012

Related U.S. Application Data

(63) Continuation of application No. 12/686,344, filed on Jan. 12, 2010, now abandoned.

(60) Provisional application No. 61/144,110, filed on Jan. 12, 2009, provisional application No. 61/144,105, filed on Jan. 12, 2009, provisional application No. 61/249,416, filed on Oct. 7, 2009, provisional application No. 61/249,441, filed on Oct. 7, 2009.

(51) Int. Cl.

| | |
|---|---|
| *C12P 21/08* | (2006.01) |
| *C12N 15/74* | (2006.01) |
| *C12N 9/00* | (2006.01) |
| *C12N 15/62* | (2006.01) |
| *C07H 21/04* | (2006.01) |
| *C07K 16/28* | (2006.01) |
| *C07K 16/46* | (2006.01) |
| *C07K 14/00* | (2006.01) |

(52) U.S. Cl.
USPC ......... 435/69.1; 435/71.1; 435/328; 435/334; 536/23.4; 536/23.53; 424/134.1; 424/192.1

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,379,145 A | 4/1983 | Masuho et al. |
| 4,671,958 A | 6/1987 | Rodwell et al. |
| 4,816,567 A | 3/1989 | Cabilly et al. |
| 4,867,973 A | 9/1989 | Goers et al. |
| 4,952,394 A | 8/1990 | Senter |
| 4,975,278 A | 12/1990 | Senter et al. |
| 5,010,176 A | 4/1991 | Barton |
| 5,144,012 A | 9/1992 | Johnson et al. |
| 5,162,218 A | 11/1992 | Schultz |
| 5,223,409 A | 6/1993 | Ladner et al. |
| 5,272,253 A | 12/1993 | Koppel et al. |
| 5,306,731 A | 4/1994 | Epstein |
| 5,403,484 A | 4/1995 | Ladner et al. |
| 5,459,061 A | 10/1995 | Sato et al. |
| 5,468,785 A | 11/1995 | Greuel et al. |
| 5,571,698 A | 11/1996 | Ladner et al. |
| 5,637,288 A | 6/1997 | Goldenberg et al. |
| 5,665,358 A | 9/1997 | Barton et al. |
| 5,679,548 A | 10/1997 | Barbas et al. |
| 5,725,856 A | 3/1998 | Hudziak et al. |
| 5,770,195 A | 6/1998 | Hudziak et al. |
| 5,772,997 A | 6/1998 | Hudziak et al. |
| 5,824,782 A | 10/1998 | Holzer et al. |
| 5,834,247 A | 11/1998 | Comb et al. |
| 5,837,500 A | 11/1998 | Ladner et al. |
| 5,866,341 A | 2/1999 | Spinella et al. |
| 5,922,845 A | 7/1999 | Deo et al. |
| 5,985,626 A | 11/1999 | Barbas et al. |
| 5,990,286 A | 11/1999 | Khawli et al. |
| 6,015,557 A | 1/2000 | Tobinick et al. |
| 6,054,297 A | 4/2000 | Carter et al. |
| 6,066,719 A | 5/2000 | Zapata |
| 6,080,575 A | 6/2000 | Heidtmann et al. |

(Continued)

FOREIGN PATENT DOCUMENTS

| | | | |
|---|---|---|---|
| EP | 0 329185 | B1 | 4/1994 |
| EP | 0 444158 | B1 | 1/1996 |

(Continued)

OTHER PUBLICATIONS

Wu et al., J Mol Biol 294: 151-162, 1999.*
Dufner et al., Trends Biotechnol 24(11): 523-529, 2006.*
Ngo et al., 1994, The Protein Folding Problem and Tertiary Structure Prediction, pp. 492-495.*
Skolnick et al., Trends in Biotech. 18(1):34-39, 2000.*
Anderson et al. Selective photothermolysis: precise microsurgery by selective absorption of pulsed radiation. Science. Apr. 29, 1983;220(4596):524-7.
Armentano et al. Induction of covalent binding antibodies. Immunol Lett. Feb. 28, 2006;103(1):51-7.

(Continued)

*Primary Examiner* — Phuong Huynh
(74) *Attorney, Agent, or Firm* — Mintz Levin Cohn Ferris Glovsky and Popeo, P.C.; Ivor R. Elrifi

(57) ABSTRACT

The present disclosure provides modified antibodies which contain an antibody or antibody fragment (AB) modified with a masking moiety (MM). Such modified antibodies can be further coupled to a cleavable moiety (CM), resulting in activatable antibodies (AAs), wherein the CM is capable of being cleaved, reduced, photolysed, or otherwise modified. AAs can exhibit an activatable conformation such that the AB is more accessible to a target after, for example, removal of the MM by cleavage, reduction, or photolysis of the CM in the presence of an agent capable of cleaving, reducing, or photolysing the CM. The disclosure further provides methods of making and using such modified antibodies and activatable antibodies.

38 Claims, 37 Drawing Sheets

(56) References Cited

U.S. PATENT DOCUMENTS

| | | |
|---|---|---|
| 6,107,059 A | 8/2000 | Hart |
| 6,165,464 A | 12/2000 | Hudziak et al. |
| 6,217,866 B1 | 4/2001 | Schlessinger et al. |
| 6,235,883 B1 | 5/2001 | Jakobovits et al. |
| 6,258,562 B1 | 7/2001 | Salfeld et al. |
| 6,265,540 B1 | 7/2001 | Isaacs et al. |
| 6,268,488 B1 | 7/2001 | Barbas et al. |
| 6,342,221 B1 | 1/2002 | Thorpe et al. |
| 6,399,063 B1 | 6/2002 | Hudziak et al. |
| 6,407,213 B1 | 6/2002 | Carter et al. |
| 6,534,061 B1 | 3/2003 | Goddard et al. |
| 6,548,249 B1 | 4/2003 | Anderson et al. |
| 6,670,147 B1 | 12/2003 | Heidtmann et al. |
| 6,682,736 B1 | 1/2004 | Hanson et al. |
| 6,884,879 B1 | 4/2005 | Baca et al. |
| 6,903,196 B1 | 6/2005 | Roben et al. |
| 6,955,900 B1 | 10/2005 | Barbas et al. |
| 6,979,538 B2 | 12/2005 | Ladner et al. |
| 6,984,720 B1 | 1/2006 | Korman et al. |
| 6,992,174 B2 | 1/2006 | Gillies et al. |
| 7,029,874 B2 | 4/2006 | Baker et al. |
| 7,060,269 B1 | 6/2006 | Baca et al. |
| 7,060,808 B1 | 6/2006 | Goldstein et al. |
| 7,087,409 B2 | 8/2006 | Barbas et al. |
| 7,098,002 B1 | 8/2006 | Rubenstein et al. |
| 7,118,879 B2 | 10/2006 | Ladner et al. |
| 7,157,418 B1 | 1/2007 | McDonald et al. |
| 7,169,901 B2 | 1/2007 | Baca et al. |
| 7,208,293 B2 | 4/2007 | Ladner et al. |
| 7,214,776 B2 | 5/2007 | Hsei et al. |
| 7,226,596 B2 | 6/2007 | Bodary et al. |
| 7,256,038 B2 | 8/2007 | Daugherty et al. |
| 7,297,334 B2 | 11/2007 | Baca et al. |
| 7,304,143 B2 | 12/2007 | Goddard et al. |
| 7,341,720 B2 | 3/2008 | Stefano |
| 7,365,166 B2 | 4/2008 | Baca et al. |
| 7,375,193 B2 | 5/2008 | Baca et al. |
| 7,452,535 B2 | 11/2008 | Davis et al. |
| 7,465,790 B2 | 12/2008 | Waldmann et al. |
| 7,521,541 B2 | 4/2009 | Eigenbrot et al. |
| 7,591,994 B2 | 9/2009 | Govindan et al. |
| 7,598,350 B2 | 10/2009 | Liu et al. |
| 7,608,591 B2 | 10/2009 | Liu et al. |
| 7,851,432 B2 | 12/2010 | Chari et al. |
| 7,855,275 B2 | 12/2010 | Eigenbrot et al. |
| 7,999,083 B2 | 8/2011 | Govindan et al. |
| 2002/0048578 A1 | 4/2002 | Waldmann et al. |
| 2002/0168690 A1 | 11/2002 | Miller et al. |
| 2003/0021791 A1 | 1/2003 | Kassis et al. |
| 2003/0134824 A1 | 7/2003 | Breslow et al. |
| 2004/0014652 A1 | 1/2004 | Trouet et al. |
| 2004/0053829 A1 | 3/2004 | Pfizenmaier et al. |
| 2004/0082039 A1 | 4/2004 | Gillies et al. |
| 2004/0110682 A1 | 6/2004 | Heidtmann et al. |
| 2004/0146516 A1 | 7/2004 | Roben et al. |
| 2004/0147444 A1 | 7/2004 | Chemajovsky et al. |
| 2004/0185053 A1 | 9/2004 | Govindan |
| 2004/0213797 A1 | 10/2004 | Bodmer et al. |
| 2004/0265274 A1 | 12/2004 | Wei et al. |
| 2005/0042680 A1 | 2/2005 | Filpula et al. |
| 2005/0106100 A1 | 5/2005 | Harris et al. |
| 2005/0136049 A1 | 6/2005 | Ledbetter et al. |
| 2005/0196754 A1 | 9/2005 | Drmanac et al. |
| 2005/0208558 A1 | 9/2005 | Venter et al. |
| 2005/0255042 A1 | 11/2005 | Lam et al. |
| 2005/0255555 A1 | 11/2005 | Johns et al. |
| 2005/0277160 A1 | 12/2005 | Shiba et al. |
| 2005/0287155 A1 | 12/2005 | Santi et al. |
| 2006/0018911 A1 | 1/2006 | Ault-Riche et al. |
| 2006/0078901 A1 | 4/2006 | Buchreiser et al. |
| 2006/0121570 A1 | 6/2006 | Barbas et al. |
| 2006/0228348 A1 | 10/2006 | Stefano |
| 2006/0246066 A1 | 11/2006 | Morgan et al. |
| 2006/0252130 A1 | 11/2006 | Boehm et al. |
| 2006/0265274 A1 | 11/2006 | Commins et al. |
| 2007/0041904 A1 | 2/2007 | Jiang et al. |
| 2007/0061916 A1 | 3/2007 | Kovalic et al. |
| 2007/0065158 A1 | 3/2007 | Shindou et al. |
| 2007/0065878 A1 | 3/2007 | Daugherty et al. |
| 2007/0083334 A1 | 4/2007 | Mintz et al. |
| 2008/0107660 A1 | 5/2008 | Self |
| 2009/0023602 A1 | 1/2009 | Fellouse et al. |
| 2009/0123467 A1 | 5/2009 | Bedi et al. |
| 2009/0304719 A1* | 12/2009 | Daugherty et al. .......... 424/178.1 |
| 2010/0189651 A1* | 7/2010 | Stagliano et al. .............. 424/9.1 |
| 2010/0221212 A1 | 9/2010 | Stagliano et al. |
| 2011/0178279 A1 | 7/2011 | Williams et al. |
| 2012/0149061 A1* | 6/2012 | Stagliano et al. ............ 435/69.6 |
| 2012/0207756 A1* | 8/2012 | Stagliano et al. .......... 424/134.1 |
| 2012/0237512 A1* | 9/2012 | Daugherty et al. .......... 424/134.1 |
| 2012/0237977 A1* | 9/2012 | Daugherty et al. .......... 435/69.6 |
| 2012/0244154 A1* | 9/2012 | Daugherty et al. ........ 424/134.1 |

FOREIGN PATENT DOCUMENTS

| | | |
|---|---|---|
| EP | 0586002 B1 | 1/2000 |
| EP | 0706799 B1 | 11/2001 |
| EP | 0 623679 B1 | 6/2003 |
| EP | 1550729 B1 | 7/2005 |
| EP | 1579873 A1 | 9/2005 |
| EP | 1770099 A1 | 4/2007 |
| WO | WO-95/11703 A1 | 5/1995 |
| WO | WO-96/05863 A1 | 2/1996 |
| WO | WO-96/34892 A1 | 11/1996 |
| WO | WO-97/31024 A1 | 8/1997 |
| WO | WO-00/04192 B1 | 1/2000 |
| WO | WO-00/18962 B1 | 4/2000 |
| WO | WO-00/23472 A2 | 4/2000 |
| WO | WO-00/34519 B1 | 6/2000 |
| WO | WO-01/00244 A1 | 1/2001 |
| WO | WO-02/30460 A2 | 4/2002 |
| WO | WO-02/060488 A1 | 8/2002 |
| WO | WO-02/066058 A1 | 8/2002 |
| WO | WO-02/066656 A2 | 8/2002 |
| WO | WO-03/012105 A2 | 2/2003 |
| WO | WO-03/020212 A2 | 3/2003 |
| WO | WO-2004/009638 A1 | 1/2004 |
| WO | WO-2005/007198 A2 | 1/2005 |
| WO | WO-2005/042034 A1 | 5/2005 |
| WO | WO-2005/051315 A2 | 6/2005 |
| WO | WO-2005/117986 A1 | 12/2005 |
| WO | WO-2006/060533 A1 | 6/2006 |
| WO | WO-2006/090813 A1 | 8/2006 |
| WO | WO-2007/014744 A2 | 2/2007 |
| WO | WO-2007/026972 A2 | 3/2007 |
| WO | WO-2007/027935 A2 | 3/2007 |
| WO | WO-2007/066106 A2 | 6/2007 |
| WO | WO-2007/099348 A2 | 9/2007 |
| WO | WO-2007/105027 A1 | 9/2007 |
| WO | WO-2007/106415 A2 | 9/2007 |
| WO | WO-2007/109254 A2 | 9/2007 |
| WO | 2009025846 * | 2/2009 |
| WO | WO-2009/018500 A1 | 2/2009 |
| WO | WO-2009/025846 A2 | 2/2009 |
| WO | WO-2009/026274 A1 | 2/2009 |
| WO | WO-2009/039409 A1 | 3/2009 |
| WO | WO-2009/088805 A2 | 7/2009 |
| WO | 2010081173 * | 7/2010 |
| WO | WO-2010/077643 A1 | 7/2010 |
| WO | WO-2010/083536 A1 | 7/2010 |
| WO | WO-2010/085845 A1 | 8/2010 |
| WO | WO-2011/015918 A1 | 2/2011 |
| WO | WO-2011/015921 A1 | 2/2011 |
| WO | WO-2011/101435 A1 | 8/2011 |
| WO | WO-2011/133658 A1 | 10/2011 |

OTHER PUBLICATIONS

Baron, Narula. From Cloning to a Commercial Realization: Human Alpha Interferon. Biotechnology. 1990; 10(3):179-190.

Bartenschlager et al. Substrate determinants for cleavage in cis and in trans by the hepatitis C virus NS3 proteinase. J Virol. 1995. 69(1):198-205.

Bessette et al. Construction of designed protein libraries using gene assembly mutagenesis. Methods Mol Biol. 2003;231:29-37.

(56) References Cited

OTHER PUBLICATIONS

Bessette et al. Rapid isolation of high-affinity protein binding peptides using bacterial display. Protein Eng Des Sel. Oct. 17, 2004(10):731-9.
Bessette, U.S. Appl. No. 61/249,416, entitled "Activatable Antibody Complexes," filed Oct. 7, 2009.
Boder et al. Directed evolution of antibody fragments with monovalent femtomolar antigen-binding affinity. Proc Natl Acad Sci U S A. Sep. 26, 2000;97(20):10701-5.
Boder et al. Yeast surface display for screening combinatorial polypeptide libraries. Nat Biotechnol. Jun. 1997;15(6):553-7.
Bupp et al. Altering retroviral tropism using a random-display envelope library. Mol Ther. Mar. 2002;5(3):329-35.
Caliceti et al. Preparation and properties of monomethoxy poly(ethylene glycol) doxorubicin conjugates linked by an amino acid or a peptide as spacer. Farmaco Jul. 1993;48(7):919-32.
Caron et al. Murine and humanized constructs of monoclonal antibody M195 (anti-CD33) for the therapy of acute myelogenoUS-leukemia. Cancer. Feb. 1, 1994;73(3 Suppl):1049-56.
Chang et al. Intratumoral delivery of IL-18 naked DNA induces T-cell activation and Th1 response in a mouse hepatic cancer model. BMC Cancer. May 23, 2007;87(7):1-6.
Chari et al. C242-DM1: A'tumor-activated prodrug that shows exceptional activity in human colon tumor xenograft models at non-toxic doses. Proceedings of the American Association for Cancer Research Annual Meeting, Mar. 1998, 39:643 (89th annual meeting of the American Association for Cancer Research).
Chari et al. Integration of SB-40875 into combination treatments of human colon xenograft models of SCID mice. Proceedings of the American Association for Cancer Research Annual Meeting, Mar. 2000, 41:291 (9181 annual meeting of the American Association for Cancer Research.
Chari. Targeted Cancer Therapy: Conferring Specificity to Cytotoxic Drugs. Accounts of Chemical Research. Jan. 2008; 41(1):98-107.
Chari. Targeted delivery of chemotherapeutics: Tumor-activated prodrug therapy. Advanced Drug Delivery Reviews Apr. 6, 1998;31(1-2):89-104.
Chen et al. Selection and analysis of an optimized anti-VEGF antibody: crystal structure of an affinity-matured fab in complex with antigen. J Mol Biol. Nov. 5, 1999;293(4):865-881.
Chmura et al. Antibodies with infinite affinity. Proc Natl Acad Sci U S A. Jul. 17, 2001;98(15):8480-4.
Cho et al. N-terminal processing is essential for release of epithin, a mouse type II membrane serine protease. J Biol Chem. 2001. 276(48):44581-9.
Co et al. Chimeric and humanized antibodies with specificity for the CD33 antigen. J Immunol. Feb. 15, 1992;148(4):1149-54.
Cooper et al. Galactose oxidase from PolyporUS-circinatus, Fr. J Biol Chem. Mar. 1959;234(3):445-8.
Daugherty et al. Flow cytometric screening of cell-based libraries. J Immunol Methods. Sep. 21, 2000;243(1-2):211-27.
Daugherty et al. Quantitative analysis of the effect of the mutation frequency on the affinity maturation of single chain Fv antibodies. Proc Natl Acad Sci U S A. Feb. 29, 2000;97(5):2029-34.
Daugherty, et al., U.S. Appl. No. 60/957,449, entitled "Activatable Binding Polypeptides and Methods of Identification and Use Thereof," filed Aug. 22, 2007.
Daugherty, et al., U.S. Appl. No. 60/957,453, entitled "Activatable Binding Polypeptides Capable of Binding Multiple Targets and Methods of Identification and Use Thereof," filed Aug. 22, 2007.
Daugherty, U.S. Appl. No. 61/052,986, entitled "Protease Activated Probody Constructs and Methods of Use," filed May 13, 2008.
Donaldson et al. Design and development of masked therapeutic antibodies to limit off-target effects13 Application to anti-EGFR antibodies. Cancer Biology & Therapy. Nov. 2009. 8(22):1-6.
Facchiano et al. Identification of a novel domain of fibroblast growth factor 2 controlling its angiogenic properties. The Journal of Biological Chemistry. 2003. 278(10):8751-8760.
Ford et al. Fusion tails for the recovery and purification of recombinant proteins. Protein expression and purification 1991, 2:95-107.

Fricker. MMP-8: a new target for atherosclerosis? Drug Discov Today. Jan. 15, 2005;7(2):86-8.
Funahashi et al. A notch1 ectodomain construct inhibits endothelial notch signaling, tumor growth, and angiogenesis. Cancer Res. 2008. 68(12):4727-35.
Georgiou et al. Display of heterologoUS-proteins on the surface of microorganisms: from the screening of combinatorial libraries to live recombinant vaccines. Nat Biotechnol. Jan. 1997;15(1):29-34.
Georgiou. Analysis of large libraries of protein mutants using flow cytometry. Adv Protein Chem. 2000;55:293-315.
Gerspach et al. Restoration of membrane TNF-like activity by cell surface targeting and matrix metalloproteinase-mediated processing of a TNF prodrug. Cell Death and Differentiation. 2006.13:273-284.
Gilliland et al. Elimination of the Immunogenicity of Therapeutic Antibodies. Journal of Immunology. 1999. 162:3663-3671.
Gilliland et al. Rapid and reliable cloning of antibody variable regions and generation of recombinant single chain antibody fragments. Tissue Antigens. Jan. 1996;47(1):1-20.
Grussenmeyer et al. Complexes of polyoma virUS-medium T antigen and cellular proteins. Proc Natl Acad Sci U S A. Dec. 1985;82(23):7952-4.
Guay et al. Potency and selectivity of inhibition of cathepsin K, L and S by their respective propeptides. Eur J Biochem. 2000. 267(20):6311-8.
Hagedorn et al., A short peptide domain of platelet factor 4-Blocks angiogenic key events induced by FGF-2. FASEB J. Mar. 15, 2001(3):550-2.
Hale. Synthetic peptide mimotope of the CAMPATH-1 (CD52) antigen, a small glycosylphosphatidylinositol-anchored glycoprotein. Inrimunotechnology. Dec. 1995; 1(3):175-187.
Harris et al. Generation of Anti-complement "Prodrugs". The Journal of Biological Chemistry. Sep.2003. 278(38):36068-36076.
Hillmen et al. The complement inhibitor eculizumab in paroxysmal nocturnal hemoglobinuria. N Engl J Med. Sep. 21, 2006;355(12):1233-43.
Hopp et al. A Short Polypeptide Marker Sequence Useful for Recombinant Protein Identification and Purification. Nature Biotechnology 1988 6:1204 -1210.
Horton et al. Engineering hybrid genes without the use of restriction enzymes: gene splicing by overlap extension. Gene. Apr. 15, 1989;77(1):61-8.
Iiyama et al. Patterns of Vascular Cell Adhesion Molecule-1 and Intercellular Adhesion Molecule-1 Expression in Rabbit and Mouse Atherosclerotic Lesions and at Sites Predisposed to Lesion Formation. Circulation Research, Am Heart Assoc.1999;85:199-207.
Immordino et al. Stealth liposomes: review of the basic science, rationale, and clinical applications, existing and potential. Int J Nanomedicine. Sep. 2006;1(3):297-315.
Isaacs et al. Helplessness as a Strategy for Avoiding Antiglobulin responses to Therapeutic Monoclonal Antiboties. Therapeutic Immunology. Dec. 1994; 1(6):303-312.
Jensen-Jarolim et al. Peptide mimotopes displayed by phage inhibit antibody binding to bet v 1, the major birch pollen allergen, and induce specific IgG response in mice. FASEB J. Dec. 1998;12(15):1635-42.
Johnson et al. Development of a humanized monoclonal antibody (MEDI-493) with potent in vitro and in vivo activity against respiratory syncytial virus. J Infect Dis. Nov. 1997;176(5):1215-24.
Kam et al. MUC1 synthetic peptide inhibition of intercellular adhesion molecule-1 and MUC1 binding requires six tandem repeats. Cancer Res. 1998. 58(23):5577-81.
Kamath, et al., U.S. Appl. No. 61/249,441, entitled "Methods and Compositions For Serum Half-Life Extension of Antibodies and Antibody Derivatives," filed Oct. 7, 2009.
Karush et al. Interaction of a bivalent ligand with IgM anti-lactose antibody. Biochemistry. May 29, 1979;18(11):2226-32.
Knight et al. Construction and initial characterization of a mouse-human chimeric anti-TNF antibody. Mol Immunol. Nov. 1993;30(16):1443-53.
La Rocca et al. Zymographic detection and clinical correlations of MMP-2 and MMP-9 in breast cancer sera. Br J Cancer. Apr. 5, 2004;90(7):1414-21.

(56) References Cited

OTHER PUBLICATIONS

Lambert et al. Pharmacokinetics, in vivo stability, and toxicity of the tumoractivated prodrug. Proceedings of the American Association for Cancer Research Annual Meeting, Mar. 1998, 39:522 (89th annual meeting of the American Association for Cancer Research).

Lamoyi et al. Preparation of F(ab')2 fragments from mouse IgG of various subclasses. J Immunol Methods. Jan. 28, 1983;56(2):235-43.

Leger et al. Humanization of a mouse antibody against human alpha-4 integrin: a potential therapeutic for the treatment of multiple sclerosis. Hum Antibodies. 1997;8(1):3-16.

Liu et al. Overexpression of legumain in tumors is significant for invasion/metastasis and a candidate enzymatic target for prodrug therapy. Cancer Res. Jun. 1, 2003;63(11):2957-64.

Lowman et al. Selecting high-affinity binding proteins by monovalent phage display. Biochemistry. Nov. 12, 1991;30(45):10832-8.

Lozano et al. Solution structure and interaction with basic and acidic fibroblast growth factor of a 3-kDa human platelet factor-4 fragment with antiangiogenic activity. The Journal of Biological Chemistry. 2001. 276(38):35723-35734.

Mathieu et al. Substrate specificity of schistosome versUS-human legumain determined by P1-P3 peptide libraries. Mol Biochem Parasitol. Apr. 30, 2002;121(1):99-105.

Mattheakis et al. An in vitro polysome display system for identifying ligands from very large peptide libraries. Proc Natl Acad Sci U S A. Sep. 13, 1994;91(19):9022-6.

Mitra et al. Reagents for the crosslinking of proteins by equilibrium transfer alkylation. J. Am. Chem. Soc., 1979;101(11):3097-3110.

Muller et al. Random peptide libraries displayed on adeno-associated virus to select for targeted gene therapy vectors. Nat Biotechnol. 21(9):1040-6. Epub Aug. 3, 2003.

Nagahira et al. Humanization of a mouse neutralizing monoclonal antibody against tumor necrosis factor-alpha (TNF-alpha). J Immunol Methods. Jan. 1, 1999;222(1-2):83-92.

Nicaise et al. Affinity transfer by CDR grafting on a nonimmunoglobulin scaffold. Protein Sci. 2004. 13(7):1882-91.

Nicolaisen-Strouss et al. Natural feline leukemia virUS-variant escapes neutralization by a monoclonal antibody via an amino acid change outside the antibody-binding epitope. Journal of Virology. 1987. 61(11):3410-3415.

Nilsson et al. Expression and purification of recombinant insulin-like growth factors from *Escherichia coli*. Methods Enzymol. 1991;198:3-16.

Nilsson et al. Immobilization and purification of enzymes with staphylococcal protein A gene fusion vectors. EMBO J. Apr. 1985;4(4):1075-80.

Olsen et al. High-throughput FACS method for directed evolution of substrate specificity. Methods Mol Biol. 2003;230:329-42.

Palandoken et al. Amiloride peptide conjugates: prodrugs for sodium-piton exchange inhibition. J. Pharmacol. Exp. Ther. Mar. 2005 312(3):961-967.

Parham. On the fragmentation of monoclonal IgG1, IgG2a, and IgG2b from BALB/c mice. J Immunol. Dec. 1983;131(6):2895-902.

Presta et al. Humanization of an anti-vascular endothelial growth factor monoclonal antibody for the therapy of solid tumors and other disorders. Cancer Res. Oct. 15, 1997;57(20):4593-9.

Putnam et al. Complete amino acid sequence of the Mu heavy chain of a human IgM immunoglobulin. Science. Oct. 19, 1973;182(109):287-91.

Rader et al. Chemically programmed monoclonal antibodies for cancer therapy: adaptor immunotherapy based on a covalent antibody catalyst. Proc Natl Acad Sci U S A. Apr. 29, 2003;100(9):5396-400.

Ribas et al.Tremelimumab (CP-675,206), a Cytotoxic T Lymphocyte-Associated Antigen 4-Blocking Monoclonal Antibody in Clinical Development for Patients with Cancer. Oncologist, Jul. 2007;12:873-883.

Rice et al. Bacterial display using circularly permuted outer membrane protein OmpX yields high affinity peptide ligands. Protein Sci. Apr. 2006;15(4):825-36.

Rodwell et al. Linker Technology: Antibody-Mediated Delivery Systems. Biotechnology. 1985. 3:889-894.

Samel et al. Generation of a FasL-based Proapoptotic Fusion Protein Devoid of Systemic Toxicity due to Cell-surface Antigen-restricted Activation. The Journal of Biological Chemistry. Aug. 2003. 278(34):32077-32082.

Scheraga. Predicting three-dimensional structures of oligopeptides, In:Reviews in Computational Chemistry. vol. III, Lipkowitz and Boyd, eds., New York; 1992:73-142.

Scott et al. Searching for peptide ligands with an epitope library. Science. Jul. 27, 1990;249(4967):386-90.

Self et al. Light-Directed Activation of Human T-Cells. ChemMedChem. 2007 2:1587-1.

Self, Thompson. How specific are therapeutic monoclonal antibodies? www.thelancet.com. Apr. 2006. 367(960):1038-1039.

Self, Thompson. Light activatable antibodies: Models for remotely activatable proteins. Nature Medicine. Jul. 1996. 2(7):817-820.

Shusta et al. Biosynthetic polypeptide libraries. Curr Opin Biotechnol. Apr. 1999;10(2):117-22.

Sidhu et al. Exploring protein-protein interactions with phage display. Chembiochem. 2003. 4(1):14-25.

Smith et al. Protein loop grafting to construct a variant of tissue-type plasminogen activator that binds platelet integrin alpha Iib beta 3. J Biol Chem. 1995. 270(51):30486-90.

Smith et al. Single-step purification of polypeptides expressed in *Escherichia coli* as fusions with glutathione S-transferase. Gene. Jul. 15, 1988;67(1):31-40.

Stagliano, et al. U.S. Appl. No. 61/154,730, entitled "Proproteins and Methods of Use Thereof," filed Feb. 23, 2009.

Stagliano, et al. U.S. Appl. No. 61/144,105, entitled "Activatable Antibodies and Methods of Identification and Use Thereof," filed Jan. 12, 2009.

Stagliano, et al. U.S. Appl. No. 61/144,110, entitled "Activatable Antibody Conjugates and Methods of Identification and Use Thereof," filed Jan. 12, 2009.

Stanworth, et al. Handbook of experimental immunology, vol. 1, 2nd ed., Weir ed., chapter 10,—Blackwell Scientific Publications, London; 1973.

Takagi et al. A new approach for alteration of protease functions: pro-sequence engineering. Appl Microbiol Biotechnol. 2003. 63(1):1-9.

Thompson et al. A simple procedure for the photoregulation of chymotrypsin activity. Photochemical & Photobiological Sciences. 2006. 5:326-330.

Thompson et al. Light Activation of Anti-CD3 in vivo Reduces the Growth of an Aggressive Ovarian Carcinoma. ChemMedChem. 2007. 2:1591-1593.

Thompson et al. Photocleavable Nitrobenzyl-Protein Conjugates. Biochemical and Biophysical Research Communications. Jun. 1994. 201(3):1213-1219.

Thompson et al. The construction and in vitro testing of photo-activatable cancer targeting folated anti-CD3 conjugates. Biochemical and Biophysical Research Communication. 2008. 366:526-531.

Thompson et al. The Construction of a Functional Photoactivatable Cancer Targeting Bispecific Antibody Conjugate. ChemMedChem. 2007. 2:1162-1164.

Thompson, et al. The modulation of Protein A-IgG(Fc) binding by the reversible addition of 2-nitrobenzyl groups. Biochemical Society Transactions. May 1995; vol. 23(2):155S.

Trouet et al. CPI-0004Na: An extracellular tumor-activated prodrug of doxorubicin. Proceedings of the American Association for Cancer Research Annual Meeting, Mar. 2000, 41:522 (9151 annual meeting of the American Association for Cancer Research, San Francisco).

Trouet et al. Extracellularly tumor-activated prodrugs for the selective chemotherapy of cancer: application to doxorubicin and preliminary in vitro and in vivo studies. Cancer Research Apr. 2001. 61(7):2843-6.

Tuve et al. Combination of tumor site-located CTL-associated antigen-4 blockade and systemic regulatory T-cell depletion induces tumor-destructive immune responses. Cancer Res. Jun. 15, 2007;67(12):5929-39.

Vartak, Gemeinhart. Matrix metalloproteases: Underutilized targets for drug delivery. Journal of Drug Targeting. Jan. 2007. 15(1):1-20.

(56) References Cited

OTHER PUBLICATIONS

Weisel, Medved. The Structure and Function of the aC Domains of Fibrinogen. Annals New York Academy of Sciences. 2001. 312-327.

Werther et al. Humanization of an anti-lymphocyte function-associated antigen (LFA)-1 monoclonal antibody and reengineering of the humanized antibody for binding to rhesUS-LFA-1. J Immunol. Dec. 1, 1996;157(11):4986-95.

Wiebe et al. Concepts for the design of anti-HIV nucleoside prodrugs for treating cephalic HIV infection. Advanced Drug Delivery Reviews Oct. 18, 1998;39(1-3):63-80.

Wiiest et al. TNF-Selectokine: a novel prodrug generated for tumor targeting and stie-specific activation of tumor necrosis factor. Oncogene. 2002. 21:4257-4265.

Wilson et al. The use of mRNA display to select high-affinity protein-binding peptides. Proc Natl Acad Sci U S A. 98(7):3750-5. Epub Mar. 13, 2001.

Xie et al. Identification of the fibroblast growth factor (FGF)-interacting domain in a secreted FGF-binding protein by phage display. The Journal of Biological Chemistry. 2006. 281(2):1137-1144.

Yang et al. Ipilimumab (anti-CTLA4 antibody) causes regression of metastatic renal cell cancer associated with enteritis and hypophysitis. J Immunother. Nov.-Dec. 2007;30(8):825-30.

Zhou et al. Specific Antibodies to the External Vestibule of Voltage-gated Potassium Channels-Block Current. J. Gen. Physiol. 1998. 111:555-563.

\* cited by examiner

Figure 2
A.
B.
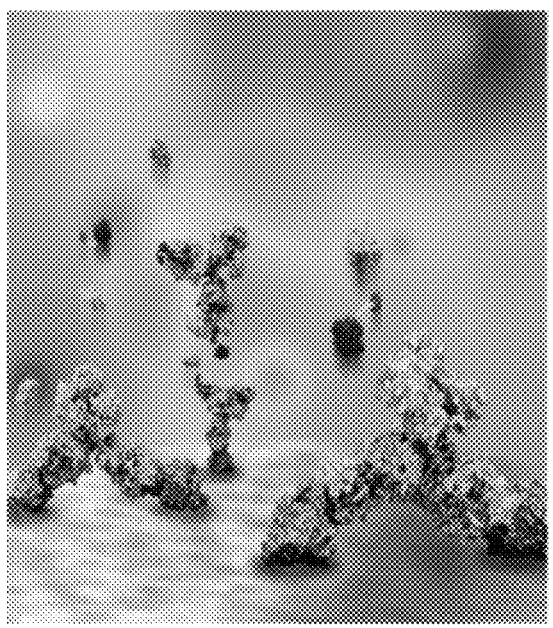

Figure 11
For1a
　　For1c link
　　　　For1d linkV$_L$
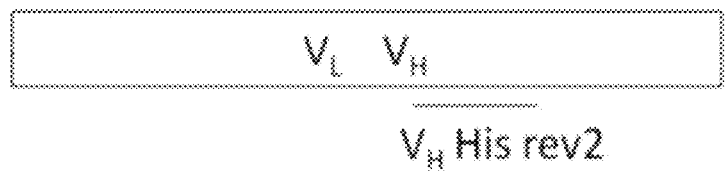
　　　　　　　　　　V$_H$ His rev2
For1a
　　For1c link
　　　　For1e linkV$_H$
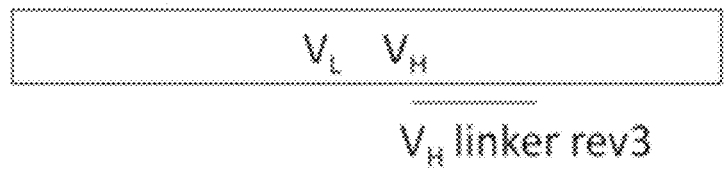
　　　　　　　　　　V$_H$ linker rev3

SEQUENCE LISTING

```
<160> NUMBER OF SEQ ID NOS: 362

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 1

Cys Ile Ser Pro Arg Gly Cys
1               5

<210> SEQ ID NO 2
<211> LENGTH: 18
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (2)..(2)
<223> OTHER INFORMATION: Asn or Pro
<220> FEATURE:
<221> NAME/KEY: MOD_RES
```

```
<222> LOCATION: (4)..(4)
<223> OTHER INFORMATION: His, Val or Phe
<220> FEATURE:
<221> NAME/KEY: MOD_RES
<222> LOCATION: (5)..(5)
<223> OTHER INFORMATION: Tyr or Thr
<220> FEATURE:
<221> NAME/KEY: MOD_RES
<222> LOCATION: (6)..(6)
<223> OTHER INFORMATION: Phe, Trp, Thr or Leu
<220> FEATURE:
<221> NAME/KEY: MOD_RES
<222> LOCATION: (7)..(7)
<223> OTHER INFORMATION: Tyr, Gly, Thr or Ser
<220> FEATURE:
<221> NAME/KEY: MOD_RES
<222> LOCATION: (8)..(8)
<223> OTHER INFORMATION: Thr, Ser, Tyr or His

<400> SEQUENCE: 2

Cys Xaa His Xaa Xaa Xaa Xaa Xaa Cys Gly Cys Ile Ser Pro Arg Gly
1               5                   10                  15

Cys Gly

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (9)..(14)
<223> OTHER INFORMATION: Any amino acid

<400> SEQUENCE: 3

Xaa Cys Xaa Xaa Tyr Gln Cys Leu Xaa Xaa Xaa Xaa Xaa Xaa
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (10)..(11)
<223> OTHER INFORMATION: Any amino acid

<400> SEQUENCE: 4

Xaa Xaa Gln Pro Xaa Pro Pro Arg Val Xaa Xaa
1               5                   10

<210> SEQ ID NO 5
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (9)..(12)
<223> OTHER INFORMATION: Any amino acid

<400> SEQUENCE: 5

Pro Xaa Pro Gly Phe Pro Tyr Cys Xaa Xaa Xaa Xaa
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (1)..(4)
<223> OTHER INFORMATION: Any amino acid
<220> FEATURE:
<221> NAME/KEY: MOD_RES
<222> LOCATION: (6)..(7)
<223> OTHER INFORMATION: Any amino acid

<400> SEQUENCE: 6

Xaa Xaa Xaa Xaa Gln Xaa Xaa Pro Trp Pro Pro
1               5                   10

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (14)..(16)
<223> OTHER INFORMATION: Any amino acid

<400> SEQUENCE: 7

Gly Xaa Gly Xaa Cys Tyr Thr Ile Leu Glu Xaa Xaa Cys Xaa Xaa Xaa
1               5                   10                  15
Arg

<210> SEQ ID NO 8
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      consensus peptide
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (14)..(17)
<223> OTHER INFORMATION: Any amino acid

<400> SEQUENCE: 8

Gly Xaa Xaa Xaa Cys Tyr Xaa Ile Xaa Glu Xaa Xaa Cys Xaa Xaa Xaa
1               5                   10                  15

Xaa

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (14)..(17)
<223> OTHER INFORMATION: Any amino acid

<400> SEQUENCE: 9

Gly Xaa Xaa Xaa Cys Tyr Xaa Ile Xaa Glu Xaa Trp Cys Xaa Xaa Xaa
1               5                   10                  15

Xaa

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
```

```
<222> LOCATION: (6)..(7)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (15)..(17)
<223> OTHER INFORMATION: Any amino acid

<400> SEQUENCE: 10

Xaa Xaa Xaa Cys Cys Xaa Xaa Tyr Xaa Ile Xaa Xaa Cys Cys Xaa Xaa
1               5                   10                  15

Xaa

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (1)..(5)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (11)..(15)
<223> OTHER INFORMATION: Any amino acid

<400> SEQUENCE: 11

Xaa Xaa Xaa Xaa Xaa Tyr Xaa Ile Leu Glu Xaa Xaa Xaa Xaa Xaa
1               5                   10                  15

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Ser Gly Gly Ser
1               5

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Gly Ser
1

<210> SEQ ID NO 14
<211> LENGTH: 4
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 14

Gly Gly Ser Gly
1

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Gly Ser Gly Gly
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Ser Gly Ser Gly
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Ser Gly Gly Gly
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Gly Gly Ser Gly
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Ser Ser Ser Gly
1               5
```

```
<210> SEQ ID NO 20
<211> LENGTH: 8
<212> TYPE: PRT
<213> ORGANISM: Unknown
<220> FEATURE:
<223> OTHER INFORMATION: Description of Unknown: Pro-urokinase
      peptide

<400> SEQUENCE: 20

Pro Arg Phe Lys Ile Ile Gly Gly
1               5

<210> SEQ ID NO 21
<211> LENGTH: 8
<212> TYPE: PRT
<213> ORGANISM: Unknown
<220> FEATURE:
<223> OTHER INFORMATION: Description of Unknown: Pro-urokinase
      peptide

<400> SEQUENCE: 21

Pro Arg Phe Arg Ile Ile Gly Gly
1               5

<210> SEQ ID NO 22
<211> LENGTH: 9
<212> TYPE: PRT
<213> ORGANISM: Unknown
<220> FEATURE:
<223> OTHER INFORMATION: Description of Unknown: TGFbeta
      peptide

<400> SEQUENCE: 22

Ser Ser Arg His Arg Arg Ala Leu Asp
1               5

<210> SEQ ID NO 23
<211> LENGTH: 14
<212> TYPE: PRT
<213> ORGANISM: Unknown
<220> FEATURE:
<223> OTHER INFORMATION: Description of Unknown: Plasminogen
      peptide

<400> SEQUENCE: 23

Arg Lys Ser Ser Ile Ile Ile Arg Met Arg Asp Val Val Leu
1               5                   10

<210> SEQ ID NO 24
<211> LENGTH: 15
<212> TYPE: PRT
<213> ORGANISM: Unknown
<220> FEATURE:
<223> OTHER INFORMATION: Description of Unknown: Staphylokinase
      peptide

<400> SEQUENCE: 24

Ser Ser Ser Phe Asp Lys Gly Lys Tyr Lys Lys Gly Asp Asp Ala
1               5                   10                  15

<210> SEQ ID NO 25
<211> LENGTH: 15
<212> TYPE: PRT
<213> ORGANISM: Unknown
<220> FEATURE:
<223> OTHER INFORMATION: Description of Unknown: Staphylokinase
      peptide

<400> SEQUENCE: 25
```

```
Ser Ser Ser Phe Asp Lys Gly Lys Tyr Lys Arg Gly Asp Asp Ala
1               5                   10                  15

<210> SEQ ID NO 26
<211> LENGTH: 4
<212> TYPE: PRT
<213> ORGANISM: Unknown
<220> FEATURE:
<223> OTHER INFORMATION: Description of Unknown: Factor Xa cleavable
      peptide

<400> SEQUENCE: 26

Ile Glu Gly Arg
1

<210> SEQ ID NO 27
<211> LENGTH: 4
<212> TYPE: PRT
<213> ORGANISM: Unknown
<220> FEATURE:
<223> OTHER INFORMATION: Description of Unknown: Factor Xa cleavable
      peptide

<400> SEQUENCE: 27

Ile Asp Gly Arg
1

<210> SEQ ID NO 28
<211> LENGTH: 7
<212> TYPE: PRT
<213> ORGANISM: Unknown
<220> FEATURE:
<223> OTHER INFORMATION: Description of Unknown: Factor Xa cleavable
      peptide

<400> SEQUENCE: 28

Gly Gly Ser Ile Asp Gly Arg
1               5

<210> SEQ ID NO 29
<211> LENGTH: 6
<212> TYPE: PRT
<213> ORGANISM: Unknown
<220> FEATURE:
<223> OTHER INFORMATION: Description of Unknown: Gelatinase A
      peptide

<400> SEQUENCE: 29

Pro Leu Gly Leu Trp Ala
1               5

<210> SEQ ID NO 30
<211> LENGTH: 8
<212> TYPE: PRT
<213> ORGANISM: Bos sp.

<400> SEQUENCE: 30

Gly Pro Gln Gly Ile Ala Gly Gln
1               5

<210> SEQ ID NO 31
<211> LENGTH: 8
<212> TYPE: PRT
<213> ORGANISM: Bos sp.

<400> SEQUENCE: 31

Gly Pro Gln Gly Leu Leu Gly Ala
```

```
<210> SEQ ID NO 32
<211> LENGTH: 5
<212> TYPE: PRT
<213> ORGANISM: Bos sp.

<400> SEQUENCE: 32

Gly Ile Ala Gly Gln
1               5

<210> SEQ ID NO 33
<211> LENGTH: 8
<212> TYPE: PRT
<213> ORGANISM: Homo sapiens

<400> SEQUENCE: 33

Gly Pro Leu Gly Ile Ala Gly Ile
1               5

<210> SEQ ID NO 34
<211> LENGTH: 8
<212> TYPE: PRT
<213> ORGANISM: Homo sapiens

<400> SEQUENCE: 34

Gly Pro Glu Gly Leu Arg Val Gly
1               5

<210> SEQ ID NO 35
<211> LENGTH: 8
<212> TYPE: PRT
<213> ORGANISM: Homo sapiens

<400> SEQUENCE: 35

Tyr Gly Ala Gly Leu Gly Val Val
1               5

<210> SEQ ID NO 36
<211> LENGTH: 8
<212> TYPE: PRT
<213> ORGANISM: Homo sapiens

<400> SEQUENCE: 36

Ala Gly Leu Gly Val Val Glu Arg
1               5

<210> SEQ ID NO 37
<211> LENGTH: 8
<212> TYPE: PRT
<213> ORGANISM: Homo sapiens

<400> SEQUENCE: 37

Ala Gly Leu Gly Ile Ser Ser Thr
1               5

<210> SEQ ID NO 38
<211> LENGTH: 8
<212> TYPE: PRT
<213> ORGANISM: Rattus sp.

<400> SEQUENCE: 38

Glu Pro Gln Ala Leu Ala Met Ser
1               5
```

```
<210> SEQ ID NO 39
<211> LENGTH: 8
<212> TYPE: PRT
<213> ORGANISM: Rattus sp.

<400> SEQUENCE: 39

Gln Ala Leu Ala Met Ser Ala Ile
1               5

<210> SEQ ID NO 40
<211> LENGTH: 8
<212> TYPE: PRT
<213> ORGANISM: Rattus sp.

<400> SEQUENCE: 40

Ala Ala Tyr His Leu Val Ser Gln
1               5

<210> SEQ ID NO 41
<211> LENGTH: 8
<212> TYPE: PRT
<213> ORGANISM: Rattus sp.

<400> SEQUENCE: 41

Met Asp Ala Phe Leu Glu Ser Ser
1               5

<210> SEQ ID NO 42
<211> LENGTH: 8
<212> TYPE: PRT
<213> ORGANISM: Rattus sp.

<400> SEQUENCE: 42

Glu Ser Leu Pro Val Val Ala Val
1               5

<210> SEQ ID NO 43
<211> LENGTH: 8
<212> TYPE: PRT
<213> ORGANISM: Rattus sp.

<400> SEQUENCE: 43

Ser Ala Pro Ala Val Glu Ser Glu
1               5

<210> SEQ ID NO 44
<211> LENGTH: 8
<212> TYPE: PRT
<213> ORGANISM: Homo sapiens

<400> SEQUENCE: 44

Asp Val Ala Gln Phe Val Leu Thr
1               5

<210> SEQ ID NO 45
<211> LENGTH: 8
<212> TYPE: PRT
<213> ORGANISM: Homo sapiens

<400> SEQUENCE: 45

Val Ala Gln Phe Val Leu Thr Glu
1               5

<210> SEQ ID NO 46
<211> LENGTH: 8
<212> TYPE: PRT
```

<213> ORGANISM: Homo sapiens

<400> SEQUENCE: 46

Ala Gln Phe Val Leu Thr Glu Gly
1               5

<210> SEQ ID NO 47
<211> LENGTH: 8
<212> TYPE: PRT
<213> ORGANISM: Homo sapiens

<400> SEQUENCE: 47

Pro Val Gln Pro Ile Gly Pro Gln
1               5

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 48

His His His His His His
1               5

<210> SEQ ID NO 49
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
gatattcaac tgacccagag cccttcttcc ctgagtgcca gcgtgggtga ccgtgttacg     60
atcacttgct cggccagcca agatatttct aactacctga attggtacca gcagaagcca    120
ggaaaggcac aaaagtcct gatctacttc acaagttcac tgcattccgg cgtaccgtcg     180
cgctttagcg gttctggcag tggtaccgac ttcaccctga ctatctcgag tctgcaacct    240
gaggattttg ctacatatta ctgtcagcaa tattcgaccg tgccgtggac gttcgggcag    300
ggcaccaaag tggagattaa ggggggtgga ggcagcgggg aggtggctc aggcggtgga     360 gggtctggcg aggtccagct ggtagaaagc ggggcggac tggtccaacc gggcggatcc     420
ctgcgtctga gctgcgcggc ctcgggttac gactttactc actacggaat gaactgggtt    480
cgccaagccc ctggtaaagg tctggaatgg gtcggatgga ttaatacata cactggagaa    540
cctacttatg ctgctgattt caaacgtcgc tttactttct ctctggatac aagtaagtca    600
accgcctatc tgcaaatgaa cagcctgcgt gcagaggaca cggctgtgta ctattgtgcg    660
aaatatcctt attattatgg aacttcccac tggtatttcg atgtatgggg ccagggtact    720
ctggttacag tgtcg                                                     735

<210> SEQ ID NO 50
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Gln Leu Thr Gln Ser Pro Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Gly Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Tyr Asp Phe Thr His Tyr Gly Met Asn Trp Val
145                 150                 155                 160

Arg Gln Ala Pro Gly Lys Gly Leu Glu Trp Val Gly Trp Ile Asn Thr
                165                 170                 175

Tyr Thr Gly Glu Pro Thr Tyr Ala Ala Asp Phe Lys Arg Arg Phe Thr
            180                 185                 190

Phe Ser Leu Asp Thr Ser Lys Ser Thr Ala Tyr Leu Gln Met Asn Ser
        195                 200                 205

Leu Arg Ala Glu Asp Thr Ala Val Tyr Tyr Cys Ala Lys Tyr Pro Tyr
210                 215                 220

Tyr Tyr Gly Thr Ser His Trp Tyr Phe Asp Val Trp Gly Gln Gly Thr
225                 230                 235                 240

Leu Val Thr Val Ser
                245

<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ala Thr Ala Val Trp Asn Ser Met Val Lys Gln Ser Cys Tyr Met Gln
1               5                   10                  15

Gly

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly His Gly Met Cys Tyr Thr Ile Leu Glu Asp His Cys Asp Arg Val
1               5                   10                  15

Arg

```
<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Pro Cys Ser Glu Trp Gln Ser Met Val Gln Pro Arg Cys Tyr Tyr Gly
1               5                   10                  15

Gly

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asn Val Glu Cys Cys Gln Asn Tyr Asn Leu Trp Asn Cys Cys Gly Gly
1               5                   10                  15

Arg

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Val His Ala Trp Glu Gln Leu Val Ile Gln Glu Leu Tyr His Cys
1               5                   10                  15

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Val Gly Leu Cys Tyr Thr Ile Leu Glu Gln Trp Cys Glu Met Gly
1               5                   10                  15

Arg

<210> SEQ ID NO 57
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Pro Pro Cys Cys Arg Asp Tyr Ser Ile Leu Glu Cys Cys Lys Ser
1               5                   10                  15

Asp

<210> SEQ ID NO 58
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Ala Met Ala Cys Tyr Asn Ile Phe Glu Tyr Trp Cys Ser Ala Met
1               5                   10                  15

Lys

<210> SEQ ID NO 59
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gaattcatgg gccatcacca tcaccatcac ggtgggg                              37

<210> SEQ ID NO 60
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gtgagtaagc ttttattacg acactgtaac cagagtaccc tgg                      43

<210> SEQ ID NO 61
<211> LENGTH: 71
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gtggcatgtg cacttggcca ccttggccca ctcgagctgg ccagactggc cctgaaaata    60
cagattttcc c                                                         71

<210> SEQ ID NO 62
<211> LENGTH: 81
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gagtgggcca aggtggccaa gtgcacatgc cactgggctt cctgggtccg ggcggttctg    60
atattcaact gacccagagc c                                              81

<210> SEQ ID NO 63
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
```
ttcgagctcg aacaacaaca acaataacaa taacaacaac     40

<210> SEQ ID NO 64
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gctttcaccg caggtacttc cgtagctggc cagtctggcc     40

<210> SEQ ID NO 65
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
cgctccatgg gccaccttgg ccgctgccac cagaaccgcc     40

<210> SEQ ID NO 66
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gcccagccgg ccatggccgg ccagtctggc cagctcgagt     40

<210> SEQ ID NO 67
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ccagtgccaa gcttttagtg gtgatggtga tgatgcgaca ctgtaaccag agtaccctgg     60
cc                                                                    62

<210> SEQ ID NO 68
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
cttgtcacga attcgggcca gtctggccag ctcgagt     37

<210> SEQ ID NO 69
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
cagatctaac catggcgccg ctaccgcccg acactgtaac cagagtaccc tg          52

<210> SEQ ID NO 70
<211> LENGTH: 860
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
atgggccatc accatcacca tcacggtggg gaaaatctgt attttcaggg ccagtctggc    60
cagctcgagt gggccaaggt ggccaagtgc acatgccact gggcttcctg ggtccgggcg   120
gttctgatat tcaactgacc cagagcccctt cttccctgag tgccagcgtg ggtgaccgtg   180
ttacgatcac ttgctcggcc agccaagata tttctaacta cctgaattgg taccagcaga   240
agccaggaaa ggcaccaaaa gtcctgatct acttcacaag ttcactgcat ccggcgtac    300 cgtcgcgctt tagcggttct ggcagtggta ccgacttcac cctgactatc tcgagtctgc   360
aacctgagga ttttgctaca tattactgtc agcaatattc gaccgtgccg tggacgttcg   420
ggcagggcac caaagtggag attaaggggg gtggaggcag cgggggaggt ggctcaggcg   480
gtggagggtc tggcgaggtc cagctggtag aaagcggggg cggactggtc caaccgggcg   540
gatccctgcg tctgagctgc gcggcctcgg gttacgactt tactcactac ggaatgaact   600
gggttcgcca agcccctggt aaaggtctgg aatgggtcgg atggattaat acatacactg   660
gagaacctac ttatgctgct gatttcaaac gtcgctttac tttctctctg gatacaagta   720
agtcaaccgc ctatctgcaa atgaacagcc tgcgtgcaga ggacacggct gtgtactatt   780 gtgcgaaaata tccttattat tatggaactt cccactggta tttcgatgta tggggccagg   840
gtactctggt tacagtgtcg                                              860

<210> SEQ ID NO 71
<211> LENGTH: 918
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
atgggccatc accatcacca tcacggtggg gaaaatctgt attttcaggg ccagtctggc    60
cagccgtgtt ctgagtggca gtcgatggtg cagccgcgtt gctattatgg gggcggttct   120
ggtggcagcg gccaaggtgg ccaagtgcac atgccactgg gcttcctggg tccgggcggt   180
tctgatattc aactgaccca gagcccttct tccctgagtg ccagcgtggg tgaccgtgtt   240
acgatcactt gctcggccag ccaagatatt tctaactacc tgaattggta ccagcagaag   300
ccaggaaagg caccaaaagt cctgatctac ttcacaagtt cactgcattc cggcgtaccg   360
tcgcgcttta gcggttctgg cagtggtacc gacttcaccc tgactatctc gagtctgcaa   420
cctgaggatt ttgctacata ttactgtcag caatattcga ccgtgccgtg gacgttcggg   480
cagggcacca aagtggagat taaggggggt ggaggcagcg ggggaggtgg ctcaggcggt   540
ggagggtctg gcgaggtcca gctggtagaa agcggggggcg gactggtcca accgggcgga   600
tccctgcgtc tgagctgcgc ggcctcgggt tacgacttta ctcactacgg aatgaactgg   660
gttcgccaag cccctggtaa aggtctggaa tgggtcggat ggattaatac atacactgga   720
gaacctactt atgctgctga tttcaaacgt cgctttactt tctctctgga tacaagtaag   780
tcaaccgcct atctgcaaat gaacagcctg cgtgcagagg acacggctgt gtactattgt    840
gcgaaatatc cttattatta tggaacttcc cactggtatt tcgatgtatg gggccaggt    900 actctggtta cagtgtcg                                                  918

<210> SEQ ID NO 72
<211> LENGTH: 306
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Met Gly His His His His His Gly Gly Glu Asn Leu Tyr Phe Gln
1               5                   10                  15

Gly Gln Ser Gly Gln Pro Cys Ser Glu Trp Gln Ser Met Val Gln Pro
                20                  25                  30

Arg Cys Tyr Tyr Gly Gly Ser Gly Gly Ser Gly Gln Gly Gly Gln
            35                  40                  45

Val His Met Pro Leu Gly Phe Leu Gly Pro Gly Gly Ser Asp Ile Gln
50                  55                  60

Leu Thr Gln Ser Pro Ser Ser Leu Ser Ala Ser Val Gly Asp Arg Val
65                  70                  75                  80

Thr Ile Thr Cys Ser Ala Ser Gln Asp Ile Ser Asn Tyr Leu Asn Trp
                85                  90                  95

Tyr Gln Gln Lys Pro Gly Lys Ala Pro Lys Val Leu Ile Tyr Phe Thr
            100                 105                 110

Ser Ser Leu His Ser Gly Val Pro Ser Arg Phe Ser Gly Ser Gly Ser
        115                 120                 125

Gly Thr Asp Phe Thr Leu Thr Ile Ser Ser Leu Gln Pro Glu Asp Phe
130                 135                 140

Ala Thr Tyr Tyr Cys Gln Gln Tyr Ser Thr Val Pro Trp Thr Phe Gly
145                 150                 155                 160

Gln Gly Thr Lys Val Glu Ile Lys Gly Gly Gly Gly Ser Gly Gly Gly
                165                 170                 175

Gly Ser Gly Gly Gly Gly Ser Gly Glu Val Gln Leu Val Glu Ser Gly
            180                 185                 190

Gly Gly Leu Val Gln Pro Gly Gly Ser Leu Arg Leu Ser Cys Ala Ala
        195                 200                 205

Ser Gly Tyr Asp Phe Thr His Tyr Gly Met Asn Trp Val Arg Gln Ala
210                 215                 220

Pro Gly Lys Gly Leu Glu Trp Val Gly Trp Ile Asn Thr Tyr Thr Gly
225                 230                 235                 240

Glu Pro Thr Tyr Ala Ala Asp Phe Lys Arg Arg Phe Thr Phe Ser Leu
                245                 250                 255

Asp Thr Ser Lys Ser Thr Ala Tyr Leu Gln Met Asn Ser Leu Arg Ala
            260                 265                 270

Glu Asp Thr Ala Val Tyr Tyr Cys Ala Lys Tyr Pro Tyr Tyr Gly
        275                 280                 285

Thr Ser His Trp Tyr Phe Asp Val Trp Gly Gln Gly Thr Leu Val Thr
290                 295                 300

Val Ser
305

<210> SEQ ID NO 73

<211> LENGTH: 921
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 73

```
atgggccatc accatcacca tcacggtggg gaaaatctgt attttcaggg ccagtctggc    60
cagcggccgc cgtgttgccg tgattatagt attttggagt gctgtaagag tgatggcggt   120
tctggtggca gcggccaagg tggccaagtg cacatgccac tgggcttcct gggtccgggc   180
ggttctgata ttcaactgac ccagagccct tcttccctga gtgccagcgt gggtgaccgt   240
gttacgatca cttgctcggc cagccaagat atttctaact acctgaattg gtaccagcag   300
aagccaggaa aggcaccaaa agtcctgatc tacttcacaa gttcactgca ttccggcgta   360
ccgtcgcgct ttagcggttc tggcagtggt accgacttca ccctgactat ctcgagtctg   420
caacctgagg attttgctac atattactgt cagcaatatt cgaccgtgcc gtggacgttc   480
gggcagggca ccaaagtgga gattaagggg ggtggaggca gcggggggagg tggctcaggc   540
ggtggagggt ctggcgaggt ccagctggta gaaagcgggg gcggactggt ccaaccgggc   600
ggatccctgc gtctgagctg cgcggcctcg ggttacgact ttactcacta cggaatgaac   660
tgggttcgcc aagcccctgg taaaggtctg gaatgggtcg gatggattaa tacatacact   720
ggagaaccta cttatgctgc tgatttcaaa cgtcgcttta ctttctctct ggatacaagt   780
aagtcaaccg cctatctgca aatgaacagc ctgcgtgcag aggacacggc tgtgtactat   840
tgtgcgaaat atccttatta ttatggaact tcccactggt atttcgatgt atggggccag   900
ggtactctgg ttacagtgtc g                                              921
```

<210> SEQ ID NO 74
<211> LENGTH: 307
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

```
Met Gly His His His His His Gly Gly Glu Asn Leu Tyr Phe Gln
1               5                   10                  15

Gly Gln Ser Gly Gln Arg Pro Pro Cys Cys Arg Asp Tyr Ser Ile Leu
            20                  25                  30

Glu Cys Cys Lys Ser Asp Gly Gly Ser Gly Gly Ser Gly Gln Gly Gly
        35                  40                  45

Gln Val His Met Pro Leu Gly Phe Leu Gly Pro Gly Ser Asp Ile
    50                  55                  60

Gln Leu Thr Gln Ser Pro Ser Ser Leu Ser Ala Ser Val Gly Asp Arg
65                  70                  75                  80

Val Thr Ile Thr Cys Ser Ala Ser Gln Asp Ile Ser Asn Tyr Leu Asn
                85                  90                  95

Trp Tyr Gln Gln Lys Pro Gly Lys Ala Pro Lys Val Leu Ile Tyr Phe
            100                 105                 110

Thr Ser Ser Leu His Ser Gly Val Pro Ser Arg Phe Ser Gly Ser Gly
        115                 120                 125

Ser Gly Thr Asp Phe Thr Leu Thr Ile Ser Ser Leu Gln Pro Glu Asp
    130                 135                 140

Phe Ala Thr Tyr Tyr Cys Gln Gln Tyr Ser Thr Val Pro Trp Thr Phe
```

```
                145                 150                 155                 160
Gly Gln Gly Thr Lys Val Glu Ile Lys Gly Gly Gly Ser Gly Gly
                    165                 170                 175
Gly Gly Ser Gly Gly Gly Gly Ser Gly Glu Val Gln Leu Val Glu Ser
                180                 185                 190
Gly Gly Gly Leu Val Gln Pro Gly Gly Ser Leu Arg Leu Ser Cys Ala
                195                 200                 205
Ala Ser Gly Tyr Asp Phe Thr His Tyr Gly Met Asn Trp Val Arg Gln
    210                 215                 220
Ala Pro Gly Lys Gly Leu Glu Trp Val Gly Trp Ile Asn Thr Tyr Thr
225                 230                 235                 240
Gly Glu Pro Thr Tyr Ala Ala Asp Phe Lys Arg Arg Phe Thr Phe Ser
                245                 250                 255
Leu Asp Thr Ser Lys Ser Thr Ala Tyr Leu Gln Met Asn Ser Leu Arg
                260                 265                 270
Ala Glu Asp Thr Ala Val Tyr Tyr Cys Ala Lys Tyr Pro Tyr Tyr Tyr
            275                 280                 285
Gly Thr Ser His Trp Tyr Phe Asp Val Trp Gly Gln Gly Thr Leu Val
    290                 295                 300
Thr Val Ser
305

<210> SEQ ID NO 75
<211> LENGTH: 888
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
ggccagtctg gccagccgtg ttctgagtgg cagtcgatgg tgcagccgcg ttgctattat      60
gggggcggtt ctggtggcag cggccaaggt ggccaagtgc acatgccact gggcttcctg     120
ggtccgggcg ttctgatat tcaactgacc cagagccctt cttccctgag tgccagcgtg     180
ggtgaccgtg ttacgatcac ttgctcggcc agccaagata tttctaacta cctgaattgg     240
taccagcaga agccaggaaa ggcaccaaaa gtcctgatct acttcacaag ttcactgcat     300
tccggcgtac cgtcgcgctt tagcggttct ggcagtggta ccgacttcac cctgactatc     360
tcgagtctgc aacctgagga ttttgctaca tattactgtc agcaatattg gaccgtgccg     420
tggacgttcg gcagggcac caaagtggag attaaggggg gtggaggcag cgggggaggt     480
ggctcaggcg gtggagggtc tggcgaggtc cagctggtag aaagcggggg cggactggtc     540
caaccgggcg gatccctgcg tctgagctgc gcggcctcgg gttacgactt tactcactac     600
ggaatgaact gggttcgcca agcccctggt aaaggtctgg aatgggtcgg atggattaat     660
acatacactg gagaacctac ttatgctgct gatttcaaac gtcgctttac tttctctctg     720
gatacaagta agtcaaccgc ctatctgcaa atgaacagcc tgcgtgcaga ggacacggct     780
gtgtactatt gtgcgaaata tccttattat tatggaactt cccactggta tttcgatgta     840
tggggccagg gtactctggt tacagtgtcg catcatcacc atcaccac                 888

<210> SEQ ID NO 76
<211> LENGTH: 296
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 76

Gly Gln Ser Gly Gln Pro Cys Ser Glu Trp Gln Ser Met Val Gln Pro
1               5                   10                  15

Arg Cys Tyr Tyr Gly Gly Gly Ser Gly Gly Ser Gly Gln Gly Gly Gln
            20                  25                  30

Val His Met Pro Leu Gly Phe Leu Gly Pro Gly Gly Ser Asp Ile Gln
        35                  40                  45

Leu Thr Gln Ser Pro Ser Ser Leu Ser Ala Ser Val Gly Asp Arg Val
    50                  55                  60

Thr Ile Thr Cys Ser Ala Ser Gln Asp Ile Ser Asn Tyr Leu Asn Trp
65                  70                  75                  80

Tyr Gln Gln Lys Pro Gly Lys Ala Pro Lys Val Leu Ile Tyr Phe Thr
                85                  90                  95

Ser Ser Leu His Ser Gly Val Pro Ser Arg Phe Ser Gly Ser Gly Ser
            100                 105                 110

Gly Thr Asp Phe Thr Leu Thr Ile Ser Ser Leu Gln Pro Glu Asp Phe
        115                 120                 125

Ala Thr Tyr Tyr Cys Gln Gln Tyr Ser Thr Val Pro Trp Thr Phe Gly
    130                 135                 140

Gln Gly Thr Lys Val Glu Ile Lys Gly Gly Gly Gly Ser Gly Gly Gly
145                 150                 155                 160

Gly Ser Gly Gly Gly Gly Ser Gly Glu Val Gln Leu Val Glu Ser Gly
                165                 170                 175

Gly Gly Leu Val Gln Pro Gly Gly Ser Leu Arg Leu Ser Cys Ala Ala
            180                 185                 190

Ser Gly Tyr Asp Phe Thr His Tyr Gly Met Asn Trp Val Arg Gln Ala
        195                 200                 205

Pro Gly Lys Gly Leu Glu Trp Val Gly Trp Ile Asn Thr Tyr Thr Gly
    210                 215                 220

Glu Pro Thr Tyr Ala Ala Asp Phe Lys Arg Arg Phe Thr Phe Ser Leu
225                 230                 235                 240

Asp Thr Ser Lys Ser Thr Ala Tyr Leu Gln Met Asn Ser Leu Arg Ala
                245                 250                 255

Glu Asp Thr Ala Val Tyr Tyr Cys Ala Lys Tyr Pro Tyr Tyr Tyr Gly
            260                 265                 270

Thr Ser His Trp Tyr Phe Asp Val Trp Gly Gln Gly Thr Leu Val Thr
        275                 280                 285

Val Ser His His His His His His
    290                 295

<210> SEQ ID NO 77
<211> LENGTH: 894
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
ggccagtctg gccagcggcc gccgtgttgc cgtgattata gtattttgga gtgctgtaag     60
agtgatggcg gttctggtgg cagcggccaa ggtggccaag tgcacatgcc actgggcttc    120
ctgggtccgg gcggttctga tattcaactg acccagagcc cttcttccct gagtgccagc    180
gtgggtgacc gtgttacgat cacttgctcg ccagccaag atatttctaa ctacctgaat    240

```
tggtaccagc agaagccagg aaaggcacca aaagtcctga tctacttcac aagttcactg    300
cattccggcg taccgtcgcg ctttagcggt tctggcagtg gtaccgactt caccctgact    360
atctcgagtc tgcaacctga ggattttgct acatattact gtcagcaata ttcgaccgtg    420
ccgtggacgt tcgggcaggg caccaaagtg gagattaagg ggggtggagg cagcggggga    480
ggtggctcag gcggtggagg gtctggcgag gtccagctgg tagaaagcgg gggcggactg    540
gtccaaccgg gcggatccct gcgtctgagc tgcgcggcct cgggttacga ctttactcac    600
tacggaatga actgggttcg ccaagcccct ggtaaaggtc tggaatgggt cggatggatt    660
aatacataca ctggagaacc tacttatgct gctgatttca acgtcgctt tactttctct    720 ctggatacaa gtaagtcaac cgcctatctg caaatgaaca gcctgcgtgc agaggacacg    780
gctgtgtact attgtgcgaa atatccttat tattatggaa cttcccactg gtatttcgat    840
gtatggggcc agggtactct ggttacagtg tcgcatcatc accatcacca ctaa           894
```

<210> SEQ ID NO 78
<211> LENGTH: 297
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 78

```
Gly Gln Ser Gly Gln Arg Pro Pro Cys Cys Arg Asp Tyr Ser Ile Leu
1               5                   10                  15

Glu Cys Cys Lys Ser Asp Gly Gly Ser Gly Ser Gly Gln Gly Gly
            20                  25                  30

Gln Val His Met Pro Leu Gly Phe Leu Gly Pro Gly Gly Ser Asp Ile
        35                  40                  45

Gln Leu Thr Gln Ser Pro Ser Ser Leu Ser Ala Ser Val Gly Asp Arg
    50                  55                  60

Val Thr Ile Thr Cys Ser Ala Ser Gln Asp Ile Ser Asn Tyr Leu Asn
65                  70                  75                  80

Trp Tyr Gln Gln Lys Pro Gly Lys Ala Pro Lys Val Leu Ile Tyr Phe
                85                  90                  95

Thr Ser Ser Leu His Ser Gly Val Pro Ser Arg Phe Ser Gly Ser Gly
            100                 105                 110

Ser Gly Thr Asp Phe Thr Leu Thr Ile Ser Ser Leu Gln Pro Glu Asp
        115                 120                 125

Phe Ala Thr Tyr Tyr Cys Gln Gln Tyr Ser Thr Val Pro Trp Thr Phe
    130                 135                 140

Gly Gln Gly Thr Lys Val Glu Ile Lys Gly Gly Gly Ser Gly Gly
145                 150                 155                 160

Gly Gly Ser Gly Gly Gly Ser Gly Glu Val Gln Leu Val Glu Ser
                165                 170                 175

Gly Gly Gly Leu Val Gln Pro Gly Gly Ser Leu Arg Leu Ser Cys Ala
            180                 185                 190

Ala Ser Gly Tyr Asp Phe Thr His Tyr Gly Met Asn Trp Val Arg Gln
        195                 200                 205

Ala Pro Gly Lys Gly Leu Glu Trp Val Gly Trp Ile Asn Thr Tyr Thr
    210                 215                 220

Gly Glu Pro Thr Tyr Ala Ala Asp Phe Lys Arg Arg Phe Thr Phe Ser
225                 230                 235                 240

Leu Asp Thr Ser Lys Ser Thr Ala Tyr Leu Gln Met Asn Ser Leu Arg
                245                 250                 255
```

```
Ala Glu Asp Thr Ala Val Tyr Tyr Cys Ala Lys Tyr Pro Tyr Tyr Tyr
        260                 265                 270

Gly Thr Ser His Trp Tyr Phe Asp Val Trp Gly Gln Gly Thr Leu Val
        275                 280                 285

Thr Val Ser His His His His His His
        290                 295
```

<210> SEQ ID NO 79
<211> LENGTH: 1578
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79

```
ggccagtctg gccagccgtg ttctgagtgg cagtcgatgg tgcagccgcg ttgctattat      60
gggggcggtt ctggtggcag cggccaaggt ggccaagtgc acatgccact gggcttcctg     120
ggtccgggcg gttctgatat tcaactgacc cagagccctt cttccctgag tgccagcgtg     180
ggtgaccgtg ttacgatcac ttgctcggcc agccaagata tttctaacta cctgaattgg     240
taccagcaga agccaggaaa ggcaccaaaa gtcctgatct acttcacaag ttcactgcat     300
tccggcgtac cgtcgcgctt tagcggttct ggcagtggta ccgacttcac cctgactatc     360
tcgagtctgc aacctgagga ttttgctaca tattactgtc agcaatattc gaccgtgccg     420
tggacgttcg gcagggcac  caaagtggag attaagggggg gtggaggcag cgggggaggt     480
ggctcaggcg gtggagggtc tggcgaggtc cagctggtag aaagcggggg cggactggtc     540
caaccgggcg gatccctgcg tctgagctgc gcggcctcgg gttacgactt tactcactac     600
ggaatgaact gggttcgcca agcccctggt aaaggtctgg aatgggtcgg atggattaat     660
acatacactg gagaacctac ttatgctgct gatttcaaac gtcgctttac tttctctctg     720
gatacaagta agtcaaccgc ctatctgcaa atgaacagcc tgcgtgcaga ggacacggct     780
gtgtactatt gtgcgaaata tccttattat tatggaactt cccactggta tttcgatgta     840
tggggccagg gtactctggt tacagtgtcg ggcggtagcg gcgccatggt tagatctgac     900
aaaactcaca catgcccacc gtgcccagca cctgaactcc tggggggacc gtcagtcttc     960
ctcttccccc caaaacccaa ggacaccctc atgatctccc ggacccctga ggtcacatgc    1020
gtggtggtgg acgtgagcca cgaagaccct gaggtcaagt tcaactggta cgtggacggc    1080
gtggaggtgc ataatgccaa gacaaagccg cgggaggagc agtacaacag cacgtaccgt    1140
gtggtcagcg tcctcaccgt cctgcaccag gactggctga atggcaagga gtacaagtgc    1200
aaggtctcca acaaagccct cccagccccc atcgagaaaa ccatctccaa agccaaaggg    1260
cagccccgag aaccacaggt gtacaccctg cccccatccc gggaggagat gaccaagaac    1320
caggtcagcc tgacctgcct ggtcaaaggc ttctatccca gcgacatcgc cgtggagtgg    1380
gagagcaatg ggcagccgga gaacaactac aagaccacgc ctcccgtgct ggactccgac    1440
ggctccttct tcctctacag caagctcacc gtggacaaga gcaggtggca gcaggggaac    1500
gtcttctcat gctccgtgat gcatgagggt ctgcacaacc actacacgca gaagagcctc    1560
tccctgtctc cgggtaaa                                                  1578
```

<210> SEQ ID NO 80
<211> LENGTH: 526
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

```
Gly Gln Ser Gly Gln Pro Cys Ser Glu Trp Gln Ser Met Val Gln Pro
1               5                   10                  15

Arg Cys Tyr Tyr Gly Gly Gly Ser Gly Gly Ser Gly Gln Gly Gly Gln
            20                  25                  30

Val His Met Pro Leu Gly Phe Leu Gly Pro Gly Gly Ser Asp Ile Gln
        35                  40                  45

Leu Thr Gln Ser Pro Ser Ser Leu Ser Ala Ser Val Gly Asp Arg Val
    50                  55                  60

Thr Ile Thr Cys Ser Ala Ser Gln Asp Ile Ser Asn Tyr Leu Asn Trp
65                  70                  75                  80

Tyr Gln Gln Lys Pro Gly Lys Ala Pro Lys Val Leu Ile Tyr Phe Thr
                85                  90                  95

Ser Ser Leu His Ser Gly Val Pro Ser Arg Phe Ser Gly Ser Gly Ser
            100                 105                 110

Gly Thr Asp Phe Thr Leu Thr Ile Ser Ser Leu Gln Pro Glu Asp Phe
        115                 120                 125

Ala Thr Tyr Tyr Cys Gln Gln Tyr Ser Thr Val Pro Trp Thr Phe Gly
    130                 135                 140

Gln Gly Thr Lys Val Glu Ile Lys Gly Gly Gly Ser Gly Gly Gly
145                 150                 155                 160

Gly Ser Gly Gly Gly Ser Gly Glu Val Gln Leu Val Glu Ser Gly
                165                 170                 175

Gly Gly Leu Val Gln Pro Gly Gly Ser Leu Arg Leu Ser Cys Ala Ala
            180                 185                 190

Ser Gly Tyr Asp Phe Thr His Tyr Gly Met Asn Trp Val Arg Gln Ala
            195                 200                 205

Pro Gly Lys Gly Leu Glu Trp Val Gly Trp Ile Asn Thr Tyr Thr Gly
        210                 215                 220

Glu Pro Thr Tyr Ala Ala Asp Phe Lys Arg Arg Phe Thr Phe Ser Leu
225                 230                 235                 240

Asp Thr Ser Lys Ser Thr Ala Tyr Leu Gln Met Asn Ser Leu Arg Ala
                245                 250                 255

Glu Asp Thr Ala Val Tyr Tyr Cys Ala Lys Tyr Pro Tyr Tyr Tyr Gly
            260                 265                 270

Thr Ser His Trp Tyr Phe Asp Val Trp Gly Gln Gly Thr Leu Val Thr
        275                 280                 285

Val Ser Gly Gly Ser Gly Ala Met Val Arg Ser Asp Lys Thr His Thr
    290                 295                 300

Cys Pro Pro Cys Pro Ala Pro Glu Leu Leu Gly Gly Pro Ser Val Phe
305                 310                 315                 320

Leu Phe Pro Pro Lys Pro Lys Asp Thr Leu Met Ile Ser Arg Thr Pro
                325                 330                 335

Glu Val Thr Cys Val Val Val Asp Val Ser His Glu Asp Pro Glu Val
            340                 345                 350

Lys Phe Asn Trp Tyr Val Asp Gly Val Glu Val His Asn Ala Lys Thr
        355                 360                 365

Lys Pro Arg Glu Glu Gln Tyr Asn Ser Thr Tyr Arg Val Val Ser Val
    370                 375                 380

Leu Thr Val Leu His Gln Asp Trp Leu Asn Gly Lys Glu Tyr Lys Cys
385                 390                 395                 400
```

```
Lys Val Ser Asn Lys Ala Leu Pro Ala Pro Ile Glu Lys Thr Ile Ser
            405                 410                 415

Lys Ala Lys Gly Gln Pro Arg Glu Pro Gln Val Tyr Thr Leu Pro Pro
        420                 425                 430

Ser Arg Glu Glu Met Thr Lys Asn Gln Val Ser Leu Thr Cys Leu Val
            435                 440                 445

Lys Gly Phe Tyr Pro Ser Asp Ile Ala Val Glu Trp Glu Ser Asn Gly
        450                 455                 460

Gln Pro Glu Asn Asn Tyr Lys Thr Thr Pro Pro Val Leu Asp Ser Asp
465                 470                 475                 480

Gly Ser Phe Phe Leu Tyr Ser Lys Leu Thr Val Asp Lys Ser Arg Trp
                485                 490                 495

Gln Gln Gly Asn Val Phe Ser Cys Ser Val Met His Glu Gly Leu His
            500                 505                 510

Asn His Tyr Thr Gln Lys Ser Leu Ser Leu Ser Pro Gly Lys
        515                 520                 525
```

<210> SEQ ID NO 81
<211> LENGTH: 1581
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81

```
ggccagtctg gccagcggcc gccgtgttgc cgtgattata gtattttgga gtgctgtaag      60
agtgatggcg gttctggtgg cagcggccaa ggtggccaag tgcacatgcc actgggcttc     120
ctgggtccgg gcggttctga tattcaactg acccagagcc cttcttccct gagtgccagc     180
gtgggtgacc gtgttacgat cacttgctcg gccagccaag atatttctaa ctacctgaat     240
tggtaccagc agaagccagg aaaggcacca aaagtcctga tctacttcac aagttcactg     300
cattccggcg taccgtcgcg ctttagcggt tctggcagtg gtaccgactt caccctgact     360
atctcgagtc tgcaacctga ggattttgct acatattact gtcagcaata ttcgaccgtg     420
ccgtggacgt tcgggcaggg caccaaagtg gagattaagg ggggtggagg cagcggggga     480
ggtggctcag gcggtggagg gtctggcgag gtccagctgg tagaaagcgg gggcggactg     540
gtccaaccgg gcggatccct gcgtctgagc tgcgcggcct cgggttacga ctttactcac     600 tacgaatga actgggttcg ccaagcccct ggtaaaggtc tggaatgggt cggatggatt     660
aatacataca ctggagaacc tacttatgct gctgatttca acgtcgctt tactttctct     720 ctggatacaa gtaagtcaac cgcctatctg caaatgaaca gcctgcgtgc agaggacacg     780
gctgtgtact attgtgcgaa atatccttat tattatggaa cttcccactg gtatttcgat     840
gtatggggcc agggtactct ggttacagtg tcgggcggta gcggcgccat ggttagatct     900
gacaaaactc acacatgccc accgtgccca gcacctgaac tcctgggggg accgtcagtc     960
ttcctcttcc ccccaaaacc caaggacacc ctcatgatct cccggacccc tgaggtcaca    1020
tgcgtggtgg tggacgtgag ccacgaagac cctgaggtca agttcaactg gtacgtggac    1080
ggcgtggagg tgcataatgc caagacaaag ccgcgggagg agcagtacaa cagcacgtac    1140
cgtgtggtca gcgtcctcac cgtcctgcac caggactggc tgaatggcaa ggagtacaag    1200
tgcaaggtct ccaacaaagc cctcccagcc ccatcgaga aaaccatctc caaagccaaa    1260
gggcagcccc gagaaccaca ggtgtacacc ctgcccccat cccgggagga gatgaccaag    1320
```

-continued

```
aaccaggtca gcctgacctg cctggtcaaa ggcttctatc ccagcgacat cgccgtggag    1380
tgggagagca atgggcagcc ggagaacaac tacaagacca cgcctcccgt gctggactcc    1440
gacggctcct tcttcctcta cagcaagctc accgtggaca gagcaggtg gcagcagggg    1500 aacgtcttct catgctccgt gatgcatgag ggtctgcaca accactacac gcagaagagc    1560
ctctccctgt ctccgggtaa a                                              1581
```

<210> SEQ ID NO 82
<211> LENGTH: 527
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

```
Gly Gln Ser Gly Gln Arg Pro Pro Cys Cys Arg Asp Tyr Ser Ile Leu
1               5                   10                  15

Glu Cys Cys Lys Ser Asp Gly Gly Ser Gly Ser Gly Gln Gly Gly
            20                  25                  30

Gln Val His Met Pro Leu Gly Phe Leu Gly Pro Gly Ser Asp Ile
        35                  40                  45

Gln Leu Thr Gln Ser Pro Ser Ser Leu Ser Ala Ser Val Gly Asp Arg
    50                  55                  60

Val Thr Ile Thr Cys Ser Ala Ser Gln Asp Ile Ser Asn Tyr Leu Asn
65                  70                  75                  80

Trp Tyr Gln Gln Lys Pro Gly Lys Ala Pro Lys Val Leu Ile Tyr Phe
                85                  90                  95

Thr Ser Ser Leu His Ser Gly Val Pro Ser Arg Phe Ser Gly Ser Gly
            100                 105                 110

Ser Gly Thr Asp Phe Thr Leu Thr Ile Ser Ser Leu Gln Pro Glu Asp
        115                 120                 125

Phe Ala Thr Tyr Tyr Cys Gln Gln Tyr Ser Thr Val Pro Trp Thr Phe
    130                 135                 140

Gly Gln Gly Thr Lys Val Glu Ile Lys Gly Gly Gly Gly Ser Gly Gly
145                 150                 155                 160

Gly Gly Ser Gly Gly Gly Gly Ser Gly Glu Val Gln Leu Val Glu Ser
                165                 170                 175

Gly Gly Gly Leu Val Gln Pro Gly Gly Ser Leu Arg Leu Ser Cys Ala
            180                 185                 190

Ala Ser Gly Tyr Asp Phe Thr His Tyr Gly Met Asn Trp Val Arg Gln
        195                 200                 205

Ala Pro Gly Lys Gly Leu Glu Trp Val Gly Trp Ile Asn Thr Tyr Thr
    210                 215                 220

Gly Glu Pro Thr Tyr Ala Ala Asp Phe Lys Arg Arg Phe Thr Phe Ser
225                 230                 235                 240

Leu Asp Thr Ser Lys Ser Thr Ala Tyr Leu Gln Met Asn Ser Leu Arg
                245                 250                 255

Ala Glu Asp Thr Ala Val Tyr Tyr Cys Ala Lys Tyr Pro Tyr Tyr Tyr
            260                 265                 270

Gly Thr Ser His Trp Tyr Phe Asp Val Trp Gly Gln Gly Thr Leu Val
        275                 280                 285

Thr Val Ser Gly Gly Ser Gly Ala Met Val Arg Ser Asp Lys Thr His
    290                 295                 300

Thr Cys Pro Pro Cys Pro Ala Pro Glu Leu Leu Gly Gly Pro Ser Val
305                 310                 315                 320
```

-continued

```
Phe Leu Phe Pro Pro Lys Pro Lys Asp Thr Leu Met Ile Ser Arg Thr
                325                 330                 335
Pro Glu Val Thr Cys Val Val Val Asp Val Ser His Glu Asp Pro Glu
            340                 345                 350
Val Lys Phe Asn Trp Tyr Val Asp Gly Val Glu Val His Asn Ala Lys
        355                 360                 365
Thr Lys Pro Arg Glu Glu Gln Tyr Asn Ser Thr Tyr Arg Val Val Ser
    370                 375                 380
Val Leu Thr Val Leu His Gln Asp Trp Leu Asn Gly Lys Glu Tyr Lys
385                 390                 395                 400
Cys Lys Val Ser Asn Lys Ala Leu Pro Ala Pro Ile Glu Lys Thr Ile
                405                 410                 415
Ser Lys Ala Lys Gly Gln Pro Arg Glu Pro Gln Val Tyr Thr Leu Pro
            420                 425                 430
Pro Ser Arg Glu Glu Met Thr Lys Asn Gln Val Ser Leu Thr Cys Leu
        435                 440                 445
Val Lys Gly Phe Tyr Pro Ser Asp Ile Ala Val Glu Trp Glu Ser Asn
    450                 455                 460
Gly Gln Pro Glu Asn Asn Tyr Lys Thr Thr Pro Pro Val Leu Asp Ser
465                 470                 475                 480
Asp Gly Ser Phe Phe Leu Tyr Ser Lys Leu Thr Val Asp Lys Ser Arg
                485                 490                 495
Trp Gln Gln Gly Asn Val Phe Ser Cys Ser Val Met His Glu Gly Leu
            500                 505                 510
His Asn His Tyr Thr Gln Lys Ser Leu Ser Leu Ser Pro Gly Lys
        515                 520                 525

<210> SEQ ID NO 83
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(57)

<400> SEQUENCE: 83 atg att ttg ttg tgc gcg gcg ggt cgg acg tgg gtg gag gct tgc gct    48
Met Ile Leu Leu Cys Ala Ala Gly Arg Thr Trp Val Glu Ala Cys Ala
1               5                   10                  15 aat ggt agg                                                        57
Asn Gly Arg <210> SEQ ID NO 84
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Met Ile Leu Leu Cys Ala Ala Gly Arg Thr Trp Val Glu Ala Cys Ala
1               5                   10                  15

Asn Gly Arg

<210> SEQ ID NO 85
<211> LENGTH: 42
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(42)

<400> SEQUENCE: 85 gct gag cgg ttg tgc gcg tgg gcg ggg cgg ttc tgt ggc agc          42
Ala Glu Arg Leu Cys Ala Trp Ala Gly Arg Phe Cys Gly Ser
1               5                   10

<210> SEQ ID NO 86
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ala Glu Arg Leu Cys Ala Trp Ala Gly Arg Phe Cys Gly Ser
1               5                   10

<210> SEQ ID NO 87
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(45)

<400> SEQUENCE: 87 tgg gcg gat gtt atg cct ggg tcg ggt gtg ttg ccg tgg acg tcg      45
Trp Ala Asp Val Met Pro Gly Ser Gly Val Leu Pro Trp Thr Ser
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Trp Ala Asp Val Met Pro Gly Ser Gly Val Leu Pro Trp Thr Ser
1               5                   10                  15

<210> SEQ ID NO 89
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(60)

<400> SEQUENCE: 89 agt gat ggt cgt atg ggg agt ttg gag ctt tgt gcg ttg tgg ggg cgg     48
Ser Asp Gly Arg Met Gly Ser Leu Glu Leu Cys Ala Leu Trp Gly Arg
1               5                   10                  15 ttc tgt ggc agc                                                     60
```

```
Phe Cys Gly Ser
        20

<210> SEQ ID NO 90
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ser Asp Gly Arg Met Gly Ser Leu Glu Leu Cys Ala Leu Trp Gly Arg
1               5                   10                  15

Phe Cys Gly Ser
        20

<210> SEQ ID NO 91
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(45)

<400> SEQUENCE: 91 ccg tgt tct gag tgg cag tcg atg gtg cag ccg cgt tgc tat tat         45
Pro Cys Ser Glu Trp Gln Ser Met Val Gln Pro Arg Cys Tyr Tyr
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Pro Cys Ser Glu Trp Gln Ser Met Val Gln Pro Arg Cys Tyr Tyr
1               5                   10                  15

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other

<400> SEQUENCE: 93
gtyttrtgng tnacytcrca                                                20

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
                        primer
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (21)..(21)
<223> OTHER INFORMATION: a, c, t, g, unknown or other

<400> SEQUENCE: 94
acdatyttyt trtcnacytt ngt                                              23

<210> SEQ ID NO 95
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
cgtcgatgag ctctagaatt cgcatgtgca agtccgatgg tccccccccc ccccc          55

<210> SEQ ID NO 96
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (36)..(36)
<223> OTHER INFORMATION: a, c, t, g, unknown or other

<400> SEQUENCE: 96
cgtcatgtcg acggatccaa gcttacyttc cayttnacrt tdatrtc                   47

<210> SEQ ID NO 97
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(28)
<223> OTHER INFORMATION: a, c, t, g, unknown or other
<220> FEATURE:
<221> NAME/KEY: modified_base
<222> LOCATION: (31)..(31)
<223> OTHER INFORMATION: a, c, t, g, unknown or other
<220> FEATURE:
<221> NAME/KEY: modified_base
<222> LOCATION: (34)..(34)
<223> OTHER INFORMATION: a, c, t, g, unknown or other
<220> FEATURE:
<221> NAME/KEY: modified_base
<222> LOCATION: (37)..(37)
<223> OTHER INFORMATION: a, c, t, g, unknown or other
<220> FEATURE:
<221> NAME/KEY: modified_base
<222> LOCATION: (40)..(40)
<223> OTHER INFORMATION: a, c, t, g, unknown or other
<220> FEATURE:
<221> NAME/KEY: modified_base
<222> LOCATION: (46)..(46)
<223> OTHER INFORMATION: a, c, t, g, unknown or other

<400> SEQUENCE: 97
cgtcatgtcg acggatccaa gcttrcangc nggngcnarn ggrtanac                  48
```

<210> SEQ ID NO 98
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Met Glu Ser His Ile His Val Phe Met Ser Leu Phe Leu Trp Val Ser
1               5                   10                  15

Gly Ser Cys Ala Asp Ile Met Met Thr Gln Ser Pro Ser Ser Leu Ser
                20                  25                  30

Val Ser Ala Gly Glu Lys Ala Thr Ile Ser Cys Lys Ser Ser Gln Ser
            35                  40                  45

Leu Phe Asn Ser Asn Ala Lys Thr Asn Tyr Leu Asn Trp Tyr Leu Gln
        50                  55                  60

Lys Pro Gly Gln Ser Pro Lys Leu Leu Ile Tyr Tyr Ala Ser Thr Arg
65                  70                  75                  80

His Thr Gly Val Pro Asp Arg Phe Arg Gly Ser Gly Thr Asp Phe Thr
                85                  90                  95

Leu Thr Ile Ser Ser Val Gln Asp Glu Asp Leu Ala Phe Tyr Tyr Cys
                100                 105                 110

Gln Gln Trp Tyr Asp Tyr Pro Tyr Thr Phe Gly Ala Gly Thr Lys Val
        115                 120                 125

Glu Ile Lys
    130

<210> SEQ ID NO 99
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99
atggaatcac atatccatgt cttcatgtcc ttgttccttt gggtgtctgg ttcctgtgca      60
gacatcatga tgacccagtc tccttcatcc ctgagtgtgt cagcgggaga gaaagccact     120
atcagctgca agtccagtca gagtctttt  aacagtaacg ccaaaacgaa ctacttgaac     180
tggtatttgc agaaaccagg gcagtctcct aaactgctga tctattatgc atccactagg     240
catactgggg tccctgatcg cttcagaggc agtggatctg ggacggattt cactctcacc     300
atcagcagtg tccaggatga agacctggca ttttattact gtcagcagtg gtatgactac     360
ccatacacgt tcggagctgg gaccaaggtg gaaatcaaa                             399

<210> SEQ ID NO 100
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Lys Met Arg Leu Leu Gly Leu Leu Tyr Leu Val Thr Ala Leu Pro Gly
1               5                   10                  15

Val Leu Ser Gln Ile Gln Leu Gln Glu Ser Gly Pro Gly Leu Val Asn
                20                  25                  30

```
Pro Ser Gln Ser Leu Ser Leu Ser Cys Ser Val Thr Gly Tyr Ser Ile
        35                  40                  45

Thr Ser Gly Tyr Gly Trp Asn Trp Ile Arg Gln Phe Pro Gly Gln Lys
    50                  55                  60

Val Glu Trp Met Gly Phe Ile Tyr Tyr Glu Gly Ser Thr Tyr Tyr Asn
 65                 70                  75                  80

Pro Ser Ile Lys Ser Arg Ile Ser Ile Thr Arg Asp Thr Ser Lys Asn
                85                  90                  95

Gln Phe Phe Leu Gln Val Asn Ser Val Thr Thr Glu Asp Thr Ala Thr
                100                 105                 110

Tyr Tyr Cys Ala Arg Gln Thr Gly Tyr Phe Asp Tyr Trp Gly Gln Gly
            115                 120                 125

Thr Met Val Thr Val Ser Ser
        130             135

<210> SEQ ID NO 101
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
aagatgagac tgttgggtct tctgtacctg gtgacagccc ttcctggtgt cctgtcccag    60
atccagcttc aggagtcagg acctggcctg gtgaacccct cacaatcact gtccctctct   120
tgctctgtca ctggttactc catcaccagt ggttatggat ggaactggat caggcagttc   180
ccagggcaga aggtggagtg gatgggattc atatattatg agggtagcac ctactacaac   240
ccttccatca gagccgcat ctccatcacc agagacacat cgaagaacca gttcttcctg   300
caggtgaatt ctgtgaccac tgaggacaca gccacatatt actgtgcgag acaaactggg   360
tactttgatt actggggcca aggaaccatg gtcaccgtct cctca                   405

<210> SEQ ID NO 102
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Gly Gly Ser Gly Gly Gly Ser Gly Gly Gly Ser
1               5                   10

<210> SEQ ID NO 103
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
caaggaccat agcatatgga catcatgatg acccagtct                          39

<210> SEQ ID NO 104
<211> LENGTH: 50
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 104
acttccgcct ccacctgatc caccaccacc tttgatttcc accttggtcc            50

<210> SEQ ID NO 105
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
ggatcaggtg gaggcggaag tggaggtggc ggttcccaga tccagcttca ggagtcagga    60

<210> SEQ ID NO 106
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
ggccggatcc aagcttttag tggtgatggt gatgatgtga ggagacggtg accatggttc    60
c                                                                    61

<210> SEQ ID NO 107
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
acaaggacca tagcatatgc agatccagct tcaggagtca                          40

<210> SEQ ID NO 108
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
acttccgcct ccacctgatc caccaccacc tgaggagacg gtgaccatgg ttcc          54

<210> SEQ ID NO 109
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
ggtggatcag gtggaggcgg aagtggaggt ggcggttccg acatcatgat gacccagtct    60
cct                                                                  63

<210> SEQ ID NO 110
<211> LENGTH: 62
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 110
cggccggatc caagcttta gtggtgatgg tgatgatgtt tgatttccac cttggtccca    60
gc                                                                 62

<210> SEQ ID NO 111
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Gly Ser Gly Gly Ser
1               5

<210> SEQ ID NO 112
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
gccagtctgg ccggtagggc tcgagcggcc aagtgcacat gccactgggc ttcctgggtc    60

<210> SEQ ID NO 113
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
gccactgggc ttcctgggtc cgggtggaag cggcggctca gacatcatga tgacccagtc    60

<210> SEQ ID NO 114
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
gccactgggc ttcctgggtc cgggtggaag cggcggctca cagatccagc ttcaggagtc    60
a                                                                  61

<210> SEQ ID NO 115
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
ttcaccaaca aggaccatag catatgggcc agtctggccg gtagggc                 47
```

<210> SEQ ID NO 116
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
ggccggatcc aagctttag tggtgatggt gatgatgtga ggagacggtg accatggttc    60
c                                                                   61

<210> SEQ ID NO 117
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
acttccgcct ccacctgatc caccaccacc tgaggagacg gtgaccatgg ttcc          54

<210> SEQ ID NO 118
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gly Gly Ser Gly Gly Ser Gly Gly Ser Ser Gly Gln Val His Met Pro
1               5                   10                  15

Leu Gly Phe Leu Gly Pro Gly Gly Ser Gly Gly Ser
            20                  25

<210> SEQ ID NO 119
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
ggcggttctg gtggcagcgg tggctcgagc ggccaagtgc acatgccact gggcttcctg    60
ggtccgggtg gaagcggcgg ctca                                          84

<210> SEQ ID NO 120
<211> LENGTH: 291
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Met Ile Leu Leu Cys Ala Ala Gly Arg Thr Trp Val Glu Ala Cys Ala
1               5                   10                  15

Asn Gly Arg Gly Gly Ser Gly Gly Ser Gly Gly Ser Ser Gly Gln Val
            20                  25                  30

His Met Pro Leu Gly Phe Leu Gly Pro Gly Gly Ser Gly Gly Ser Gln
        35                  40                  45

Ile Gln Leu Gln Glu Ser Gly Pro Gly Leu Val Asn Pro Ser Gln Ser

```
                50                  55                  60
Leu Ser Leu Ser Cys Ser Val Thr Gly Tyr Ser Ile Thr Ser Gly Tyr
 65                  70                  75                  80

Gly Trp Asn Trp Ile Arg Gln Phe Pro Gly Gln Lys Val Glu Trp Met
                 85                  90                  95

Gly Phe Ile Tyr Tyr Glu Gly Ser Thr Tyr Tyr Asn Pro Ser Ile Lys
                100                 105                 110

Ser Arg Ile Ser Ile Thr Arg Asp Thr Ser Lys Asn Gln Phe Phe Leu
                115                 120                 125

Gln Val Asn Ser Val Thr Thr Glu Asp Thr Ala Thr Tyr Tyr Cys Ala
            130                 135                 140

Arg Gln Thr Gly Tyr Phe Asp Tyr Trp Gly Gln Gly Thr Met Val Thr
145                 150                 155                 160

Val Ser Ser Gly Gly Gly Gly Ser Gly Gly Gly Ser Gly Gly Gly
                165                 170                 175

Gly Ser Asp Ile Met Met Thr Gln Ser Pro Ser Ser Leu Ser Val Ser
            180                 185                 190

Ala Gly Glu Lys Ala Thr Ile Ser Cys Lys Ser Ser Gln Ser Leu Phe
            195                 200                 205

Asn Ser Asn Ala Lys Thr Asn Tyr Leu Asn Trp Tyr Leu Gln Lys Pro
        210                 215                 220

Gly Gln Ser Pro Lys Leu Leu Ile Tyr Tyr Ala Ser Thr Arg His Thr
225                 230                 235                 240

Gly Val Pro Asp Arg Phe Arg Gly Ser Gly Ser Gly Thr Asp Phe Thr
                245                 250                 255

Leu Thr Ile Ser Ser Val Gln Asp Glu Asp Leu Ala Phe Tyr Tyr Cys
            260                 265                 270

Gln Gln Trp Tyr Asp Tyr Pro Tyr Thr Phe Gly Ala Gly Thr Lys Val
            275                 280                 285

Glu Ile Lys
    290

<210> SEQ ID NO 121
<211> LENGTH: 894
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121
atgattttgt tgtgcgcggc gggtcggacg tgggtggagg cttgcgctaa tggtaggggc      60
ggttctggtg gcagcggtgg ctcgagcggc caagtgcaca tgccactggg cttcctgggt     120
ccgggtggaa gcggcggctc acagatccag cttcaggagt caggacctgg cctggtgaac     180
ccctcacaat cactgtccct ctcttgctct gtcactggtt actccatcac cagtggttat     240
ggatggaact ggatcaggca gttcccaggg cagaaggtgg agtggatggg attcatatat     300
tatgagggta gcacctacta caacccttcc atcaagagcc gcatctccat caccagagac     360
acatcgaaga accagttctt cctgcaggtg aattctgtga ccactgagga cacagccaca     420
tattactgtg cgagacaaac tgggtacttt gattactggg ccaaggaac catggtcacc     480 gtctcctcag gtggtggtgg atcaggtgga ggcggaagtg gaggtggcgg ttccgacatc     540
atgatgaccc agtctccttc atccctgagt gtgtcagcgg gagagaaagc cactatcagc     600
tgcaagtcca gtcagagtct tttcaacagt aacgccaaaa cgaactactt gaactggtat     660
```

```
ttgcagaaac cagggcagtc tcctaaactg ctgatctatt atgcatccac taggcatact    720
ggggtccctg atcgcttcag aggcagtgga tctgggacgg atttcactct caccatcagc    780
agtgtccagg atgaagacct ggcattttat tactgtcagc agtggtatga ctacccatac    840
acgttcggag ctgggaccaa ggtggaaatc aaacatcatc accatcacca ctaa          894
```

```
<210> SEQ ID NO 122
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
tcagatctaa ccatggcttt gatttccacc ttggtcc                              37

<210> SEQ ID NO 123
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
tcagatctaa ccatggctga ggagacggtg accatgg                              37

<210> SEQ ID NO 124
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
cacttgtcac gaattcgatg attttgttgt gcgcggc                              37

<210> SEQ ID NO 125
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
cacttgtcac gaattcgtgg gcggatgtta tgcctg                               36

<210> SEQ ID NO 126
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
cacttgtcac gaattcggct gagcggttgt gcgcgtg                              37

<210> SEQ ID NO 127
<211> LENGTH: 37
<212> TYPE: DNA
<213> ORGANISM: Artificial Sequence
<220> FEATURE:
<223> OTHER INFORMATION: Description of Artificial Sequence: Synthetic
```

```
    primer

<400> SEQUENCE: 127
cacttgtcac gaattcgagt gatggtcgta tggggag                             37

<210> SEQ ID NO 128
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
cacttgtcac gaattcgccg tgttctgagt ggcagtcg                            38

<210> SEQ ID NO 129
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 129
gaaattgtgt tgacacagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcaccgct cactttcggc   300
ggagggacca aggtggaaat caaacgttcc ggagggtcga ccataacttc gtataatgta   360
tactatacga agttatcctc gagcggtacc caggtgcagc tggtgcagac tggggaggc   420 gtggtccagc ctgggaggtc cctgagactc tcctgtgcag cctctggatc cacctttagc   480
agctatgcca tgagctgggt ccgccaggct ccagggaagg ggctggagtg ggtctcagct   540
attagtggta gtggtggtag cacatactac gcagactccg tgaagggccg gttcaccatc   600
tccagagaca attccaagaa cacgctgtat ctgcaaatga acagcctgag agccgaggac   660
acggccgtat attactgtgc gacaaactcc ctttactggt acttcgatct ctggggccgt   720
ggcaccctgg tcactgtctc ttcagctagc                                   750

<210> SEQ ID NO 130
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
```

```
                65                  70                  75                  80
Pro Glu Asp Phe Ala Val Tyr Tyr Cys Gln Gln Tyr Gly Ser Ser Pro
                    85                  90                  95
Leu Thr Phe Gly Gly Gly Thr Lys Val Glu Ile Lys Arg Ser Gly
                100                 105                 110
Gly Ser Thr Ile Thr Ser Tyr Asn Val Tyr Tyr Thr Lys Leu Ser Ser
                115                 120                 125
Ser Gly Thr Gln Val Gln Leu Val Gln Thr Gly Gly Val Val Gln
            130                 135                 140
Pro Gly Arg Ser Leu Arg Leu Ser Cys Ala Ala Ser Gly Ser Thr Phe
145                 150                 155                 160
Ser Ser Tyr Ala Met Ser Trp Val Arg Gln Ala Pro Gly Lys Gly Leu
                165                 170                 175
Glu Trp Val Ser Ala Ile Ala Gly Ser Gly Gly Ser Thr Tyr Tyr Ala
                180                 185                 190
Asp Ser Val Lys Gly Arg Phe Thr Ile Ser Arg Asp Asn Ser Lys Asn
                195                 200                 205
Thr Leu Tyr Leu Gln Met Asn Ser Leu Arg Ala Glu Asp Thr Ala Val
                210                 215                 220
Tyr Tyr Cys Ala Thr Asn Ser Leu Tyr Trp Tyr Phe Asp Leu Trp Gly
225                 230                 235                 240
Arg Gly Thr Leu Val Thr Val Ser Ser Ala Ser
                245                 250

<210> SEQ ID NO 131
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
cttgtcacga attcggatat tcaactgacc cagagc                              36

<210> SEQ ID NO 132
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
gtgcagccac cgtacgctta atctccactt tggtg                               35

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
tgcttgctca actctacgtc                                                20

<210> SEQ ID NO 134
<211> LENGTH: 40
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 134
gctttcaccg caggtacttc cgtagctggc cagtctggcc                              40

<210> SEQ ID NO 135
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
cgctccatgg gccaccttgg ccgctgccac cgctcgagcc                              40

<210> SEQ ID NO 136
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
cacttgtcac gaattcggag gtccagctgg tagaaag                                 37

<210> SEQ ID NO 137
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
ggcccttggt gctagcgctc gacactgtaa ccagagtac                               39

<210> SEQ ID NO 138
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138
gatattcaac tgacccagag cccttcttcc ctgagtgcca gcgtgggtga ccgtgttacg        60
atcacttgct cggccagcca agatatttct aactacctga attggtacca gcagaagcca       120
ggaaaggcac caaaagtcct gatctacttc acaagttcac tgcattccgg cgtaccgtcg       180
cgctttagcg gttctggcag tggtaccgac ttcaccctga ctatctcgag tctgcaacct       240
gaggattttg ctacatatta ctgtcagcaa tattcgaccg tgccgtggac gttcgggcag       300
ggcaccaaag tggagattaa gcgtacggtg gctgcaccat ctgtcttcat cttcccgcca       360
tctgatgagc agttgaaatc tggaactgcc tctgttgtgt gcctgctgaa taacttctat       420
cccagagagg ccaaagtaca gtggaaggtg gataacgccc tccaatcggg taactcccag       480
gagagtgtca cagagcagga cagcaaggac agcacctaca gcctcagcag cacccctgacg      540 ctgagcaaag cagactacga gaaacacaaa gtctacgcct gcgaagtcac ccatcagggc       600
ctgagctcgc ccgtcacaaa gagcttcaac aggggagagt gttag                       645
```

```
<210> SEQ ID NO 139
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 140
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Pro Cys Ser Glu Trp Gln Ser Met Val Gln Pro Arg Cys Tyr Tyr Gly
1               5                   10                  15

<210> SEQ ID NO 141
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Pro Cys Ser Glu Trp Gln Ser Met Val Gln Pro Arg Cys Tyr Tyr Gly
1               5                   10                  15
```

```
<210> SEQ ID NO 142
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Ser Cys Thr Ala Trp Gln Ser Met Val Glu Gln Arg Cys Tyr Phe Gly
1               5                   10                  15

<210> SEQ ID NO 143
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Pro Cys Ser Lys Trp Glu Ser Met Val Glu Gln Arg Cys Tyr Phe Ala
1               5                   10                  15

<210> SEQ ID NO 144
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Pro Cys Ser Ala Trp Gln Ser Met Val Glu Gln Arg Cys Tyr Phe Gly
1               5                   10                  15

<210> SEQ ID NO 145
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Pro Cys Ser Lys Trp Glu Ser Met Val Leu Gln Ser Cys Tyr Phe Gly
1               5                   10                  15

<210> SEQ ID NO 146
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Thr Cys Ser Ala Trp Gln Ser Met Val Glu Gln Arg Cys Tyr Phe Gly
1               5                   10                  15

<210> SEQ ID NO 147
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147
```

```
Thr Cys Ser Gln Trp Glu Ser Met Val Glu Pro Arg Cys Tyr Phe Gly
1               5                   10                  15
```

<210> SEQ ID NO 148
<211> LENGTH: 780
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 148

```
ggccagtctg gccagccgtg ttctgagtgg cagtcgatgg tgcagccgcg ttgctattat    60
ggggcggtt ctggtggcag cggccaaggt ggccaagtgc acatgccact gggcttcctg    120
ggtccgggcg gttctgatat tcaactgacc cagagccctt cttccctgag tgccagcgtg    180
ggtgaccgtg ttacgatcac ttgctcggcc agccaagata tttctaacta cctgaattgg    240
taccagcaga agccaggaaa ggcaccaaaa gtcctgatct acttcacaag ttcactgcat    300
tccggcgtac cgtcgcgctt tagcggttct ggcagtggta ccgacttcac cctgactatc    360
tcgagtctgc aacctgagga ttttgctaca tattactgtc agcaatattc gaccgtgccg    420
tggacgttcg gcagggcac caaagtggag attaagcgta cggtggctgc accatctgtc    480
ttcatcttcc cgccatctga tgagcagttg aaatctggaa ctgcctctgt tgtgtgcctg    540
ctgaataact ctatcccag agaggccaaa gtacagtgga aggtggataa cgccctccaa    600
tcgggtaact cccaggagag tgtcacagag caggacagca aggacagcac ctacagcctc    660
agcagcaccc tgacgctgag caaagcagac tacgagaaac acaaagtcta cgcctgcgaa    720
gtcacccatc agggcctgag ctcgcccgtc acaaagagct tcaacagggg agagtgttag    780
```

<210> SEQ ID NO 149
<211> LENGTH: 259
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

```
Gly Gln Ser Gly Gln Pro Cys Ser Glu Trp Gln Ser Met Val Gln Pro
1               5                   10                  15

Arg Cys Tyr Tyr Gly Gly Gly Ser Gly Gly Ser Gly Gln Gly Gly Gln
                20                  25                  30

Val His Met Pro Leu Gly Phe Leu Gly Pro Gly Gly Ser Asp Ile Gln
            35                  40                  45

Leu Thr Gln Ser Pro Ser Ser Leu Ser Ala Ser Val Gly Asp Arg Val
        50                  55                  60

Thr Ile Thr Cys Ser Ala Ser Gln Asp Ile Ser Asn Tyr Leu Asn Trp
65                  70                  75                  80

Tyr Gln Gln Lys Pro Gly Lys Ala Pro Lys Val Leu Ile Tyr Phe Thr
                85                  90                  95

Ser Ser Leu His Ser Gly Val Pro Ser Arg Phe Ser Gly Ser Gly Ser
            100                 105                 110

Gly Thr Asp Phe Thr Leu Thr Ile Ser Ser Leu Gln Pro Glu Asp Phe
        115                 120                 125

Ala Thr Tyr Tyr Cys Gln Gln Tyr Ser Thr Val Pro Trp Thr Phe Gly
    130                 135                 140

Gln Gly Thr Lys Val Glu Ile Lys Arg Thr Val Ala Ala Pro Ser Val
```

```
                    145                 150                 155                 160
Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys

<210> SEQ ID NO 150
<211> LENGTH: 780
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 150
ggccagtctg gccagtcgtg tacggcgtgg cagtcgatgg tggagcagcg ttgctatttt    60
gggggctcga gcggtggcag cggccaaggt ggccaagtgc acatgccact gggcttcctg   120
ggtccgggcg gttctgatat tcaactgacc cagagccctt cttccctgag tgccagcgtg   180
ggtgaccgtg ttacgatcac ttgctcggcc agcaagata tttctaacta cctgaattgg   240
taccagcaga agccaggaaa ggcaccaaaa gtcctgatct acttcacaag ttcactgcat   300
tccggcgtac cgtcgcgctt tagcggttct ggcagtggta ccgacttcac cctgactatc   360
tcgagtctgc aacctgagga ttttgctaca tattactgtc agcaatattc gaccgtgccg   420
tggacgttcg gcagggcac caaagtggag attaagcgta cggtggctgc accatctgtc   480
ttcatcttcc cgccatctga tgagcagttg aaatctggaa ctgcctctgt tgtgtgcctg   540
ctgaataact tctatcccag agaggccaaa gtacagtgga aggtggataa cgccctccaa   600
tcgggtaact cccaggagag tgtcacagag caggacagca aggacagcac ctacagcctc   660
agcagcaccc tgacgctgag caaagcagac tacgagaaac acaaagtcta cgcctgcgaa   720
gtcacccatc agggcctgag ctcgcccgtc acaaagagct caacaggggg agagtgttag   780

<210> SEQ ID NO 151
<211> LENGTH: 259
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Gly Gln Ser Gly Gln Ser Cys Thr Ala Trp Gln Ser Met Val Glu Gln
1               5                   10                  15

Arg Cys Tyr Phe Gly Gly Ser Gly Gly Ser Gly Gln Gly Gly Gln
            20                  25                  30

Val His Met Pro Leu Gly Phe Leu Gly Pro Gly Gly Ser Asp Ile Gln
        35                  40                  45

Leu Thr Gln Ser Pro Ser Ser Leu Ser Ala Ser Val Gly Asp Arg Val
```

```
                50                  55                  60
Thr Ile Thr Cys Ser Ala Ser Gln Asp Ile Ser Asn Tyr Leu Asn Trp
 65                  70                  75                  80

Tyr Gln Gln Lys Pro Gly Lys Ala Pro Lys Val Leu Ile Tyr Phe Thr
                 85                  90                  95

Ser Ser Leu His Ser Gly Val Pro Ser Arg Phe Ser Gly Ser Gly Ser
                100                 105                 110

Gly Thr Asp Phe Thr Leu Thr Ile Ser Ser Leu Gln Pro Glu Asp Phe
                115                 120                 125

Ala Thr Tyr Tyr Cys Gln Gln Tyr Ser Thr Val Pro Trp Thr Phe Gly
130                 135                 140

Gln Gly Thr Lys Val Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
                180                 185                 190

Trp Lys Val Asp Asn Ala Leu Gln Ser Gly Asn Ser Gln Glu Ser Val
                195                 200                 205

Thr Glu Gln Asp Ser Lys Asp Ser Thr Tyr Ser Leu Ser Ser Thr Leu
210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys

<210> SEQ ID NO 152
<211> LENGTH: 780
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 152
ggccagtctg gccagccgtg ttctgcgtgg cagtctatgg tggagcagcg ttgctatttt      60
gggggctcga gcggtggcag cggccaaggt ggccaagtgc acatgccact gggcttcctg     120
ggtccgggcg gttctgatat tcaactgacc cagagccctt cttccctgag tgccagcgtg     180
ggtgaccgtg ttacgatcac ttgctcggcc agccaagata tttctaacta cctgaattgg     240
taccagcaga agccaggaaa ggcaccaaaa gtcctgatct acttcacaag ttcactgcat     300
tccggcgtac cgtcgcgctt tagcggttct ggcagtggta ccgacttcac cctgactatc     360
tcgagtctgc aacctgagga ttttgctaca tattactgtc agcaatattc gaccgtgccg     420
tggacgttcg ggcagggcac caaagtggag attaagcgta cggtggctgc accatctgtc     480
ttcatcttcc cgccatctga tgagcagttg aaatctggaa ctgcctctgt tgtgtgcctg     540
ctgaataact tctatcccag agaggccaaa gtacagtgga aggtggataa cgccctccaa     600
tcgggtaact cccaggagag tgtcacagag caggacagca aggacagcac ctacagcctc     660
agcagcaccc tgacgctgag caaagcagac tacgagaaac acaaagtcta cgcctgcgaa     720
gtcacccatc agggcctgag ctcgcccgtc acaaagagct tcaacagggg agagtgttag     780

<210> SEQ ID NO 153
<211> LENGTH: 259
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Gly Gln Ser Gly Gln Pro Cys Ser Ala Trp Gln Ser Met Val Glu Gln
1               5                   10                  15

Arg Cys Tyr Phe Gly Gly Ser Ser Gly Gly Ser Gly Gln Gly Gly Gln
            20                  25                  30

Val His Met Pro Leu Gly Phe Leu Gly Pro Gly Gly Ser Asp Ile Gln
        35                  40                  45

Leu Thr Gln Ser Pro Ser Ser Leu Ser Ala Ser Val Gly Asp Arg Val
    50                  55                  60

Thr Ile Thr Cys Ser Ala Ser Gln Asp Ile Ser Asn Tyr Leu Asn Trp
65                  70                  75                  80

Tyr Gln Gln Lys Pro Gly Lys Ala Pro Lys Val Leu Ile Tyr Phe Thr
                85                  90                  95

Ser Ser Leu His Ser Gly Val Pro Ser Arg Phe Ser Gly Ser Gly Ser
            100                 105                 110

Gly Thr Asp Phe Thr Leu Thr Ile Ser Ser Leu Gln Pro Glu Asp Phe
        115                 120                 125

Ala Thr Tyr Tyr Cys Gln Gln Tyr Ser Thr Val Pro Trp Thr Phe Gly
    130                 135                 140

Gln Gly Thr Lys Val Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys

<210> SEQ ID NO 154
<211> LENGTH: 780
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 154
ggccagtctg gccagccgtg ttctaagtgg aatcgatgg tgctgcagag ttgctatttt      60
ggcggctcga gcggtggcag cggccaaggt ggccaagtgc acatgccact gggcttcctg    120
ggtccgggcg gttctgatat tcaactgacc cagagccctt cttccctgag tgccagcgtg    180
ggtgaccgtg ttacgatcac ttgctcggcc agccaagata tttctaacta cctgaattgg    240
taccagcaga agccaggaaa ggcaccaaaa gtcctgatct acttcacaag ttcactgcat    300
tccggcgtac cgtcgcgctt tagcggttct ggcagtggta ccgacttcac cctgactatc    360

```
tcgagtctgc aacctgagga ttttgctaca tattactgtc agcaatattc gaccgtgccg    420
tggacgttcg ggcagggcac caaagtggag attaagcgta cggtggctgc accatctgtc    480
ttcatcttcc cgccatctga tgagcagttg aaatctggaa ctgcctctgt tgtgtgcctg    540
ctgaataact tctatcccag agaggccaaa gtacagtgga aggtggataa cgccctccaa    600
tcgggtaact cccaggagag tgtcacagag caggacagca aggacagcac ctacagcctc    660
agcagcaccc tgacgctgag caaagcagac tacgagaaac acaaagtcta cgcctgcgaa    720
gtcacccatc agggcctgag ctcgcccgtc acaaagagct tcaacagggg agagtgttag    780
```

<210> SEQ ID NO 155
<211> LENGTH: 259
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Gly Gln Ser Gly Gln Pro Cys Ser Lys Trp Glu Ser Met Val Leu Gln
1               5                   10                  15

Ser Cys Tyr Phe Gly Gly Ser Ser Gly Gly Ser Gly Gln Gly Gly Gln
            20                  25                  30

Val His Met Pro Leu Gly Phe Leu Gly Pro Gly Gly Ser Asp Ile Gln
        35                  40                  45

Leu Thr Gln Ser Pro Ser Ser Leu Ser Ala Ser Val Gly Asp Arg Val
50                  55                  60

Thr Ile Thr Cys Ser Ala Ser Gln Asp Ile Ser Asn Tyr Leu Asn Trp
65                  70                  75                  80

Tyr Gln Gln Lys Pro Gly Lys Ala Pro Lys Val Leu Ile Tyr Phe Thr
                85                  90                  95

Ser Ser Leu His Ser Gly Val Pro Ser Arg Phe Ser Gly Ser Gly Ser
            100                 105                 110

Gly Thr Asp Phe Thr Leu Thr Ile Ser Ser Leu Gln Pro Glu Asp Phe
        115                 120                 125

Ala Thr Tyr Tyr Cys Gln Gln Tyr Ser Thr Val Pro Trp Thr Phe Gly
    130                 135                 140

Gln Gly Thr Lys Val Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys

<210> SEQ ID NO 156
<211> LENGTH: 35
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 156
ccgcaggtac ctcgagcgct agccagtctg gccag                                    35

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
tgcttgctca actctacgtc                                                     20

<210> SEQ ID NO 158
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
aacttgttta ttgcagctt                                                      19

<210> SEQ ID NO 159
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
gagttttgtc ggatccacca gagccaccgc tgccaccgct cgagcc                        46

<210> SEQ ID NO 160
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
gcgtatgcag gatccggcgg cgatattctg ctgacccaga                               40

<210> SEQ ID NO 161
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
cacgctcaga atcaccgggc tctgggtcag cagaatatcg                               40

<210> SEQ ID NO 162
<211> LENGTH: 40
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 162
gcccggtgat tctgagcgtg agcccgggcg aacgtgtgag                                 40

<210> SEQ ID NO 163
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
ggctcgcgcg gcagctaaag ctcacacgtt cgcccgggct                                 40

<210> SEQ ID NO 164
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
ctttagctgc cgcgcgagcc agagcattgg caccaacatt                                 40

<210> SEQ ID NO 165
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
gtgcgctgct gataccaatg aatgttggtg ccaatgctct                                 40

<210> SEQ ID NO 166
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
cattggtatc agcagcgcac caacggcagc ccgcgcctgc                                 40

<210> SEQ ID NO 167
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
ttcgctcgca tatttaatca gcaggcgcgg gctgccgttg                                 40

<210> SEQ ID NO 168
<211> LENGTH: 40
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 168
tgattaaata tgcgagcgaa agcattagcg gcattccgag            40

<210> SEQ ID NO 169
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
tgccgctgcc gctaaagcgg ctcggaatgc cgctaatgct            40

<210> SEQ ID NO 170
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
ccgctttagc ggcagcggca gcggcaccga ttttaccctg            40

<210> SEQ ID NO 171
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
ctttccacgc tgttaatgct cagggtaaaa tcggtgccgc            40

<210> SEQ ID NO 172
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
agcattaaca gcgtggaaag cgaagatatt gcggattatt            40

<210> SEQ ID NO 173
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
gttgttgttc tgctggcaat aataatccgc aatatcttcg            40

<210> SEQ ID NO 174
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
attgccagca gaacaacaac tggccgacca cctttggcgc                                   40

<210> SEQ ID NO 175
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
tcagttccag tttggtgccc gcgccaaagg tggtcggcca                                   40

<210> SEQ ID NO 176
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
gggcaccaaa ctggaactga aacgcggccg ccatcaccat                                   40

<210> SEQ ID NO 177
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
ctcccacgcg tatggtgatg atggtgatgg cggccgcgtt                                   40

<210> SEQ ID NO 178
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
cgtatgcaag atctggtagc ggtacccagg tgcagctgaa                                   40

<210> SEQ ID NO 179
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
ccaggcccgg gccgctctgt ttcagctgca cctgggtacc                                   40

<210> SEQ ID NO 180
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
acagagcggc ccgggcctgg tgcagccgag ccagagcctg                                   40

<210> SEQ ID NO 181
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
ctcacggtgc aggtaatgct caggctctgg ctcggctgca                     40

<210> SEQ ID NO 182
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
agcattacct gcaccgtgag cggctttagc ctgaccaact                     40

<210> SEQ ID NO 183
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
gcgcacccaa tgcacgccat agttggtcag gctaaagccg                     40

<210> SEQ ID NO 184
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
atggcgtgca ttgggtgcgc cagagcccgg gcaaaggcct                     40

<210> SEQ ID NO 185
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
aaatcacgcc cagccattcc aggcctttgc ccgggctctg                     40

<210> SEQ ID NO 186
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
ggaatggctg ggcgtgattt ggagcggcgg caacaccgat                     40

```
<210> SEQ ID NO 187
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
ctggtaaacg gggtgttata atcggtgttg ccgccgctcc                          40

<210> SEQ ID NO 188
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
tataacaccc cgtttaccag ccgcctgagc attaacaaag                          40

<210> SEQ ID NO 189
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
cacctggctt ttgctgttat ctttgttaat gctcaggcgg                          40

<210> SEQ ID NO 190
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
ataacagcaa aagccaggtg tttttaaaa tgaacagcct                           40

<210> SEQ ID NO 191
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
tcgcggtatc gttgctttgc aggctgttca ttttaaaaaa                          40

<210> SEQ ID NO 192
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
gcaaagcaac gataccgcga tttattattg cgcgcgcgcg                          40

<210> SEQ ID NO 193
<211> LENGTH: 40
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
tcataatcat aataggtcag cgcgcgcgcg caataataaa                            40

<210> SEQ ID NO 194
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
ctgacctatt atgattatga atttgcgtat tggggccagg                            40

<210> SEQ ID NO 195
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
gctcacggtc accagggtgc cctggccccca atacgcaaat                           40

<210> SEQ ID NO 196
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
gcaccctggt gaccgtgagc gcgggtggta gcggtagcgg                            40

<210> SEQ ID NO 197
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
taccgccgcc tccagatcct ccgctaccgc taccacccgc                            40

<210> SEQ ID NO 198
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
aggatctgga ggcggcggta gtagtggtgg aggatccggt                            40

<210> SEQ ID NO 199
<211> LENGTH: 40
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 199
tggtgatggc ggccgcggcc accggatcct ccaccactac                            40

<210> SEQ ID NO 200
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
cgagctagct ccctctacgc tcccctgttg aagctctttg                            40

<210> SEQ ID NO 201
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
acaagcgcgt tgagcccaaa tcttgtg                                          27

<210> SEQ ID NO 202
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
cagttcatcc cgggatgggg gcagggtg                                         28

<210> SEQ ID NO 203
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
ccccatcccg ggatgaactg accaagaacc aggtcagc                              38

<210> SEQ ID NO 204
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
ctggccacct aggactcatt taccc                                            25

<210> SEQ ID NO 205
<211> LENGTH: 38
<212> TYPE: DNA
<213> ORGANISM: Artificial Sequence
<220> FEATURE:
<223> OTHER INFORMATION: Description of Artificial Sequence: Synthetic

```
                            primer

<400> SEQUENCE: 205
gcactggtct cgaattcgga tattctgctg acccagag                          38

<210> SEQ ID NO 206
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
ggtgcggtct ccgtacgttt cagttccagt ttggtg                            36

<210> SEQ ID NO 207
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
gcactggtct cgaattcgca ggtgcagctg aaacagag                          38

<210> SEQ ID NO 208
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
gagacggtct cgctagccgc gctcacggtc accag                             35

<210> SEQ ID NO 209
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
tgcgtatgca agatctggta gcggtaccga tattctgctg acccagag               48

<210> SEQ ID NO 210
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
actactaccg ccgcctccag atcctccgct accgctacca cctttcagtt ccagtttggt  60
g                                                                  61

<210> SEQ ID NO 211
<211> LENGTH: 59
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 211
tctggaggcg gcggtagtag tggtggaggc tcaggcggcc aggtgcagct gaaacagag      59

<210> SEQ ID NO 212
<211> LENGTH: 37
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 212
gatggtgatg gcggccgcgc gcgctcacgg tcaccag      37

<210> SEQ ID NO 213
<211> LENGTH: 40
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 213
tgtcggatcc accgctaccg cccgcgctca cggtcaccag      40

<210> SEQ ID NO 214
<211> LENGTH: 75
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 214
tcacgaattc gcaaggccag tctggccagg gctcgagcgg tggcagcggt ggctctggtg      60
gatccggcgg tggca      75

<210> SEQ ID NO 215
<211> LENGTH: 75
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 215
tggtggatcc ggcggtggca gcggtggtgg ctccggcggt accggcggta gcggtagatc      60
tgacaaaact cacac      75

<210> SEQ ID NO 216
<211> LENGTH: 43
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 216
gatccccgtc tccgccagtc aaaatgatgc cggaaggcgg tac      43

<210> SEQ ID NO 217
<211> LENGTH: 35
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 217
cgccttccgg catcattttg actggcggag acggg                               35

<210> SEQ ID NO 218
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Cys Ile Ser Pro Arg Gly Cys Pro Asp Gly Pro Tyr Val Met
1               5                   10

<210> SEQ ID NO 219
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Cys Ile Ser Pro Arg Gly Cys Glu Pro Gly Thr Tyr Val Pro Thr
1               5                   10                  15

<210> SEQ ID NO 220
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Cys Ile Ser Pro Arg Gly Cys Pro Gly Gln Ile Trp His Pro Pro
1               5                   10                  15

<210> SEQ ID NO 221
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 221
caggtgcagc tgaaacagag cggcccgggc ctggtgcagc cgagccagag cctgagcatt    60
acctgcaccg tgagcggctt tagcctgacc aactatggcg tgcattgggt gcgccagagc   120
ccgggcaaag gcctggaatg gctgggcgtg atttggagcg gcggcaacac cgattataac   180
accccgttta ccagccgcct gagcattaac aaagataaca gcaaaagcca ggtgtttttt   240
aaaatgaaca gcctgcaaag caacgatacc gcgatttatt attgcgcgcg cgcgctgacc   300
tattatgatt atgaatttgc gtattggggc cagggcaccc tggtgaccgt gagcgcggct   360
agcaccaagg gcccatcggt cttccccctg gcaccctcct ccaagagcac ctctgggggc   420
acagcggccc tgggctgcct ggtcaaggac tacttccccg aaccggtgac ggtgtcgtgg   480
aactcaggcg ccctgaccag cggcgtgcac accttcccgg ctgtcctaca gtcctcagga   540
ctctactccc tcagcagcgt ggtgaccgtg ccctccagca gcttgggcac ccagacctac   600
```

```
atctgcaacg tgaatcacaa gcccagcaac accaaggtgg acaagcgcgt tgagcccaaa    660
tcttgtgaca aaactcacac atgcccaccg tgcccagcac ctgaactcct ggggggaccg    720
tcagtcttcc tcttcccccc aaaacccaag acacccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc ccccatcccg ggatgaactg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctacagc aagctcaccg tggacaagag caggtggcag   1260
caggggaacg tcttctcatg ctccgtgatg catgaggctc tgcacaacca ctacacgcag   1320
aagagcctct ccctgtctcc gggtaaa                                      1347
```

<210> SEQ ID NO 222
<211> LENGTH: 449
<212> TYPE: PRT
<213> ORGANISM: Artificial Sequence
<220> FEATURE:
<223> OTHER INFORMATION: Description of Artificial Sequence: Synthetic
   polypeptide

<400> SEQUENCE: 222

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Asp Glu Leu Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 223
<211> LENGTH: 756
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 223
caaggccagt ctggccagtg catctcgccc cgtggttgtg gaggctcgag cggtggcagc      60
ggtggctctg gtggatcccc gtctccgcca gtcaaaatga tgccggaagg cggtacccag     120
atcttgctga cccagagccc ggtgattctg agcgtgagcc cgggcgaacg tgtgagcttt     180
agctgccgcg cgagccagag cattggcacc aacattcatt ggtatcagca gcgcaccaac     240
ggcagcccgc gcctgctgat taaatatgcg agcgaaagca ttagcggcat tccgagccgc     300
tttagcggca gcggcagcgg caccgatttt accctgagca ttaacagcgt ggaaagcgaa     360
gatattgcgg attattattg ccagcagaac aacaactggc cgaccacctt ggcgcgggc     420 accaaactgg aactgaaacg tacggtggct gcaccatctg tcttcatctt cccgccatct     480
gatgagcagt tgaaatctgg aactgcctct gttgtgtgcc tgctgaataa cttctatccc     540
agagaggcca agtacagtg gaaggtggat aacgccctcc aatcgggtaa ctcccaggag     600
agtgtcacag agcaggacag caaggacagc acctacagcc tcagcagcac cctgacgctg     660
agcaaagcag actacgagaa acacaaagtc tacgcctgcg aagtcaccca tcagggcctg     720
agctcgcccg tcacaaagag cttcaacagg ggagcg                              756
```

<210> SEQ ID NO 224
<211> LENGTH: 252
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 224

Gln Gly Gln Ser Gly Gln Cys Ile Ser Pro Arg Gly Cys Gly Gly Ser
1               5                   10                  15

Ser Gly Gly Ser Gly Gly Ser Gly Gly Ser Pro Ser Pro Pro Val Lys
            20                  25                  30

Met Met Pro Glu Gly Gly Thr Gln Ile Leu Leu Thr Gln Ser Pro Val
        35                  40                  45

Ile Leu Ser Val Ser Pro Gly Glu Arg Val Ser Phe Ser Cys Arg Ala
    50                  55                  60

Ser Gln Ser Ile Gly Thr Asn Ile His Trp Tyr Gln Gln Arg Thr Asn
65                  70                  75                  80

Gly Ser Pro Arg Leu Leu Ile Lys Tyr Ala Ser Glu Ser Ile Ser Gly
                85                  90                  95

Ile Pro Ser Arg Phe Ser Gly Ser Gly Ser Gly Thr Asp Phe Thr Leu
            100                 105                 110

Ser Ile Asn Ser Val Glu Ser Glu Asp Ile Ala Asp Tyr Tyr Cys Gln
        115                 120                 125

Gln Asn Asn Asn Trp Pro Thr Thr Phe Gly Ala Gly Thr Lys Leu Glu
    130                 135                 140

Leu Lys Arg Thr Val Ala Ala Pro Ser Val Phe Ile Phe Pro Pro Ser
145                 150                 155                 160

Asp Glu Gln Leu Lys Ser Gly Thr Ala Ser Val Val Cys Leu Leu Asn
                165                 170                 175

Asn Phe Tyr Pro Arg Glu Ala Lys Val Gln Trp Lys Val Asp Asn Ala
            180                 185                 190

Leu Gln Ser Gly Asn Ser Gln Glu Ser Val Thr Glu Gln Asp Ser Lys
        195                 200                 205

Asp Ser Thr Tyr Ser Leu Ser Ser Thr Leu Thr Leu Ser Lys Ala Asp
    210                 215                 220

Tyr Glu Lys His Lys Val Tyr Ala Cys Glu Val Thr His Gln Gly Leu
225                 230                 235                 240

Ser Ser Pro Val Thr Lys Ser Phe Asn Arg Gly Ala
                245                 250

<210> SEQ ID NO 225
<211> LENGTH: 771
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 225
caaggccagt ctggccaggg ttcacattgt ctcattccta ttaacatggg cgcgccgtca    60
tgcggctcga gcggtggcag cggtggctct ggtggatccg gcggtggcag cggtggtggc   120
tccggcggta cccagatctt gctgacccag agcccggtga ttctgagcgt gagcccgggc   180
gaacgtgtga gctttagctg ccgcgcgagc cagagcattg gcaccaacat tcattggtat   240
cagcagcgca ccaacggcag cccgcgcctg ctgattaaat atgcgagcga aagcattagc   300

```
ggcattccga gccgctttag cggcagcggc agcggcaccg attttaccct gagcattaac      360
agcgtggaaa gcgaagatat tgcggattat tattgccagc agaacaacaa ctggccgacc      420
acctttggcg cgggcaccaa actggaactg aaacgtacgg tggctgcacc atctgtcttc      480
atcttcccgc catctgatga gcagttgaaa tctggaactg cctctgttgt gtgcctgctg      540
aataacttct atcccagaga ggccaaagta cagtggaagg tggataacgc cctccaatcg      600
ggtaactccc aggagagtgt cacagagcag gacagcaagg acagcaccta cagcctcagc      660
agcaccctga cgctgagcaa agcagactac gagaaacaca agtctacgc ctgcgaagtc       720 acccatcagg gcctgagctc gcccgtcaca aagagcttca caggggagc g                771
```

<210> SEQ ID NO 226
<211> LENGTH: 257
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 226

```
Gln Gly Gln Ser Gly Gln Gly Ser His Cys Leu Ile Pro Ile Asn Met
1               5                   10                  15

Gly Ala Pro Ser Cys Gly Ser Ser Gly Gly Ser Gly Gly Ser Gly Gly
            20                  25                  30

Ser Gly Gly Gly Ser Gly Gly Gly Ser Gly Gly Thr Gln Ile Leu Leu
        35                  40                  45

Thr Gln Ser Pro Val Ile Leu Ser Val Ser Pro Gly Glu Arg Val Ser
    50                  55                  60

Phe Ser Cys Arg Ala Ser Gln Ser Ile Gly Thr Asn Ile His Trp Tyr
65                  70                  75                  80

Gln Gln Arg Thr Asn Gly Ser Pro Arg Leu Leu Ile Lys Tyr Ala Ser
                85                  90                  95

Glu Ser Ile Ser Gly Ile Pro Ser Arg Phe Ser Gly Ser Gly Ser Gly
            100                 105                 110

Thr Asp Phe Thr Leu Ser Ile Asn Ser Val Glu Ser Glu Asp Ile Ala
        115                 120                 125

Asp Tyr Tyr Cys Gln Gln Asn Asn Asn Trp Pro Thr Thr Phe Gly Ala
    130                 135                 140

Gly Thr Lys Leu Glu Leu Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Ala
```

<210> SEQ ID NO 227

```
<211> LENGTH: 828
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 227
caaggccagt ctggccagtg catctcgccc cgtggttgtg gaggctcgag cgctagccag    60
tctggccagg gttcacattg tctcattcct attaacatgg gcgcgccgtc atgcggctcg   120
agcggtggca gcggtggctc tggtggatcc ccgtctccgc cagtcaaaat gatgccggaa   180
ggcggtaccc agatcttgct gacccagagc ccggtgattc tgagcgtgag cccgggcgaa   240
cgtgtgagct ttagctgccg cgcgagccag agcattggca ccaacattca ttggtatcag   300
cagcgcacca acggcagccc gcgcctgctg attaaatatg cgagcgaaag cattagcggc   360
attccgagcc gctttagcgg cagcggcagc ggcaccgatt ttaccctgag cattaacagc   420
gtggaaagcg aagatattgc ggattattat tgccagcaga caacaactg ccgaccacc    480 tttggcgcgg gcaccaaact ggaactgaaa cgtacggtgg ctgccaccat cgtcttcatc   540
ttcccgccat ctgatgagca gttgaaatct ggaactgcct ctgttgtgtg cctgctgaat   600
aacttctatc ccagagaggc caaagtacag tggaaggtgg ataacgccct ccaatcgggt   660
aactcccagg agagtgtcac agagcaggac agcaaggaca gcacctacag cctcagcagc   720
accctgacgc tgagcaaagc agactacgag aaacacaaag tctacgcctg cgaagtcacc   780
catcagggcc tgagctcgcc cgtcacaaag agcttcaaca ggggagcg                828

<210> SEQ ID NO 228
<211> LENGTH: 276
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Gln Gly Gln Ser Gly Gln Cys Ile Ser Pro Arg Gly Cys Gly Gly Ser
1               5                   10                  15

Ser Ala Ser Gln Ser Gly Gln Gly Ser His Cys Leu Ile Pro Ile Asn
            20                  25                  30

Met Gly Ala Pro Ser Cys Gly Ser Gly Gly Ser Gly Gly Ser Gly
        35                  40                  45

Gly Ser Pro Ser Pro Pro Val Lys Met Met Pro Glu Gly Gly Thr Gln
    50                  55                  60

Ile Leu Leu Thr Gln Ser Pro Val Ile Leu Ser Val Ser Pro Gly Glu
65                  70                  75                  80

Arg Val Ser Phe Ser Cys Arg Ala Ser Gln Ser Ile Gly Thr Asn Ile
                85                  90                  95

His Trp Tyr Gln Gln Arg Thr Asn Gly Ser Pro Arg Leu Leu Ile Lys
            100                 105                 110

Tyr Ala Ser Glu Ser Ile Ser Gly Ile Pro Ser Arg Phe Ser Gly Ser
        115                 120                 125

Gly Ser Gly Thr Asp Phe Thr Leu Ser Ile Asn Ser Val Glu Ser Glu
    130                 135                 140

Asp Ile Ala Asp Tyr Tyr Cys Gln Gln Asn Asn Asn Trp Pro Thr Thr
145                 150                 155                 160

Phe Gly Ala Gly Thr Lys Leu Glu Leu Lys Arg Thr Val Ala Ala Pro
                165                 170                 175
```

Ser Val Phe Ile Phe Pro Pro Ser Asp Glu Gln Leu Lys Ser Gly Thr
                180                 185                 190

Ala Ser Val Val Cys Leu Leu Asn Asn Phe Tyr Pro Arg Glu Ala Lys
            195                 200                 205

Val Gln Trp Lys Val Asp Asn Ala Leu Gln Ser Gly Asn Ser Gln Glu
        210                 215                 220

Ser Val Thr Glu Gln Asp Ser Lys Asp Ser Thr Tyr Ser Leu Ser Ser
225                 230                 235                 240

Thr Leu Thr Leu Ser Lys Ala Asp Tyr Glu Lys His Lys Val Tyr Ala
                245                 250                 255

Cys Glu Val Thr His Gln Gly Leu Ser Ser Pro Val Thr Lys Ser Phe
            260                 265                 270

Asn Arg Gly Ala
        275

<210> SEQ ID NO 229
<211> LENGTH: 771
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 229
caaggccagt ctggccagtg catctcacct cgtggttgtc cggacggccc atacgtcatg      60
tacggctcga gcggtggcag cggtggctct ggtggatccg gcggtggcag cggtggtggc     120
tccggcggta cccagatctt gctgacccag agcccggtga ttctgagcgt gagcccgggc     180
gaacgtgtga gctttagctg ccgcgcgagc cagagcattg gcaccaacat tcattggtat     240
cagcagcgca ccaacggcag cccgcgcctg ctgattaaat atgcgagcga aagcattagc     300
ggcattccga ccgctttag cggcagcggc agcggcaccg attttaccct gagcattaac     360
agcgtggaaa gcgaagatat tgcggattat tattgccagc agaacaacaa ctggccgacc     420
acctttggcg cgggcaccaa actggaactg aaacgtacgg tggctgcacc atctgtcttc     480
atcttcccgc catctgatga gcagttgaaa tctggaactg cctctgttgt gtgcctgctg     540
aataacttct atcccagaga ggccaaagta cagtggaagg tggataacgc cctccaatcg     600
ggtaactccc aggagagtgt cacagagcag gacagcaagg acagcaccta cagcctcagc     660
agcaccctga cgctgagcaa agcagactac gagaaacaca agtctacgc ctgcgaagtc     720 acccatcagg gcctgagctc gcccgtcaca aagagcttca caggggagc g              771

<210> SEQ ID NO 230
<211> LENGTH: 257
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Ser Gly Gly
            20                  25                  30

Ser Gly Gly Gly Ser Gly Gly Gly Ser Gly Gly Thr Gln Ile Leu Leu
        35                  40                  45

Thr Gln Ser Pro Val Ile Leu Ser Val Ser Pro Gly Glu Arg Val Ser

```
                50                  55                  60
Phe Ser Cys Arg Ala Ser Gln Ser Ile Gly Thr Asn Ile His Trp Tyr
 65                  70                  75                  80

Gln Gln Arg Thr Asn Gly Ser Pro Arg Leu Leu Ile Lys Tyr Ala Ser
                 85                  90                  95

Glu Ser Ile Ser Gly Ile Pro Ser Arg Phe Ser Gly Ser Gly Ser Gly
                100                 105                 110

Thr Asp Phe Thr Leu Ser Ile Asn Ser Val Glu Ser Glu Asp Ile Ala
                115                 120                 125

Asp Tyr Tyr Cys Gln Gln Asn Asn Asn Trp Pro Thr Thr Phe Gly Ala
            130                 135                 140

Gly Thr Lys Leu Glu Leu Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
                195                 200                 205

Glu Gln Asp Ser Lys Asp Ser Thr Tyr Ser Leu Ser Ser Thr Leu Thr
            210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Ala

<210> SEQ ID NO 231
<211> LENGTH: 771
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 231
caaggccagt ctggccagtg catctcacct cgtggttgtg agcctggcac ctatgttcca      60
acaggctcga gcggtggcag cggtggctct ggtggatccg gcggtggcag cggtggtggc     120
tccggcggta cccagatctt gctgacccag agcccggtga ttctgagcgt gagcccgggc     180
gaacgtgtga gctttagctg ccgcgcgagc cagagcattg caccaacat tcattggtat     240 cagcagcgca ccaacggcag cccgcgcctg ctgattaaat atgcgagcga aagcattagc     300
ggcattccga ccgctttag cggcagcggc agcggcaccg attttaccct gagcattaac     360
agcgtggaaa gcgaagatat tgcggattat tattgccagc agaacaacaa ctggccgacc     420
acctttggcg cgggcaccaa actggaactg aaacgtacgg tggctgcacc atctgtcttc     480
atcttcccgc catctgatga gcagttgaaa tctggaactg cctctgttgt gtgcctgctg     540
aataacttct atcccagaga ggccaaagta cagtggaagg tggataacgc cctccaatcg     600
ggtaactccc aggagagtgt cacagagcag gacagcaagg acagcaccta cagcctcagc     660
agcaccctga cgctgagcaa agcagactac gagaaacaca agtctacgc ctgcgaagtc     720 acccatcagg gcctgagctc gcccgtcaca aagagcttca caggggagc g              771

<210> SEQ ID NO 232
<211> LENGTH: 257
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Gln Gly Gln Ser Gly Gln Cys Ile Ser Pro Arg Gly Cys Glu Pro Gly
1               5                   10                  15

Thr Tyr Val Pro Thr Gly Ser Ser Gly Ser Gly Ser Gly Gly
            20                  25                  30

Ser Gly Gly Gly Ser Gly Gly Gly Ser Gly Gly Thr Gln Ile Leu Leu
        35                  40                  45

Thr Gln Ser Pro Val Ile Leu Ser Val Ser Pro Gly Glu Arg Val Ser
    50                  55                  60

Phe Ser Cys Arg Ala Ser Gln Ser Ile Gly Thr Asn Ile His Trp Tyr
65                  70                  75                  80

Gln Gln Arg Thr Asn Gly Ser Pro Arg Leu Leu Ile Lys Tyr Ala Ser
                85                  90                  95

Glu Ser Ile Ser Gly Ile Pro Ser Arg Phe Ser Gly Ser Gly Ser Gly
            100                 105                 110

Thr Asp Phe Thr Leu Ser Ile Asn Ser Val Glu Ser Glu Asp Ile Ala
        115                 120                 125

Asp Tyr Tyr Cys Gln Gln Asn Asn Asn Trp Pro Thr Thr Phe Gly Ala
130                 135                 140

Gly Thr Lys Leu Glu Leu Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Ala

<210> SEQ ID NO 233
<211> LENGTH: 771
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 233
caaggccagt ctggccagtg catctcacct cgtggttgtc cgggccaaat ttggcatcca      60
cctggctcga gcggtggcag cggtggctct ggtggatccg gcggtggcag cggtggtggc     120
tccggcggta cccagatctt gctgacccag agcccggtga ttctgagcgt gagcccgggc     180
gaacgtgtga gctttagctg ccgcgcgagc cagagcattg gcaccaacat tcattggtat     240
cagcagcgca ccaacggcag cccgcgcctg ctgattaaat atgcgagcga aagcattagc     300
ggcattccga gccgctttag cggcagcggc agcggcaccg attttaccct gagcattaac     360

```
agcgtggaaa gcgaagatat tgcggattat tattgccagc agaacaacaa ctggccgacc      420
acctttggcg cgggcaccaa actggaactg aaacgtacgg tggctgcacc atctgtcttc      480
atcttcccgc catctgatga gcagttgaaa tctggaactg cctctgttgt gtgcctgctg      540
aataacttct atcccagaga ggccaaagta cagtggaagg tggataacgc cctccaatcg      600
ggtaactccc aggagagtgt cacagagcag gacagcaagg acagcaccta cagcctcagc      660
agcaccctga cgctgagcaa agcagactac gagaaacaca aagtctacgc ctgcgaagtc      720
acccatcagg gcctgagctc gcccgtcaca aagagcttca cagggagc g               771
```

<210> SEQ ID NO 234
<211> LENGTH: 257
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Gln Gly Gln Ser Gly Gln Cys Ile Ser Pro Arg Gly Cys Pro Gly Gln
1               5                   10                  15

Ile Trp His Pro Pro Gly Ser Ser Gly Gly Ser Gly Gly Ser Gly Gly
            20                  25                  30

Ser Gly Gly Ser Gly Gly Ser Gly Gly Thr Gln Ile Leu Leu
        35                  40                  45

Thr Gln Ser Pro Val Ile Leu Ser Val Ser Pro Gly Glu Arg Val Ser
 50                  55                  60

Phe Ser Cys Arg Ala Ser Gln Ser Ile Gly Thr Asn Ile His Trp Tyr
65                  70                  75                  80

Gln Gln Arg Thr Asn Gly Ser Pro Arg Leu Leu Ile Lys Tyr Ala Ser
                85                  90                  95

Glu Ser Ile Ser Gly Ile Pro Ser Arg Phe Ser Gly Ser Gly
                100                 105                 110

Thr Asp Phe Thr Leu Ser Ile Asn Ser Val Glu Ser Glu Asp Ile Ala
            115                 120                 125

Asp Tyr Tyr Cys Gln Gln Asn Asn Asn Trp Pro Thr Thr Phe Gly Ala
130                 135                 140

Gly Thr Lys Leu Glu Leu Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Ala

<210> SEQ ID NO 235
<211> LENGTH: 8
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sequence may encompass 1-2 'Ser Gly Gly Gly'
      repeating units

<400> SEQUENCE: 235

Ser Gly Gly Gly Ser Gly Gly Gly
1               5

<210> SEQ ID NO 236
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Gly Ser His Cys Leu Ile Pro Ile Asn Met Gly Ala Pro Ser Cys
1               5                   10                  15

<210> SEQ ID NO 237
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Cys Ile Ser Pro Arg Gly Cys Gly Gly Ser Ser Ala Ser Gln Ser Gly
1               5                   10                  15

Gln Gly Ser His Cys Leu Ile Pro Ile Asn Met Gly Ala Pro Ser Cys
            20                  25                  30

<210> SEQ ID NO 238
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Cys Ile Ser Pro Arg Gly Cys Pro Asp Gly Pro Tyr Val Met Tyr
1               5                   10                  15

<210> SEQ ID NO 239
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Cys Ile Ser Pro Arg Gly Cys Glu Pro Gly Thr Tyr Val Pro Thr
1               5                   10                  15

<210> SEQ ID NO 240
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 240

Cys Ile Ser Pro Arg Gly Cys Pro Gly Gln Ile Trp His Pro Pro
1               5                   10                  15

<210> SEQ ID NO 241
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Cys Asn His His Tyr Phe Tyr Thr Cys Gly Cys Ile Ser Pro Arg Gly
1               5                   10                  15

Cys Pro Gly

<210> SEQ ID NO 242
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Ala Asp His Val Phe Trp Gly Ser Tyr Gly Cys Ile Ser Pro Arg Gly
1               5                   10                  15

Cys Pro Gly

<210> SEQ ID NO 243
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Cys His His Val Tyr Trp Gly His Cys Gly Cys Ile Ser Pro Arg Gly
1               5                   10                  15

Cys Pro Gly

<210> SEQ ID NO 244
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Cys Pro His Phe Thr Thr Thr Ser Cys Gly Cys Ile Ser Pro Arg Gly
1               5                   10                  15

Cys Pro Gly

<210> SEQ ID NO 245
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Cys Asn His His Tyr His Tyr Tyr Cys Gly Cys Ile Ser Pro Arg Gly
1               5                   10                  15

Cys Pro Gly

<210> SEQ ID NO 246
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Cys Pro His Val Ser Phe Gly Ser Cys Gly Cys Ile Ser Pro Arg Gly
1               5                   10                  15

Cys Pro Gly

<210> SEQ ID NO 247
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Cys Pro Tyr Tyr Thr Leu Ser Tyr Cys Gly Cys Ile Ser Pro Arg Gly
1               5                   10                  15

Cys Pro Gly

<210> SEQ ID NO 248
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Cys Asn His Val Tyr Phe Gly Thr Cys Gly Cys Ile Ser Pro Arg Gly
1               5                   10                  15

Cys Pro Gly

<210> SEQ ID NO 249
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Cys Asn His Phe Thr Leu Thr Thr Cys Gly Cys Ile Ser Pro Arg Gly
1               5                   10                  15

Cys Pro Gly

<210> SEQ ID NO 250
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

```
Cys His His Phe Thr Leu Thr Thr Cys Gly Cys Ile Ser Pro Arg Gly
1               5                   10                  15

Cys Pro Gly

<210> SEQ ID NO 251
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Tyr Asn Pro Cys Ala Thr Pro Met Cys Cys Ile Ser Pro Arg Gly Cys
1               5                   10                  15

Pro Gly

<210> SEQ ID NO 252
<211> LENGTH: 18
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 252

Cys Asn His His Tyr Phe Tyr Thr Cys Gly Cys Ile Ser Pro Arg Gly
1               5                   10                  15

Cys Gly

<210> SEQ ID NO 253
<211> LENGTH: 18
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 253

Cys Asn His His Tyr His Tyr Tyr Cys Gly Cys Ile Ser Pro Arg Gly
1               5                   10                  15

Cys Gly

<210> SEQ ID NO 254
<211> LENGTH: 18
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 254

Cys Asn His Val Tyr Phe Gly Thr Cys Gly Cys Ile Ser Pro Arg Gly
1               5                   10                  15

Cys Gly

<210> SEQ ID NO 255
<211> LENGTH: 18
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 255
```

Cys His His Val Tyr Trp Gly His Cys Gly Cys Ile Ser Pro Arg Gly
1               5                   10                  15

Cys Gly

<210> SEQ ID NO 256
<211> LENGTH: 18
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 256

Cys Pro His Phe Thr Thr Thr Ser Cys Gly Cys Ile Ser Pro Arg Gly
1               5                   10                  15

Cys Gly

<210> SEQ ID NO 257
<211> LENGTH: 18
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 257

Cys Asn His Phe Thr Leu Thr Thr Cys Gly Cys Ile Ser Pro Arg Gly
1               5                   10                  15

Cys Gly

<210> SEQ ID NO 258
<211> LENGTH: 18
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 258

Cys His His Phe Thr Leu Thr Thr Cys Gly Cys Ile Ser Pro Arg Gly
1               5                   10                  15

Cys Gly

<210> SEQ ID NO 259
<211> LENGTH: 18
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 259

Cys Pro Tyr Tyr Thr Leu Ser Tyr Cys Gly Cys Ile Ser Pro Arg Gly
1               5                   10                  15

Cys Gly

<210> SEQ ID NO 260
<211> LENGTH: 18
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 260

```
Cys Pro His Val Ser Phe Gly Ser Cys Gly Cys Ile Ser Pro Arg Gly
1               5                   10                  15

Cys Gly

<210> SEQ ID NO 261
<211> LENGTH: 18
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 261

Ala Asp His Val Phe Trp Gly Ser Tyr Gly Cys Ile Ser Pro Arg Gly
1               5                   10                  15

Cys Gly

<210> SEQ ID NO 262
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 262

Tyr Asn Pro Cys Ala Thr Pro Met Cys Cys Ile Ser Pro Arg Gly Cys
1               5                   10                  15

Gly

<210> SEQ ID NO 263
<211> LENGTH: 18
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 263

Cys His His Val Tyr Trp Gly His Cys Gly Cys Ile Ser Pro Arg Gly
1               5                   10                  15

Cys Gly

<210> SEQ ID NO 264
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 264

Cys Ile Ser Pro Arg Gly Cys Gly Gln Pro Ile Pro Ser Val Lys
1               5                   10                  15

<210> SEQ ID NO 265
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 265

Cys Ile Ser Pro Arg Gly Cys Thr Gln Pro Tyr His Val Ser Arg
```

<210> SEQ ID NO 266
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 266

Cys Ile Ser Pro Arg Gly Cys Asn Ala Val Ser Gly Leu Gly Ser
1               5                   10                  15

<210> SEQ ID NO 267
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 267

Thr Gly Arg Gly Pro Ser Trp Val
1               5

<210> SEQ ID NO 268
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 268

Ser Ala Arg Gly Pro Ser Arg Trp
1               5

<210> SEQ ID NO 269
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 269

Thr Ala Arg Gly Pro Ser Phe Lys
1               5

<210> SEQ ID NO 270
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 270

Thr Ala Arg Gly Pro Ser Trp
1               5

<210> SEQ ID NO 271
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus peptide

```
<400> SEQUENCE: 271

Leu Ser Gly Arg Ser Asp Asn His
1               5

<210> SEQ ID NO 272
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 272

Gly Gly Trp His Thr Gly Arg Asn
1               5

<210> SEQ ID NO 273
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 273

His Thr Gly Arg Ser Gly Ala Leu
1               5

<210> SEQ ID NO 274
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 274

Pro Leu Thr Gly Arg Ser Gly Gly
1               5

<210> SEQ ID NO 275
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 275

Leu Thr Gly Arg Ser Gly Ala
1               5

<210> SEQ ID NO 276
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 276

Ala Ala Arg Gly Pro Ala Ile His
1               5

<210> SEQ ID NO 277
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      consensus peptide

<400> SEQUENCE: 277

Arg Gly Pro Ala Phe Asn Pro Met
1               5

<210> SEQ ID NO 278
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 278

Ser Ser Arg Gly Pro Ala Tyr Leu
1               5

<210> SEQ ID NO 279
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 279

Arg Gly Pro Ala Thr Pro Ile Met
1               5

<210> SEQ ID NO 280
<211> LENGTH: 4
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 280

Arg Gly Pro Ala
1

<210> SEQ ID NO 281
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Glu His Pro Arg Val Lys Val Val Ser Glu
1               5                   10

<210> SEQ ID NO 282
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Pro Pro Pro Asp Met Lys Leu Phe Pro Gly
1               5                   10
```

```
<210> SEQ ID NO 283
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Pro Pro Pro Val Leu Lys Leu Leu Glu Trp
1               5                   10

<210> SEQ ID NO 284
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Val Leu Pro Glu Leu Arg Ser Val Phe Ser
1               5                   10

<210> SEQ ID NO 285
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Ala Pro Pro Ser Phe Lys Leu Val Asn Ala
1               5                   10

<210> SEQ ID NO 286
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Pro Pro Pro Glu Val Arg Ser Phe Ser Val
1               5                   10

<210> SEQ ID NO 287
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Ala Leu Pro Ser Val Lys Met Val Ser Glu
1               5                   10

<210> SEQ ID NO 288
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288
```

```
Glu Thr Pro Ser Val Lys Thr Met Gly Arg
1               5                   10

<210> SEQ ID NO 289
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Ala Ile Pro Arg Val Arg Leu Phe Asp Val
1               5                   10

<210> SEQ ID NO 290
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Gly Leu Gly Thr Pro Arg Gly Leu Phe Ala
1               5                   10

<210> SEQ ID NO 291
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Asp Arg Pro Lys Val Lys Thr Met Asp Phe
1               5                   10

<210> SEQ ID NO 292
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Arg Val Pro Lys Val Lys Val Met Leu Asp
1               5                   10

<210> SEQ ID NO 293
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Ala Pro Pro Leu Val Lys Ser Met Val Val
1               5                   10

<210> SEQ ID NO 294
<211> LENGTH: 10
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 294

Arg Glu Pro Phe Met Lys Ser Leu Pro Trp
1               5                   10

<210> SEQ ID NO 295
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Pro Val Pro Arg Leu Lys Leu Ile Lys Asp
1               5                   10

<210> SEQ ID NO 296
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Lys Gly Pro Lys Val Lys Val Val Thr Leu
1               5                   10

<210> SEQ ID NO 297
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Glu Arg Pro Gly Val Lys Ser Leu Val Leu
1               5                   10

<210> SEQ ID NO 298
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Asn Glx Pro Arg Val Arg Leu Val Leu Pro
1               5                   10

<210> SEQ ID NO 299
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Pro Arg Pro Phe Val Lys Ser Val Asp Gln
1               5                   10

<210> SEQ ID NO 300

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Arg Phe Pro Ser Leu Lys Ser Phe Pro Leu
1               5                   10

<210> SEQ ID NO 301
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Glu Ser Pro Val Met Lys Ser Met Ala Leu
1               5                   10

<210> SEQ ID NO 302
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Val Ala Pro Gln Leu Lys Ser Leu Val Pro
1               5                   10

<210> SEQ ID NO 303
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Ala Pro Pro Leu Val Lys Ser Met Val Val
1               5                   10

<210> SEQ ID NO 304
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Asn Met Pro Ser Phe Lys Leu Val Thr Gly
1               5                   10

<210> SEQ ID NO 305
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Asp Arg Pro Glu Met Lys Ser Leu Ser Gly
```

<210> SEQ ID NO 306
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Glu Gln Pro Glu Val Lys Met Val Lys Gly
1               5                   10

<210> SEQ ID NO 307
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Ala Val Pro Lys Val Arg Val Val Pro Glu
1               5                   10

<210> SEQ ID NO 308
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Asp Leu Pro Leu Val Lys Ser Leu Pro Ser
1               5                   10

<210> SEQ ID NO 309
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Glu Ala Pro Lys Val Lys Ala Leu Pro Lys
1               5                   10

<210> SEQ ID NO 310
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Gly Phe Pro His Met Lys Thr Phe Gln His
1               5                   10

<210> SEQ ID NO 311
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 311

Tyr Asp Pro Glx Val Lys Val Val Leu Ala
1               5                   10

<210> SEQ ID NO 312
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Ala Ser Pro Thr Met Lys Thr Val Gly Leu
1               5                   10

<210> SEQ ID NO 313
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Asp Val Pro Pro Met Lys Thr Leu Arg Pro
1               5                   10

<210> SEQ ID NO 314
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Ala Phe Pro Asp Met Arg Ser Val Arg Ser
1               5                   10

<210> SEQ ID NO 315
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Ser Ala Pro Tyr Phe Arg Met Met Asp Met
1               5                   10

<210> SEQ ID NO 316
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Glu Lys Pro Arg Met Lys Leu Phe Gln Gly
1               5                   10

<210> SEQ ID NO 317
<211> LENGTH: 10
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 317

Tyr Val Pro Arg Val Lys Ala Leu Glu Met
1               5                   10

<210> SEQ ID NO 318
<211> LENGTH: 786
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 318

```
ggccagtctg gccagccgtg ttctgagtgg cagtcgatgg tgcagccgcg ttgctattat      60
gggggcggtt ctggtggcag cggccaaggt ggccaaggta ctggccgtgg tccaagctgg     120
gttggcagta gcggcggttc tgatattcaa ctgacccaga gcccttcttc cctgagtgcc     180
agcgtgggtg accgtgttac gatcacttgc tcggccagcc aagatatttc taactacctg     240
aattggtacc agcagaagcc aggaaaggca ccaaaagtcc tgatctactt cacaagttca     300
ctgcattccg gcgtaccgtc gcgctttagc ggttctggca gtggtaccga cttcaccctg     360
actatctcga gtctgcaacc tgaggatttt gctacatatt actgtcagca atattcgacc     420
gtgccgtgga cgttcgggca gggcaccaaa gtggagatta agcgtacggt ggctgcacca     480
tctgtcttca tcttcccgcc atctgatgag cagttgaaat ctggaactgc ctctgttgtg     540
tgcctgctga taacttcta tcccagagag gccaaagtac agtggaaggt ggataacgcc     600
ctccaatcgg gtaactccca ggagagtgtc acagagcagg acagcaagga cagcacctac     660
agcctcagca gcaccctgac gctgagcaaa gcagactacg agaaacacaa agtctacgcc     720
tgcgaagtca cccatcaggg cctgagctcg cccgtcacaa agagcttcaa caggggagag     780
tgttag                                                                786
```

<210> SEQ ID NO 319
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 319

Gly Gln Ser Gly Gln Pro Cys Ser Glu Trp Gln Ser Met Val Gln Pro
1               5                   10                  15

Arg Cys Tyr Tyr Gly Gly Gly Ser Gly Gly Ser Gly Gln Gly Gly Gln
                20                  25                  30

Gly Thr Gly Arg Gly Pro Ser Trp Val Gly Ser Ser Gly Gly Ser Asp
            35                  40                  45

Ile Gln Leu Thr Gln Ser Pro Ser Ser Leu Ser Ala Ser Val Gly Asp
        50                  55                  60

Arg Val Thr Ile Thr Cys Ser Ala Ser Gln Asp Ile Ser Asn Tyr Leu
65                  70                  75                  80

Asn Trp Tyr Gln Gln Lys Pro Gly Lys Ala Pro Lys Val Leu Ile Tyr
                85                  90                  95

Phe Thr Ser Ser Leu His Ser Gly Val Pro Ser Arg Phe Ser Gly Ser
                100                 105                 110

Gly Ser Gly Thr Asp Phe Thr Leu Thr Ile Ser Ser Leu Gln Pro Glu
            115                 120                 125

Asp Phe Ala Thr Tyr Tyr Cys Gln Gln Tyr Ser Thr Val Pro Trp Thr
        130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260

<210> SEQ ID NO 320
<211> LENGTH: 786
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 320
ggccagtctg gccagccgtg ttctgagtgg cagtcgatgg tgcagccgcg ttgctattat      60
gggggcggtt ctggtggcag cggccaaggt ggccaaggtc tgagcggccg ttccgataat     120
catggcagta gcggcggttc tgatattcaa ctgacccaga gcccttcttc cctgagtgcc     180
agcgtgggtg accgtgttac gatcacttgc tcggccagcc aagatatttc taactacctg     240
aattggtacc agcagaagcc aggaaaggca ccaaaagtcc tgatctactt cacaagttca     300
ctgcattccg gcgtaccgtc gcgctttagc ggttctggca gtggtaccga cttcaccctg     360
actatctcga gtctgcaacc tgaggatttt gctacatatt actgtcagca atattcgacc     420
gtgccgtgga cgttcgggca gggcaccaaa gtggagatta gcgtacggt ggctgcacca      480 tctgtcttca tcttcccgcc atctgatgag cagttgaaat ctggaactgc ctctgttgtg     540
tgcctgctga taacttcta tcccagagag gccaaagtac agtggaaggt ggataacgcc      600
ctccaatcgg gtaactccca ggagagtgtc acagagcagg acagcaagga cagcacctac     660
agcctcagca gcaccctgac gctgagcaaa gcagactacg agaaacacaa agtctacgcc     720
tgcgaagtca cccatcaggg cctgagctcg cccgtcacaa agagcttcaa caggggagag     780
tgttag                                                               786

<210> SEQ ID NO 321
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 321

Gly Gln Ser Gly Gln Pro Cys Ser Glu Trp Gln Ser Met Val Gln Pro
1               5                   10                  15

Arg Cys Tyr Tyr Gly Gly Ser Gly Ser Gly Gln Gly Gly Gln
            20              25              30

Gly Leu Ser Gly Arg Ser Asp Asn His Gly Ser Ser Gly Ser Asp
        35                  40                  45

Ile Gln Leu Thr Gln Ser Pro Ser Ser Leu Ser Ala Ser Val Gly Asp
50                  55                  60

Arg Val Thr Ile Thr Cys Ser Ala Ser Gln Asp Ile Ser Asn Tyr Leu
65                  70                  75                  80

Asn Trp Tyr Gln Gln Lys Pro Gly Lys Ala Pro Lys Val Leu Ile Tyr
                85                  90                  95

Phe Thr Ser Ser Leu His Ser Gly Val Pro Ser Arg Phe Ser Gly Ser
            100                 105                 110

Gly Ser Gly Thr Asp Phe Thr Leu Thr Ile Ser Ser Leu Gln Pro Glu
        115                 120                 125

Asp Phe Ala Thr Tyr Tyr Cys Gln Gln Tyr Ser Thr Val Pro Trp Thr
130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
            165                 170                 175

Ala Ser Val Val Cys Leu Leu Asn Asn Phe Tyr Pro Arg Glu Ala Lys
        180                 185                 190

Val Gln Trp Lys Val Asp Asn Ala Leu Gln Ser Gly Asn Ser Gln Glu
    195                 200                 205

Ser Val Thr Glu Gln Asp Ser Lys Asp Ser Thr Tyr Ser Leu Ser Ser
210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
            245                 250                 255

Asn Arg Gly Glu Cys
            260

```
<210> SEQ ID NO 322
<211> LENGTH: 786
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 322
ggccagtctg gccagccgtg ttctgagtgg cagtcgatgg tgcagccgcg ttgctattat      60
gggggcggtt ctggtggcag cggccaaggt ggccaaccac tgactggtcg tagcggtggt     120
ggaggaagta gcggcggttc tgatattcaa ctgacccaga gcccttcttc cctgagtgcc     180
agcgtgggtg accgtgttac gatcacttgc tcggccagcc aagatatttc taactacctg     240
aattggtacc agcagaagcc aggaaaggca ccaaaagtcc tgatctactt cacaagttca     300
ctgcattccg gcgtaccgtc gcgctttagc ggttctggca gtggtaccga cttcaccctg     360
actatctcga gtctgcaacc tgaggatttt gctacatatt actgtcagca atattcgacc     420
gtgccgtgga cgttcgggca gggcaccaaa gtggagatta agcgtacggt ggctgccacca    480 tctgtcttca cttcccgcc atctgatgag cagttgaaat ctggaactgc ctctgttgtg      540
```

```
tgcctgctga ataacttcta tcccagagag gccaaagtac agtggaaggt ggataacgcc    600
ctccaatcgg gtaactccca ggagagtgtc acagagcagg acagcaagga cagcacctac    660
agcctcagca gcaccctgac gctgagcaaa gcagactacg agaaacacaa agtctacgcc    720
tgcgaagtca cccatcaggg cctgagctcg cccgtcacaa agagcttcaa caggggagag    780
tgttag                                                               786
```

```
<210> SEQ ID NO 323
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 323
```

Gly Gln Ser Gly Gln Pro Cys Ser Glu Trp Gln Ser Met Val Gln Pro
1               5                   10                  15

Arg Cys Tyr Tyr Gly Gly Ser Gly Gly Ser Gly Gln Gly Gly Gln
            20                  25                  30

Pro Leu Thr Gly Arg Ser Gly Gly Gly Ser Ser Gly Gly Ser Asp
        35                  40                  45

Ile Gln Leu Thr Gln Ser Pro Ser Ser Leu Ser Ala Ser Val Gly Asp
50                  55                  60

Arg Val Thr Ile Thr Cys Ser Ala Ser Gln Asp Ile Ser Asn Tyr Leu
65                  70                  75                  80

Asn Trp Tyr Gln Gln Lys Pro Gly Lys Ala Pro Lys Val Leu Ile Tyr
                85                  90                  95

Phe Thr Ser Ser Leu His Ser Gly Val Pro Ser Arg Phe Ser Gly Ser
            100                 105                 110

Gly Ser Gly Thr Asp Phe Thr Leu Thr Ile Ser Ser Leu Gln Pro Glu
        115                 120                 125

Asp Phe Ala Thr Tyr Tyr Cys Gln Gln Tyr Ser Thr Val Pro Trp Thr
130                 135                 140

Phe Gly Gln Gly Thr Lys Val Glu Ile Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260

```
<210> SEQ ID NO 324
<211> LENGTH: 786
<212> TYPE: DNA
<213> ORGANISM: Artificial Sequence
<220> FEATURE:
<223> OTHER INFORMATION: Description of Artificial Sequence: Synthetic
```

-continued polynucleotide

<400> SEQUENCE: 324

```
ggccagtctg gccagccgtg ttctgagtgg cagtcgatgg tgcagccgcg ttgctattat      60
gggggcggtt ctggtggcag cggccaaggt ggccaagaaa ctccatctgt aaagactatg     120
ggccgtagta gcggcggttc tgatattcaa ctgacccaga gccttcttc cctgagtgcc      180
agcgtgggtg accgtgttac gatcacttgc tcggccagcc aagatatttc taactacctg     240
aattggtacc agcagaagcc aggaaaggca ccaaaagtcc tgatctactt cacaagttca     300
ctgcattccg gcgtaccgtc gcgctttagc ggttctggca gtggtaccga cttcaccctg     360
actatctcga gtctgcaacc tgaggatttt gctacatatt actgtcagca atattcgacc     420
gtgccgtgga cgttcgggca gggcaccaaa gtggagatta agcgtacggt ggctgcacca     480
tctgtcttca tcttcccgcc atctgatgag cagttgaaat ctggaactgc ctctgttgtg     540
tgcctgctga taacttcta tcccagagag gccaaagtac agtggaaggt ggataacgcc      600
ctccaatcgg gtaactccca ggagagtgtc acagagcagg acagcaagga cagcacctac     660
agcctcagca gcaccctgac gctgagcaaa gcagactacg agaaacacaa agtctacgcc     720
tgcgaagtca cccatcaggg cctgagctcg cccgtcacaa agagcttcaa caggggagag     780
tgttag                                                                786
```

<210> SEQ ID NO 325
<211> LENGTH: 261
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 325

```
Gly Gln Ser Gly Gln Pro Cys Ser Glu Trp Gln Ser Met Val Gln Pro
  1               5                  10                  15
Arg Cys Tyr Tyr Gly Gly Gly Ser Gly Gly Ser Gly Gln Gly Gly Gln
                 20                  25                  30
Glu Thr Pro Ser Val Lys Thr Met Gly Arg Ser Ser Gly Gly Ser Asp
             35                  40                  45
Ile Gln Leu Thr Gln Ser Pro Ser Ser Leu Ser Ala Ser Val Gly Asp
         50                  55                  60
Arg Val Thr Ile Thr Cys Ser Ala Ser Gln Asp Ile Ser Asn Tyr Leu
 65                  70                  75                  80
Asn Trp Tyr Gln Gln Lys Pro Gly Lys Ala Pro Lys Val Leu Ile Tyr
                 85                  90                  95
Phe Thr Ser Ser Leu His Ser Gly Val Pro Ser Arg Phe Ser Gly Ser
            100                 105                 110
Gly Ser Gly Thr Asp Phe Thr Leu Thr Ile Ser Ser Leu Gln Pro Glu
        115                 120                 125
Asp Phe Ala Thr Tyr Tyr Cys Gln Gln Tyr Ser Thr Val Pro Trp Thr
    130                 135                 140
Phe Gly Gln Gly Thr Lys Val Glu Ile Lys Arg Thr Val Ala Ala Pro
145                 150                 155                 160
Ser Val Phe Ile Phe Pro Pro Ser Asp Glu Gln Leu Lys Ser Gly Thr
                165                 170                 175
Ala Ser Val Val Cys Leu Leu Asn Asn Phe Tyr Pro Arg Glu Ala Lys
            180                 185                 190
Val Gln Trp Lys Val Asp Asn Ala Leu Gln Ser Gly Asn Ser Gln Glu
```

```
                    195                 200                 205
Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260

<210> SEQ ID NO 326
<211> LENGTH: 786
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 326
ggccagtctg gccagccgtg ttctgagtgg cagtcgatgg tgcagccgcg ttgctattat      60
gggggcggtt ctggtggcag cggccaaggt ggccaaggtt ccccacatat gaaaactttc     120
cagcatagta gcggcggttc tgatattcaa ctgacccaga gcccttcttc cctgagtgcc     180
agcgtgggtg accgtgttac gatcacttgc tcggccagcc aagatatttc taactacctg     240
aattggtacc agcagaagcc aggaaaggca ccaaaagtcc tgatctactt cacaagttca     300
ctgcattccg gcgtaccgtc gcgctttagc ggttctggca gtggtaccga cttcaccctg     360
actatctcga gtctgcaacc tgaggatttt gctacatatt actgtcagca atattcgacc     420
gtgccgtgga cgttcgggca gggcaccaaa gtggagatta gcgtacggt ggctgcacca     480 tctgtcttca tcttcccgcc atctgatgag cagttgaaat ctggaactgc ctctgttgtg     540
tgcctgctga taacttcta tcccagagag gccaaagtac agtggaaggt ggataacgcc     600
ctccaatcgg gtaactccca ggagagtgtc acagagcagg acagcaagga cagcacctac     660
agcctcagca gcaccctgac gctgagcaaa gcagactacg agaaacacaa agtctacgcc     720
tgcgaagtca cccatcaggg cctgagctcg cccgtcacaa agagcttcaa caggggagag     780
tgttag                                                                786

<210> SEQ ID NO 327
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

Gly Gln Ser Gly Gln Pro Cys Ser Glu Trp Gln Ser Met Val Gln Pro
1               5                   10                  15

Arg Cys Tyr Tyr Gly Gly Gly Ser Gly Gly Ser Gly Gln Gly Gly Gln
                20                  25                  30

Gly Phe Pro His Met Lys Thr Phe Gln His Ser Ser Gly Gly Ser Asp
            35                  40                  45

Ile Gln Leu Thr Gln Ser Pro Ser Ser Leu Ser Ala Ser Val Gly Asp
        50                  55                  60

Arg Val Thr Ile Thr Cys Ser Ala Ser Gln Asp Ile Ser Asn Tyr Leu
65                  70                  75                  80

Asn Trp Tyr Gln Gln Lys Pro Gly Lys Ala Pro Lys Val Leu Ile Tyr
```

```
                     85                  90                  95
Phe Thr Ser Ser Leu His Ser Gly Val Pro Ser Arg Phe Ser Gly Ser
                100                 105                 110
Gly Ser Gly Thr Asp Phe Thr Leu Thr Ile Ser Ser Leu Gln Pro Glu
            115                 120                 125
Asp Phe Ala Thr Tyr Tyr Cys Gln Gln Tyr Ser Thr Val Pro Trp Thr
        130                 135                 140
Phe Gly Gln Gly Thr Lys Val Glu Ile Lys Arg Thr Val Ala Ala Pro
145                 150                 155                 160
Ser Val Phe Ile Phe Pro Pro Ser Asp Glu Gln Leu Lys Ser Gly Thr
                165                 170                 175
Ala Ser Val Val Cys Leu Leu Asn Asn Phe Tyr Pro Arg Glu Ala Lys
            180                 185                 190
Val Gln Trp Lys Val Asp Asn Ala Leu Gln Ser Gly Asn Ser Gln Glu
        195                 200                 205
Ser Val Thr Glu Gln Asp Ser Lys Asp Ser Thr Tyr Ser Leu Ser Ser
210                 215                 220
Thr Leu Thr Leu Ser Lys Ala Asp Tyr Glu Lys His Lys Val Tyr Ala
225                 230                 235                 240
Cys Glu Val Thr His Gln Gly Leu Ser Ser Pro Val Thr Lys Ser Phe
                245                 250                 255
Asn Arg Gly Glu Cys
            260

<210> SEQ ID NO 328
<211> LENGTH: 780
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 328
ggccagtctg gccagccgtg ttctgagtgg cagtcgatgg tgcagccgcg ttgctattat    60
gggggcggtt ctggtggcag cggccaaggt ggccaagcag ctaatctggg cagcggagga   120
agtagcggcg gttctgatat tcaactgacc cagagccctt cttccctgag tgccagcgtg   180
ggtgaccgtg ttacgatcac ttgctcggcc agccaagata tttctaacta cctgaattgg   240
taccagcaga agccaggaaa ggcaccaaaa gtcctgatct acttcacaag ttcactgcat   300
tccggcgtac cgtcgcgctt tagcggttct ggcagtggta ccgacttcac cctgactatc   360
tcgagtctgc aacctgagga ttttgctaca tattactgtc agcaatattc gaccgtgccg   420
tggacgttcg gcagggcac caaagtggag attaagcgta cggtggctgc accatctgtc   480
ttcatcttcc cgccatctga tgagcagttg aaatctggaa ctgcctctgt tgtgtgcctg   540
ctgaataact tctatcccag agaggccaaa gtacagtgga aggtggataa cgccctccaa   600
tcgggtaact cccaggagag tgtcacagag caggacagca aggacagcac ctacagcctc   660
agcagcaccc tgacgctgag caaagcagac tacgagaaac acaaagtcta cgcctgcgaa   720
gtcacccatc agggcctgag ctcgcccgtc acaaagagct caacaggggg agagtgttag   780

<210> SEQ ID NO 329
<211> LENGTH: 259
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 329

Gly Gln Ser Gly Gln Pro Cys Ser Glu Trp Gln Ser Met Val Gln Pro
1               5                   10                  15

Arg Cys Tyr Tyr Gly Gly Gly Ser Gly Gly Ser Gly Gln Gly Gly Gln
            20                  25                  30

Ala Ala Asn Leu Gly Ser Gly Gly Ser Ser Gly Gly Ser Asp Ile Gln
        35                  40                  45

Leu Thr Gln Ser Pro Ser Ser Leu Ser Ala Ser Val Gly Asp Arg Val
50                  55                  60

Thr Ile Thr Cys Ser Ala Ser Gln Asp Ile Ser Asn Tyr Leu Asn Trp
65              70                  75                  80

Tyr Gln Gln Lys Pro Gly Lys Ala Pro Lys Val Leu Ile Tyr Phe Thr
            85                  90                  95

Ser Ser Leu His Ser Gly Val Pro Ser Arg Phe Ser Gly Ser Gly Ser
            100                 105                 110

Gly Thr Asp Phe Thr Leu Thr Ile Ser Ser Leu Gln Pro Glu Asp Phe
            115                 120                 125

Ala Thr Tyr Tyr Cys Gln Gln Tyr Ser Thr Val Pro Trp Thr Phe Gly
        130                 135                 140

Gln Gly Thr Lys Val Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys

<210> SEQ ID NO 330
<211> LENGTH: 780
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 330
ggccagtctg gccagccgtg ttctgagtgg cagtcgatgg tgcagccgcg ttgctattat      60
gggggcggtt ctggtggcag cggccaaggt ggccaaccga ctaatctggg cagcggagga     120
agtagcggcg gttctgatat tcaactgacc cagagccctt cttccctgag tgccagcgtg     180
ggtgaccgtg ttacgatcac ttgctcggcc agccaagata tttctaacta cctgaattgg     240
taccagcaga agccaggaaa ggcaccaaaa gtcctgatct acttcacaag ttcactgcat     300
tccggcgtac cgtcgcgctt tagcggttct ggcagtggta ccgacttcac cctgactatc     360
tcgagtctgc aacctgagga ttttgctaca tattactgtc agcaatattc gaccgtgccg     420
tggacgttcg ggcagggcac caaagtggag attaagcgta cggtggctgc accatctgtc     480

```
ttcatcttcc cgccatctga tgagcagttg aaatctggaa ctgcctctgt tgtgtgcctg      540
ctgaataact tctatcccag agaggccaaa gtacagtgga aggtggataa cgccctccaa      600
tcgggtaact cccaggagag tgtcacagag caggacagca aggacagcac ctacagcctc      660
agcagcaccc tgacgctgag caaagcagac tacgagaaac acaaagtcta cgcctgcgaa      720
gtcacccatc agggcctgag ctcgcccgtc acaaagagct tcaacagggg agagtgttag      780
```

<210> SEQ ID NO 331
<211> LENGTH: 259
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 331

```
Gly Gln Ser Gly Gln Pro Cys Ser Glu Trp Gln Ser Met Val Gln Pro
1               5                  10                   15

Arg Cys Tyr Tyr Gly Gly Gly Ser Gly Ser Gly Gln Gly Gly Gln
            20                  25                  30

Pro Thr Asn Leu Gly Ser Gly Gly Ser Ser Gly Gly Ser Asp Ile Gln
        35                  40                  45

Leu Thr Gln Ser Pro Ser Ser Leu Ser Ala Ser Val Gly Asp Arg Val
50                  55                  60

Thr Ile Thr Cys Ser Ala Ser Gln Asp Ile Ser Asn Tyr Leu Asn Trp
65                  70                  75                  80

Tyr Gln Gln Lys Pro Gly Lys Ala Pro Lys Val Leu Ile Tyr Phe Thr
                85                  90                  95

Ser Ser Leu His Ser Gly Val Pro Ser Arg Phe Ser Gly Ser Gly Ser
            100                 105                 110

Gly Thr Asp Phe Thr Leu Thr Ile Ser Ser Leu Gln Pro Glu Asp Phe
        115                 120                 125

Ala Thr Tyr Tyr Cys Gln Gln Tyr Ser Thr Val Pro Trp Thr Phe Gly
    130                 135                 140

Gln Gly Thr Lys Val Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys
```

<210> SEQ ID NO 332
<211> LENGTH: 780
<212> TYPE: DNA
<213> ORGANISM: Artificial Sequence
<220> FEATURE:
<223> OTHER INFORMATION: Description of Artificial Sequence: Synthetic
      polynucleotide -continued

<400> SEQUENCE: 332

```
ggccagtctg gccagccgtg ttctgagtgg cagtcgatgg tgcagccgcg ttgctattat      60
gggggcggtt ctggtggcag cggccaaggt ggccaaccga ctaatggtgg cagcggagga     120
agtagcggcg ttctgatat tcaactgacc cagagccctt cttccctgag tgccagcgtg     180
ggtgaccgtg ttacgatcac ttgctcggcc agccaagata tttctaacta cctgaattgg     240
taccagcaga agccaggaaa ggcaccaaaa gtcctgatct acttcacaag ttcactgcat     300
tccggcgtac cgtcgcgctt tagcggttct ggcagtggta ccgacttcac cctgactatc     360
tcgagtctgc aacctgagga ttttgctaca tattactgtc agcaatattc gaccgtgccg     420
tggacgttcg gcagggcac caaagtggag attaagcgta cggtggctgc accatctgtc     480
ttcatcttcc cgccatctga tgagcagttg aaatctggaa ctgcctctgt tgtgtgcctg     540
ctgaataact tctatcccag agaggccaaa gtacagtgga aggtggataa cgccctccaa     600
tcgggtaact cccaggagag tgtcacagag caggacagca aggacagcac ctacagcctc     660
agcagcaccc tgacgctgag caaagcagac tacgagaaac acaaagtcta cgcctgcgaa     720
gtcacccatc agggcctgag ctcgcccgtc acaaagagct tcaacagggg agagtgttag     780
```

<210> SEQ ID NO 333
<211> LENGTH: 259
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 333

```
Gly Gln Ser Gly Gln Pro Cys Ser Glu Trp Gln Ser Met Val Gln Pro
 1               5                  10                  15

Arg Cys Tyr Tyr Gly Gly Gly Ser Gly Gly Ser Gly Gln Gly Gly Gln
                20                  25                  30

Pro Thr Asn Gly Gly Ser Gly Gly Ser Ser Gly Gly Ser Asp Ile Gln
                35                  40                  45

Leu Thr Gln Ser Pro Ser Ser Leu Ser Ala Ser Val Gly Asp Arg Val
    50                  55                  60

Thr Ile Thr Cys Ser Ala Ser Gln Asp Ile Ser Asn Tyr Leu Asn Trp
65                  70                  75                  80

Tyr Gln Gln Lys Pro Gly Lys Ala Pro Lys Val Leu Ile Tyr Phe Thr
                85                  90                  95

Ser Ser Leu His Ser Gly Val Pro Ser Arg Phe Ser Gly Ser Gly Ser
                100                 105                 110

Gly Thr Asp Phe Thr Leu Thr Ile Ser Ser Leu Gln Pro Glu Asp Phe
            115                 120                 125

Ala Thr Tyr Tyr Cys Gln Gln Tyr Ser Thr Val Pro Trp Thr Phe Gly
    130                 135                 140

Gln Gly Thr Lys Val Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
                180                 185                 190

Trp Lys Val Asp Asn Ala Leu Gln Ser Gly Asn Ser Gln Glu Ser Val
            195                 200                 205

Thr Glu Gln Asp Ser Lys Asp Ser Thr Tyr Ser Leu Ser Ser Thr Leu
    210                 215                 220
```

```
Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
            245                 250                 255

Gly Glu Cys
```

<210> SEQ ID NO 334
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

```
Asp Glu Val Asp
1
```

<210> SEQ ID NO 335
<211> LENGTH: 780
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 335

```
ggccagtctg gccagccgtg ttctgagtgg cagtcgatgg tgcagccgcg ttgctattat      60
gggggcggtt ctggtggcag cggccaaggt ggccaagacg aagtcgatgg cagcggagga     120
agtagcggcg gttctgatat tcaactgacc cagagccctt cttccctgag tgccagcgtg     180
ggtgaccgtg ttacgatcac ttgctcggcc agccaagata tttctaacta cctgaattgg     240
taccagcaga agccaggaaa ggcaccaaaa gtcctgatct acttcacaag ttcactgcat     300
tccggcgtac cgtcgcgctt tagcggttct ggcagtggta ccgacttcac cctgactatc     360
tcgagtctgc aacctgagga ttttgctaca tattactgtc agcaatattc gaccgtgccg     420
tggacgttcg gcagggcac caaagtggag attaagcgta cggtggctgc accatctgtc     480
ttcatcttcc cgccatctga tgagcagttg aaatctggaa ctgcctctgt tgtgtgcctg     540
ctgaataact tctatcccag agaggccaaa gtacagtgga aggtggataa cgccctccaa     600
tcgggtaact cccaggagag tgtcacagag caggacagca aggacagcac ctacagcctc     660
agcagcaccc tgacgctgag caaagcagac tacgagaaac acaaagtcta cgcctgcgaa     720
gtcacccatc agggcctgag ctcgcccgtc acaaagagct tcaacagggg agagtgttag     780
```

<210> SEQ ID NO 336
<211> LENGTH: 259
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 336

```
Gly Gln Ser Gly Gln Pro Cys Ser Glu Trp Gln Ser Met Val Gln Pro
1               5                   10                  15

Arg Cys Tyr Tyr Gly Gly Gly Ser Gly Gly Ser Gly Gln Gly Gly Gln
            20                  25                  30

Asp Glu Val Asp Gly Ser Gly Gly Ser Ser Gly Gly Ser Asp Ile Gln
        35                  40                  45
```

```
Leu Thr Gln Ser Pro Ser Ser Leu Ser Ala Ser Val Gly Asp Arg Val
 50                  55                  60

Thr Ile Thr Cys Ser Ala Ser Gln Asp Ile Ser Asn Tyr Leu Asn Trp
 65                  70                  75                  80

Tyr Gln Gln Lys Pro Gly Lys Ala Pro Lys Val Leu Ile Tyr Phe Thr
                 85                  90                  95

Ser Ser Leu His Ser Gly Val Pro Ser Arg Phe Ser Gly Ser Gly Ser
                100                 105                 110

Gly Thr Asp Phe Thr Leu Thr Ile Ser Ser Leu Gln Pro Glu Asp Phe
            115                 120                 125

Ala Thr Tyr Tyr Cys Gln Gln Tyr Ser Thr Val Pro Trp Thr Phe Gly
        130                 135                 140

Gln Gly Thr Lys Val Glu Ile Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys

<210> SEQ ID NO 337
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 337
aggttgcaga ctcgagatag tcagggtgaa gtc                                33

<210> SEQ ID NO 338
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 338
tcctccgctg cccagattag ctgcttggcc accttggccg ctgccac                 47

<210> SEQ ID NO 339
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 339
gcagctaatc tgggcagcgg aggaagtagc ggcggttctg atattcaact g            51
```

```
<210> SEQ ID NO 340
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 340
tcctccgctg cccagattag tcggttggcc accttggccg ctgccac                47

<210> SEQ ID NO 341
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 341
ccgactaatc tgggcagcgg aggaagtagc ggcggttctg atattcaact g            51

<210> SEQ ID NO 342
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 342
tcctccgctg ccaccattag tcggttggcc accttggccg ctgccac                47

<210> SEQ ID NO 343
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 343
ccgactaatg gtggcagcgg aggaagtagc ggcggttctg atattcaact g            51

<210> SEQ ID NO 344
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 344
gacgaagtcg atggcagcgg aggaagtagc ggcggttctg atattcaact g            51

<210> SEQ ID NO 345
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 345
tcctccgctg ccatcgactt cgtcttggcc accttggccg ctgccac                47

<210> SEQ ID NO 346
```

```
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 346
```

| | | | | | | | | | | | | | | | |
|---|---|---|---|---|---|---|---|---|---|---|---|---|---|---|---|
|Asp|Ile|Gln|Leu|Thr|Gln|Ser|Pro|Ser|Ser|Leu|Ser|Ala|Ser|Val|Gly|
|1| | | |5| | | | |10| | | | |15| |
|Asp|Arg|Val|Thr|Ile|Thr|Cys|Ser|Ala|Ser|Gln|Asp|Ile|Ser|Asn|Tyr|
| | | |20| | | | |25| | | | |30| | |
|Leu|Asn|Trp|Tyr|Gln|Gln|Lys|Pro|Gly|Lys|Ala|Pro|Lys|Val|Leu|Ile|
| | |35| | | | |40| | | | |45| | | |
|Tyr|Phe|Thr|Ser|Ser|Leu|His|Ser|Gly|Val|Pro|Ser|Arg|Phe|Ser|Gly|
| |50| | | | |55| | | | |60| | | | |
|Ser|Gly|Ser|Gly|Thr|Asp|Phe|Thr|Leu|Thr|Ile|Ser|Ser|Leu|Gln|Pro|
|65| | | | |70| | | | |75| | | | |80|
|Glu|Asp|Phe|Ala|Thr|Tyr|Tyr|Cys|Gln|Gln|Tyr|Ser|Thr|Val|Pro|Trp|
| | | | |85| | | | |90| | | | |95| |
|Thr|Phe|Gly|Gln|Gly|Thr|Lys|Val|Glu|Ile|Lys|Gly|Gly|Gly|Ser|Gly|
| | | |100| | | | |105| | | | |110| | |
|Gly|Gly|Ser|Gly|Gly|Ser|Gly|Gly|Gly|Ser|Gly|Gly|Gly|Gly|Gly|Gly|
| | |115| | | | |120| | | | |125| | | |
|Ser|Gly|Gly|Gly|Gly|Ser|Gly|Glu|Val|Gln|Leu|Val|Glu|Ser|Gly|Gly|
| |130| | | | |135| | | | |140| | | | |
|Gly|Leu|Val|Gln|Pro|Gly|Gly|Ser|Leu|Arg|Leu|Ser|Cys|Ala|Ala|Ser|
|145| | | | |150| | | | |155| | | | |160|
|Gly|Tyr|Asp|Phe|Thr|His|Tyr|Gly|Met|Asn|Trp|Val|Arg|Gln|Ala|Pro|
| | | | |165| | | | |170| | | | |175| |
|Gly|Lys|Gly|Leu|Glu|Trp|Val|Gly|Trp|Ile|Asn|Thr|Tyr|Thr|Gly|Glu|
| | | |180| | | | |185| | | | |190| | |
|Pro|Thr|Tyr|Ala|Ala|Asp|Phe|Lys|Arg|Arg|Phe|Thr|Phe|Ser|Leu|Asp|
| | |195| | | | |200| | | | |205| | | |
|Thr|Ser|Lys|Ser|Thr|Ala|Tyr|Leu|Gln|Met|Asn|Ser|Leu|Arg|Ala|Glu|
| |210| | | | |215| | | | |220| | | | |
|Asp|Thr|Ala|Val|Tyr|Tyr|Cys|Ala|Lys|Tyr|Pro|Tyr|Tyr|Tyr|Gly|Thr|
|225| | | | |230| | | | |235| | | | |240|
|Ser|His|Trp|Tyr|Phe|Asp|Val|Trp|Gly|Gln|Gly|Thr|Leu|Val|Thr|Val|
| | | | |245| | | | |250| | | | |255| |
|Ser|Gly|Gly|Ser|Gly|Ala|Met|Val|Arg|Ser|Asp|Lys|Thr|His|Thr|Cys|
| | | |260| | | | |265| | | | |270| | |
|Pro|Pro|Cys|Pro|Ala|Pro|Glu|Leu|Leu|Gly|Gly|Pro|Ser|Val|Phe|Leu|
| | |275| | | | |280| | | | |285| | | |
|Phe|Pro|Pro|Lys|Pro|Lys|Asp|Thr|Leu|Met|Ile|Ser|Arg|Thr|Pro|Glu|
| |290| | | | |295| | | | |300| | | | |
|Val|Thr|Cys|Val|Val|Val|Asp|Val|Ser|His|Glu|Asp|Pro|Glu|Val|Lys|
|305| | | | |310| | | | |315| | | | |320|
|Phe|Asn|Trp|Tyr|Val|Asp|Gly|Val|Glu|Val|His|Asn|Ala|Lys|Thr|Lys|
| | | | |325| | | | |330| | | | |335| |
|Pro|Arg|Glu|Glu|Gln|Tyr|Asn|Ser|Thr|Tyr|Arg|Val|Val|Ser|Val|Leu|
| | | |340| | | | |345| | | | |350| | |
|Thr|Val|Leu|His|Gln|Asp|Trp|Leu|Asn|Gly|Lys|Glu|Tyr|Lys|Cys|Lys|
| | |355| | | | |360| | | | |365| | | |
|Val|Ser|Asn|Lys|Ala|Leu|Pro|Ala|Pro|Ile|Glu|Lys|Thr|Ile|Ser|Lys|
| |370| | | | |375| | | | |380| | | | |

```
Ala Lys Gly Gln Pro Arg Glu Pro Gln Val Tyr Thr Leu Pro Pro Ser
385                 390                 395                 400

Arg Glu Glu Met Thr Lys Asn Gln Val Ser Leu Thr Cys Leu Val Lys
            405                 410                 415

Gly Phe Tyr Pro Ser Asp Ile Ala Val Glu Trp Glu Ser Asn Gly Gln
        420                 425                 430

Pro Glu Asn Asn Tyr Lys Thr Thr Pro Pro Val Leu Asp Ser Asp Gly
    435                 440                 445

Ser Phe Phe Leu Tyr Ser Lys Leu Thr Val Asp Lys Ser Arg Trp Gln
450                 455                 460

Gln Gly Asn Val Phe Ser Cys Ser Val Met His Glu Gly Leu His Asn
465                 470                 475                 480

His Tyr Thr Gln Lys Ser Leu Ser Leu Ser Pro Gly Lys
                485                 490

<210> SEQ ID NO 347
<211> LENGTH: 538
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 347

Gly Gln Ser Gly Gln Pro Cys Ser Glu Trp Gln Ser Met Val Gln Pro
1               5                   10                  15

Arg Cys Tyr Tyr Gly Gly Gly Ser Gly Ser Gly Gly Gly Gly Gly Gln
                20                  25                  30

Val His Met Pro Leu Gly Phe Leu Gly Pro Gly Gly Ser Asp Ile Gln
            35                  40                  45

Leu Thr Gln Ser Pro Ser Ser Leu Ser Ala Ser Val Gly Asp Arg Val
    50                  55                  60

Thr Ile Thr Cys Ser Ala Ser Gln Asp Ile Ser Asn Tyr Leu Asn Trp
65                  70                  75                  80

Tyr Gln Gln Lys Pro Gly Lys Ala Pro Lys Val Leu Ile Tyr Phe Thr
                85                  90                  95

Ser Ser Leu His Ser Gly Val Pro Ser Arg Phe Ser Gly Ser Gly Ser
            100                 105                 110

Gly Thr Asp Phe Thr Leu Thr Ile Ser Ser Leu Gln Pro Glu Asp Phe
        115                 120                 125

Ala Thr Tyr Tyr Cys Gln Gln Tyr Ser Thr Val Pro Trp Thr Phe Gly
    130                 135                 140

Gln Gly Thr Lys Val Glu Ile Lys Gly Gly Gly Ser Gly Gly Gly Ser
145                 150                 155                 160

Gly Gly Gly Ser Gly Gly Gly Ser Gly Gly Gly Ser Gly Gly Gly Gly
                165                 170                 175

Gly Gly Ser Gly Glu Val Gln Leu Val Glu Ser Gly Gly Gly Leu Val
            180                 185                 190

Gln Pro Gly Gly Ser Leu Arg Leu Ser Cys Ala Ala Ser Gly Tyr Asp
        195                 200                 205

Phe Thr His Tyr Gly Met Asn Trp Val Arg Gln Ala Pro Gly Lys Gly
    210                 215                 220

Leu Glu Trp Val Gly Trp Ile Asn Thr Tyr Thr Gly Glu Pro Thr Tyr
225                 230                 235                 240

Ala Ala Asp Phe Lys Arg Arg Phe Thr Phe Ser Leu Asp Thr Ser Lys
                245                 250                 255
```

```
Ser Thr Ala Tyr Leu Gln Met Asn Ser Leu Arg Ala Glu Asp Thr Ala
            260                 265                 270

Val Tyr Tyr Cys Ala Lys Tyr Pro Tyr Tyr Gly Thr Ser His Trp
        275                 280                 285

Tyr Phe Asp Val Trp Gly Gln Gly Thr Leu Val Thr Val Ser Gly Gly
    290                 295                 300

Ser Gly Ala Met Val Arg Ser Asp Lys Thr His Thr Cys Pro Pro Cys
305                 310                 315                 320

Pro Ala Pro Glu Leu Leu Gly Gly Pro Ser Val Phe Leu Phe Pro Pro
                325                 330                 335

Lys Pro Lys Asp Thr Leu Met Ile Ser Arg Thr Pro Glu Val Thr Cys
                340                 345                 350

Val Val Val Asp Val Ser His Glu Asp Pro Glu Val Lys Phe Asn Trp
            355                 360                 365

Tyr Val Asp Gly Val Glu Val His Asn Ala Lys Thr Lys Pro Arg Glu
    370                 375                 380

Glu Gln Tyr Asn Ser Thr Tyr Arg Val Val Ser Val Leu Thr Val Leu
385                 390                 395                 400

His Gln Asp Trp Leu Asn Gly Lys Glu Tyr Lys Cys Lys Val Ser Asn
                405                 410                 415

Lys Ala Leu Pro Ala Pro Ile Glu Lys Thr Ile Ser Lys Ala Lys Gly
                420                 425                 430

Gln Pro Arg Glu Pro Gln Val Tyr Thr Leu Pro Pro Ser Arg Glu Glu
            435                 440                 445

Met Thr Lys Asn Gln Val Ser Leu Thr Cys Leu Val Lys Gly Phe Tyr
    450                 455                 460

Pro Ser Asp Ile Ala Val Glu Trp Glu Ser Asn Gly Gln Pro Glu Asn
465                 470                 475                 480

Asn Tyr Lys Thr Thr Pro Pro Val Leu Asp Ser Asp Gly Ser Phe Phe
                485                 490                 495

Leu Tyr Ser Lys Leu Thr Val Asp Lys Ser Arg Trp Gln Gln Gly Asn
                500                 505                 510

Val Phe Ser Cys Ser Val Met His Glu Gly Leu His Asn His Tyr Thr
            515                 520                 525

Gln Lys Ser Leu Ser Leu Ser Pro Gly Lys
    530                 535

<210> SEQ ID NO 348
<211> LENGTH: 526
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 348

Gly Gln Ser Gly Gln Pro Cys Ser Glu Trp Gln Ser Met Val Gln Pro
1               5                   10                  15

Arg Cys Tyr Tyr Gly Gly Gly Ser Gly Gly Ser Gly Gln Gly Gly Gln
            20                  25                  30

Gln Gly Pro Met Phe Lys Ser Leu Trp Asp Gly Gly Ser Asp Ile Gln
        35                  40                  45

Leu Thr Gln Ser Pro Ser Ser Leu Ser Ala Ser Val Gly Asp Arg Val
    50                  55                  60

Thr Ile Thr Cys Ser Ala Ser Gln Asp Ile Ser Asn Tyr Leu Asn Trp
65                  70                  75                  80
```

-continued

Tyr Gln Gln Lys Pro Gly Lys Ala Pro Lys Val Leu Ile Tyr Phe Thr
                    85              90                  95
Ser Ser Leu His Ser Gly Val Pro Ser Arg Phe Ser Gly Ser Gly Ser
            100             105             110
Gly Thr Asp Phe Thr Leu Thr Ile Ser Ser Leu Gln Pro Glu Asp Phe
        115                 120             125
Ala Thr Tyr Tyr Cys Gln Gln Tyr Ser Thr Val Pro Trp Thr Phe Gly
    130             135                 140
Gln Gly Thr Lys Val Glu Ile Lys Gly Gly Gly Ser Gly Gly Gly
145             150             155             160
Gly Ser Gly Gly Gly Ser Gly Glu Val Gln Leu Val Glu Ser Gly
            165             170             175
Gly Gly Leu Val Gln Pro Gly Gly Ser Leu Arg Leu Ser Cys Ala Ala
            180             185             190
Ser Gly Tyr Asp Phe Thr His Tyr Gly Met Asn Trp Val Arg Gln Ala
        195             200             205
Pro Gly Lys Gly Leu Glu Trp Val Gly Trp Ile Asn Thr Tyr Thr Gly
    210             215             220
Glu Pro Thr Tyr Ala Ala Asp Phe Lys Arg Arg Phe Thr Phe Ser Leu
225             230             235             240
Asp Thr Ser Lys Ser Thr Ala Tyr Leu Gln Met Asn Ser Leu Arg Ala
            245             250             255
Glu Asp Thr Ala Val Tyr Tyr Cys Ala Lys Tyr Pro Tyr Tyr Tyr Gly
        260             265             270
Thr Ser His Trp Tyr Phe Asp Val Trp Gly Gln Gly Thr Leu Val Thr
    275             280             285
Val Ser Gly Gly Ser Gly Ala Met Val Arg Ser Asp Lys Thr His Thr
    290             295             300
Cys Pro Pro Cys Pro Ala Pro Glu Leu Leu Gly Gly Pro Ser Val Phe
305             310             315             320
Leu Phe Pro Pro Lys Pro Lys Asp Thr Leu Met Ile Ser Arg Thr Pro
            325             330             335
Glu Val Thr Cys Val Val Val Asp Val Ser His Glu Asp Pro Glu Val
        340             345             350
Lys Phe Asn Trp Tyr Val Asp Gly Val Glu Val His Asn Ala Lys Thr
    355             360             365
Lys Pro Arg Glu Glu Gln Tyr Asn Ser Thr Tyr Arg Val Val Ser Val
370             375             380
Leu Thr Val Leu His Gln Asp Trp Leu Asn Gly Lys Glu Tyr Lys Cys
385             390             395             400
Lys Val Ser Asn Lys Ala Leu Pro Ala Pro Ile Glu Lys Thr Ile Ser
            405             410             415
Lys Ala Lys Gly Gln Pro Arg Glu Pro Gln Val Tyr Thr Leu Pro Pro
        420             425             430
Ser Arg Glu Glu Met Thr Lys Asn Gln Val Ser Leu Thr Cys Leu Val
    435             440             445
Lys Gly Phe Tyr Pro Ser Asp Ile Ala Val Glu Trp Glu Ser Asn Gly
    450             455             460
Gln Pro Glu Asn Asn Tyr Lys Thr Thr Pro Pro Val Leu Asp Ser Asp
465             470             475             480
Gly Ser Phe Phe Leu Tyr Ser Lys Leu Thr Val Asp Lys Ser Arg Trp
            485             490             495
Gln Gln Gly Asn Val Phe Ser Cys Ser Val Met His Glu Gly Leu His

```
                    500                 505                 510
Asn His Tyr Thr Gln Lys Ser Leu Ser Leu Ser Pro Gly Lys
        515                 520                 525

<210> SEQ ID NO 349
<211> LENGTH: 533
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 349

Pro Cys Ser Glu Trp Gln Ser Met Val Gln Pro Arg Cys Tyr Tyr Gly
1               5                   10                  15

Gly Ser Gly Gly Gly Ser Gly Gln Ser Gly Gln Gly Gly Ser Gly Gly
            20                  25                  30

Ser Gly Gln Gly Gly Gln Gly Ser Asp Ile Gln Leu Thr Gln Ser Pro
        35                  40                  45

Ser Ser Leu Ser Ala Ser Val Gly Asp Arg Val Thr Ile Thr Cys Ser
    50                  55                  60

Ala Ser Gln Asp Ile Ser Asn Tyr Leu Asn Trp Tyr Gln Gln Lys Pro
65                  70                  75                  80

Gly Lys Ala Pro Lys Val Leu Ile Tyr Phe Thr Ser Ser Leu His Ser
                85                  90                  95

Gly Val Pro Ser Arg Phe Ser Gly Ser Gly Ser Gly Thr Asp Phe Thr
            100                 105                 110

Leu Thr Ile Ser Ser Leu Gln Pro Glu Asp Phe Ala Thr Tyr Tyr Cys
        115                 120                 125

Gln Gln Tyr Ser Thr Val Pro Trp Thr Phe Gly Gln Gly Thr Lys Val
    130                 135                 140

Glu Ile Lys Gly Gly Gly Ser Gly Gly Gly Ser Gly Gly Gly Ser Gly
145                 150                 155                 160

Gly Gly Ser Gly Gly Gly Gly Ser Gly Gly Gly Ser Gly Gly Gly Glu
                165                 170                 175

Val Gln Leu Val Glu Ser Gly Gly Gly Leu Val Gln Pro Gly Gly Ser
            180                 185                 190

Leu Arg Leu Ser Cys Ala Ala Ser Gly Tyr Asp Phe Thr His Tyr Gly
        195                 200                 205

Met Asn Trp Val Arg Gln Ala Pro Gly Lys Gly Leu Glu Trp Val Gly
    210                 215                 220

Trp Ile Asn Thr Tyr Thr Gly Glu Pro Thr Tyr Ala Ala Asp Phe Lys
225                 230                 235                 240

Arg Arg Phe Thr Phe Ser Leu Asp Thr Ser Lys Ser Thr Ala Tyr Leu
                245                 250                 255

Gln Met Asn Ser Leu Arg Ala Glu Asp Thr Ala Val Tyr Tyr Cys Ala
            260                 265                 270

Lys Tyr Pro Tyr Tyr Tyr Gly Thr Ser His Trp Tyr Phe Asp Val Trp
        275                 280                 285

Gly Gln Gly Thr Leu Val Thr Val Ser Gly Gly Ser Gly Ala Met Val
    290                 295                 300

Arg Ser Asp Lys Thr His Thr Cys Pro Pro Cys Pro Ala Pro Glu Leu
305                 310                 315                 320

Leu Gly Gly Pro Ser Val Phe Leu Phe Pro Pro Lys Pro Lys Asp Thr
                325                 330                 335

Leu Met Ile Ser Arg Thr Pro Glu Val Thr Cys Val Val Val Asp Val
```

-continued

```
                    340                 345                 350
Ser His Glu Asp Pro Glu Val Lys Phe Asn Trp Tyr Val Asp Gly Val
            355                 360                 365

Glu Val His Asn Ala Lys Thr Lys Pro Arg Glu Glu Gln Tyr Asn Ser
        370                 375                 380

Thr Tyr Arg Val Val Ser Val Leu Thr Val Leu His Gln Asp Trp Leu
385                 390                 395                 400

Asn Gly Lys Glu Tyr Lys Cys Lys Val Ser Asn Lys Ala Leu Pro Ala
                405                 410                 415

Pro Ile Glu Lys Thr Ile Ser Lys Ala Lys Gly Gln Pro Arg Glu Pro
            420                 425                 430

Gln Val Tyr Thr Leu Pro Pro Ser Arg Glu Glu Met Thr Lys Asn Gln
        435                 440                 445

Val Ser Leu Thr Cys Leu Val Lys Gly Phe Tyr Pro Ser Asp Ile Ala
    450                 455                 460

Val Glu Trp Glu Ser Asn Gly Gln Pro Glu Asn Asn Tyr Lys Thr Thr
465                 470                 475                 480

Pro Pro Val Leu Asp Ser Asp Gly Ser Phe Phe Leu Tyr Ser Lys Leu
                485                 490                 495

Thr Val Asp Lys Ser Arg Trp Gln Gln Gly Asn Val Phe Ser Cys Ser
            500                 505                 510

Val Met His Glu Gly Leu His Asn His Tyr Thr Gln Lys Ser Leu Ser
        515                 520                 525

Leu Ser Pro Gly Lys
    530
```

```
<210> SEQ ID NO 350
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 350

Gly Gln Ser Gly Gln Pro Cys Ser Glu Trp Gln Ser Met Val Gln Pro
1               5                   10                  15

Arg Cys Tyr Tyr Gly Gly Gly Ser Gly Gly Ser Gly Gln Gly Gly Gln
            20                  25                  30

Val His Met Pro Leu Gly Phe Leu Gly Pro Gly Gly Ser
        35                  40                  45

<210> SEQ ID NO 351
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sequence may encompass 1-2 'Gly Gly Gly Ser'
      repeating units

<400> SEQUENCE: 351

Gly Gly Gly Ser Gly Gly Gly Ser
1               5

<210> SEQ ID NO 352
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 352

Ile Gly Arg Cys Pro Ile Cys Phe Met Arg Pro Ala His Glu Glu
1               5                   10                  15

<210> SEQ ID NO 353
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Leu Gly Arg Cys Pro Ile Cys Gly Pro Gln Asn Asn Ser Arg Ala
1               5                   10                  15

<210> SEQ ID NO 354
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Cys Pro Met Ser Ser Val Arg Leu Cys Tyr Glu Phe Asn Gln Glu
1               5                   10                  15

<210> SEQ ID NO 355
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Thr Leu Thr Pro Glu His Thr Arg Gln Trp Tyr Leu Glu Lys Tyr
1               5                   10                  15

<210> SEQ ID NO 356
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Cys Thr Pro Thr Leu Thr Arg Asp Gly Trp Leu His Cys Pro Ser
1               5                   10                  15

<210> SEQ ID NO 357
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Trp Cys Arg Pro Thr Gln Ser Tyr Glu His Ile Cys Pro Lys Glu
1               5                   10                  15
```

```
<210> SEQ ID NO 358
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Leu Ile Cys Asp Leu Tyr Pro Thr Val Asn Ala Thr Arg Cys Lys
1               5                   10                  15

<210> SEQ ID NO 359
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

His Val His Phe Asn Phe Lys Glu Trp Cys Arg Asn Ile Arg Cys
1               5                   10                  15

<210> SEQ ID NO 360
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Pro Ile Tyr Asp Tyr Ala Phe Tyr Gln Ser Asp Ala Tyr Arg Ser
1               5                   10                  15

<210> SEQ ID NO 361
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Ala Ala Asn Leu
1

<210> SEQ ID NO 362
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Pro Thr Asn Leu
1
```

MODIFIED ANTIBODY COMPOSITIONS, METHODS OF MAKING AND USING THEREOF

CROSS-REFERENCE

This application claims the benefit of U.S. Provisional Applications Nos. 61/144,110, filed Jan. 12, 2009; 61/144,105, filed Jan. 12, 2009; 61/249,441, filed Oct. 7, 2009; and 61/249,416, filed Oct. 7, 2009; which applications are incorporated herein by reference in their entirety.

SEQUENCE LISTING

The contents of the text file named "514C01USSeqList.txt," which was created on Dec. 9, 2011 and is 212 KB in size, are hereby incorporated by reference in their entirety.

BACKGROUND OF THE INVENTION

Protein-based therapies have changed the face of medicine, finding application in a variety of different diseases. In particular antibody-based therapies have proven effective treatments for some diseases but in some cases, toxicities due to broad target expression have limited their therapeutic effectiveness.

As with any drugs, however, the need and desire for drugs having improved specificity and selectivity for their targets is of great interest, especially in developing second generation of antibody-based drugs having known targets to which they bind. Increased targeting of antibody to the disease site could reduce systemic mechanism-based toxicities and lead to broader therapeutic utility.

In the realm of small molecule drugs, strategies have been developed to provide prodrugs of an active chemical entity. Such prodrugs are administered in a relatively inactive (or significantly less active) form. Once administered, the prodrug is metabolized in vivo into the active compound. Such prodrug strategies can provide for increased selectivity of the drug for its intended target and for a reduction of adverse effects. Drugs used to target hypoxic cancer cells, through the use of redox-activation, utilize the large quantities of reductase enzyme present in the hypoxic cell to convert the drug into its cytotoxic form, essentially activating it. Since the prodrug has low cytotoxicity prior to this activation, there is a markedly decreased risk of damage to non-cancerous cells, thereby providing for reduced side-effects associated with the drug. There is a need in the field for a strategy for providing features of a prodrug to antibody-based therapeutics.

SUMMARY OF THE INVENTION

The present disclosure provides for modified and activatable antibody compositions useful for therapeutics and diagnostics. The activatable antibody compositions exhibit increased bioavailability and biodistribution compared to conventional antibody therapeutics with prodrug features. Also provided are methods for use in diagnostics and therapeutics, as well as screening for and construction of such compositions.

In one aspect, the present disclosure provides a modified antibody comprising an antibody or antibody fragment (AB), capable of specifically binding its target, coupled to a masking moiety (MM), wherein the coupling of the MM reduces the ability of the AB to bind its target such that that the dissociation constant ($K_d$) of the AB coupled to the MM towards the target is at least 100 times greater, at least 1000 times greater, or at least 10,000 times greater than the $K_d$ of the AB not coupled to the MM towards the target.

In another aspect, the present disclosure provides a modified antibody comprising an antibody or antibody fragment (AB), capable of specifically binding its target, coupled to a masking moiety (MM), wherein the coupling of the MM to the AB reduces the ability of the AB to bind the target by at least 90%, as compared to the ability of the AB not coupled to the MM to bind the target, when assayed in vitro using a target displacement assay. Such coupling of the MM to the AB reduces the ability of the AB to bind its target for at least 12 hours or for at least 24 hours or for at least 72 hours.

In another aspect, the modified antibody is further coupled to a cleavable moiety (CM). The CM is capable of being cleaved by an enzyme, or the CM is capable of being reduced by a reducing agent, or the CM is capable of being photolysed. The CM is capable of being specifically cleaved, reduced, or photolysed at a rate of about at least $1\times10^4$ $M^{-1}S^{-1}$, or at least $5\times10^4$ $M^{-1}S$, or at least $10\times10^4$ $M^{-1}S$. In one embodiment, the CM of the modified antibody is be within the MM.

The dissociation constant ($K_d$) of the MM towards the AB in the modified antibodies provided herein is usually at least 100 times greater than the $K_d$ of the AB towards the target. Generally, the $K_d$ of the MM towards the AB is lower than 10 nM, or lower than 5 nM, or about 1 nM.

In some embodiments, the MM of the modified antibody reduces the AB's ability to bind its target by specifically binding to the antigen-binding domain of the AB. Such binding can be non-covalent. The MM of the modified antibody can reduce the AB's ability to bind its target allosterically or sterically. In specific embodiments, the MM of the modified antibody does not comprise more than 50% amino acid sequence similarity to a natural binding partner of the AB.

In specific embodiments, the AB of the modified antibody is an antibody fragment that is selected from the group consisting of a Fab' fragment, a F(ab') 2 fragment, a scFv, a scAB a dAb, a single domain heavy chain antibody, and a single domain light chain antibody.

In related embodiments, the AB of the modified antibody is selected from the group consisting of the antibodies in Table 2 or specifically the source of the AB is cetuximab, panitumumab, infliximab, adalimumab, efalizumab, ipilimumab, tremelimumab, adecatumumab, Hu5c8, alemtuzumab, ranibizumab, tositumomab, ibritumomab tiuxetan, rituximab, infliximab, bevacizumab, or figitumumab. In a specific embodiment, the modified antibody is not alemtuzumab.

In related embodiments, the target of the AB is selected from the group consisting of the targets in Table 1. In exemplary embodiments, the target is EGFR, TNFalpha, CD11a, CSFR, CTLA-4, EpCAM, VEGF, CD40, CD20, Notch 1, Notch 2, Notch 3, Notch 4, Jagged 1, Jagged 2, CD52, MUC1, IGF1R, transferrin, gp130, VCAM-1, CD44, DLL4, or IL4. In one specific embodiment the target is not CD52.

In a specific embodiment, the modified antibody further comprises a second AB wherein the target for the second AB is selected from the group consisting of the targets in Table 1.

In related embodiments, the CM is a substrate for an enzyme selected from the group consisting of the enzymes in Table 3. In specific embodiments the CM is a substrate for legumain, plasmin, TMPRSS-3/4, MMP-9, MT1-MMP, cathepsin, caspase, human neutrophil elastase, beta-secretase, uPA, or PSA. In such embodiments, where the modified AB comprises a CM, the AB is selected from the group consisting of the antibodies in Table 2; and specifically can be from cetuximab, panitumumab, infliximab, adalimumab, efalizumab, ipilimumab, tremelimumab, adecatumumab, Hu5c8, alemtuzumab, ranibizumab, tositomomab, ibritumomab tiuxetan, rituximab, infliximab, bevacizumab, or figitumumab. In one exemplary embodiment, the AB is not alemtuzumab.

In one embodiment where the modified antibody comprises an AB, coupled to a CM and a MM, the target is selected from the group consisting of the targets in Table 1; or the target is EGFR, TNFalpha, CD11a, CSFR, CTLA-4, EpCAM, VEGF, CD40, CD20, Notch 1, Notch 2, Notch 3, Notch 4, Jagged 1, Jagged 2, CD52, MUC1, IGF1R, transferrin, gp130, VCAM-1, CD44, DLL4, or IL4. In one exemplary embodiment, the target is not CD52.

The modified antibody can be further coupled to a second cleavable moiety (CM), capable of being specifically modified by an enzyme. In this embodiment, the second cleavable is a substrate for legumain, plasmin, TMPRSS-3/4, MMP-9, MT1-MMP, cathepsin, caspase, human neutrophil elastase, beta-secretase, uPA, or PSA.

In another specific embodiment, the modified antibody further comprises a linker peptide, wherein the linker peptide is positioned between the AB and the MM; or the modified antibody further comprises a linker peptide, wherein the linker peptide is positioned between the MM and the CM; or the modified antibody further comprises a linker peptide, wherein the linker peptide is positioned between the AB and the CM; or the modified antibody further comprises two linker peptides, wherein the first linker peptide is between the AB and the CM and the second linker peptide is positioned between the MM and the CM. The linker is selected from the group consisting of a cleavable linker, a non-cleavable linker, and a branched linker.

In certain embodiments, the modified antibody further comprises a detectable moiety. In one specific embodiment, the detectable moiety is a diagnostic agent.

In one particular embodiment, the modified antibodies described herein further comprise an agent conjugated to the AB. In one aspect, the agent is a therapeutic agent, for example an antineoplastic agent. In such embodiments, the agent is conjugated to a carbohydrate moiety of the AB, wherein the carbohydrate moiety can be located outside the antigen-binding region of the AB. Alternatively the agent is conjugated to a sulfhydryl group of the AB.

The modified antibodies provided herein exhibit a serum half-life of at least 5 days when administered to an organism.

The consensus sequence of the MM of some of the modified antibodies provided herein is CISPRGC (SEQ ID NO: 1), C(N/P)H(H/V/F)(Y/T)(F/W/T/L)(Y/G/T/S)(T/S/Y/H)CG-CISPRGCG (SEQ ID NO: 2), xCxxYQCLxxxxxx (SEQ ID NO: 3), XXQPxPPRVXX (SEQ ID NO: 4), PxPGFPYCxxxx (SEQ ID NO: 5), xxxxQxxPWPP (SEQ ID NO: 6), GxGx-CYTILExxCxxxR (SEQ ID NO: 7), GxxxCYxIxExxCxxxx (SEQ ID NO: 8), GxxxCYxIxExWCxxxx (SEQ ID NO: 9), xxxCCxxYxIxxCCxxx (SEQ ID NO: 10), or xxxxxYx-ILExxxxx (SEQ ID NO: 11). In a specific embodiment, the consensus sequence is specific for binding to an anti-VEGF antibody, an anti-EFGR antibody, or an anti-CTLA-4 antibody.

In a related aspect, the present disclosure provides for an activatable antibody (AA) comprising an antibody or antibody fragment (AB), capable of specifically binding its target; a masking moiety (MM) coupled to the AB, capable of inhibiting the specific binding of the AB to its target; and a cleavable moiety (CM) coupled to the AB, capable of being specifically cleaved by an enzyme; wherein when the AA is not in the presence of sufficient enzyme activity to cleave the CM, the MM reduces the specific binding of the AB to its target by at least 90% when compared to when the AA is in the presence of sufficient enzyme activity to cleave the CM and the MM does not inhibit the specific binding of the AB to its target. In specific embodiments, the binding of the AB to its target is reduced for at least 12 hours, or for at least 24 hours, or for at least 72 hours.

In one embodiment, in the AA, the dissociation constant ($K_d$) of the AB coupled to the MM and CM towards the target is at least 100 times greater than the $K_d$ of the AB not coupled to the MM and CM towards the target. In a related embodiment, the dissociation constant ($K_d$) of the MM towards the AB is at least 100 times greater than the $K_d$ of the AB towards the target. Generally, the $K_d$ of the MM towards the AB is lower than 10 nM, or lower than 5 nM, or about 1 nM.

In some embodiments of the AA, the MM is capable of specifically binding to the antigen-binding domain of the AB.

In some embodiments of the AA the CM is capable of being specifically cleaved by an enzyme at a rate of about at least $1 \times 10^4$ $M^{-1}S^{-1}$, or at least $5 \times 10^4$ $M^{-1}S$, or at least $10 \times 10^4$ $M^{-1}S$.

In certain embodiments, of the AA where the AB is an antibody fragment, the antibody fragment is selected from the group consisting of a Fab' fragment, a F(ab') 2 fragment, a scFv, a scAB a dAb, a single domain heavy chain antibody, and a single domain light chain antibody.

In certain embodiments, the AB of the AA is selected from the group consisting of the antibodies in Table 2. In specific embodiments, the AB is cetuximab, panitumumab, infliximab, adalimumab, efalizumab, ipilimumab, tremelimumab, adecatumumab, Hu5c8, alemtuzumab, ranibizumab, tositomomab, ibritumomab tiuxetan, rituximab, infliximab, bevacizumab, or figitumumab.

In certain embodiments, the target of the AA is selected from the group consisting of the targets in Table 1. In specific embodiments, the target is EGFR, TNFalpha, CD11a, CSFR, CTLA-4, EpCAM, VEGF, CD40, CD20, Notch 1, Notch 2, Notch 3, Notch 4, Jagged 1, Jagged 2, CD52, MUC1, IGF1R, transferrin, gp130, VCAM-1, CD44, DLL4, or IL4.

In one specific embodiment the AB is not alemtuzumab and target is not CD52.

In certain embodiments, the CM of the AA is a substrate for legumain, plasmin, TMPRSS-3/4, MMP-9, MT1-MMP, cathepsin, caspase, human neutrophil elastase, beta-secretase, uPA, or PSA. In specific embodiments, the AA is further coupled to a second cleavable moiety (CM), capable of being specifically modified by an enzyme. In this embodiment, the second CM is a substrate for legumain, plasmin, TMPRSS-3/4, MMP-9, MT1-MMP, cathepsin, caspase, human neutrophil elastase, beta-secretase, uPA, or PSA.

In some embodiments of the AAs provided herein, the CM is located within the MM.

In some embodiments of the AAs provided herein, the MM does not comprise more than 50% amino acid sequence similarity to a natural binding partner of the AB.

In some embodiments the AA further comprises a linker peptide, wherein the linker peptide is positioned between the MM and the CM. In specific embodiments, the linker peptide is positioned between the AB and the CM.

In certain embodiments, the AAs provided herein further comprise a detectable moiety or an agent conjugated to the AB.

In yet another aspect, the present disclosure provides for an activatable antibody complex (AAC) comprising: two antibodies or antibody fragments (AB1 and AB2), each capable of specifically binding its target; at least one masking moiety (MM) coupled to either AB1 or AB2, capable of inhibiting the specific binding of AB1 and AB2 to their targets; and at least one cleavable moiety (CM) coupled to either AB1 or AB2, capable of being specifically cleaved by an enzyme whereby activating the AAC composition; wherein when the AAC is in an uncleaved state, the MM inhibits the specific binding of AB1 and AB2 to their targets and when the AAC is in a cleaved state, the MM does not inhibit the specific binding of AB1 and AB2 to their targets.

In one embodiment, the AAC is bispecific, wherein AB1 and AB2 bind the same epitope on the same target; or the AB1 and AB2 bind to different epitopes on the same target; or the AB1 and AB2 bind to different epitopes on different targets.

In one embodiment of the AAC, the CM is capable of being specifically cleaved by an enzyme at a rate of about at least $1 \times 10^4 \, M^{-1} S^{-1}$.

In the embodiments where AB1 or AB2 of the AAC is an antibody fragment, the antibody fragment is selected from the group consisting of a Fab' fragment, a F(ab') 2 fragment, a scFv, a scAB a dAb, a single domain heavy chain antibody, and a single domain light chain antibody.

In an embodiment of the AAC, the AB1 and/or AB 2 are selected from the group consisting of the antibodies in Table 2. In a specific embodiment, the AB1 and/or AB2 is cetuximab, panitumumab, infliximab, adalimumab, efalizumab, ipilimumab, tremelimumab, adecatumumab, Hu5c8, alemtuzumab, ranibizumab, tositumomab, ibritumomab tiuxetan, rituximab, infliximab, bevacizumab, or figitumumab.

In an embodiment of the AAC, the target for the AB1 and/or AB2 is selected from the group consisting of the targets in Table 1. In a related embodiment, the target of the AB1 and/or AB2 is EGFR, TNFalpha, CD11a, CSFR, CTLA-4, EpCAM, VEGF, CD40, CD20, Notch 1, Notch 2, Notch 3, Notch 4, Jagged 1, Jagged 2, CD52, MUC1, IGF1R, transferrin, gp130, VCAM-1, CD44, DLL4, or IL4. In a specific embodiment, the AB1 and AB2 are capable of binding to EGFR and VEGF, a Notch Receptor and EGFR, a Jagged ligand and EGFR or cMET and VEGF, respectively.

In a related AAC embodiment, the CM is a substrate for an enzyme selected from the group consisting of the enzymes in Table 3. In a specific embodiment, the CM is a substrate for legumain, plasmin, TMPRSS-3/4, MMP-9, MT1-MMP, cathepsin, caspase, human neutrophil elastase, beta-secretase, uPA, or PSA. In yet another specific embodiment, the AAC is further coupled to a second cleavable moiety (CM), capable of being specifically cleaved by an enzyme and the second CM is a substrate for legumain, plasmin, TMPRSS-3/4, MMP-9, MT1-MMP, cathepsin, caspase, human neutrophil elastase, beta-secretase, uPA, or PSA.

In specific embodiments of the AAC, the MM does not comprise more than 50% amino acid sequence similarity to a natural binding partner of the AB.

In other specific embodiments of the AAC, the AAC further comprises a detectable moiety or is further conjugated to an agent.

Also provided herein is a method of treating or diagnosing a condition in a subject including administering to the subject a composition comprising: an antibody or antibody fragment (AB), capable of specifically binding its target; a masking moiety (MM) coupled to the AB, capable of inhibiting the specific binding of the AB to its target; and a cleavable moiety (CM) coupled to the AB, capable of being specifically cleaved by an enzyme; wherein upon administration to the subject, when the AA is not in the presence of sufficient enzyme activity to cleave the CM, the MM reduces the specific binding of the AB to its target by at least 90% when compared to when the AA is in the presence of sufficient enzyme activity to cleave the CM and the MM does not inhibit the specific binding of the AB to its target.

In this method, the AB is selected from the group consisting of a Fab' fragment, a F(ab') 2 fragment, a scFv, a scAB a dAb, a single domain heavy chain antibody, and a single domain light chain antibody.

In as specific embodiment, the condition is cancer.

In another specific embodiment, the MM is not the natural binding partner of the AB.

In various embodiments of the method, the AB is selected from the group consisting of the antibodies in Table 2. Specifically in some embodiments, the AB is cetuximab, panitumumab, infliximab, adalimumab, efalizumab, ipilimumab, tremelimumab, adecatumumab, Hu5c8, alemtuzumab, ranibizumab, tositumomab, ibritumomab tiuxetan, rituximab, infliximab, bevacizumab, or figitumumab.

In various embodiments of the method, the target is selected from the group of targets in Table 1. In specific embodiments, the target is EGFR, TNFalpha, CD11a, CSFR, CTLA-4, EpCAM, VEGF, CD40, CD20, Notch 1, Notch 2, Notch 3, Notch 4, Jagged 1, Jagged 2, CD52, MUC1, IGF1R, transferrin, gp130, VCAM-1, CD44, DLL4, or IL4.

In a very specific embodiment of the method the AB is not alemtuzumab and the target is not CD52.

In various embodiments of the method, the CM is a substrate for an enzyme selected from the group consisting of the enzymes in Table 3. In specific embodiments, the CM is a substrate for legumain, plasmin, TMPRSS-3/4, MMP-9, MT1-MMP, cathepsin, caspase, human neutrophil elastase, beta-secretase, uPA, or PSA.

Also provided herein is a method of inhibiting angiogenesis in a mammalian subject, the method comprising administering to a subject in need thereof a therapeutically effective amount of a pharmaceutical composition comprising a modified AB, an AA, an AAC, or an AACJ wherein the target is EGFR, TNFalpha, CD11a, CSFR, CTLA-4, EpCAM, VEGF, CD40, CD20, Notch 1, Notch 2, Notch 3, Notch 4, Jagged 1, Jagged 2, CD52, MUC1, IGF1R, transferrin, gp130, VCAM-1, CD44, DLL4, or IL4. In a specific embodiment, the AB is cetuximab, panitumumab, infliximab, adalimumab, efalizumab, ipilimumab, tremelimumab, adecatumumab, Hu5c8, alemtuzumab, ranibizumab, tositumomab, ibritumomab tiuxetan, rituximab, infliximab, bevacizumab, or figitumumab; the CM is a substrate for legumain, plasmin, TMPRSS-3/4, MMP-9, MT1-MMP, cathepsin, caspase, human neutrophil elastase, beta-secretase, uPA, or PSA.

Also provided herein is a method of making an activatable antibody (AA) composition comprising: providing an antibody or antibody fragment (AB) capable of specifically binding its target; coupling a masking moiety (MM) to the AB, capable of inhibiting the specific binding of the AB to its target; and coupling a cleavable moiety (CM) to the AB, capable of being specifically cleaved by an enzyme; wherein the dissociation constant ($K_d$) of the AB coupled to the MM towards the target is at least 100 times greater than the $K_d$ of the AB not coupled to the MM towards the target.

In one embodiment of the method, the AB is or is derived from an antibody selected from the group consisting of the antibodies in Table 2. In a specific embodiment, the AB is or is derived from cetuximab, panitumumab, infliximab, adalimumab, efalizumab, ipilimumab, tremelimumab, adecatumumab, Hu5c8, alemtuzumab, ranibizumab, tositumomab, ibritumomab tiuxetan, rituximab, infliximab, bevacizumab, or figitumumab.

In one very specific embodiment, the AB is not alemtuzumab and the target is not CD52.

In another embodiment of the method, the CM is a substrate for an enzyme selected from the group consisting of the enzymes in Table 3. In a specific embodiment, the CM is a substrate for legumain, plasmin, TMPRSS-3/4, MMP-9, MT1-MMP, cathepsin, caspase, human neutrophil elastase, beta-secretase, uPA, or PSA.

Also provided herein is a method of screening candidate peptides to identify a masking moiety (MM) peptide capable of binding an antibody or antibody fragment (AB) comprising: providing a library of peptide scaffolds, wherein each peptide scaffold comprises: a transmembrane protein (TM); and a candidate peptide; contacting an AB with the library; identifying at least one candidate peptide capable of binding the AB; and determining whether the dissociation constant ($K_d$) of the candidate peptide towards the AB is between 1-10 nM.

In various embodiments of the method, the library comprises viruses, cells or spores. Specifically in one embodiment, the library comprises *E. coli*. In another embodiment, the peptide scaffold further comprises a detectable moiety.

Also provided is another screening method to identify a masking moiety (MM) peptide capable of masking an antibody or antibody fragment (AB) with an optimal masking efficiency comprising: providing a library comprising a plurality of ABs, each coupled to a candidate peptide, wherein the ABs are capable of specifically binding a target; incubating each library member with the target; and comparing the binding affinity of each library member towards the target with the binding affinity of each AB not coupled to a candidate peptide towards the target. In a specific embodiment, the optimal binding efficiency is when the binding affinity of a library member to the target is 10% compared to the binding affinity of the unmodified AB to the target.

In one aspect, also provided herein is an antibody therapeutic having an improved bioavailability wherein the affinity of binding of the antibody therapeutic to its target is lower in a first tissue when compared to the binding of the antibody therapeutic to its target in a second tissue. In a related aspect, also provided herein is a pharmaceutical composition comprising: an antibody or antibody fragment (AB), capable of specifically binding its target; and a pharmaceutically acceptable excipient; wherein the affinity of the antibody or antibody fragment to the target in a first tissue is lower than the affinity of the antibody or antibody fragment to the target in a second tissue. In a specific embodiment, the affinity in the first tissue is 10-1,000 times lower than the affinity in the second tissue. In one embodiment, the AB is coupled to a masking moiety (MM), capable of reducing the binding of the AB to its target and a cleavable moiety (CM), capable of specifically being cleaved by an enzyme.

In related embodiments, the target is EGFR, TNFalpha, CD11a, CSFR, CTLA-4, EpCAM, VEGF, CD40, CD20, Notch 1, Notch 2, Notch 3, Notch 4, Jagged 1, Jagged 2, CD52, MUC1, IGF1R, transferrin, gp130, VCAM-1, CD44, DLL4, or IL4. In related embodiments, the CM is a substrate for legumain, plasmin, TMPRSS-3/4, MMP-9, MT1-MMP, cathepsin, caspase, human neutrophil elastase, beta-secretase, uPA, or PSA. In related embodiments, the antibody or antibody fragment is cetuximab, panitumumab, infliximab, adalimumab, efalizumab, ipilimumab, tremelimumab, adecatumumab, Hu5c8, alemtuzumab, ranibizumab, tositumomab, ibritumomab tiuxetan, rituximab, infliximab, bevacizumab, or figitumumab.

In a specific embodiment, the first tissue is a healthy tissue and the second tissue is a diseased tissue; or the first tissue is an early stage tumor and the second tissue is a late stage tumor; the first tissue is a benign tumor and the second tissue is a malignant tumor; or the first tissue and second tissue are spatially separated; or the first tissue is epithelial tissue and the second tissue is breast, head, neck, lung, pancreatic, nervous system, liver, prostate, urogenital, or cervical tissue.

In one embodiment, the antibody therapeutic is further coupled to an agent. In a specific embodiment, the agent is an antineoplastic agent.

Also provided herein are specific compositions for diagnostic and therapeutic use. Provided herein is a composition comprising a legumain-activatable antibody or antibody fragment (AB) coupled to a masking moiety (MM); a composition comprising a plasmin-activatable antibody or antibody fragment (AB) coupled to a masking moiety (MM); a composition comprising a caspase-activatable antibody or antibody fragment (AB) coupled to a masking moiety (MM); a composition comprising a TMPRSS-3/4-activatable antibody or antibody fragment (AB) coupled to a masking moiety (MM); a composition comprising a PSA-activatable antibody or antibody fragment (AB) coupled to a masking moiety (MM); a composition comprising a cathepsin-activatable antibody or antibody fragment (AB) coupled to a masking moiety (MM); a composition comprising a human neutrophil elastase-activatable antibody or antibody fragment (AB) coupled to a masking moiety (MM); a composition comprising a beta-secretase-activatable antibody or antibody fragment (AB) coupled to a masking moiety (MM); a composition comprising an uPA-activatable antibody or antibody fragment (AB) coupled to a masking moiety (MM); a composition comprising a TMPRSS-3/4-activatable antibody or antibody fragment (AB) coupled to a masking moiety (MM); a composition comprising a MT1-MMP-activatable antibody or antibody fragment (AB) coupled to a masking moiety (MM); a composition comprising an activatable EGFR antibody or antibody fragment (AB) coupled to a masking moiety (MM); a composition comprising an activatable TNFalpha antibody or antibody fragment (AB) coupled to a masking moiety (MM); a composition comprising an activatable CD11a antibody or antibody fragment (AB) coupled to a masking moiety (MM); a composition comprising an activatable CSFR antibody or antibody fragment (AB) coupled to a masking moiety (MM); a composition comprising an activatable CTLA-4 antibody or antibody fragment (AB) coupled to a masking moiety (MM); a composition comprising an activatable EpCAM antibody or antibody fragment (AB) coupled to a masking moiety (MM); a composition comprising an activatable CD40L antibody or antibody fragment (AB) coupled to a masking moiety (MM); a composition comprising an activatable Notch1 antibody or antibody fragment (AB) coupled to a masking moiety (MM); a composition comprising an activatable Notch3 antibody or antibody fragment (AB) coupled to a masking moiety (MM); a composition comprising an activatable Jagged1 antibody or antibody fragment (AB) coupled to a masking moiety (MM); a composition comprising an activatable Jagged2 antibody or antibody fragment (AB) coupled to a masking moiety (MM); a composition comprising an activatable cetuximab antibody or antibody fragment (AB) coupled to a masking moiety (MM); a composition comprising an activatable vectibix antibody or antibody fragment (AB) coupled to a masking moiety (MM); a composition comprising an activatable infliximab antibody or antibody fragment (AB) coupled to a masking moiety (MM); a composition comprising an activatable adalimumab antibody or antibody fragment (AB) coupled to a masking moiety (MM); a composition comprising an activatable efalizumab antibody or antibody fragment (AB) coupled to a masking moiety (MM); a composition comprising an activatable ipilimumab antibody or antibody fragment (AB) coupled to a masking moiety (MM); a composition comprising an activatable tremelimumab antibody or antibody fragment (AB) coupled to a masking moiety (MM); or a composition comprising an activatable adecatumumab antibody or antibody fragment (AB) coupled to a masking moiety (MM).

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 shows the activity of an exemplary AA in vivo. Panel A shows healthy tissue where the AA is not able to bind, side effects are minimal; Panel B shows diseased tissue where the AA is activated by a disease-specific protease/reducing agent allowing the AA to bind to target and be efficacious.

FIG. 11 shows the use of PCR to add sites for MM cloning, CM cleavage sequence, (GGS)2 (SEQ ID NO: 111) linker on the N-terminus of the anti-CTLA4 scFv $V_HV_L$ and $V_LV_H$ constructs.

DETAILED DESCRIPTION OF THE INVENTION

Figure 1:
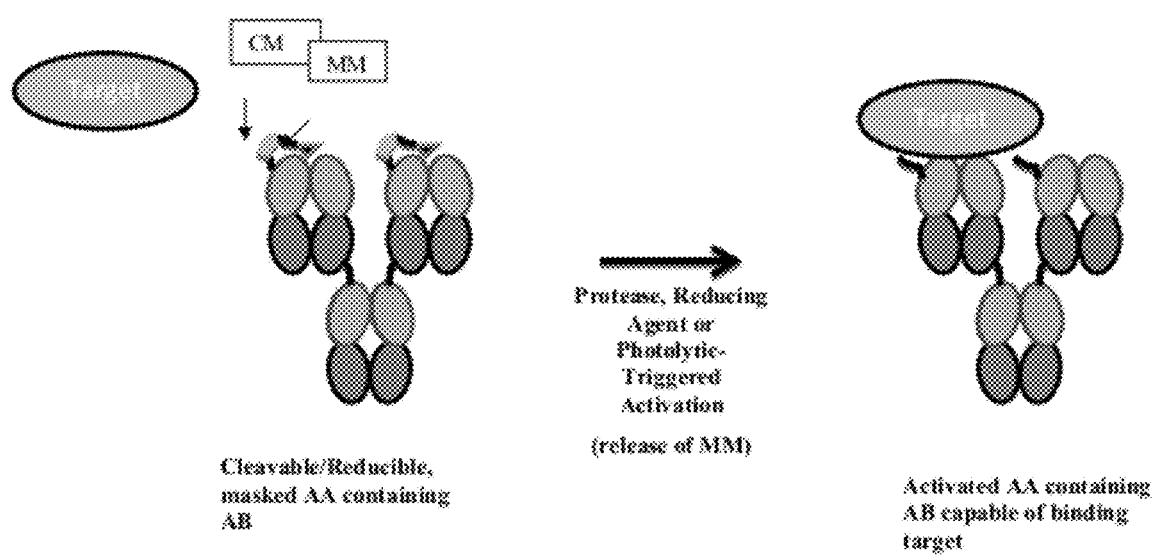
FIG. 1 shows a protease-activated AA containing an antibody (an AB), a masking moiety (MM), and a cleavable moiety (CM).

The present disclosure provides modified antibody compositions and that are useful for therapeutics and diagnostics. The compositions described herein allow for greater biodistribution and improved bioavailability.

Modified and Activatable Antibodies

The modified antibody compositions described herein contain at least an antibody or antibody fragment thereof (collectively referred to as AB throughout the disclosure), capable of specifically binding a target, wherein the AB is modified by a masking moiety (MM).

When the AB is modified with a MM and is in the presence of the target, specific binding of the AB to its target is reduced or inhibited, as compared to the specific binding of the AB not modified with an MM or the specific binding of the parental AB to the target.

The $K_d$ of the AB modified with a MM towards the target can be at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB not modified with an MM or the parental AB towards the target. Conversely, the binding affinity of the AB modified with a MM towards the target can be at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB not modified with an MM or the parental AB towards the target.

The dissociation constant ($K_d$) of the MM towards the AB is generally greater than the $K_d$ of the AB towards the target. The $K_d$ of the MM towards the AB can be at least 5, 10, 25, 50, 100, 250, 500, 1,000, 2,500, 5,000, 10,000, 100,000, 1,000,000 or even 10,000,000 times greater than the $K_d$ of the AB towards the target. Conversely, the binding affinity of the MM towards the AB is generally lower than the binding affinity of the AB towards the target. The binding affinity of MM towards the AB can be at least 5, 10, 25, 50, 100, 250, 500, 1,000, 2,500, 5,000, 10,000, 100,000, 1,000,000 or even 10,000,000 times lower than the binding affinity of the AB towards the target.

When the AB is modified with a MM and is in the presence of the target, specific binding of the AB to its target can be reduced or inhibited, as compared to the specific binding of the AB not modified with an MM or the specific binding of the parental AB to the target. When compared to the binding of the AB not modified with an MM or the binding of the parental AB to the target, the AB's ability to bind the target when modified with an MM can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, 96, hours, or 5, 10, 15, 30, 45, 60, 90, 120, 150, 180 days, or 1, 2, 3, 4, 5, 6, 7, 8, 9, 10, 11, 12 months or greater when measured in vivo or in a Target Displacement in vitro immunoabsorbant assay, as described herein.

The MM can inhibit the binding of the AB to the target. The MM can bind the antigen binding domain of the AB and inhibit binding of the AB to its target. The MM can sterically inhibit the binding of the AB to the target. The MM can allosterically inhibit the binding of the AB to its target. In these embodiments when the AB is modified or coupled to a MM and in the presence of target, there is no binding or substantially no binding of the AB to the target, or no more than 0.001%, 0.01%, 0.1%, 1%, 2%, 3%, 4%, 5%, 6%, 7%, 8%, 9%, 10%, 15%, 20%, 25%, 30%, 35%, 40%, or 50% binding of the AB to the target, as compared to the binding of the AB not modified with an MM, the parental AB, or the AB not coupled to an MM to the target, for at least 2, 4, 6, 8, 12, 28, 24, 30, 36, 48, 60, 72, 84, 96, hours, or 5, 10, 15, 30, 45, 60, 90, 120, 150, 180 days, or 1, 2, 3, 4, 5, 6, 7, 8, 9, 10, 11, 12 months or greater when measured in vivo or in a Target Displacement in vitro immunoabsorbant assay, as described herein.

When an AB is coupled to or modified by a MM, the MM can 'mask' or reduce, or inhibit the specific binding of the AB to its target. When an AB is coupled to or modified by a MM, such coupling or modification can effect a structural change which reduces or inhibits the ability of the AB to specifically bind its target.

An AB coupled to or modified with an MM can be represented by the following formulae (in order from an amino (N) terminal region to carboxyl (C) terminal region:

(MM)-(AB)

(AB)-(MM)

(MM)-L-(AB)

(AB)-L-(MM)

where MM is a masking moiety, the AB is an antibody or antibody fragment thereof, and the L is a linker. In many embodiments it may be desirable to insert one or more linkers, e.g., flexible linkers, into the composition so as to provide for flexibility.

In certain embodiments the MM is not a natural binding partner of the AB. The MM may be a modified binding partner for the AB which contains amino acid changes that at least slightly decrease affinity and/or avidity of binding to the AB. In some embodiments the MM contains no or substantially no homology to the AB's natural binding partner. In other embodiments the MM is no more than 5%, 10%, 15%, 20%, 25%, 30%, 35%, 40%, 45%, 50%, 55%, 60%, 65%, 70%, 75%, or 80% similar to the natural binding partner of the AB.

The present disclosure also provides activatable antibodies (AAs) where the AB modified by an MM can further include one or more cleavable moieties (CM). Such AAs exhibit activatable/switchable binding, to the AB's target. AAs generally include an antibody or antibody fragment (AB), modified by or coupled to a masking moiety (MM) and a modifiable or cleavable moiety (CM). In some embodiments, the CM contains an amino acid sequence that serves as a substrate for a protease of interest. In other embodiments, the CM provides a cysteine-cysteine disulfide bond that is cleavable by reduction. In yet other embodiments the CM provides a photolytic substrate that is activatable by photolysis.

A schematic of an exemplary AA is provided in FIG. 1. As illustrated, the elements of the AA are arranged so that the CM is positioned such that in a cleaved (or relatively active state) and in the presence of a target, the AB binds a target, while in an uncleaved (or relatively inactive state) in the presence of the target, specific binding of the AB to its target is reduced or inhibited. The specific binding of the AB to its target can be reduced due to the due to the inhibition or masking of the AB's ability to specifically bind its target by the MM.

The $K_d$ of the AB modified with a MM and a CM towards the target can be at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB not modified with an MM and a CM or the parental AB towards the target. Conversely, the binding affinity of the AB modified with a MM and a CM towards the target can be at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000, 000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000, 000 times lower than the binding affinity of the AB not modified with an MM and a CM or the parental AB towards the target.

When the AB is modified with a MM and a CM and is in the presence of the target but not in the presence of a modifying agent (for example an enzyme, protease, reduction agent, light), specific binding of the AB to its target can be reduced or inhibited, as compared to the specific binding of the AB not modified with an MM and a CM or the parental AB to the target. When compared to the binding of the parental AB or the binding of an AB not modified with an MM and a CM to its target, the AB's ability to bind the target when modified with an MM and a CM can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, 96 hours, or 5, 10, 15, 30, 45, 60, 90, 120, 150, 180 days, or 1, 2, 3, 4, 5, 6, 7, 8, 9, 10, 11, 12 months or greater when measured in vivo or in a Target Displacement in vitro immunoabsorbant assay, as described herein.

As used herein, the term cleaved state refers to the condition of the AA following modification of the CM by a protease and/or reduction of a cysteine-cysteine disulfide, bond of the CM, and/or photoactivation. The term uncleaved state, as used herein, refers to the condition of the AA in the absence of cleavage of the CM by a protease and/or in the absence reduction of a cysteine-cysteine disulfide bond of the CM, and/or in the absence of light. As discussed above, the term AA is used herein to refer to an AA in both its uncleaved (native) state, as well as in its cleaved state. It will be apparent to the ordinarily skilled artisan that in some embodiments a cleaved AA may lack an MM due to cleavage of the CM by protease, resulting in release of at least the MM (e.g., where the MM is not joined to the AA by a covalent bond (e.g., a disulfide bond between cysteine residues).

By activatable or switchable is meant that the AA exhibits a first level of binding to a target when in a inhibited, masked or uncleaved state (i.e., a first conformation), and a second level of binding to the target in the uninhibited, unmasked and/or cleaved state (i.e., a second conformation), where the second level of target binding is greater than the first level of binding. In general, the access of target to the AB of the AA is greater in the presence of a cleaving agent capable of cleaving the CM than in the absence of such a cleaving agent. Thus, when the AA is in the uncleaved state, the AB is inhibited from target binding and can be masked from target binding (i.e., the first conformation is such the AB can not bind the target), and in the cleaved state the AB is not inhibited or is unmasked to target binding.

The CM and AB of the AA may be selected so that the AB represents a binding moiety for a target of interest, and the CM represents a substrate for a protease that is co-localized with the target at a treatment site in a subject. Alternatively or in addition, the CM is a cysteine-cysteine disulfide bond that is cleavable as a result of reduction of this disulfide bond. AAs contain at least one of a protease-cleavable CM or a cysteine-cysteine disulfide bond, and in some embodiments include both kinds of CMs. The AAs can alternatively or further include a photolabile substrate, activatable by a light source. The AAs disclosed herein find particular use where, for example, a protease capable of cleaving a site in the CM is present at relatively higher levels in target-containing tissue of a treatment site (for example diseased tissue; for example for therapeutic treatment or diagnostic treatment) than in tissue of non-treatment sites (for example in healthy tissue), as exemplified in FIG. 2. The AAs disclosed herein also find particular use where, for example, a reducing agent capable of reducing a site in the CM is present at relatively higher levels in target-containing tissue of a treatment or diagnostic site than in tissue of non-treatment non-diagnostic sites. The AAs disclosed herein also find particular use where, for example, a light source, for example, by way of laser, capable of photolysing a site in the CM is introduced to a target-containing tissue of a treatment or diagnostic site.

In some embodiments AAs can provide for reduced toxicity and/or adverse side effects that could otherwise result from binding of the AB at non-treatment sites if the AB were not masked or otherwise inhibited from binding its target. Where the AA contains a CM that is cleavable by a reducing agent that facilitates reduction of a disulfide bond, the ABs of such AAs may selected to exploit activation of an AB where a target of interest is present at a desired treatment site characterized by elevated levels of a reducing agent, such that the environment is of a higher reduction potential than, for example, an environment of a non-treatment site.

In general, an AA can be designed by selecting an AB of interest and constructing the remainder of the AA so that, when conformationally constrained, the MM provides for masking of the AB or reduction of binding of the AB to its target. Structural design criteria to be taken into account to provide for this functional feature.

In certain embodiments dual-target binding AAs are provided in the present disclosure. Such dual target binding AAs contain two ABs, which may bind the same or different target. In specific embodiments, dual-targeting AAs contain bispecific antibodies or antibody fragments. In one specific exemplary embodiment, the AA contains an IL17 AB and an IL23 AB. In other specific embodiments the AA contains a IL12 AB and a IL23 AB, or a EGFR AB and a VEGF AB, or a IGF1R AB and EGFR AB, or a cMET AB and IGF1R AB, or a EGFR AB and a VEGF AB, or a Notch Receptor AB and a EGFR AB, or a Jagged ligand AB and a EGFR AB, or a cMET AB and a VEGF AB.

Dual target binding AAs can be designed so as to have a CM cleavable by a cleaving agent that is co-localized in a target tissue with one or both of the targets capable of binding to the ABs of the AA. Dual target binding AAs with more than one AB to the same or different targets can be designed so as to have more than one CM, wherein the first CM is cleavable by a cleaving agent in a first target tissue and wherein the second CM is cleavable by a cleaving agent in a second target tissue, with one or more of the targets capable of binding to the ABs of the AA. The first and second target tissues can be spatially separated, for example, at different sites in the organism. The first and second target tissues can be the same tissue temporally separated, for example the same tissue at two different points in time, for example the first time point can be when the tissue is a healthy tumor, and the second time point can be when the tissue is a necrosed tumor.

AAs exhibiting a switchable phenotype of a desired dynamic range for target binding in an inhibited versus an uninhibited conformation are provided. Dynamic range generally refers to a ratio of (a) a maximum detected level of a parameter under a first set of conditions to (b) a minimum detected value of that parameter under a second set of conditions. For example, in the context of an AA, the dynamic range refers to the ratio of (a) a maximum detected level of target protein binding to an AA in the presence of protease capable of cleaving the CM of the AA to (b) a minimum detected level of target protein binding to an AA in the absence of the protease. The dynamic range of an AA can be calculated as the ratio of the equilibrium dissociation constant of an AA cleaving agent (e.g., enzyme) treatment to the equilibrium dissociation constant of the AA cleaving agent treatment. The greater the dynamic range of an AA, the better the switchable phenotype of the AA. AAs having relatively higher dynamic range values (e.g., greater than 1) exhibit more desirable switching phenotypes such that target protein binding by the AA occurs to a greater extent (e.g., predominantly occurs) in the presence of a cleaving agent (e.g., enzyme) capable of cleaving the CM of the AA than in the absence of a cleaving agent.

AAs can be provided in a variety of structural configurations. Exemplary formulae for AAs are provided below. It is specifically contemplated that the N- to C-terminal order of the AB, MM and CM may be reversed within an AA. It is also specifically contemplated that the CM and MM may overlap in amino acid sequence, e.g., such that the CM is contained within the MM.

For example, AAs can be represented by the following formula (In order from an amino (N) terminal region to carboxyl (C) terminal region:

(MM)-(CM)-(AB)

(AB)-(CM)-(MM)

where MM is a masking moiety, CM is a cleavable moiety, and AB is an antibody or fragment thereof. It should be noted that although MM and CM are indicated as distinct components in the formula above, in all exemplary embodiments (including formulae) disclosed herein it is contemplated that the amino acid sequences of the MM and the CM could overlap, e.g., such that the CM is completely or partially contained within the MM. In addition, the formulae above provide for additional amino acid sequences that may be positioned N-terminal or C-terminal to the AA elements.

In many embodiments it may be desirable to insert one or more linkers, e.g., flexible linkers, into the AA construct so as to provide for flexibility at one or more of the MM-CM junction, the CM-AB junction, or both. For example, the AB, MM, and/or CM may not contain a sufficient number of residues (e.g., Gly, Ser, Asp, Asn, especially Gly and Ser, particularly Gly) to provide the desired flexibility. As such, the switchable phenotype of such AA constructs may benefit from introduction of one or more amino acids to provide for a flexible linker. In addition, as described below, where the AA is provided as a conformationally constrained construct, a flexible linker can be operably inserted to facilitate formation and maintenance of a cyclic structure in the uncleaved AA.

For example, in certain embodiments an AA comprises one of the following formulae (where the formula below represent an amino acid sequence in either N- to C-terminal direction or C- to N-terminal direction):

(MM)-$L_1$-(CM)-(AB)

(MM)-(CM)-$L_1$-(AB)

(MM)-$L_1$-(CM)-$L_2$-(AB)

cyclo[$L_1$-(MM)-$L_2$-(CM)-$L_3$-(AB)]

wherein MM, CM, and AB are as defined above; wherein $L_1$, $L_2$, and $L_3$ are each independently and optionally present or absent, are the same or different flexible linkers that include at least 1 flexible amino acid (e.g., Gly); and wherein cyclo where present, the AA is in the form of a cyclic structure due to the presence of a disulfide bond between a pair of cysteines in the AA. In addition, the formulae above provide for additional amino acid sequences that may be positioned N-terminal or C-terminal to the AA elements. It should be understood that in the formula cyclo[$L_1$-(MM)-$L_2$-(CM)-$L_3$-(AB)], the cysteines responsible for the disulfide bond may be positioned in the AA to allow for one or two tails, thereby generating a lasso or omega structure when the AA is in a disulfide-bonded structure (and thus conformationally constrained state). The amino acid sequence of the tail(s) can provide for additional AA features, such as binding to a target receptor to facilitate localization of the AA, increasing serum half-life of the AA, and the like. Targeting moieties (e.g., a ligand for a receptor of a cell present in a target tissue) and serum half-life extending moieties (e.g., polypeptides that bind serum proteins, such as immunoglobulin (e.g., IgG) or serum albumin (e.g., human serum albumin (HSA).

Elements of Modified and Activatable Antibodies (a) Antibodies or Antibody Fragments (Collectively Referred to as ABs)

According to the present invention, ABs directed against any antigen or hapten may be used. ABs used in the present invention may be directed against any determinant, e.g., tumor, bacterial, fungal, viral, parasitic, mycoplasmal, histocompatibility, differentiation and other cell membrane antigens, pathogen surface antigens, toxins, enzymes, allergens, drugs, intracellular targets, and any biologically active molecules. Additionally, a combination of ABs reactive to different antigenic determinants may be used.

As used herein, the AB is a full length antibody or an antibody fragment containing an antigen binding domain, which is capable of binding, especially specific binding, to a target of interest, usually a protein target of interest. A schematic of an AA is provided in FIG. 1. In such embodiments, the AB can be but is not limited to variable or hypervariable regions of light and/or heavy chains of an antibody ($V_L$, $V_H$), variable fragments (Fv), Fab' fragments, F(ab') 2 fragments, Fab fragments, single chain antibodies (scAb), single chain variable regions (scFv), complementarity determining regions (CDR), domain antibodies (dAbs), single domain heavy chain immunoglobulins of the BHH or BNAR type, single domain light chain immunoglobulins, or other polypeptides known in the art containing an AB capable of binding target proteins or epitopes on target proteins. In further embodiments, the AB may be a chimera or hybrid combination containing more than on AB, for example a first AB and a second AB such that each AB is capable of binding to the same or different target. In some embodiments, the AB is a bispecific antibody or fragment thereof, designed to bind two different antigens. In some embodiments there is a first MM and CM and/or a second MM and CM coupled to the first AB and the second AB, respectively, in the activatable form.

The origin of the AB can be a naturally occurring antibody or fragment thereof, a non-naturally occurring antibody or fragment thereof, a synthetic antibody or fragment thereof, a hybrid antibody or fragment thereof, or an engineered antibody or fragment thereof. The antibody can be a humanized antibody or fragment thereof.

In certain embodiments, more than one AB is contained in the AA. In some embodiments the ABs can be derived from bispecific antibodies or fragments thereof. In other embodiments the AA can be synthetically engineered so as to incorporate ABs derived from two different antibodies or fragments thereof. In such embodiments, the ABs can be designed to bind two different targets, two different antigens, or two different epitopes on the same target. An AB containing a plurality of ABs capable of binding more than one target site are usually designed to bind to different binding sites on a target or targets of interest such that binding of a first AB of the AA does not substantially interfere with binding of a second AB of the AA to a target. AAs containing multiple ABs can further include multiple AB-MM units, which may optionally be separated by additional CMs so that upon exposure to a modifying agent, the ABs are no longer inhibited from specifically binding their targets, or are 'unmasked'.

In some embodiments, use of antibody fragments as sources for the AB allow permeation of target sites at an increased rate. The Fab' fragments of IgG immunoglobulins are obtained by cleaving the antibody with pepsin [resulting in a bivalent fragment, (Fab') 2] or with papain [resulting in 2 univalent fragments, (2 Fab)]. Parham, 1983, J. Immunol. 131: 2895-2902; Lamoyi and Nisonoff, 1983, J. Immunol. Meth. 56: 235-243. The bivalent (Fab') 2 fragment can be split by mild reduction of one or a few disulfide bonds to yield univalent Fab' fragments. The Fab and (Fab') 2 fragments are smaller than a whole antibody, still containing an AB and, therefore can permeate the target site or tissue more easily when used as the AB. This may offer an advantage for in vivo delivery in certain embodiments because many such fragments do not cross a placental barrier. As a result, using this embodiment of the present invention, an AA may be delivered at an in vivo site (such as a tumor) to a pregnant female without exposing the fetus.

Methods for generating an antibody (or fragment thereof) for a given target are well known in the art. The structure of antibodies and fragments thereof, variable regions of heavy and light chains of an antibody ($V_H$ and $V_L$), Fv, F(ab') 2, Fab fragments, single chain antibodies (scAb), single chain variable regions (scFv), complementarity determining regions (CDR), and domain antibodies (dAbs) are well understood. Methods for generating a polypeptide having a desired antigen-binding domain of a target antigen are known in the art.

Figure 3:
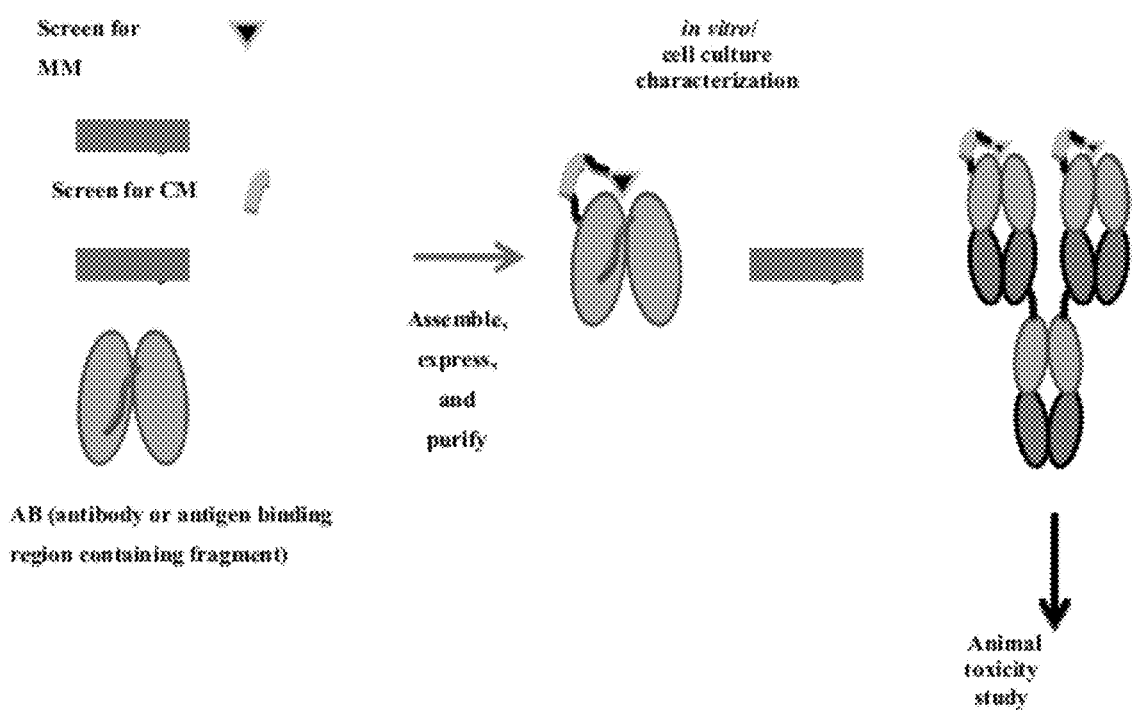
FIG. 3 illustrates a process to produce a protease-activated AA, involving: screening for MMs; screening for CMs; assembling the MM, CM, and an AB; expressing and purifying the assembled construct; and assaying the assembled construct for activity and toxicity in vitro and in vivo.
Figure 4:
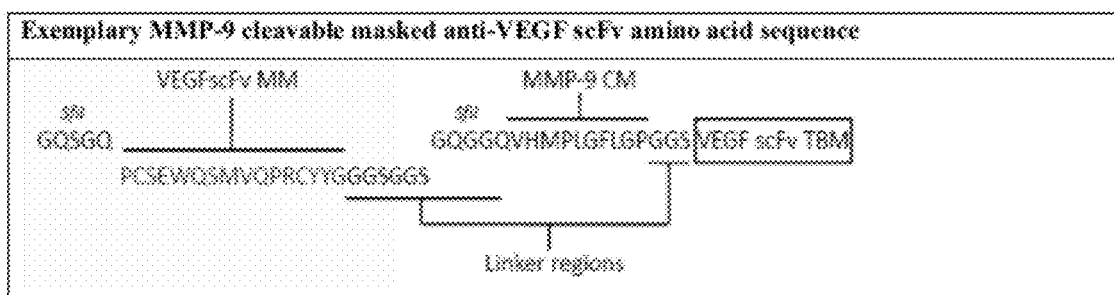
FIG. 4 provides an exemplary MMP-9 cleavable masked anti-VEGF scFv amino acid sequence (SEQ ID NO: 350).

Methods for modifying antibodies or antibody fragments to couple additional polypeptides are also well-known in the art. For instance, peptides such as MMs, CMs or linkers may be coupled to modify antibodies to generate the modified ABs and AAs of the disclosure. AAs that contain protease-activated ABs can be developed and produced with standard methods, as described in the schematic in FIG. 3.

The antibody or fragment thereof (collectively referred to as AB) is capable of specifically binding a protein target. An AB of the invention can specifically bind to its target with a dissociation constant ($K_d$) of no more than 1000 nM, 100 nM, 50 nM, 10 nM, 5 nM, 1 nM, 500 pM, 400 pM, 350 pM, 300 pM, 250 pM, 200 pM, 150 pM, 100 pM, 50 pM, 25 pM, 10 pM, 5 pM, 1 pM, 0.5 pM, or 0.1 pM.

Exemplary classes of targets of an AB include, but are not necessarily limited to, cell surface receptors and secreted binding proteins (e.g., growth factors), soluble enzymes, structural proteins (e.g. collagen, fibronectin) and the like. In some embodiments, AAs contemplated by the present disclosure are those having an AB capable of binding an extracellular target, usually an extracellular protein target. In other embodiments AAs can be designed such that they are capable of cellular uptake and are designed to be switchable inside a cell.

In exemplary embodiments, in no way limiting, the AB is a binding partner for any target listed in Table 1. In specific exemplary embodiments, the AB is a binding partner for EGFR, TNFalpha, CD11a, CSFR, CTLA-4, EpCAM, VEGF, CD40, CD20, Notch 1, Notch 2, Notch 3, Notch 4, Jagged 1, Jagged 2, CD52, MUC1, IGF1R, transferrin, gp130, VCAM-1, CD44, DLL4, or IL4. In one specific embodiment the AB is not a binding partner for CD52.

In exemplary embodiments, in no way limiting, exemplary sources for ABs are listed in Table 2. In specific exemplary embodiments, the source for an AB of the invention is cetuximab, panitumumab, infliximab, adalimumab, efalizumab, ipilimumab, tremelimumab, adecatumumab, Hu5c8, alemtuzumab, ranibizumab, tositumomab, ibritumomab tiuxetan, rituximab, infliximab, bevacizumab, or figitumumab. In one specific embodiment, the source for the AB is not alemtuzumab or is not Campath™.

TABLE 1

Exemplary Targets

| | | | | |
|---|---|---|---|---|
| 1-92-LFA-3 | cMet | HGF | IL4 | PSMA |
| Anti-Lewis-Y | Collagen | hGH | IL4R | RAAG12 |
| Apelin J receptor | CSFR | Hyaluronidase | IL6 | Sphingosine 1 Phosphate |
| C5 complement | CSFR-1 | IFNalpha | Insulin Receptor | TGFbeta |
| CD11a | CTLA-4 | IFNbeta | Jagged Ligands | TNFalpha |
| CD172A | CXCR4 | IFNgamma | Jagged 1 | TNFalpha |
| CD19 | DL44 | IgE | Jagged 2 | TNFR |
| CD20 | DLL4 | IgE Receptor | MUC1 | TRAIL-R1 |
| CD22 | EGFR | IGF | Na/K ATPase | TRAIL-R2 |
| CD25 | EpCAM | IGF1R | NGF | Transferrin |
| CD28 | EPHA2 | IL11 | Notch Receptors | Transferrin receptor |
| CD3 | ERBB3 | IL12 | Notch 1 | TRK-A |
| CD30 | F protein of RSV | IL13 | Notch 2 | TRK-B |
| CD33 | FAP | IL15 | Notch 3 | VCAM-1 |
| CD40 | FGF-2 | IL17 | Notch 4 | VEGF |
| CD40L | FGFR1 | IL18 | PDGF-AA | VEGF-A |
| CD41 | FGFR2 | IL1B | PDGF-BB | VEGF-B |
| CD44 | FGFR3 | IL1R | PDGFRalpha | VEGF-C |
| CD52 | FGFR4 | IL2 | PDGFRalpha | VEGF-D |
| CD64 | Folate receptor | IL21 | PDGFRbeta | VEGFR1 |
| CD80 | GP IIb/IIIa receptors | IL23 | PDGFRbeta | VEGFR2 |
| CD86 | Gp130 | IL23R | Phosphatidylserine | VEGFR3 |
| CLAUDIN-3 | GPIIB/IIIA | IL29 | P1GF | alpha4beta1 integrin |
| CLAUDIN-4 | HER2/neu | IL2R | PSCA | alpha4beta7 integrin |

TABLE 2

Exemplary sources for ABs

| Antibody Trade Name (antibody name) | Target |
|---|---|
| Avastin ™ (bevacizumab) | VEGF |
| Lucentis ™ (ranibizumab) | VEGF |
| Erbitux ™ (cetuximab) | EGFR |
| Vectibix ™ (panitumumab) | EGFR |
| Remicade ™ (infliximab) | TNFα |
| Humira ™ (adalimumab) | TNFα |
| Tysabri ™ (natalizumab) | Integrinα4 |
| Simulect ™ (basiliximab) | IL2R |
| Soliris ™ (eculizumab) | Complement C5 |
| Raptiva ™ (efalizumab) | CD11a |
| Bexxar ™ (tositumomab) | CD20 |
| Zevalin ™ (ibritumomab tiuxetan) | CD20 |
| Rituxan ™ (rituximab) | CD20 |
| Zenapax ™ (daclizumab) | CD25 |
| Myelotarg ™ (gemtuzumab) | CD33 |
| Mylotarg ™ (gemtuzumab ozogamicin) | CD33 |
| Campath ™ (alemtuzumab) | CD52 |
| ReoPro ™ (abiciximab) | Glycoprotein receptor IIb/IIIa |
| Xolair ™ (omalizumab) | IgE |
| Herceptin ™ (trastuzumab) | Her2 |
| Synagis ™ (palivizumab) | F protein of RSV |
| (ipilimumab) | CTLA-4 |
| (tremelimumab) | CTLA-4 |
| Hu5c8 | CD40L |
| (pertumumab) | Her2-neu |
| (ertumaxomab) | CD3/Her2-neu |
| Orencia ™ (abatacept) | CTLA-4 |
| (tanezumab) | NGF |
| (bavituximab) | Phosphatidylserine |
| (zalutumumab) | EGFR |

TABLE 2-continued

Exemplary sources for ABs

| Antibody Trade Name (antibody name) | Target |
|---|---|
| (mapatumumab) | Tumor Necrosis Factor-Related Apoptosis-Inducing Ligand Receptor-1 (TRAIL-R1) |
| (matuzumab) | EGFR |
| (nimotuzumab) | EGFR |
| ICR62 | EGFR |
| mAb 528 | EGFR |
| CH806 | EGFR |
| MDX-447 | EGFR/CD64 |
| (edrecolomab) | EpCAM |
| RAV12 | RAAG12 |
| huJ591 | PSMA |
| Enbrel ™ (etanercept) | TNF-R |
| Amevive ™ (alefacept) | 1-92-LFA-3 |
| Antril ™, Kineret ™ (ankinra) | IL-1Ra |
| GC1008 | TGFbeta Notch 1 Jagged 1 |
| (adecatumumab) | EpCAM |
| (figitumumab) | IGF1R |
| (tocilizumab) | IL-6 |

The exemplary sources for some of the ABs listed in Table 2 are detailed in the following references which are incorporated by reference herein for their description of one or more of the referenced AB sources: Remicade™ (infliximab): U.S. Pat. No. 6,015,557, Nagahira K, Fukuda Y, Oyama Y, Kurihara T, Nasu T, Kawashima H, Noguchi C, Oikawa S, Nakanishi T. Humanization of a mouse neutralizing monoclonal antibody against tumor necrosis factor-alpha (TNF-alpha). J Immunol Methods. 1999 Jan. 1; 222(1-2):83-92.) Knight D M, Trinh H, Le J, Siegel S, Shealy D, McDonough M, Scallon B, Moore M A, Vilcek J, Daddona P, et al. Construction and initial characterization of a mouse-human chimeric anti-TNF antibody. Mol Immunol. 1993 November; 30(16):1443-53. Humira™ (adalimumab): Sequence in U.S. Pat. No. 6,258, 562. Raptiva™ (efalizumab): Sequence listed in Werther W A, Gonzalez T N, O'Connor S J, McCabe S, Chan B, Hotaling T, Champe M, Fox J A, Jardieu P M, Berman P W, Presta L G. Humanization of an anti-lymphocyte function-associated antigen (LFA)-1 monoclonal antibody and reengineering of the humanized antibody for binding to rhesus LFA-1. J. Immunol. 1996 Dec. 1; 157(11):4986-95. Mylotarg™ (gemtuzumab ozogamicin): (Sequence listed in CO MS, Avdalovic N M, Caron P C, Avdalovic M V, Scheinberg D A, Queen C: Chimeric and humanized antibodies with specificity for the CD33 antigen. J Immunol 148:1149, 1991) (Caron P C, Schwartz M A, Co M S, Queen C, Finn R D, Graham M C, Divgi C R, Larson S M, Scheinberg D A. Murine and humanized constructs of monoclonal antibody M195 (anti-CD33) for the therapy of acute myelogenous leukemia. Cancer. 1994 Feb. 1; 73(3 Suppl):1049-56). Soliris™ (eculizumab): Hillmen P, Young N, Schubert J, Brodsky R, Socié G, Muus P, Röth A, Szer J, Elebute M, Nakamura R, Browne P, Risitano A, Hill A, Schrezenmeier H, Fu C, Maciejewski J, Rollins S, Mojcik C, Rother R, Luzzatto L (2006). The complement inhibitor eculizumab in paroxysmal nocturnal hemoglobinuria. N Engl J Med 355 (12): 1233-43. Tysabri™ (natalizumab): Sequence listed in Leger O J, Yednock T A, Tanner L, Horner H C, Hines D K, Keen S, Saldanha J, Jones S T, Fritz L C, Bendig M M. Humanization of a mouse antibody against human alpha-4 integrin: a potential therapeutic for the treatment of multiple sclerosis. Hum Antibodies. 1997; 8(1):3-16. Synagis™ (palivizumab): Sequence listed in Johnson S, Oliver C, Prince G A, Hemming V G, Pfarr D S, Wang S C, Dormitzer M, O'Grady J, Koenig S, Tamura J K, Woods R, Bansal G, Couchenour D, Tsao E, Hall W C, Young J F. Development of a humanized monoclonal antibody (MEDI-493) with potent in vitro and in vivo activity against respiratory syncytial virus. J Infect Dis. 1997 November; 176(5): 1215-24. Ipilimumab: *J. Immunother:* 2007; 30(8): 825-830 Ipilimumab (Anti-CTLA4 Antibody) Causes Regression of Metastatic Renal Cell Cancer Associated With Enteritis and Hypophysitis; James C. Yang, Marybeth Hughes, Udai Kammula, Richard Royal, Richard M. Sherry, Suzanne L. Topalian, Kimberly B. Suri, Catherine Levy, Tamika Allen, Sharon Mavroukakis, Israel Lowy, Donald E. White, and Steven A. Rosenberg. Tremelimumab: *Oncologist* 2007; 12; 153-883; Blocking Monoclonal Antibody in Clinical Development for Patients with Cancer; Antoni Ribas, Douglas C. Hanson, Dennis A. Noe, Robert Millham, Deborah J. Guyot, Steven H. Bernstein, Paul C. Canniff, Amarnath Sharma and Jesus Gomez-Navarro.

(b) Masking Moiety (MM)

The masking moiety (MM) of the present disclosure generally refers to an amino acid sequence coupled to the AB and positioned such that it reduces the AB's ability to specifically bind its target. In some cases the MM is coupled to the AB by way of a linker.

When the AB is modified with a MM and is in the presence of the target, specific binding of the AB to its target is reduced or inhibited, as compared to the specific binding of the AB not modified with an MM or the specific binding of the parental AB to the target.

The $K_d$ of the AB modified with a MM towards the AB's target is generally greater than the $K_d$ of the AB not modified with a MM or the $K_d$ of parental AB towards the target. Conversely, the binding affinity of the AB modified with a MM towards the target is generally lower than the binding affinity of the AB not modified with a MM or the parental AB towards the target.

The dissociation constant ($K_d$) of the MM towards the AB is generally greater than the $K_d$ of the AB towards the target. Conversely, the binding affinity of the MM towards the AB is generally lower than the binding affinity of the AB towards the target.

When the AB is modified with a MM and is in the presence of the target, specific binding of the AB to its target can be reduced or inhibited, as compared to the specific binding of the AB not modified with an MM or the specific binding of the parental AB to the target. When the AB is modified with a CM and a MM and is in the presence of the target but not sufficient enzyme or enzyme activity to cleave the CM, specific binding of the modified AB to the target is reduced or inhibited, as compared to the specific binding of the AB modified with a CM and a MM in the presence of the target and sufficient enzyme or enzyme activity to cleave the CM.

The MM can inhibit the binding of the AB to the target. The MM can bind the antigen binding domain of the AB and inhibit binding of the AB to its target. The MM can sterically inhibit the binding of the AB to the target. The MM can allosterically inhibit the binding of the AB to its target. In these embodiments when the AB is modified or coupled to a MM and in the presence of target, there is no binding or substantially no binding of the AB to the target, or no more than 0.001%, 0.01%, 0.1%, 1%, 2%, 3%, 4%, 5%, 6%, 7%, 8%, 9%, 10%, 15%, 20%, 25%, 30%, 35%, 40%, or 50% binding of the AB to the target, as compared to the binding of the AB not modified with an MM, the binding of the parental AB, or the binding of the AB not coupled to an MM to the target, for at least 2, 4, 6, 8, 12, 28, 24, 30, 36, 48, 60, 72, 84, 96 hours, or 5, 10, 15, 30, 45, 60, 90, 120, 150, 180 days, or 1, 2, 3, 4, 5, 6, 7, 8, 9, 10, 11, 12 months or greater when measured in vivo or in a Target Displacement in vitro immunoabsorbant assay, as described herein.

In certain embodiments the MM is not a natural binding partner of the AB. The MM may be a modified binding partner for the AB which contains amino acid changes that at least slightly decrease affinity and/or avidity of binding to the AB. In some embodiments the MM contains no or substantially no homology to the AB's natural binding partner. In other embodiments the MM is no more than 5%, 10%, 15%, 20%, 25%, 30%, 35%, 40%, 45%, 50%, 55%, 60%, 65%, 70%, 75%, or 80% similar to the natural binding partner of the AB.

When the AB is in a 'masked' state, even in the presence of a target for the AB, the MM interferes with or inhibits the binding of the AB to the target. However, in the unmasked state of the AB, the MM's interference with target binding to the AB is reduced, thereby allowing greater access of the AB to the target and providing for target binding.

For example, when the modified antibody is an AA and comprises a CM, the AB can be unmasked upon cleavage of the CM, in the presence of enzyme, preferably a disease-specific enzyme. Thus, the MM is one that when the AA is uncleaved provides for masking of the AB from target binding, but does not substantially or significantly interfere or compete for binding of the target to the AB when the AA is in the cleaved conformation. Thus, the combination of the MM and the CM facilitates the switchable/activatable phenotype, with the MM decreasing binding of target when the AA is uncleaved, and cleavage of the CM by protease providing for increased binding of target.

The structural properties of the MM will vary according to a variety of factors such as the minimum amino acid sequence required for interference with AB binding to target, the target protein-AB binding pair of interest, the size of the AB, the length of the CM, whether the CM is positioned within the MM and also serves to mask the AB in the uncleaved AA, the presence or absence of linkers, the presence or absence of a cysteine within or flanking the AB that is suitable for providing a CM of a cysteine-cysteine disulfide bond, and the like.

One strategy for masking an antibody or fragment thereof (AB) in an AA is to provide the AA in a loop that sterically hinders access of target to the AB. In this strategy, cysteines are positioned at or near the N-terminus, C-terminus, or AB of the AA, such that upon formation of a disulfide bond between the cysteines, the AB is masked.

In some embodiments, the MM is coupled to the AA by covalent binding. In another embodiment, the AA composition is prevented from binding to the target by binding the MM to an N-terminus of the AA. In yet another embodiment, the AA is coupled to the MM by cysteine-cysteine disulfide bridges between the MM and the AA.

The MM can be provided in a variety of different forms. In certain embodiments, the MM can be selected to be a known binding partner of the AB, provided that the MM binds the AB with less affinity and/or avidity than the target protein to which the AB is designed to bind following cleavage of the CM so as to reduce interference of MM in target-AB binding. Stated differently, as discussed above, the MM is one that masks the AB from target binding when the AA is uncleaved, but does not substantially or significantly interfere or compete for binding for target when the AA is in the cleaved conformation. In a specific embodiment, the AB and MM do not contain the amino acid sequences of a naturally-occurring binding partner pair, such that at least one of the AB and MM does not have the amino acid sequence of a member of a naturally occurring binding partner The efficiency of the MM to inhibit the binding of the AB to its target when coupled can be measured by a Masking Efficiency measure, using an immunoabsorbant Target Displacement Assay, as described herein in the Examples section of the disclosure. Masking efficiency of MMs is determined by at least two parameters: affinity of the MM for the antibody or fragment thereof and the spatial relationship of the MM relative to the binding interface of the AB to its target.

Regarding affinity, by way of example, an MM may have high affinity but only partially inhibit the binding site on the AB, while another MM may have a lower affinity for the AB but fully inhibit target binding. For short time periods, the lower affinity MM may show sufficient masking; in contrast, over time, that same MM may be displaced by the target (due to insufficient affinity for the AB).

In a similar fashion, two MMs with the same affinity may show different extents of masking based on how well they promote inhibition of the binding site on the AB or prevention of the AB from binding its target. In another example, a MM with high affinity may bind and change the structure of the AB so that binding to its target is completely inhibited while another MM with high affinity may only partially inhibit binding. As a consequence, discovery of an effective MM cannot be based only on affinity but can include an empirical measure of Masking Efficiency. The time-dependent target displacement of the MM in the AA can be measured to optimize and select for MMs. A novel Target Displacement Assay is described herein for this purpose.

In some embodiments the MM can be identified through a screening procedure from a library of candidates AAs having variable MMs. For example, an AB and CM can be selected to provide for a desired enzyme/target combination, and the amino acid sequence of the MM can be identified by the screening procedure described below to identify an MM that provides for a switchable phenotype. For example, a random peptide library (e.g., from about 2 to about 40 amino acids or more) may be used in the screening methods disclosed herein to identify a suitable MM. In specific embodiments, MMs with specific binding affinity for an antibody or fragment thereof (AB) can be identified through a screening procedure that includes providing a library of peptide scaffolds consisting of candidate MMs wherein each scaffold is made up of a transmembrane protein and the candidate MM. The library is then contacted with an entire or portion of an AB such as a full length antibody, a naturally occurring antibody fragment, or a non-naturally occurring fragment containing an AB (also capable of binding the target of interest), and identifying one or more candidate MMs having detectably bound AB. Screening can include one more rounds of magnetic-activated sorting (MACS) or fluorescence-activated sorting (FACS). Screening can also included determination of the dissociation constant ($K_d$) of MM towards the AB and subsequent determination of the Masking Efficiency.

In this manner, AAs having an MM that inhibits binding of the AB to the target in an uncleaved state and allows binding of the AB to the target in a cleaved state can be identified, and can further provide for selection of an AA having an optimal dynamic range for the switchable phenotype. Methods for identifying AAs having a desirable switching phenotype are described in more detail below.

Alternatively, the MM may not specifically bind the AB, but rather interfere with AB-target binding through non-specific interactions such as steric hindrance. For example, the MM may be positioned in the uncleaved AA such that the tertiary or quaternary structure of the AA allows the MM to mask the AB through charge-based interaction, thereby holding the MM in place to interfere with target access to the AB.

AAs can also be provided in a conformationally constrained structure, such as a cyclic structure, to facilitate the switchable phenotype. This can be accomplished by including a pair of cysteines in the AA construct so that formation of a disulfide bond between the cysteine pairs places the AA in a loop or cyclic structure. Thus the AA remains cleavable by the desired protease while providing for inhibition of target binding to the AB. Upon cleavage of the CM, the cyclic structure is opened, allowing access of target to the AB.

The cysteine pairs can be positioned in the AA at any position that provides for a conformationally constrained AA, but that, following CM reduction, does not substantially or significantly interfere with target binding to the AB. For example, the cysteine residues of the cysteine pair are positioned in the MM and a linker flanked by the MM and AB, within a linker flanked by the MM and AB, or other suitable configurations. For example, the MM or a linker flanking an MM can include one or more cysteine residues, which cysteine residue forms a disulfide bridge with a cysteine residue positioned opposite the MM when the AA is in a folded state. It is generally desirable that the cysteine residues of the cysteine pair be positioned outside the AB so as to avoid interference with target binding following cleavage of the AA. Where a cysteine of the cysteine pair to be disulfide bonded is positioned within the AB, it is desirable that it be positioned to as to avoid interference with AB-target binding following exposure to a reducing agent.

Exemplary AAs capable of forming a cyclic structure by disulfide bonds between cysteines can be of the general formula (which may be from either N- to C-terminal or from C- to N-terminal direction):

$$X_{n1}\text{-}(Cys_1)\text{-}X_m\text{-}CM\text{-}AB\text{-}(Cys_2)\text{-}X_{n2}$$

$$X_{n1}\text{-}cyclo[(Cys_1)\text{-}X_m\text{-}CM\text{-}AB\text{-}(Cys_2)]\text{-}X_{n2}$$

wherein $X_{n1}$ and $X_{n2}$ are independently, optionally present or absent and, when present, independently represent any amino acid, and can optionally include an amino acid sequence of a flexible linker (e.g., at least one Gly, Ser, Asn, Asp, usually at least one Gly or Ser, usually at least one Gly), and $n_1$ and $n_2$ are independently selected from s zero or any integer, usually nor more than 1, 2, 3, 4, 5, 6, 7, 8, 9 or 10;

$Cys_1$ and $Cys_2$ represent first and second cysteines of a pair capable of forming a disulfide bond;

$X_m$ represents amino acids of a masking motif (MM), where X is any amino acid, wherein $X_m$ can optionally include a flexible linker (e.g., at least one Gly, Ser, Asn, Asp, usually at least one Gly or Ser, usually at least one Gly); and where m is an integer greater than 1, usually 2, 3, 4, 5, 6, 7, 8, 9, 10 or more (as described above);

CM represents a cleavable moiety (as described herein); and

AB represents an antibody or fragment thereof (as described herein).

As used in the formula above, cyclo indicates a disulfide bond in the AA that provides for a cyclic structure of the AA. Furthermore, the formula above contemplate dual target-binding AAs wherein MM refers to an AB1 and AB refers to AB2, where AB1 and AB2 are arbitrary designations for first and second ABs, and where the target capable of binding the ABs may be the same or different target, or the same or different binding sites of the same target. In such embodiments, the AB1 and/or AB2 acts as a masking moiety to interfere with target binding to an uncleaved dual target-binding AA.

As illustrated above, the cysteines can thus be positioned in the AA allow for one or two tails (represented by $X_{n1}$ and $X_{n2}$ above), thereby generating a lasso or omega structure when the AA is in a disulfide-bonded structure (and thus conformationally constrained state). The amino acid sequence of the tail(s) can provide for additional AA features, such as binding to a target receptor to facilitate localization of the AA.

In certain specific embodiments, the MM does not inhibit cellular entry of the AA.

(c) Cleavable Moiety (CM)

In some embodiments, the cleavable moiety (CM) of the AA may include an amino acid sequence that can serve as a substrate for a protease, usually an extracellular protease. In other embodiments, the CM comprises a cysteine-cysteine pair capable of forming a disulfide bond, which can be cleaved by action of a reducing agent. In other embodiments the CM comprises a substrate capable of being cleaved upon photolysis.

The CM is positioned in the AA such that when the CM is cleaved by a cleaving agent (e.g., a protease substrate of a CM is cleaved by the protease and/or the cysteine-cysteine disulfide bond is disrupted via reduction by exposure to a reducing agent) or by light-induced photolysis, in the presence of a target, resulting in a cleaved state, the AB binds the target, and in an uncleaved state, in the presence of the target, binding of the AB to the target is inhibited by the MM (FIG. 2). It should be noted that the amino acid sequence of the CM may overlap with or be included within the MM, such that all or a portion of the CM facilitates masking of the AB when the AA is in the uninhibited or uncleaved or unmasked conformation.

The CM may be selected based on a protease that is co-localized in tissue with the desired target of the AB of the AA. A variety of different conditions are known in which a target of interest is co-localized with a protease, where the substrate of the protease is known in the art. In the example of cancer, the target tissue can be a cancerous tissue, particularly cancerous tissue of a solid tumor. There are reports in the literature of increased levels of proteases having known substrates in a number of cancers, e.g., solid tumors. See, e.g., La Rocca et al, (2004) British J. of Cancer 90(7): 1414-1421. Non-liming examples of disease include: all types of cancers (breast, lung, colorectal, prostate, head and neck, pancreatic, etc), rheumatoid arthritis, Crohn's disease, melanomas, SLE, cardiovascular damage, ischemia, etc. Furthermore, anti-angiogenic targets, such as VEGF, are known. As such, where the AB of an AA is selected such that it is capable of binding an anti-angiogenic target such as VEGF, a suitable CM will be one which comprises a peptide substrate that is cleavable by a protease that is present at the cancerous treatment site, particularly that is present at elevated levels at the cancerous treatment site as compared to non-cancerous tissues. In one exemplary embodiment, the AB of an AA can bind VEGF and the CM can be a matrix metalloprotease (MMP) substrate, and thus is cleavable by an MMP. In other embodiments, the AB of an AA can bind a target of interest and the CM can be, for example, legumain, plasmin, TMPRSS-3/4, MMP-9, MT1-MMP, cathepsin, caspase, human neutrophil elastase, beta-secretase, uPA, or PSA. In other embodiments, the AA is activated by other disease-specific proteases, in diseases other than cancer such as multiple sclerosis or rheumatoid arthritis.

The unmodified or uncleaved CM can allow for efficient inhibition or masking of the AB by tethering the MM to the AB. When the CM is modified (cleaved, reduced, photolysed), the AB is no longer inhibited or unmasked and can bind its target.

The AA can comprise more than one CM such that the AA would comprise, for example, a first CM (CM1) and a second CM (CM2). The CM1 and CM2 can be different substrates for the same enzyme (for example exhibiting different binding affinities to the enzyme), or different substrates for different enzymes, or CM1 can be an enzyme substrate and CM2 can be a photolysis substrate, or CM1 can be an enzyme substrate and CM2 can be a substrate for reduction, or CM1 can be a substrate for photolysis and CM2 can be a substrate for reduction, and the like.

The CM is capable of being specifically modified (cleaved, reduced or photolysed) by an agent (ie enzyme, reducing agent, light) at a rate of about 0.001-1500×10$^4$ M$^{-1}$S$^{-1}$ or at least 0.001, 0.005, 0.01, 0.05, 0.1, 0.5, 1, 2.5, 5, 7.5, 10, 15, 20, 25, 50, 75, 100, 125, 150, 200, 250, 500, 750, 1000, 1250, or 1500×10$^4$M$^{-1}$S$^{-1}$.

For specific cleavage by an enzyme, contact between the enzyme and CM is made. When the AA comprising an AB coupled to a MM and a CM is in the presence of target and sufficient enzyme activity, the CM can be cleaved. Sufficient enzyme activity can refer to the ability of the enzyme to make contact with the CM and effect cleavage. It can readily be envisioned that an enzyme may be in the vicinity of the CM but unable to cleave because of other cellular factors or protein modification of the enzyme.

Exemplary substrates can include but are not limited to substrates cleavable by one or more of the following enzymes or proteases in Table 3.

TABLE 3

| Exemplary Enzymes/Proteases | | | |
|---|---|---|---|
| ADAM10 | Caspase 8 | Cathepsin S | MMP 8 |
| ADAM12 | Caspase 9 | FAP | MMP 9 |
| ADAM17 | Caspase 10 | Granzyme B | MMP-13 |
| ADAMTS | Caspase 11 | Guanidinobenzoatase (GB) | MMP 14 |
| ADAMTS5 | Caspase 12 | Hepsin | MT-SP1 |
| BACE | Caspase 13 | Human Neutrophil Elastase (HNE) | Neprilysin |
| Caspases | Caspase 14 | Legumain | NS3/4A |
| Caspase 1 | Cathepsins | Matriptase 2 | Plasmin |
| Caspase 2 | Cathepsin A | Meprin | PSA |
| Caspase 3 | Cathepsin B | MMP 1 | PSMA |
| Caspase 4 | Cathepsin D | MMP 2 | TACE |
| Caspase 5 | Cathepsin E | MMP 3 | TMPRSS 3/4 |
| Caspase 6 | Cathepsin K | MMP 7 | uPA |
| Caspase 7 | MT1-MMP | | |

Alternatively or in addition, the AB of an AA can be one that binds a target of interest and the CM can involve a disulfide bond of a cysteine pair, which is thus cleavable by a reducing agent such as, for example, but not limited to a cellular reducing agent such as glutathione (GSH), thioredoxins, NADPH, flavins, ascorbate, and the like, which can be present in large amounts in tissue of or surrounding a solid tumor.

(d) Linkers

Linkers suitable for use in compositions described herein are generally ones that provide flexibility of the modified AB or the AA to facilitate the inhibition of the binding of the AB to the target. Such linkers are generally referred to as flexible linkers. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers $(G)_n$, glycine-serine polymers (including, for example, $(GS)_n$, $(GSGGS)_n$ (SEQ ID NO: 12) and $(GGGS)_n$ (SEQ ID NO: 13), where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11173-142 (1992)). Exemplary flexible linkers include, but are not limited to Gly-Gly-Ser-Gly (SEQ ID NO: 14), Gly-Gly-Ser-Gly-Gly (SEQ ID NO: 15), Gly-Ser-Gly-Ser-Gly (SEQ ID NO: 16), Gly-Ser-Gly-Gly-Gly (SEQ ID NO: 17), Gly-Gly-Gly-Ser-Gly (SEQ ID NO: 18), Gly-Ser-Ser-Ser-Gly (SEQ ID NO: 19), and the like. The ordinarily skilled artisan will recognize that design of an AA can include linkers that are all or partially flexible, such that the linker can include a flexible linker as well as one or more portions that confer less flexible structure to provide for a desired AA structure.

(e) Additional Elements

In addition to the elements described above, the modified ABs and AAs can contain additional elements such as, for example, amino acid sequence N- or C-terminal of the AA. For example, AAs can include a targeting moiety to facilitate delivery to a cell or tissue of interest. Moreover, in the context of the AA libraries discussed further below, the AA can be provided in the context of a scaffold protein to facilitate display of the AA on a cell surface.

Exemplary Embodiments

The compositions and AAs provided here in can be useful for a variety of purposes including therapeutics and diagnostics.

An exemplary AA provided herein can be a legumain-activatable anti-EGFR coupled to a MM, plasmin-activatable anti-EGFR coupled to a MM, TMPRSS-3/4 activatable anti-EGFR coupled to a MM, legumain-activatable cetuximab coupled to a MM, plasmin-activatable cetuximab coupled to a MM, TMPRSS-3/4 activatable cetuximab coupled to a MM, legumain-activatable vectibix coupled to a MM, plasmin-activatable vectibix coupled to a MM, or a TMPRSS-3/4 activatable vectibix coupled to a MM. In some embodiments these AAs can be useful for the treatment of diagnosis of head and neck carcinomas, or colon, lung, or pancreatic carcinomas.

An exemplary AA provided herein can be a MMP9-activatable anti-TNFalpha coupled to a MM, MT1-MMP-activatable anti-TNFalpha coupled to a MM, cathepsin-activatable anti-TNFalpha coupled to a MM, MMP9-activatable infliximab coupled to a MM, MT1-MMP-activatable infliximab coupled to a MM, cathepsin-activatable infliximab coupled to a MM, MMP9-activatable adalimumab coupled to a MM, MT1-MMP-activatable adalimumab coupled to a MM, or a cathepsin-activatable adalimumab coupled to a MM. In some embodiments these AAs can be useful for the treatment of diagnosis of rheumatoid arthritis or multiple sclerosis.

An exemplary AA provided herein can be a legumain-activatable anti-CD11a coupled to a MM, plasmin-activatable anti-CD11a coupled to a MM, caspase-activatable anti-CD11a coupled to a MM, cathepsin-activatable anti-CD11a coupled to a MM, legumain-activatable efalizumab coupled to a MM, plasmin-activatable efalizumab coupled to a MM, caspase-activatable efalizumab coupled to a MM, cathepsin-activatable efalizumab coupled to a MM, legumain-activatable anti-CSFR coupled to a MM, plasmin-activatable anti-CSFR coupled to a MM, caspase-activatable anti-CSFR coupled to a MM, or a cathepsin-activatable anti-CSFR coupled to a MM. In some embodiments these AAs can be useful for the treatment or diagnosis of tumor associated macrophages for carcinomas.

An exemplary AA provided herein can be a plasmin-activatable anti-CTLA-4 coupled to a MM, caspase-activatable anti-CTLA-4 coupled to a MM, MT1-MMP-activatable anti-CTLA-4 coupled to a MM, plasmin-activatable ipilimumab coupled to a MM, caspase-activatable ipilimumab coupled to a MM, MT1-MMP-activatable ipilimumab coupled to a MM, plasmin-activatable tremelimumab coupled to a MM, caspase-activatable tremelimumab coupled to a MM, or a MT1-MMP-activatable tremelimumab coupled to a MM. In some embodiments these AAs can be useful for the treatment or diagnosis of malignant melanomas.

An exemplary AA provided herein can be a PSA-activatable anti-EPCAM coupled to a MM, legumain-activatable anti-EPCAM coupled to a MM, PSA-activatable adecatumumab coupled to a MM or a legumain-activatable adecatumumab coupled to a MM. In some embodiments these AAs can be useful for the treatment or diagnosis of prostate cancer.

An exemplary AA provided herein can be a human neutrophil elastase-activatable anti-CD40L coupled to a MM, or a human neutrophil elastase-activatable Hu5c8 coupled to a MM. In some embodiments these AAs can be useful for the treatment or diagnosis of lymphomas.

An exemplary AA provided herein can be a beta-secretase-activatable anti-Notch1 coupled to a MM, legumain-activatable anti-Notch1 coupled to a MM, plasmin-activatable anti-Notch1 coupled to a MM, uPA-activatable anti-Notch1 coupled to a MM, beta-secretase-activatable anti-Notch3 coupled to a MM, legumain-activatable anti-Notch3 coupled to a MM, plasmin-activatable anti-Notch3 coupled to a MM, uPA-activatable anti-Notch3 coupled to a MM, beta-secretase-activatable anti-Jagged1 coupled to a MM, legumain-activatable anti-Jagged1 coupled to a MM, plasmin-activatable anti-Jagged1 coupled to a MM, uPA-activatable anti-Jagged1 coupled to a MM, beta-secretase-activatable anti-Jagged2 coupled to a MM, legumain-activatable anti-Jagged2 coupled to a MM, plasmin-activatable anti-Jagged2 coupled to a MM, or a uPA-activatable anti-Jagged2 coupled to a MM. In some embodiments these AAs can be useful for the treatment or diagnosis of triple negative (ER, PR and Her2 negative) breast, head and neck, colon and other carcinomas.

An exemplary AA provided herein can be a MMP-activatable anti-CD52 coupled to a MM, or a MMP-activatable anti-campath coupled to a MM. In some embodiments these AAs can be useful for the treatment or diagnosis of multiple sclerosis.

An exemplary AA provided herein can be a MMP-activatable anti-MUC1 coupled to a MM, legumain-activatable anti-MUC1 coupled to a MM, plasmin-activatable anti-MUC1 coupled to a MM, or a uPA-activatable anti-MUC1 coupled to a MM. In some embodiments these AAs can be useful for the treatment or diagnosis of epithelial derived tumors.

An exemplary AA provided herein can be a legumain-activatable anti-IGF1R coupled to a MM, plasmin-activatable anti-IGF1R coupled to a MM, caspase-activatable anti-IGF1R coupled to a MM, legumain-activatable anti-figitumumab coupled to a MM, plasmin-activatable anti-figitumumab coupled to a MM, or a caspase-activatable anti-figitumumab coupled to a MM. In some embodiments these AAs can be useful for the treatment or diagnosis of non-small cell lung, and other epithelial tumors.

An exemplary AA provided herein can be a legumain-activatable anti-transferrin receptor coupled to a MM, plasmin-activatable anti-transferrin receptor coupled to a MM, or a caspase-activatable anti-transferrin receptor coupled to a MM. In some embodiments these AAs can be useful for the treatment or diagnosis of solid tumors, pancreatic tumors.

An exemplary AA provided herein can be a legumain-activatable anti-gp130 coupled to a MM, plasmin-activatable anti-gp130 coupled to a MM, or a uPA-activatable anti-gp130 coupled to a MM. In some embodiments these AAs can be useful for the treatment or diagnosis of solid tumors.

In certain other non-limiting exemplary embodiments, activatable antibody compositions include an legumain masked AB specific for Notch1, a uPA activatable masked AB specific for Jagged1, a plasmin activatable, masked anti-VEGF scFv, a MMP-9 activatable, masked anti-VCAM scFv, and a MMP-9 activatable masked anti-CTLA4.

These AAs are provided by way of example only and such enzyme activatable masked antibody AAs could be designed to any target as listed in but not limited to those in Table 1 and by using any antibody as listed in but not limited to those in Table 2.

Activatable Antibody Complexes

Figure 34:
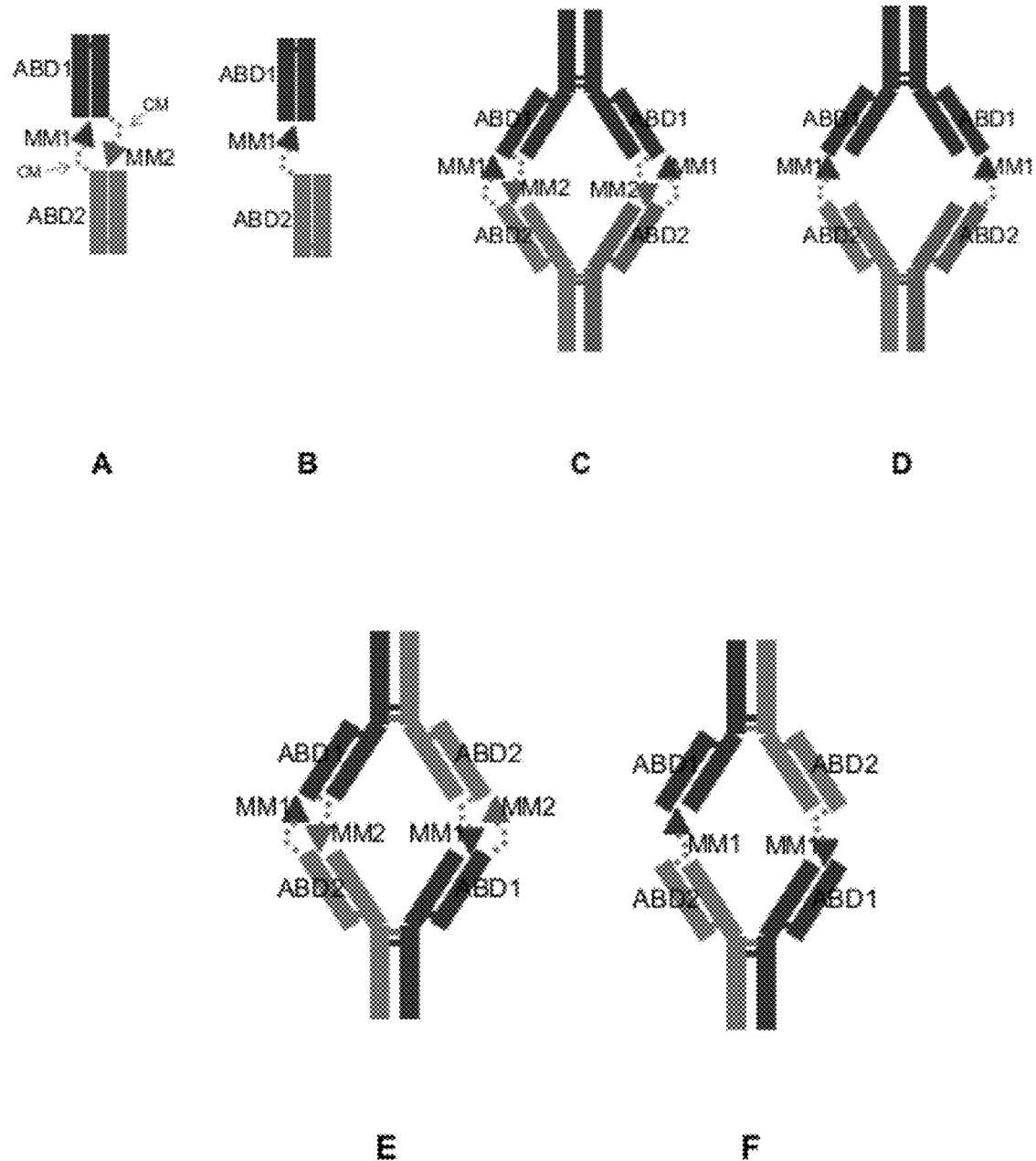
FIG. 34 shows protease-activated activatable antibody complexes (AACs) containing one or more antibodies or fragments thereof (in this figure the ABs are referred to as ABDs), a masking moiety (MM), and a cleavable moiety (CM), where ABD1 and ABD2 are arbitrary designations for first and second ABs. In such embodiments, the MM1 and MM2 bind the domains containing ABD1 and ABD2, respectively, and act as masking moieties to interfere with target binding to an uncleaved dual target-binding AAC. The target capable of binding the ABs may be the same or different target, or different binding sites of the same target. In some embodiments (FIGS. 1A, 1D, 1F), binding of MM1 to the domain containing ABD2 on the opposite molecule forms the complex capable of acting as a masking moiety of ABD1 and ABD2.
Figure 35:
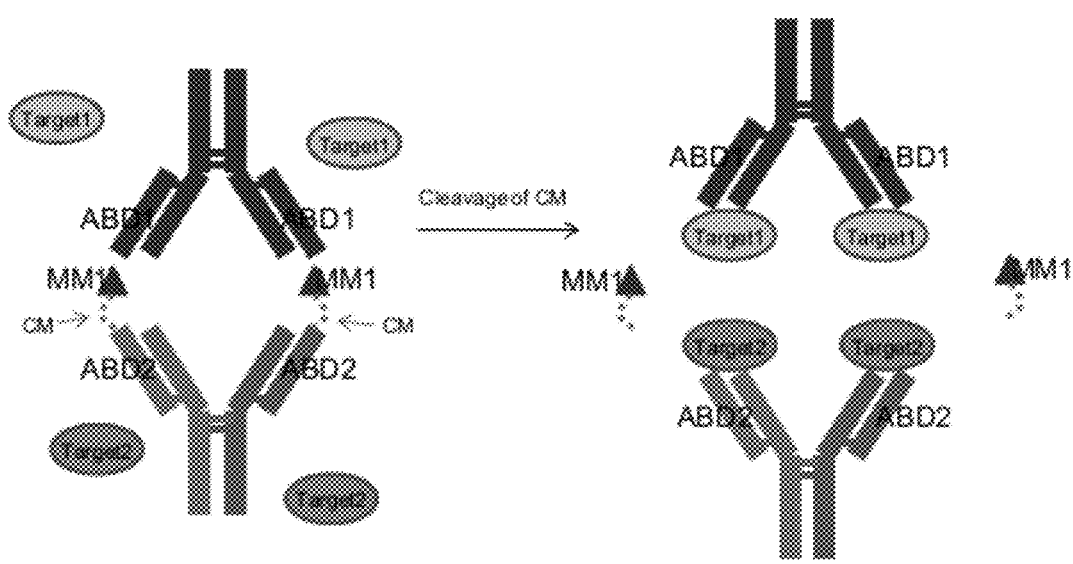
FIG. 35 shows an AAC with cross-masking occurring such that target binding by both ABs is attenuated in the uncleaved state, and target binding is increased in the presence of an agent that cleaves the CM allowing the complex to disassemble. In this figure the AB1 and AB2 are referred to as the ABD1 and ABD2, respectively.
Figure 36:
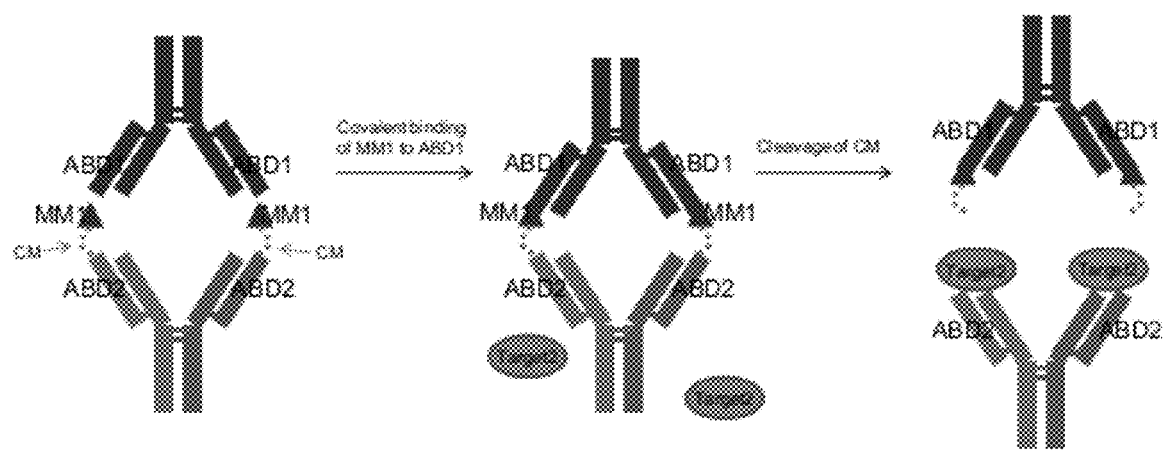
FIG. 36 shows an AAC formed by covalent linkage of MM1 with ABD1 (AB1) such that target binding by ABD2 (AB2) is attenuated in the uncleaved state, and target binding by ABD2 (AB2) is increased in the presence of an agent that cleaves the CM allowing the complex to disassemble. In this figure the AB1 and AB2 are referred to as the ABD1 and ABD2, respectively.

In one aspect of the invention, the AA exists as a complex (AAC) comprising two or more ABs, as depicted in FIGS. 34-36. The present disclosure provides complexes of activatable antibodies (AACs), which exhibit activatable/switchable binding to one or more target proteins. AACs generally include one or more antibodies or antibody fragments (ABs), masking moieties (MMs), and cleavable moieties (CMs). In some embodiments, the CM contains an amino acid sequence that serves as a substrate for a protease of interest. In other embodiments, the CM provides a cysteine-cysteine disulfide bond that is cleavable by reduction. The AAC exhibits an activatable conformation such that at least one AB is less accessible to target when unmodified than after modification of the CM, e.g., in the presence of a cleavage agent (e.g., a protease that recognizes the cleavage site of the CM) or a reducing agent (e.g. a reducing agent that reduces disulfide bonds in the CM).

The CM and AB of the AAC may be selected so that the AB represents a binding moiety for a target of interest, and the CM represents a substrate for a protease that is co-localized with the target at a treatment site in a subject. In some embodiments AACs can provide for reduced toxicity and/or adverse side effects that could otherwise result from binding of the ABs at non-treatment sites if they were not masked. In some embodiments, the AAC can further comprise a detectable moiety or a diagnostic agent. In certain embodiments the AAC is conjugated to a therapeutic agent located outside the antigen binding region. AACs can also be used in diagnostic and/or imaging methods or to detect the presence or absence of a cleaving agent in a sample.

A schematic of an AAC is provided in FIG. 34. As illustrated, the elements of the AAC are arranged so that the CM is positioned such that in a cleaved state (or relatively active state) and in the presence of a target, the AB binds a target, while in an uncleaved state (or relatively inactive state) in the presence of the target, binding of the ABs to the target is inhibited due to the masking of the ABs by the MM in the complex. As used herein, the term cleaved state refers to the condition of the AAC following cleavage of the CM by a protease and/or reduction of a cysteine-cysteine disulfide bond of the CM. The term uncleaved state, as used herein, refers to the condition of the AAC in the absence of cleavage of the CM by a protease and/or in the absence reduction of a cysteine-cysteine disulfide bond of the CM. As discussed above, the term AAC is used herein to refer to AAC in both its uncleaved (native) state, as well as in its cleaved state. It will be apparent to the ordinarily skilled artisan that in some embodiments a cleaved AAC may lack an MM due to cleavage of the CM by protease, resulting in release of at least the MM (e.g., where the MM is not joined to the AAC by a covalent bond.)

By activatable or switchable is meant that the AAC exhibits a first level of binding to a target when in a native or uncleaved state (i.e., a first conformation), and a second level of binding to the target in the cleaved state (i.e., a second conformation), where the second level of target binding is greater than the first level of binding. In general, access of target to the AB of the AAC is greater in the presence of a cleaving agent capable of cleaving the CM than in the absence of such a cleaving agent. Thus, in the native or uncleaved state the AB is masked from target binding (i.e., the first conformation is such that it interferes with access of the target to the AB), and in the cleaved state the AB is unmasked to target binding.

In general, an AAC can be designed by selecting an AB(s) of interest and constructing the remainder of the AAC so that, when conformationally constrained, the MM provides for masking of the AB. Dual target binding AACs contain two ABs, which may bind the same or different target. In specific embodiments, dual-targeting AACs contain bispecific antibodies or antibody fragments.

In certain embodiments, a complex is comprised of two activatable antibodies (AA), each containing an AB, CM, and MM such that cross-masking occurs—that is, the MM on one AA interferes with target binding by the AB on the other AA (FIG. 34A). In other embodiments, a complex is comprised of two AAs, with each AA containing an AB and one containing a CM and MM such that universal cross-masking occurs—that is, the MM effects formation of the complex and interferes with target binding by the ABs on both AAs (FIG. 34B). In other embodiments, a complex is comprised of two AAs, each containing two ABs, CMs, and MMs such that cross-masking occurs—that is, the MMs on one AA interfere with target binding by the ABs on the other AA (FIG. 34C). In other embodiments, a complex is comprised of two AAs, with one AA containing two ABs, CMs, and MMs such that universal cross-masking occurs—that is, the MMs interfere with target binding by the ABs on both AAs (FIG. 34D). In other embodiments, a complex is comprised of two molecules of a bispecific AA where the bispecific AA contains two ABs, CMs, and MMs such that cross-masking occurs in the complex—that is, the MM1 interferes with target binding by the AB1 on the opposite molecule, and the MM2 interferes with target binding by the AB2 on the opposite molecule (FIG. 34E). In other embodiments, a complex is comprised of two molecules of a bispecific AA where the bispecific AA contains two ABs, one CM, and one MM such that universal cross-masking occurs in the complex—that is, the MM interferes with target binding by both ABs (FIG. 34F).

In general, disassembly of the AAC and access of targets to at least one of the ABs of the AACs are greater in the presence of a cleaving agent capable of cleaving the CMs than in the absence of such a cleaving agent (FIG. 35). The two AAs of a complex may contain ABs that bind different targets, or that bind different epitopes on the same target.

One of the MM/AB pairs of the complex may be used for stable complex formation and have no therapeutic target on its own. A high affinity MM for the non-therapeutic AB allows a stable complex to form, even with a lower affinity MM for the therapeutic AB. The low affinity MM for the therapeutic AB, in the context of the multivalent complex, will be sufficient for masking the therapeutic AB, but after cleavage will more readily dissociate. For maximum target binding in the cleaved state, the difference in affinity of the MM and target for the AB should be maximized.

In other embodiments, an AB may form a covalent linkage to an MM on the opposite molecule of the complex. In the presence of a cleaving agent the complex disassembles such that at least one of the other ABs will bind its target (FIG. 36). Such a covalent linkage may form between reactive amino acid side chains in the MM and AB, eg. disulfide bond between cysteines, or by chemical conjugation of reactive groups to the MM and a catalytic AB. For examples of covalent binding antibodies see Chmura A. J. et al., Proc Natl Acad Sci USA. 2001 Jul. 17, 98(15): 8480-8484; Rader, C. et al., Proc Natl Acad Sci USA. 2003 Apr. 29, 100(9): 5396-5400; Armentano, F. et al., Immunology Letters 2006 Feb. 28, 103 (1): 51-57.

It should be noted that although MM and CM are indicated as distinct components, it is contemplated that the amino acid sequences of the MM and the CM could overlap, e.g., such that the CM is completely or partially contained within the MM. In many embodiments it may be desirable to insert one or more linkers, e.g., flexible linkers, into the AAC construct so as to provide for flexibility at one or more of the MM-CM junction, the CM-AB junction, or both. In addition to the elements described above, the AACs can contain additional elements such as, for example, amino acid sequence N- or C-terminal of the AAC.

Activatable Antibody Conjugates

In one aspect of the invention, the AB of the AA is further conjugated to an agent such as a therapeutic agent, thus producing activatable antibody conjugates (AACJs), a specific type of AA. The agent is attached either directly or via a linker to the AB. Such agents or linkers are selectively attached to those areas of ABs which are not a part of nor directly involved with the antigen binding site of the molecule. An exemplary AACJ is pictured in FIG. 20.

According to one embodiment of the present invention, an agent may be conjugated to an AB. When delivery and release of the agent conjugated to the AB are desired, immunoglobulin classes that are known to activate complement are used. In other applications, carrier immunoglobulins may be used which are not capable of complement activation. Such immunoglobulin carriers may include: certain classes of antibodies such IgM, IgA, IgD, IgE; certain subclasses of IgG; or certain fragments of immunoglobulins, e.g., half ABs (a single heavy: light chain pair), or Fab, Fab' or (Fab') 2 fragments.

Exemplary AACJs are AAs coupled to a therapeutic agent wherein the AB is directed to EGFR, CD44, Notch1, 2, 3 or 4 Jagged1 or 2, EpCAM, or IGF-1R.

The chemical linking methods described herein allow the resulting AACJ to retain the ability to bind antigen and to activate the complement cascade (when the unconjugated AA also had such ability). As a result, when the AACJ is administered to an individual, the subsequent formation of immune complexes with target antigens in vivo can activate the individual's serum complement system. The linker is designed to be susceptible to cleavage by complement and so the agent can be cleaved at the target site by one or more of the enzymes of the complement cascade. The majority of the release of the agent occurs following delivery to the target site.

In an exemplary embodiment, it is known that all cells of a tumor do not each possess the target antigenic determinant. Thus, delivery systems which require internalization into the target cell will effect successful delivery to those tumor cells that possess the antigenic determinant and that are capable of internalizing the conjugate. Tumor cells that do possess the antigenic determinant or are incapable of this internalization, will escape treatment. According to the method of the present invention, AACJs deliver the agent to the target cells. More importantly, however, once attached to the target cell, the method described in the present invention allows the release or activation of the active or activatable therapeutic agent. Release or activation may be mediated by the individual's activated by but not limited to the following: complement enzymes, tissue plasminogen activator, urokinase, plasmin or another enzyme having proteolytic activity, or by activation of a photosensitizer or substrate modification. Once released, the agent is then free to permeate the target sites, e.g., tumor mass. As a result, the agent will act on tumor cells that do not possess the antigenic determinant or could not internalize the conjugate. Additionally, the entire process is not dependent upon internalization of the conjugate.

(a) Methods for Conjugating Agents

The present invention utilizes several methods for attaching agents to ABs (which include antibodies and fragments thereof), two exemplary methods being attachment to the carbohydrate moieties of the AB, or attachment to sulfhydryl groups of the AB. In certain embodiments, the attachment does not significantly change the essential characteristics of the AB or the AA itself, such as immunospecificity and immunoreactivity. Additional considerations include simplicity of reaction and stability of the antibody conjugate produced. In certain embodiments the AB is first conjugated to one or more agents of interest followed by attachment of an MM and CM to produce an AACJ. In other embodiments the AB is first attached to a MM and CM following which an agent of interest is further conjugated producing an AACJ.

i. Attachment to Oxidized Carbohydrate Moieties

In certain embodiments, agents may be conjugated to the carbohydrate moiety of an AB. Some of the carbohydrate moieties are located on the Fc region of the immunoglobulin and are required in order for C1 binding to occur. The carbohydrate moiety of the Fc region of an immunoglobulin may be utilized in the scheme described herein in the embodiments where the AB is an antibody or antibody fragment that includes at least part of an Fc region. Alternatively, the Fab or Fab' fragments of any immunoglobulins which contain carbohydrate moieties may be utilized in the reaction scheme described herein. An example of such an immunoglobulin is the human IgM sequenced by Putnam et al. (1973, Science 182: 287).

The carbohydrate side chains of antibodies, Fab or Fab' fragments or other fragments containing an AB may be selectively oxidized to generate aldehydes. A variety of oxidizing agents can be used, such as periodic acid, paraperiodic acid, sodium metaperiodate and potassium metaperiodate. The resulting aldehydes may then be reacted with amine groups (e.g., ammonia derivatives such as primary amine, secondary amine, hydroxylamine, hydrazine, hydrazide, phenylhydrazine, semicarbazide or thiosemicarbazide) to form a Schiff base or reduced Schiff base (e.g., imine, enamine, oxime, hydrazone, phenylhydrazone, semicarbazone, thiosemicarbazone or reduced forms thereof). Chemical methods of oxidation of antibodies are provided in U.S. Pat. No. 4,867,973 and this patent is incorporated by reference in its entirety. Oxidation of antibodies with these oxidizing agents can be carried out by known methods. In the oxidation, the AB is used generally in the form of an aqueous solution, the concentration being generally less than 100 mg/ml, preferably 1 to 20 mg/ml. When an oxygen acid or a salt thereof is used as the oxidizing agent, it is used generally in the form of an aqueous solution, and the concentration is generally 0.001 to 10 mM, sometimes 1.0 to 10 mM. The amount of the oxygen acid or salt thereof depends on the kind of AB, but generally it is used in excess, for example, twice to ten times as much as the amount of the oxidizable carbohydrate. The optimal amount, however, can be determined by routine experimentation.

In the process for oxidizing ABs with oxygen acids or salts thereof, the optional ranges include a pH of from about 4 to 8, a temperature of from 0° to 37° C., and a reaction period of from about 15 minutes to 12 hours. During the oxidation with an oxygen acid or a salt thereof, the reaction can be carried in minimal light to prevent over oxidation.

Alternatively, the carbohydrate moiety of the AB may be modified by enzymatic techniques so as to enable attachment to or reaction with other chemical groups. One example of such an enzyme is galactose oxidase which oxidizes galactose in the presence of oxygen to form an aldehyde. Oxidation of the carbohydrate portion of ABs may also be done with the enzyme, galactose oxidase (Cooper et al., 1959, J. Biol. Chem. 234:445-448). The antibody is used in aqueous solution, the concentration being generally 0.5 to 20 mg/ml. The enzyme generally is used at about 5 to 100 units per ml of solution, at a pH ranging from about 5.5 to about 8.0. The influence of pH, substrate concentration, buffers and buffer concentrations on enzyme reaction are reported in Cooper et al., supra.

The AB conjugates, AA conjugates, or AB linker-intermediates of the invention may be produced by reacting the oxidized AB with any linker or agent having an available amine group selected from the group consisting of primary amine, secondary amine, hydrazine, hydrazide, hydroxylamine, phenylhydrazine, semicarbazide and thiosemicarbazide groups. In an exemplary method, a solution of the oxidized AB or AB linker at a concentration of from about 0.5 to 20 mg/ml is mixed with the agent or linker (molar ratios of reactive amine group to antibody aldehyde ranging from about 1 to about 10,000) and the solution incubated for from about 1 to 18 hours. Suitable temperatures are from 0° to 37° C. and pH may be from about 6 to 8. After the conjugates have been formed they can optionally be stabilized with a suitable reducing agent, such as sodium cyanoborohydride or sodium borohydride.

ii. Attachment to Sulfhydryl Groups

When the AB is a full-length antibody or includes at least part of the heavy chain, free sulfhydryl groups can be generated from the disulfide bonds of the immunoglobulin molecule. This is accomplished by mild reduction of the antibody. The disulfide bonds of IgG, which are generally susceptible to reduction, are those that link the two heavy chains. The disulfide bonds located near the antigen binding region of the antibody remain relatively unaffected. Such reduction results in the loss of ability to fix complement but does not interfere with antibody-antigen binding ability (Karush et al, 1979, Biochem. 18: 2226-2232). The free sulfhydryl groups generated in the intra-heavy chain region can then react with reactive groups of a linker or agent to form a covalent bond which will reduce interference with the antigen binding site of the immunoglobulin. Such reactive groups include, but are not limited to, reactive haloalkyl groups (including, for example, haloacetyl groups), p-mercuribenzoate groups and groups capable of Michael-type addition reactions (including, for example, maleimides and groups of the type described in Mitra and Lawton, 1979, J. Amer. Chem. Soc. 101: 3097-3110). The haloalkyl can be any alkyl group substituted with bromine, iodine or chlorine.

Details of the conditions, methods and materials suitable for mild reduction of antibodies and antibody fragments as described generally herein may be found in Stanworth and Turner, 1973, In Handbook of Experimental Immunology, Vol. 1, Second Edition, Weir (ed.), Chapter 10, Blackwell Scientific Publications, London, which chapter is incorporated herein by reference.

AB-agent conjugates (or AB-linker intermediates) which are produced by attachment to free sulfhydryl groups of reduced immunoglobulin or reduced antibody fragments do not or negligibly activate complement. Thus, these conjugates may be used in in vivo systems where cleavage and release of the agent is not desirable (e.g., an enzyme that acts on a specific substrate). Such conjugates may also be used when non-complement mediated release is desired. In such an embodiment, the agent may be linked to sulfhydryl groups on the reduced AB via linkers which are susceptible to cleavage by enzymes having proteolytic activity, including but not limited to trypsin, urokinase, plasmin, tissue plasminiogen activator and the like.

Although attachment of an agent to sulfhydryl groups of the AB reduces the complement fixation ability of the conjugate, such methods of attachment may be used to make AA conjugates for use in the complement-mediated release system. In such an embodiment, an agent joined to a complement-sensitive substrate linker can be attached to sulfhydryls of reduced ABs or AAs and delivered to the target in a mixture with non conjugated AAs that are capable of activating complement. The latter would activate complement which would cleave the agent from the former.

According to one embodiment of the present invention, for attachment to sulfhydryl groups of reduced ABs or AAs, the substrate linkers or the agents are modified by attaching an iodoalkyl group to one end of the linker. The unmodified site on the linker may or may not be covalently attached to an agent. For instance, the substrate linkers which are ester or amide linked to agents are modified by the addition of an iodoalkyl group thus forming an iodoalkyl derivative. As mentioned previously, the linker may be one that is susceptible or resistant to cleavage by activated complement, trypsin, plasmin, tissue plasminogen activator, urokinase or another specific enzyme having proteolytic activity.

(b) Agents for Conjugation to ABs

ABs may be attached to any agent which retains its essential properties after reaction with the AB, and which enables the AB to substantially retain immunospecificity and immunoreactivity allowing the AA to function as appropriate. The agent can include all chemical modifications and derivatives of agents which substantially retain their biological activity.

When it is desired to attach an aldehyde of the oxidized carbohydrate portion of an AB to an agent, the agent should contain an amine group selected from the group consisting of primary amine, secondary amine, hydrazine, hydrazide, hydroxylamine, phenylhydrazine, semicarbazide and thiosemicarbazide groups. If the agent does not contain any such amino group, the agent can be modified to introduce a suitable amine group available for coupling.

The agent to be attached to an AB for use in an AA is selected according to the purpose of the intended application (i.e., killing, prevention of cell proliferation, hormone therapy or gene therapy). Such agents may include but is not limited to, for example, pharmaceutical agents, toxins, fragments of toxins, alkylating agents, enzymes, antibiotics, antimetabolites, antiproliferative agents, hormones, neurotransmitters, DNA, RNA, siRNA, oligonucleotides, antisense RNA, aptamers, diagnostics, radioopaque dyes, radioactive isotopes, fluorogenic compounds, magnetic labels, nanoparticles, marker compounds, lectins, compounds which alter cell membrane permeability, photochemical compounds, small molecules, liposomes, micelles, gene therapy vectors, viral vectors, and the like. Non-limiting Table 4 lists some of the exemplary pharmaceutical agents that may be employed in the herein described invention but in no way is meant to be an exhaustive list. Finally, combinations of agents or combinations of different classes of agents may be used.

According to one embodiment of the present invention, photochemicals including photosensitizers and photothermolytic agents may be used as agents. Efficient photosensitizers include, but are not limited to porphyrins and modified porphyrins (e.g., hematoporphyrin, hematoporphyrin dihyddrazide, deuteroporphyrin dihydrazide and protoporphyrin dihydrazide), rose bengal, acridines, thiazines, xanthenes, anthraquinones, azines, flavin and nonmetal-containing porphyrins, porphyrin-like compounds, methylene blue, eosin, psoralin and the like. Other photosensitizers include, but are not limited to tetracyclines (e.g., dimethylchlor tetracycline) sulfonamides (e.g., sulfanilamide), griseofulvin, phenothiazines, (e.g., chlorpromazine), thiazides, sulfonylurea, and many others. Photochemicals may be designed or synthetically prepared to absorb light at specific wavelengths. Photothermolytic agents, such as Azure A, which are activated at the site of action by a light source (see Anderson and Parrish, 1983, Science 220: 524-527) may be utilized as agents.

According to another embodiment of the present invention, enzymes that catalyze substrate modification with the production of cytotoxic by-products may be used as agents. Examples of such enzymes include but are not limited to glucose oxidase, galactose oxidase, xanthene oxidase and the like.

TABLE 4

Exemplary Pharmaceutical Agents for Conjugation

| NAME/CLASS | LINKAGE | MANUFACTURERS(S) |
|---|---|---|
| I. ANTIBACTERIALS | | |
| Aminoglycosides | | |
| Streptomycin | ester/amide | |
| Neomycin | ester/amide | Dow, Lilly, Dome, Pfipharmics |
| Kanamycin | ester/amide | Bristol |
| Amikacin | ester | Bristol |
| Gentamicin | ester/amide | Upjohn, Wyeth, Schering |
| Tobramycin | ester/amide | Lilly |
| Streptomycin B | ester/amide | Squibb |
| Spectinomycin | ester | Upjohn |
| Ampicillin | amide | Squibb, Parke-Davis, Comer, Wyeth, Upjohn, Bristol, SKF |
| Sulfanilamide | amide | Merrell-National Burroughs-Wellcome, Dow, |
| Polymyxin | amide | Parke-Davis |
| Chloramphenicol | ester | Parke-Davis |
| II. ANTIVIRALS | | |
| Acyclovir | | Burroughs-Wellcome |
| Vira A | ester/amide | Parke-Davis |
| Symmetrel | amide | Endo |
| III. ANTIFUNGALS | | |
| Nystatin | ester | Squibb, Primo, Lederle, Pfizer, Holland-Rantor |
| IV. ANTINEOPLASTICS | | |
| Adriamycin | ester/amide | Adria |
| Cerubidine | ester/amide | Ives |
| Bleomycin | ester/amide | Bristol |
| Alkeran | amide | Burroughs-Wellcome |
| Velban | ester | Lilly |
| Oncovin | ester | Lilly |
| Fluorouracil | ester | Adria, Roche, Herbert |
| Methotrexate | amide | Lederle |

TABLE 4-continued

Exemplary Pharmaceutical Agents for Conjugation

| NAME/CLASS | LINKAGE | MANUFACTURERS(S) |
|---|---|---|
| Thiotepa | — | Lederle |
| Bisantrene | — | Lederle |
| Novantrone | ester | Lederle |
| Thioguanine | amide | Burroughs-Wellcome |
| Procarabizine | — | Hoffman La Roche |
| Cytarabine | — | Upjohn |
| V. RADIO-PHARMACEUTICALS | | |
| $^{125}$I | | |
| $^{131}$I | | |
| $^{99m}$Tc (Technetium) | | |
| VI. HEAVY METALS | | |
| Barium | | |
| Gold | | |
| Platinum | | |
| VII. ANTIMYCOPLASMALS | | |
| Tylosine | | |
| Spectinomycin | | |

(c) Linkers for Conjugating Agents

The present invention utilizes several methods for attaching agents to ABs: (a) attachment to the carbohydrate moieties of the AB, or (b) attachment to sulfhydryl groups of the AB. According to the invention, ABs may be covalently attached to an agent through an intermediate linker having at least two reactive groups, one to react with AB and one to react with the agent. The linker, which may include any compatible organic compound, can be chosen such that the reaction with AB (or agent) does not adversely affect AB reactivity and selectivity. Furthermore, the attachment of linker to agent might not destroy the activity of the agent. Suitable linkers for reaction with oxidized antibodies or oxidized antibody fragments include those containing an amine selected from the group consisting of primary amine, secondary amine, hydrazine, hydrazide, hydroxylamine, phenylhydrazine, semicarbazide and thiosemicarbazide groups. Such reactive functional groups may exist as part of the structure of the linker, or may be introduced by suitable chemical modification of linkers not containing such groups.

According to the present invention, suitable linkers for attachment to reduced ABs include those having certain reactive groups capable of reaction with a sulfhydryl group of a reduced antibody or fragment. Such reactive groups include, but are not limited to: reactive haloalkyl groups (including, for example, haloacetyl groups), p-mercuribenzoate groups and groups capable of Michael-type addition reactions (including, for example, maleimides and groups of the type described by Mitra and Lawton, 1979, J. Amer. Chem. Soc. 101: 3097-3110).

The agent may be attached to the linker before or after the linker is attached to the AB. In certain applications it may be desirable to first produce an AB-linker intermediate in which the linker is free of an associated agent. Depending upon the particular application, a specific agent may then be covalently attached to the linker. In other embodiments the AB is first attached to the MM, CM and associated linkers and then attached to the linker for conjugation purposes.

(i) Branched Linkers:

In specific embodiments, branched linkers which have multiple sites for attachment of agents are utilized. For multiple site linkers, a single covalent attachment to an AB would result in an AB-linker intermediate capable of binding an agent at a number of sites. The sites may be aldehyde or sulfhydryl groups or any chemical site to which agents can be attached.

Alternatively, higher specific activity (or higher ratio of agents to AB) can be achieved by attachment of a single site linker at a plurality of sites on the AB. This plurality of sites may be introduced into the AB by either of two methods. First, one may generate multiple aldehyde groups and/or sulfhydryl groups in the same AB. Second, one may attach to an aldehyde or sulfhydryl of the AB a "branched linker" having multiple functional sites for subsequent attachment to linkers. The functional sites of the branched linker or multiple site linker may be aldehyde or sulfhydryl groups, or may be any chemical site to which linkers may be attached. Still higher specific activities may be obtained by combining these two approaches, that is, attaching multiple site linkers at several sites on the AB.

(ii) Cleavable Linkers:

Peptide linkers which are susceptible to cleavage by enzymes of the complement system, such as but not limited to urokinase, tissue plasminogen activator, trypsin, plasmin, or another enzyme having proteolytic activity may be used in one embodiment of the present invention. According to one method of the present invention, an agent is attached via a linker susceptible to cleavage by complement. The antibody is selected from a class which can activate complement. The antibody-agent conjugate, thus, activates the complement cascade and releases the agent at the target site. According to another method of the present invention, an agent is attached via a linker susceptible to cleavage by enzymes having a proteolytic activity such as a urokinase, a tissue plasimogen activator, plasmin, or trypsin. Non-liming examples of cleavable linker sequences are provided in Table 5.

TABLE 5

Exemplary Linker Sequences for Conjugation

| Types of Cleavable Sequences | Amino Acid Sequence |
|---|---|
| Plasmin cleavable sequences | |
| Pro-urokinase | PRFKIIGG (SEQ ID NO: 20) |
| | PRFRIIGG (SEQ ID NO: 21) |
| TGFβ | SSRHRRALD (SEQ ID NO: 22) |
| Plasminogen | RKSSIIIRMRDVVL (SEQ ID NO: 23) |
| Staphylokinase | SSSFDKGKYKKGDDA (SEQ ID NO: 24) |
| | SSSFDKGKYKRGDDA (SEQ ID NO: 25) |
| Factor Xa cleavable sequences | IEGR (SEQ ID NO: 26) |
| | IDGR (SEQ ID NO: 27) |
| | GGSIDGR (SEQ ID NO: 28) |
| MMP cleavable sequences | |
| Gelatinase A | PLGLWA (SEQ ID NO: 29) |
| Collagenase cleavable sequences | |
| Calf skin collagen (α1(I) chain) | GPQGIAGQ (SEQ ID NO: 30) |
| Calf skin collagen (α2(I) chain) | GPQGLLGA (SEQ ID NO: 31) |
| Bovine cartilage collagen (α1(II) chain) | GIAGQ (SEQ ID NO: 32) |
| Human liver collagen (α1(III) chain) | GPLGIAGI (SEQ ID NO: 33) |
| Human α$_2$M | GPEGLRVG (SEQ ID NO: 34) |
| Human PZP | YGAGLGVV (SEQ ID NO: 35) |
| | AGLGVVER (SEQ ID NO: 36) |
| | AGLGISST (SEQ ID NO: 37) |
| Rat α$_1$M | EPQALAMS (SEQ ID NO: 38) |
| | QALAMSAI (SEQ ID NO: 39) |
| Rat α$_2$M | AAYHLVSQ (SEQ ID NO: 40) |
| | MDAFLESS (SEQ ID NO: 41) |
| Rat α$_1$I$_3$(2J) | ESLPVVAV (SEQ ID NO: 42) |
| Rat α$_1$I$_3$(27J) | SAPAVESE (SEQ ID NO: 43) |
| Human fibroblast collagenase (autolytic cleavages) | DVAQFVLT (SEQ ID NO: 44) |
| | VAQFVLTE (SEQ ID NO: 45) |
| | AQFVLTEG (SEQ ID NO: 46) |
| | PVQPIGPQ (SEQ ID NO: 47) |

In addition agents may be attached via disulfide bonds (for example, the disulfide bonds on a cysteine molecule) to the AB. Since many tumors naturally release high levels of glutathione (a reducing agent) this can reduce the disulfide bonds with subsequent release of the agent at the site of delivery. In certain specific embodiments the reducing agent that would modify a CM would also modify the linker of the conjugated AA.

(iii) Spacers and Cleavable Elements:

In still another embodiment, it may be necessary to construct the linker in such a way as to optimize the spacing between the agent and the AB of the AA. This may be accomplished by use of a linker of the general structure:

wherein
W is either —NH—CH2- or —CH2-;
Q is an amino acid, peptide; and
n is an integer from 0 to 20.

In still other embodiments, the linker may comprise a spacer element and a cleavable element. The spacer element serves to position the cleavable element away from the core of the AB such that the cleavable element is more accessible to the enzyme responsible for cleavage. Certain of the branched linkers described above may serve as spacer elements.

Throughout this discussion, it should be understood that the attachment of linker to agent (or of spacer element to cleavable element, or cleavable element to agent) need not be particular mode of attachment or reaction. Any reaction providing a product of suitable stability and biological compatibility is acceptable.

(iv) Serum Complement and Selection of Linkers:

According to one method of the present invention, when release of an agent is desired, an AB that is an antibody of a class which can activate complement is used. The resulting conjugate retains both the ability to bind antigen and activate the complement cascade. Thus, according to this embodiment of the present invention, an agent is joined to one end of the cleavable linker or cleavable element and the other end of the linker group is attached to a specific site on the AB. For example, if the agent has an hydroxy group or an amino group, it may be attached to the carboxy terminus of a peptide, amino acid or other suitably chosen linker via an ester or amide bond, respectively. For example, such agents may be attached to the linker peptide via a carbodimide reaction. If the agent contains functional groups that would interfere with attachment to the linker, these interfering functional groups can be blocked before attachment and deblocked once the product conjugate or intermediate is made. The opposite or amino terminus of the linker is then used either directly or after further modification for binding to an AB which is capable of activating complement.

Linkers (or spacer elements of linkers) may be of any desired length, one end of which can be covalently attached to specific sites on the AB of the AA. The other end of the linker or spacer element may be attached to an amino acid or peptide linker.

Thus when these conjugates bind to antigen in the presence of complement the amide or ester bond which attaches the agent to the linker will be cleaved, resulting in release of the agent in its active form. These conjugates, when administered to a subject, will accomplish delivery and release of the agent at the target site, and are particularly effective for the in vivo delivery of pharmaceutical agents, antibiotics, antimetabolites, antiproliferative agents and the like as presented in but not limited to those in Table 4.

(v) Linkers for Release without Complement Activation:

In yet another application of targeted delivery, release of the agent without complement activation is desired since activation of the complement cascade will ultimately lyse the target cell. Hence, this approach is useful when delivery and release of the agent should be accomplished without killing the target cell. Such is the goal when delivery of cell mediators such as hormones, enzymes, corticosteroids, neurotransmitters, genes or enzymes to target cells is desired. These conjugates may be prepared by attaching the agent to an AB that is not capable of activating complement via a linker that is mildly susceptible to cleavage by serum proteases. When this conjugate is administered to an individual, antigen-antibody complexes will form quickly whereas cleavage of the agent will occur slowly, thus resulting in release of the compound at the target site.

(vi) Biochemical Cross Linkers:

In other embodiments, the AA may be conjugated to one or more therapeutic agents using certain biochemical cross-linkers. Cross-linking reagents form molecular bridges that tie together functional groups of two different molecules. To link two different proteins in a step-wise manner, hetero-bifunctional cross-linkers can be used that eliminate unwanted homopolymer formation. Exemplary hetero-bifunctional cross-linkers are referenced in Table 6.

TABLE 6

Exemplary Hetero-Bifunctional Cross Linkers
HETERO-BIFUNCTIONAL CROSS-LINKERS

| Linker | Reactive Toward | Advantages and Applications | Spacer Arm Length after cross-linking |
|---|---|---|---|
| SMPT | Primary amines Sulfhydryls | Greater stability | 11.2 A |
| SPDP | Primary amines Sulfhydryls | Thiolation Cleavable cross-linking | 6.8 A |
| LC-SPDP | Primary amines Sulfhydryls | Extended spacer arm | 15.6 A |
| Sulfo-LC-SPDP | Primary amines Sulfhydryls | Extender spacer arm Water-soluble | 15.6 A |
| SMCC | Primary amines | Stable maleimide reactive group | 11.6 A |
|  | Sulfhydryls | Enzyme-antibody conjugation Hapten-carrier protein conjugation |  |
| Sulfo-SMCC | Primary amines | Stable maleimide reactive group | 11.6 A |
|  | Sulfhydryls | Water-soluble Enzyme-antibody conjugation |  |
| MBS | Primary amines Sulfhydryls | Enzyme-antibody conjugation Hapten-carrier protein conjugation | 9.9 A |
| Sulfo-MBS | Primary amines Sulfhydryls | Water-soluble | 9.9 A |
| SIAB | Primary amines Sulfhydryls | Enzyme-antibody conjugation | 10.6 A |
| Sulfo-SIAB | Primary amines Sulfhydryls | Water-soluble | 10.6 A |
| SMPB | Primary amines Sulfhydryls | Extended spacer arm Enzyme-antibody conjugation | 14.5 A |
| Sulfo-SMPB | Primary amines Sulfhydryls | Extended spacer arm Water-soluble | 14.5 A |
| EDE/Sulfo-NHS | Primary amines Carboxyl groups | Hapten-Carrier conjugation | 0 |
| ABH | Carbohydrates Nonselective | Reacts with sugar groups | 11.9 A |

(vii) Non-Cleavable Linkers or Direct Attachment:

In still other embodiments of the invention, the conjugate may be designed so that the agent is delivered to the target but not released. This may be accomplished by attaching an agent to an AB either directly or via a non-cleavable linker.

These non-cleavable linkers may include amino acids, peptides, D-amino acids or other organic compounds which may be modified to include functional groups that can subsequently be utilized in attachment to ABs by the methods described herein. A-general formula for such an organic linker could be $$W-(CH2)n-Q$$

wherein W is either —NH—CH2- or —CH2-;
Q is an amino acid, peptide; and
n is an integer from 0 to 20.

(viii) Non-Cleavable Conjugates:

Alternatively, a compound may be attached to ABs which do not activate complement. When using ABs that are incapable of complement activation, this attachment may be accomplished using linkers that are susceptible to cleavage by activated complement or using linkers that are not susceptible to cleavage by activated complement.

(d) Uses of Activatable Antibody Conjugates

The AA-agent conjugates (AACJs) of the invention are useful in therapeutics, diagnostics, substrate modification and the like.

The AACJs of the invention are useful in a variety of therapeutic in vivo applications such as but not limited to the treatment of neoplasms, including cancers, adenomas, and hyperplasias; certain immunological disorders, including autoimmune diseases, graft-versus-host diseases (e.g., after bone marrow transplantation), immune suppressive diseases, e.g., after kidney or bone marrow transplantation. Treatment of such cellular disorders involving, for example, bone marrow transplantation, may include purging (by killing) undesired cells, e.g., malignant cells or mature T lymphocytes.

Therapeutic applications center generally on treatment of various cellular disorders, including those broadly described above, by administering an effective amount of the antibody-agent conjugates of the invention. The properties of the antibody are such that it is immunospecific for and immunoreactive with a particular antigen render it ideally suited for delivery of agents to specific cells, tissues, organs or any other site having that particular antigen.

According to this aspect of the invention, the AACJ functions to deliver the conjugate to the target site.

The choice of ABs, linkers, and agents used to make the AACJs depends upon the purpose of delivery. The delivery and release or activation of agents at specific target sites may result in selective killing or inhibition of proliferation of tumor cells, cancer cells, fungi, bacteria, parasites, or virus. The targeted delivery of hormones, enzymes, or neurotransmitters to selected sites may also be accomplished. Ultimately the method of the present invention may have an application in gene therapy programs wherein DNA or specific genes may be delivered in vivo or in vitro to target cells that are deficient in that particular gene. Additionally, the conjugates may be used to reduce or prevent the activation of oncogenes, such as myc, ras and the like.

In vivo administration may involve use of agents of AACJs in any suitable adjuvant including serum or physiological saline, with or without another protein, such as human serum albumin. Dosage of the conjugates may readily be determined by one of ordinary skill, and may differ depending upon the nature of the cellular disorder and the agent used. Route of administration may be parenteral, with intravenous administration generally preferred.

(i) Substrate Modification

In an alternate embodiment of the present invention, substrate activation by the agent may be used to mediate formation of singlet oxygen or peroxides and induce cell killing. In this particular embodiment, the agent is an enzyme. For example, galactose oxidase will oxidize galactose and some galactose derivatives at the C 6 position. In the course of the oxidation reaction, molecular oxygen is converted into hydrogen peroxide which is toxic to neighboring cells. The enzyme glucose oxidase, a flavoenzyme, may also be used in the embodiment of this invention. This enzyme is highly specific for β-D-glucose and can act as an antibiotic due to peroxide formation. The enzyme may be attached to an AB either directly or via a non-cleavable linker. A subject is given an effective dosage of this AACJ and is then perfused with substrate. Cell killing is mediated through the formation of peroxides by the methods described above. The toxic effect of peroxides may be amplified by administration of a second enzyme, preferably of human origin, to convert its peroxide to a more toxic hypochlorous acid. Examples of suitable enzymes include but are not limited to myeloperoxidase, lactoperoxidase and chloroperoxidase.

Display Methods and Compositions for Identifying and/or Optimizing AAs

Methods for identifying and optimizing AAs, as well as compositions useful in such methods, are described below.

(a) Libraries of AAs or Candidate AAs Displayed on Replicable Biological Entities In general, the screening methods to identify an AA and/or to optimize an AA for a switchable phenotype can involve production of a library of replicable biological entities that display on their surface a plurality of different candidate AAs. These libraries can then be subjected to screening methods to identify candidate AAs having one or more desired characteristics of an AA.

The candidate AA libraries can contain candidate AAs that differ by one or more of the MM, linker (which may be part of the MM), CM (which may be part of the MM), and AB. In one embodiment the AAs in the library are variable for the MM and/or the linker, with the AB and CM being preselected. Where the AA is to include pairs of cysteine residues to provide a disulfide bond in the AA, the relative position of the cysteines in the AA can be varied.

The library for screening is generally provided as a library of replicable biological entities which display on their surface different candidate AAs. For example, a library of candidate AAs can include a plurality of candidate AAs displayed on the surface of population of a replicable biological entities, wherein each member of said plurality of candidate AAs comprises: (a) an antibody or fragment thereof (AB); (b) a cleavable moiety (CM); and (c) a candidate masking moiety (candidate MM), wherein the AB, CM and candidate MM are positioned such that the ability of the candidate MM to inhibit binding of the AB to a target in an uncleaved state and allow binding of the AB to the target in a cleaved state can be determined. Suitable replicable biological entities include cells (e.g., bacteria (e.g., E. coli), yeast (e.g., S. cerevesiae), protozoan cells, mammalian cells), bacteriophage, and viruses. Antibody display technologies are well known in the art.

(b) Display of Candidate AAs on the Surface of Replicable Biological Entities

A variety of display technologies using replicable biological entities are known in the art. These methods and entities include, but are not limited to, display methodologies such as mRNA and ribosome display, eukaryotic virus display, and bacterial, yeast, and mammalian cell surface display. See Wilson, D. S., et al. 2001 *PNAS USA* 98(7):3750-3755; Muller, O. J., et al. (2003) *Nat. Biotechnol.* 3:312; Bupp, K. and M. J. Roth (2002) *Mol. Ther.* 5(3):329 3513; Georgiou, G., et al., (1997) *Nat. Biotechnol.* 15(1):29 3414; and Boder, E. T. and K. D. Wittrup (1997) *Nature Biotech.* 15(6):553 557. Surface display methods are attractive since they enable application of fluorescence-activated cell sorting (FACS) for library analysis and screening. See Daugherty, P. S., et al. (2000) *J. Immuunol. Methods* 243(1 2):211 2716; Georgiou, G. (2000) *Adv. Protein Chem.* 55:293 315; Daugherty, P. S., et al. (2000) *PNAS USA* 97(5):2029 3418; Olsen, M. J., et al. (2003) *Methods Mol. Biol.* 230:329 342; Boder, E. T. et al. (2000) *PNAS USA* 97(20):10701 10705; Mattheakis, L. C., et al. (1994) *PNAS USA* 91(19): 9022 9026; and Shusta, E. V., et al. (1999) *Curr. Opin. Biotech.* 10(2):117 122. Additional display methodologies which may be used to identify a peptide capable of binding to a biological target of interest are described in U.S. Pat. No. 7,256,038, the disclosure of which is incorporated herein by reference.

A display scaffold refers to a polypeptide which when expressed in a host cell is presented on an extracellularly accessible surface of the host cell and provides for presentation of an operably linked heterologous polypeptide. For example, display scaffolds find use in the methods disclosed herein to facilitate screening of candidate AAs. Display scaffolds can be provided such that a heterologous polypeptide of interest can be readily released from the display scaffold, e.g. by action of a protease that facilitates cleavage of the fusion protein and release of a candidate AA from the display scaffold.

Phage display involves the localization of peptides as terminal fusions to the coat proteins, e.g., pIII, pIV of bacteriophage particles. See Scott, J. K. and G. P. Smith (1990) *Science* 249(4967):386 390; and Lowman, H. B., et al. (1991) *Biochem.* 30(45):10832 10838. Generally, polypeptides with a specific function of binding are isolated by incubating with a target, washing away non-binding phage, eluting the bound phage, and then re-amplifying the phage population by infecting a fresh culture of bacteria.

Exemplary phage display and cell display compositions and methods are described in U.S. Pat. Nos. 5,223,409; 5,403,484; 7,118,159; 6,979,538; 7,208,293; 5,571,698; and 5,837,500.

Additional exemplary display scaffolds and methods include those described in U.S. Patent Application Publication No: 2007/0065158, published Mar. 22, 2007.

Optionally, the display scaffold can include a protease cleavage site (different from the protease cleavage site of the CM) to allow for cleavage of an AA or candidate AA from a surface of a host cell.

In one embodiment, where the replicable biological entity is a bacterial cell, suitable display scaffolds include circularly permuted *Escherichia coli* outer membrane protein OmpX (CPX) described by Rice et al, *Protein Sci.* (2006) 15: 825-836. See also, U.S. Pat. No. 7,256,038, issued Aug. 14, 2007.

(c) Constructs Encoding AAs

The disclosure further provides nucleic acid constructs which include sequences coding for AAs and/or candidate AAs. Suitable nucleic acid constructs include, but are not limited to, constructs which are capable of expression in a prokaryotic or eukaryotic cell. Expression constructs are generally selected so as to be compatible with the host cell in which they are to be used.

For example, non-viral and/or viral constructs vectors may be prepared and used, including plasmids, which provide for replication of an AA- or candidate AA-encoding DNA and/or expression in a host cell. The choice of vector will depend on the type of cell in which propagation is desired and the purpose of propagation. Certain constructs are useful for amplifying and making large amounts of the desired DNA sequence. Other vectors are suitable for expression in cells in culture. The choice of appropriate vector is well within the skill of the art. Many such vectors are available commercially. Methods for generating constructs can be accomplished using methods well known in the art.

In order to effect expression in a host cell, the polynucleotide encoding an AA or candidate AA is operably linked to a regulatory sequence as appropriate to facilitate the desired expression properties. These regulatory sequences can include promoters, enhancers, terminators, operators, repressors, silencers, inducers, and 3' or 5' UTRs. Expression constructs generally also provide a transcriptional and translational initiation region as may be needed or desired, which may be inducible or constitutive, where the coding region is operably linked under the transcriptional control of the transcriptional initiation region, and a transcriptional and translational termination region. These control regions may be native to the species from which the nucleic acid is obtained, or may be derived from exogenous sources.

Promoters may be either constitutive or regulatable. In some situations it may be desirable to use conditionally active promoters, such as inducible promoters, e.g., temperature-sensitive promoters. Inducible elements are DNA sequence elements that act in conjunction with promoters and may bind either repressors (e.g. lacO/LAC Iq repressor system in *E. coli*) or inducers (e.g. gall/GAL4 inducer system in yeast). In such cases, transcription is virtually shut off until the promoter is de-repressed or induced, at which point transcription is turned-on.

Constructs, including expression constructs, can also include a selectable marker operative in the host to facilitate, for example, growth of host cells containing the construct of interest. Such selectable marker genes can provide a phenotypic trait for selection of transformed host cells such as dihydrofolate reductase or neomycin resistance for eukaryotic cell culture.

Expression constructs can include convenient restriction sites to provide for the insertion and removal of nucleic acid sequences encoding the AA and/or candidate AA. Alternatively or in addition, the expression constructs can include flanking sequences that can serve as the basis for primers to facilitate nucleic acid amplification (e.g., PCR-based amplification) of an AA-coding sequence of interest.

The above described expression systems may be employed with prokaryotes or eukaryotes in accordance with conventional ways, depending upon the purpose for expression. In some embodiments, a unicellular organism, such as *E. coli, B. subtilis, S. cerevisiae*, insect cells in combination with baculovirus vectors, or cells of a higher organism such as vertebrates, e.g. COS 7 cells, HEK 293, CHO, *Xenopus Oocytes*, etc., may be used as the expression host cells. Expression systems for each of these classes and types of host cells are known in the art.

(d) Methods of Making Libraries of AAs/Candidate AAs Displayed on Replicable Biological Entities The present disclosure contemplates methods of making the libraries of AAs and/or candidate AAs described herein.

In one embodiment, a method of making an AA library and/or candidate AA library comprises: (a) constructing a set of recombinant DNA vectors as described herein that encode a plurality of AAs and/or candidate AAs; (b) transforming host cells with the vectors of step (a); and (c) culturing the host cells transformed in step (b) under conditions suitable for expression and display of the fusion polypeptides.

(e) Production of Nucleic Acid Sequences Encoding Candidate AAs

Production of candidate AAs for use in the screening methods can be accomplished using methods known in the art. Polypeptide display, single chain antibody display, antibody display and antibody fragment display are methods well known in the art. In general, an element of an AA e.g., MM, to be varied in the candidate AA library is selected for randomization. The candidate AAs in the library can be fully randomized or biased in their randomization, e.g. in nucleotide/residue frequency generally or in position of amino acid(s) within an element.

Methods of Screening for AAs

The present disclosure provides methods of identifying AAs, which can be enzymatically activated AAs, reducing agent-susceptible AAs, or an AA that is activatable by either or both of enzymatic activation or reducing agent-based activation. Generally, the methods include contacting a plurality of candidate AAs with a target capable of binding an AB of the AAs and a protease capable of cleaving a CM of the AAs, selecting a first population of members of said plurality which bind to the target when exposed to protease, contacting said first population with the target in the absence of the protease, and selecting a second population of members from said first population by depleting from said first population members that bind the target in the absence of the protease, wherein said method provides for selection of candidate AAs which exhibit decreased binding to the target in the absence of the protease as compared to target binding in the presence of the protease.

In general, the method for screening for candidate AAs having a desired switchable phenotype is accomplished through a positive screening step (to identify members that bind target following exposure to protease) and a negative screening step (to identify members that do not bind target when not exposed to protease). The negative screening step can be accomplished by, for example, depleting from the population members that bind the target in the absence of the protease. It should be noted that the library screening methods described herein can be initiated by conducting the negative screening first to select for candidates that do not bind labeled target in the absence of enzyme treatment (i.e., do not bind labeled target when not cleaved), and then conducting the positive screening (i.e., treating with enzyme and selecting for members which bind labeled target in the cleaved state). However, for convenience, the screening method is described below with the positive selection as a first step.

The positive and negative screening steps can be conveniently conducted using flow cytometry to sort candidate AAs based on binding of a detectably labeled target. One round or cycle of the screening procedure involves both a positive selection step and a negative selection step. The methods may be repeated for a library such that multiple cycles (including complete and partial cycles, e.g., 1.5 cycles, 2.5 cycles, etc.) are performed. In this manner, members of the plurality of candidate AAs that exhibit the switching characteristics of an AA may be enriched in the resulting population.

In general, the screening methods are conducted by first generating a nucleic acid library encoding a plurality of candidate AAs in a display scaffold, which is in turn introduced into a display scaffold for expression on the surface of a replicable biological entity. As used herein, a plurality of candidate AAs refers to a plurality of polypeptides having amino acid sequences encoding candidate AAs, where members of the plurality are variable with respect to the amino acid sequence of at least one of the components of an AA, e.g., the plurality is variable with respect to the amino acid sequence of the MM, the CM or the AB, usually the MM.

For example, the AB and CM of the candidate AAs are held fixed and the candidate AAs in the library are variable with respect to the amino acid sequence of the MM. In another example, a library can be generated to include candidate AAs having an MM that is designed to position a cysteine residue such that disulfide bond formation with another cysteine in the candidate AA is favored (with other residues selected to provide an MM having an amino acid sequence that is otherwise fully or at least partially randomized). In another example, a library can be generated to include candidate AAs in which the MM includes a fully randomized amino acid sequence. Such libraries can contain candidate AAs designed by one or more of these criterion. By screening members of said plurality according to the methods described herein, members having candidate MMs that provide a desired switchable phenotype can be identified.

In one embodiment of the methods, each member of the plurality of candidate AAs is displayed on the surface of a replicable biological entity (exemplified here by bacterial cells). The members of the plurality are exposed to a protease capable of cleaving the CM of the candidate AAs and contacted with a target which is a binding partner of the AB of the candidate AAs. Bacterial cells displaying members comprising ABs which bind the target after exposure to the protease are identified and/or separated via detection of target binding (e.g., detection of a target-AB complex). Members comprising ABs which bind the target after protease exposure (which can lead to cleavage of the CM) are then contacted with the target in the absence of the protease. Bacterial cells displaying members comprising ABs which exhibit decreased or undetectable binding to the target in the absence of cleavage are identified and/or separated via detection of cells lacking bound target. In this manner, members of the plurality of candidate AAs which bind target in a cleaved state and exhibit decreased or undetectable target binding in an uncleaved state are identified and/or selected.

As noted above, candidate AA libraries can be constructed so as to screen for one or more aspects of the AA constructs, e.g., to provide for optimization of a switchable phenotype for one or more of the MM, the CM, and the AB. One or more other elements of the AA can be varied to facilitate optimization. For example: vary the MM, including varying the number or position of cysteines or other residues that can provide for different conformational characteristics of the AA in the absence of cleaving agent (e.g., enzyme): vary the CM to identify a substrate that is optimized for one or more desired characteristics (e.g., specificity of enzyme cleavage, and the like); and/or vary the AB to provide for optimization of switchable target binding.

In general, the elements of the candidate AA libraries are selected according to a target protein of interest, where the AA is to be activated to provide for enhanced binding of the target in the presence of a cleaving agent (e.g., enzyme) that cleaves the CM. For example, where the CM and AB are held fixed among the library members, the CM is selected such that it is cleavable by a cleaving agent (e.g., enzyme) that is co-localized with a target of interest, where the target of interest is a binding partner of the AB. In this manner, an AA can be selected such that it is selectively activated under the appropriate biological conditions, and thus at an appropriate biological location. For example, where it is desired to develop an AA to be used as an anti-angiogenic compound and exhibit a switchable phenotype for VEGF binding, the CM of the candidate AA is selected to be a substrate for an enzyme and/or a reducing agent that is co-localized with VEGF (e.g., a CM cleavable by a matrix-metalloprotease). By way of another example, where it is desired to develop an AA to be used as an anti-angiogenic compound and exhibit a switchable phenotype for Notch receptor binding, Jagged ligand binding, or EGFR binding, the CM of the candidate AA is selected to be a substrate for an enzyme and/or a reducing agent that is co-localized with the Notch receptor, Jagged ligand, or EGFR (e.g., a CM cleavable by a uPA or plasmin).

As discussed above, an AB is generally selected according to a target of interest. Many targets are known in the art. Biological targets of interest include protein targets that have been identified as playing a role in disease. Such targets include but are not limited to cell surface receptors and secreted binding proteins (e.g., growth factors), soluble enzymes, structural proteins (e.g. collagen, fibronectin), intracellular targets, and the like. Exemplary non-limiting targets are presented in Table 1, but other suitable targets will be readily identifiable by those of ordinary skill in the art. In addition, many proteases are known in the art which co-localize with targets of interest. As such, persons of ordinary skill in the art will be able to readily identify appropriate enzymes and enzyme substrates for use in the above methods.

(a) Optional Enrichment for Cell Surface Display Prior to AA Screening

Prior to the screening method, it may be desirable to enrich for cells expressing an appropriate peptide display scaffold on the cell surface. The optional enrichment allows for removal of cells from the cell library that (1) do not express peptide display scaffolds on the cell outer membrane or (2) express non-functional peptide display scaffolds on the cell outer membrane. A non-functional peptide display scaffold does not properly display a candidate AA, e.g., as a result of a stop codon or a deletion mutation.

Enrichment for cells can be accomplished by growing the cell population and inducing expression of the peptide display scaffolds. The cells are then sorted based on, for example, detection of a detectable signal or moiety incorporated into the scaffold or by use of a detectably-labeled antibody that binds to a shared portion of the display scaffold or the AA. These methods are described in greater detail in U.S. Patent Application Publication No: 2007/0065158, published Mar. 22, 2007.

(b) Screening for Target Binding by Cleaved AAs

Prior to screening, the candidate AA library can be expanded (e.g., by growth in a suitable medium in culture under suitable conditions). Subsequent to the optional expansion, or as an initial step, the library is subjected to a first screen to identify candidate AAs that bind target following exposure to protease. Accordingly, this step is often referred to herein as the positive selection step.

In order to identify members that bind target following protease cleavage, the candidate AA library is contacted with a protease capable of cleaving the CM of the displayed candidate AAs for an amount of time sufficient and under conditions suitable to provide for cleavage of the protease substrate of the CM. A variety of protease-CM combinations will be readily ascertainable by those of ordinary skill in the art, where the protease is one which is capable of cleaving the CM and one which co-localizes in vivo with a target of interest (which is a binding partner of the AB). For example, where the target of interest is a solid tumor associated target (e.g. VEGF), suitable enzymes include, for example, Matrix-Metalloproteases (e.g., MMP-2), A Disintegrin and Metalloprotease(s) (ADAMs)/ADAM with thrombospondin-like motifs (ADAMTS), Cathepsins and Kallikreins. The amino acid sequences of substrates useful as CMs in the AAs described herein are known in the art and, where desired, can be screened to identify optimal sequences suitable for use as a CM by adaptation of the methods described herein. Exemplary substrates can include but are not limited to substrates cleavable by enzymes listed in Table 3.

The candidate AA library is also exposed to target for an amount of time sufficient and under conditions suitable for target binding, which conditions can be selected according to conditions under which target binding to the AB would be expected. The candidate AA library can be exposed to the protease prior to exposure to target (e.g., to provide a population of candidate AAs which include cleaved AAs) or in combination with exposure to target, usually the latter so as to best model the expected in vivo situation in which both protease and target will be present in the same environmental milieu. Following exposure to both protease and target, the library is then screened to select members having bound target, which include candidate AAs in a target-AB complex.

Detection of target-bound candidate AAs can be accomplished in a variety of ways. For example, the target may be detectably labeled and the first population of target-bound candidate AAs may be selected by detection of the detectable label to generate a second population having bound target (e.g., a positive selection for target-bound candidate AAs).

(c) Screening for Candidate AAs that do not Bind Target in the Absence of Protease Cleavage The population of candidate AAs selected for target binding following exposure to protease can then be expanded (e.g., by growth in a suitable medium in culture under suitable conditions), and the expanded library subjected to a second screen to identify members exhibiting decreased or no detectable binding to target in the absence of protease exposure. The population resulting from this second screen will include candidate AAs that, when uncleaved, do not bind target significantly or to a detectable level. Accordingly, this step is often referred to herein as the negative selection step.

The population that resulted from the first screen is contacted with target in the absence of the protease for a time sufficient and under conditions suitable for target binding, which conditions can be selected according to conditions under which target binding to the AB would be expected. A negative selection can then be performed to identify candidate AAs that are relatively decreased for target binding, including those which exhibit no detectably target binding. This selection can be accomplished by, for example, use of a detectably labeled target, and subjecting the target-exposed population to flow cytometry analysis to sort into separate subpopulation those cells that display a candidate AA that exhibits no detectable target binding and/or which exhibit a relatively lower detectable signal. This subpopulation is thus enriched for cells having a candidate AA that exhibit decreased or undetectable binding to target in the absence of cleavage.

(d) Detectable Labels

A detectable label and detectable moiety are used interchangeably to refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, strepavidin or haptens) and the like. The term fluorescer refers to a substance or a portion thereof which is capable of exhibiting fluorescence in the detectable range. Exemplary detectable moieties suitable for use as target labels include affinity tags and fluorescent proteins.

The term affinity tag is used herein to denote a peptide segment that can be attached to a target that can be detected using a molecule that binds the affinity tag and provides a detectable signal (e.g., a fluorescent compound or protein). In principle, any peptide or protein for which an antibody or other specific binding agent is available can be used as an affinity tag. Exemplary affinity tags suitable for use include, but are not limited to, a monocytic adaptor protein (MONA) binding peptide, a T7 binding peptide, a streptavidin binding peptide, a polyhistidine tract, protein A (Nilsson et al., EMBO J. 4:1075 (1985); Nilsson et al., Methods Enzymol. 198:3 (1991)), glutathione S transferase (Smith and Johnson, Gene 67:31 (1988)), Glu-Glu affinity tag (Grussenmeyer et al., Proc. Natl. Acad. Sci. USA 82:7952 (1985)), substance P, FLAG peptide (Hopp et al., Biotechnology 6:1204 (1988)), or other antigenic epitope or binding domain. See, in general, Ford et al., Protein Expression and Purification 2:95 (1991). DNA molecules encoding affinity tags are available from commercial suppliers (e.g., Pharmacia Biotech, Piscataway, N.J.).

Any fluorescent polypeptide (also referred to herein as a fluorescent label) well known in the art is suitable for use as a detectable moiety or with an affinity tag of the peptide display scaffolds described herein. A suitable fluorescent polypeptide will be one that can be expressed in a desired host cell, such as a bacterial cell or a mammalian cell, and will readily provide a detectable signal that can be assessed qualitatively (positive/negative) and quantitatively (comparative degree of fluorescence). Exemplary fluorescent polypeptides include, but are not limited to, yellow fluorescent protein (YFP), cyan fluorescent protein (CFP), GFP, mRFP, RFP (tdimer2), HCRED, etc., or any mutant (e.g., fluorescent proteins modified to provide for enhanced fluorescence or a shifted emission spectrum), analog, or derivative thereof. Further suitable fluorescent polypeptides, as well as specific examples of those listed herein, are provided in the art and are well known.

Biotin-based labels also find use in the methods disclosed herein. Biotinylation of target molecules and substrates is well known, for example, a large number of biotinylation agents are known, including amine-reactive and thiol-reactive agents, for the biotinylation of proteins, nucleic acids, carbohydrates, carboxylic acids; see, e.g., chapter 4, Molecular Probes Catalog, Haugland, 6th Ed. 1996, hereby incorporated by reference. A biotinylated substrate can be detected by binding of a detectably labeled biotin binding partner, such as avidin or streptavidin. Similarly, a large number of haptenylation reagents are also known.

(e) Screening Methods

Any suitable method that provides for separation and recovery of AAs of interest may be utilized. For example, a cell displaying an AA of interest may be separated by FACS, immunochromatography or, where the detectable label is magnetic, by magnetic separation. As a result of the separation, the population is enriched for cells that exhibit the desired characteristic, e.g., exhibit binding to target following cleavage or have decreased or no detectable binding to target in the absence of cleavage.

For example, selection of candidate AAs having bound detectably labeled target can be accomplished using a variety of techniques known in the art. For example, flow cytometry (e.g., FACS®) methods can be used to sort detectably labeled candidate AAs from unlabeled candidate AAs. Flow cyomtery methods can be implemented to provide for more or less stringent requirements in separation of the population of candidate AAs, e.g., by modification of gating to allow for dimmer or to require brighter cell populations in order to be separated into the second population for further screening.

In another example, immunoaffinity chromatography can be used to separate target-bound candidate AAs from those that do not bind target. For example, a support (e.g., column, magnetic beads) having bound anti-target antibody can be contacted with the candidate AAs that have been exposed to protease and to target. Candidate AAs having bound target bind to the anti-target antibody, thus facilitating separation from candidate AAs lacking bound target. Where the screening step is to provide for a population enriched for uncleaved candidate AAs that have relatively decreased target binding or no detectable target binding (e.g., relative to other candidate AAs), the subpopulation of interest is those members that lack or have a relatively decreased detectably signal for bound target. For example, where an immunoaffinity technique is used in such negative selection for bound target, the subpopulation of interest is that which is not bound by the anti-target support.

(f) Screening for Dual Target-Binding AAs

Methods for screening disclosed herein can be readily adapted to identify dual target-binding AAs having two ABs. In general, the method involves a library containing a plurality of candidate AAs, wherein each member of said plurality comprises a first AB, a second AB, a first CM and/or a second CM, a first MM, and/or a second MM. The library is contacted with target capable of binding at least the first AB and a cleaving agent capable of cleaving the first CM. A first population of members of the library is selected for binding the target in the presence of the cleaving agent (e.g., protease for the CM). This selected population is then subjected to the negative screen above, in which binding of target to the library members in the absence of the cleaving agent is assessed. A second population of members is then generated by depleting the subpopulation of members that bind to said target in the absence of the cleaving agent. This can be accomplished by, for example, sorting members that are not bound to target away from those that are bound to target, as determined by detection of a detectably labeled target. This method thus provides for selection of candidate AAs which exhibit decreased binding to the target in the absence of the cleaving agent as compared to binding to said target in the presence of the cleaving agent. This method can be repeated for both targets.

Exemplary Variations of the Screening Methods to Select for Candidate AAs

The above methods may be modified to select for populations and library members that demonstrate desired characteristics.

(a) Determination of the Masking Efficiency of MMs

Masking efficiency of MMs is determined by at least two parameters: affinity of the MM for antibody or fragment thereof and the spatial relationship of the MM relative to the binding interface of the AB to its target.

Regarding affinity, by way of example, an MM may have high affinity but only partially inhibit the binding site on the AB, while another MM may have a lower affinity for the AB but fully inhibit target binding. For short time periods, the lower affinity MM may show sufficient masking; in contrast, over time, that same MM may be displaced by the target (due to insufficient affinity for the AB).

In a similar fashion, two MMs with the same affinity may show different extents of masking based on how well they promote inhibition of the binding site on the AB or prevention of the AB from binding its target. In another example, a MM with high affinity may bind and change the structure of the AB so that binding to its target is completely inhibited while another MM with high affinity may only partially inhibit binding. As a consequence, discovery of an effective MM cannot be based only on affinity but can include an empirical measure of masking efficiency. The time-dependent target displacement of the MM in the AA can be measured to optimize and select for MMs. A novel Target Displacement Assay (TDA) is described herein for this purpose.

The TDA assay can be used for the discovery and validation of efficiently masked AAs comprises empirical determination of masking efficiency, comparing the ability of the masked AB to bind the target in the presence of target to the ability of the unmasked and/or parental AB to bind the target in the presence of the target. The binding efficiency can be expressed as a % of equilibrium binding, as compared to unmasked/parental AB binding. When the AB is modified with a MM and is in the presence of the target, specific binding of the AB to its target can be reduced or inhibited, as compared to the specific binding of the AB not modified with an MM or the parental AB to the target. When compared to the binding of the AB not modified with an MM or the parental AB to the target, the AB's ability to bind the target when modified with an MM can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, 96, hours, or 5, 10, 15, 30, 45, 60, 90, 120, 150, 180 days, or 1, 2, 3, 4, 5, 6, 7, 8, 9, 10, 11, 12 months or greater when measured in vivo or in a Target Displacement in vitro immunosorbant assay, as described herein.

(b) Iterative Screens to Identify and/or Optimize AA Elements

The methods and candidate AA libraries described herein can be readily adapted to provide for identification and/or optimization of one or more elements of an AA. For example, candidate AAs that vary with respect to any one or more of AB, CM, linkers, and the like can be produced and subjected to the screening methods described herein.

(c) Reducing Agent-Activatable AAs

While the methods above describe screening methods for identifying AAs, it should be understood that an AA or candidate AA with a CM that can facilitate formation of a cysteine-cysteine disulfide bond in an AA and can also be subjected to the screening methods disclosed herein. Such AAs may or may not further include a CM (which may be the same or different CM) that may or may not comprise a protease substrate. In these embodiments, the positive screen described above may be conducted by exposing an AA or candidate AA to a reducing agent (e.g., to reducing conditions) capable of cleaving the disulfide bond of the cysteine-cysteine pair of the AA. The negative screen can then be conducted in the absence of the reducing conditions. As such, a library produced having may be enriched for AAs which are activatable by exposure to disulfide bond reducing conditions.

(d) Photo-Activatable AAs

While the methods above describe screening methods for identifying AAs, it should be understood that an AA or candidate AA with a CM that is photo-sensitive, and can be activated upon photolysis are also provided. In these embodiments, the positive screen described above may be conducted by exposing an AA or candidate AA to light. The negative screen can then be conducted in the absence of light. As such, a library produced having may be enriched for AAs which are activatable by exposure to light.

(e) Number of Cycles and Scaffold Free Screening of AAs

By increasing the number of cycles of the above methods, populations and library members that demonstrate improved switching characteristics can be identified. Any number of cycles of screening can be performed.

In addition, individual clones of candidate AAs can be isolated and subjected to screening so as to determine the dynamic range of the candidate AA. Candidate AAs can also be tested for a desired switchable phenotype separate from the scaffold, i.e., the candidate AA can be expressed or otherwise generated separate from the display scaffold, and the switchable phenotype of the candidate AA assessed in the absence of the scaffold and, where desired, in a cell-free system (e.g., using solubilized AA).

(f) Optimization of AA Components and Switching Activity

The above methods may be modified to optimize the performance of an AA, e.g., an AA identified in the screening method described herein. For example, where it is desirable to optimize the performance of the masking moiety, e.g., to provide for improved inhibition of target binding of the AB in the uncleaved state, the amino acid sequences of the AB and the CM may be fixed in a candidate AA library, and the MM varied such that members of a library have variable MMs relative to each other. The MM may be optimized in a variety of ways including alteration in the number and or type of amino acids that make up the MM. For example, each member of the plurality of candidate AAs may comprise a candidate MM, wherein the candidate MM comprises at least one cysteine amino acid residue and the remaining amino acid residues are variable between the members of the plurality. In a further example, each member of the plurality of candidate AAs may comprise a candidate MM, wherein the candidate MM comprises a cysteine amino acid residue and a random sequence of amino acid residues, e.g., a random sequence of 5 amino acids.

(g) Selection for Expanded Dynamic Range

As noted above, AAs having a desired dynamic range with respect to target binding in the unmasked/cleaved versus masked/uncleaved state are also of interest. Such AAs are those that, for example, have no detectable binding in the presence of target at physiological levels found at treatment and non-treatment sites in a subject but which, once cleaved by protease, exhibit high affinity and/or high avidity binding to target. The greater the dynamic range of an AA, the better the switchable phenotype of the AA. Thus AAs can be optimized to select for those having an expanded dynamic range for target binding in the presence and absence of a cleaving agent.

The screening methods described herein can be modified so as to enhance selection of AAs having a desired and/or optimized dynamic range. In general, this can be accomplished by altering the concentrations of target utilized in the positive selection and negative selection steps of the method such that screening for target binding of AAs exposed to protease (i.e., the screening population that includes cleaved AAs) is performed using a relatively lower target concentration than when screening for target binding of uncleaved AAs. Accordingly, the target concentration is varied between the steps so as to provide a selective pressure toward a switchable phenotype. Where desired, the difference in target concentrations used at the positive and negative selection steps can be increased with increasing cycle number.

Use of a relatively lower concentration of target in the positive selection step can serve to drive selection of those AA members that have improved target binding when in the cleaved state. For example, the screen involving protease-exposed AAs can be performed at a target concentration that is from about 2 to about 100 fold lower, about 2 to 50 fold lower, about 2 to 20 fold lower, about 2 to 10-fold lower, or about 2 to 5-folder lower than the Kd of the AB-target interaction. As a result, after selection of the population for target-bound AAs, the selected population will be enriched for AAs that exhibit higher affinity and/or avidity binding relative to other AAs in the population.

Use of a relatively higher concentration of target in the negative selection step can serve to drive selection of those AA members that have decreased or no detectable target binding when in the uncleaved state. For example, the screen involving AAs that have not been exposed to protease (in the negative selection step) can be performed at a target concentration that is from about 2 to about 100 fold higher, about 2 to 50 fold higher, about 2 to 20 fold higher, about 2 to 10-fold higher, or about 2 to 5-folder higher, than the Kd of the AB-target interaction. As a result, after selection of the population for AAs that do not detectably bind target, the selected population will be enriched for AAs that exhibit lower binding for target when in the uncleaved state relative to other uncleaved AAs in the population. Stated differently, after selection of the population for AAs that do not detectably bind target, the selected population will be enriched for AAs for which target binding to AB is inhibited, e.g., due to masking of the AB from target binding.

Where the AA is a dual target-binding AA, the screening method described above can be adapted to provide for AAs having a desired dynamic range for a first target that is capable of binding a first AB and for a second target that is capable of binding a second AB. Target binding to an AB that is located on a portion of the AA that is cleaved away from the AA presented on a display scaffold can be evaluated by assessing formation of target-AB complexes in solution (e.g., in the culture medium), e.g., immunochromatography having an anti-AA fragment antibody to capture cleaved fragment, then detecting bound, detectably labeled target captured on the column.

(h) Testing of Soluble AAs

Candidate AAs can be tested for their ability to maintain a switchable phenotype while in soluble form. One such method involves the immobilization of target to support (e.g., an array, e.g., a Biacore™ CM5 sensor chip surface). Immobilization of a target of interest can be accomplished using any suitable techniques (e.g., standard amine coupling). The surface of the support can be blocked to reduce non-specific binding. Optionally, the method can involve use of a control (e.g., a support that does not contain immobilized target (e.g., to assess background binding to the support) and/or contains a compound that serves as a negative control (e.g., to assess specificity of binding of the candidate AA to target versus non-target).

After the target is covalently immobilized, the candidate AA is contacted with the support under conditions suitable to allow for specific binding to immobilized target. The candidate AA can be contacted with the support-immobilized target in the presence and in the absence of a suitable cleavage agent in order to assess the switchable phenotype. Assessment of binding of the candidate AA in the presence of cleavage agent as compared to in the absence of cleavage agent and, optionally, compared to binding in a negative control provides a binding response, which in turn is indicative of the switchable phenotype.

(i) Screening for Individual Moieties for Use in Candidate AAs

It may be desirable to screen separately for one or more of the moieties of a candidate AA, e.g., an AB, MM or CM, prior to testing the candidate AA for a switchable phenotype. For example, known methods of identifying peptide substrates cleavable by specific proteases can be utilized to identify CMs for use in AAs designed for activation by such proteases. In addition a variety of methods are available for identifying peptide sequences which bind to a target of interest. These methods can be used, for example, to identify ABs which binds to a particular target or to identify a MM which binds to a particular AB.

The above methods include, for example, methods in which a moiety of a candidate AA, e.g., an AB, MM or CM, is displayed using a replicable biological entity.

(j) Automated Screening Methods

In certain embodiments the screening methods described herein are automated to provide convenient, real time, high volume methods of screening a library of AAs for a desired switchable activity. Automated methods can be designed to provide for iterative rounds of positive and negative selection, with the selected populations being separated and automatically subjected to the next screen for a desired number of cycles.

Assessing candidate AAs in a population may be carried out over time iteratively, following completion of a positive selection step, a negative selection step, or both. In addition, information regarding the average dynamic range of a population of candidate AAs at selected target concentrations in the positive and negative selection steps can be monitored and stored for later analysis, e.g. so as to assess the effect of selective pressure of the different target concentrations.

In some embodiments, a executable platform such as a computer software product can control operation of the detection and/or measuring means and can perform numerical operations relating to the above-described steps, and generate a desired output (e.g., flow cytometry analysis, etc.). Computer program product comprises a computer readable storage medium having computer-readable program code means embodied in the medium. Hardware suitable for use in such automated apparatus will be apparent to those of skill in the art, and may include computer controllers, automated sample handlers, fluorescence measurement tools, printers and optical displays. The measurement tool may contain one or more photodetectors for measuring the fluorescence signals from samples where fluorescently detectable molecules are utilized. The measurement tool may also contain a computer-controlled stepper motor so that each control and/or test sample can be arranged as an array of samples and automatically and repeatedly positioned opposite a photodetector during the step of measuring fluorescence intensity.

The measurement tool (e.g., FACS) can be operatively coupled to a general purpose or application-specific computer controller. The controller can comprise a computer program produce for controlling operation of the measurement tool and performing numerical operations relating to the above-described steps. The controller may accept set-up and other related data via a file, disk input or data bus. A display and printer may also be provided to visually display the operations performed by the controller. It will be understood by those having skill in the art that the functions performed by the controller may be realized in whole or in part as software modules running on a general purpose computer system. Alternatively, a dedicated stand-alone system with application specific integrated circuits for performing the above described functions and operations may be provided.

Methods of Use of AAs in Therapy

AAs can be incorporated into pharmaceutical compositions containing, for example, a therapeutically effective amount of an AA of interest and a carrier that is a pharmaceutically acceptable excipient (also referred to as a pharmaceutically acceptable carrier). Many pharmaceutically acceptable excipients are known in the art, are generally selected according to the route of administration, the condition to be treated, and other such variables that are well understood in the art. Pharmaceutically acceptable excipients have been amply described in a variety of publications, including, for example, A. Gennaro (2000) Remington: The Science and Practice of Pharmacy, 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds. $3^{rd}$ ed. Amer. Pharmaceutical Assoc. Pharmaceutical compositions can also include other components such as pH adjusting and buffering agents, tonicity adjusting agents, stabilizers, wetting agents and the like. In some embodiments, nanoparticles or liposomes carry a pharmaceutical composition comprising an AA.

Suitable components for pharmaceutical compositions of AAs can be guided by pharmaceutical compositions that may be already available for an AB of the AA. For example, where the, the AA includes an antibody to EGFR, TNFalpha, CD11a, CSFR, CTLA-4, EpCAM, VEGF, CD40, CD20, Notch 1, Notch 2, Notch 3, Notch 4, Jagged 1, Jagged 2, CD52, MUC1, IGF1R, transferrin, gp130, VCAM-1, CD44, DLL4, or IL4, for example, such AAs can be formulated in a pharmaceutical formulation according to methods and compositions suitable for use with that antibody.

In general, pharmaceutical formulations of one or more AAs are prepared for storage by mixing the AA having a desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or nonionic surfactants such as TWEEN™, PLURONICS™ or polyethylene glycol (PEG).

The formulations to be used for in vivo administration must be sterile. This is readily accomplished by filtration through sterile filtration membranes. Pharmaceutical formulations may also contain more than one active compound as necessary for the particular indication being treated, where the additional active compounds generally are those with activities complementary to an AA. Such compounds are suitably present in combination in amounts that are effective for the purpose intended.

The pharmaceutical formulation can be provided in a variety of dosage forms such as a systemically or local injectable preparation. The components can be provided in a carrier such as a microcapsule, e.g., such as that prepared by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations are also within the scope of an AA-containing formulations. Exemplary sustained-release preparations can include semi-permeable matrices of solid hydrophobic polymers containing the AA, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

When encapsulated AAs remain in the body for a long time, they may denature or aggregate as a result of exposure to moisture at physiological temperature (−37° C.), resulting in decreased biological activity and possible changes in immunogenicity. Rational strategies can be devised for stabilization depending on the mechanism involved. For example, if the aggregation mechanism is discovered to be undesirable intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

AAs can be conjugated to delivery vehicles for targeted delivery of an active agent that serves a therapeutic purpose. For example, AAs can be conjugated to nanoparticles or liposomes having drugs encapsulated therein or associated therewith. In this manner, specific, targeted delivery of the drug can be achieved. Methods of linking polypeptides to liposomes are well known in the art and such methods can be applied to link AAs to liposomes for targeted and or selective delivery of liposome contents. By way of example, polypeptides can be covalently linked to liposomes through thioether bonds. PEGylated gelatin nanoparticles and PEGylated liposomes have also been used as a support for the attachment of polypeptides, e.g., single chain antibodies. See, e.g., Immordino et al. (2006) *Int J Nanomedicine*. September; 1(3): 297-315, incorporated by reference herein for its disclosure of methods of conjugating polypeptides, e.g., antibody fragments, to liposomes.

(a) Methods of Treatment

AAs described herein can be selected for use in methods of treatment of suitable subjects according to the CM-AB combination provided in the AA. The AA can be administered by any suitable means, including oral, parenteral, subcutaneous, intraperitoneal, intrapulmonary, and intranasal, and, if desired for local injection (e.g., at the site of a solid tumor). Parenteral administration routes include intramuscular, intravenous, intraarterial, intraperitoneal, or subcutaneous administration.

The term treatment site or disease site is meant to refer to a site at which an AA is designed to be switchable, as described herein, e.g., a site at which a target for one or both ABs of an AA and a cleaving agent capable of cleaving a CM of the AA are co-localized, as pictorially represented in FIG. 2. Treatment sites include tissues that can be accessed by local administration (e.g., injection, infusion (e.g., by catheter), etc.) or by systemic administration (e.g., administration to a site remote from a treatment site). Treatment sites include those that are relatively biologically confined (e.g., an organ, sac, tumor site, and the like).

The appropriate dosage of an AA will depend on the type of disease to be treated, the severity and course of the disease, the patient's clinical history and response to the AA, and the discretion of the attending physician. AAs can suitably be administered to the patient at one time or over a series of treatments. AAs can be administered along with other treatments and modes of therapies, other pharmaceutical agents, and the like.

Depending on the type and severity of the disease, about 1 μg/kg to 15 mg/kg (e.g., 0.1-20 mg/kg) of an AA can serve as an initial candidate dosage for administration to the patient, whether, for example, by one or more separate administrations, or by continuous infusion. A typical daily dosage might range from about 1 μg/kg to 100 mg/kg or more, depending on factors such as those mentioned herein. For repeated administrations over several days or longer, depending on the condition, the treatment is sustained until a desired suppression of disease symptoms occurs. However, other dosage regimens may be useful.

The AA composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the AA, the method of administration, the scheduling of administration, and other factors known to medical practitioners. The therapeutically effective amount of an AA to be administered will be governed by such considerations, and is the minimum amount necessary to prevent, ameliorate, or treat a disease or disorder.

Generally, alleviation or treatment of a disease or disorder involves the lessening of one or more symptoms or medical problems associated with the disease or disorder. For example, in the case of cancer, the therapeutically effective amount of the drug can accomplish one or a combination of the following: reduce the number of cancer cells; reduce the tumor size; inhibit (i.e., to decrease to some extent and/or stop) cancer cell infiltration into peripheral organs; inhibit tumor metastasis; inhibit, to some extent, tumor growth; and/or relieve to some extent one or more of the symptoms associated with the cancer. In some embodiments, a composition of this invention can be used to prevent the onset or reoccurrence of the disease or disorder in a subject or mammal.

AAs can be used in combination (e.g., in the same formulation or in separate formulations) with one or more additional therapeutic agents or treatment methods (combination therapy). An AA can be administered in admixture with another therapeutic agent or can be administered in a separate formulation. Therapeutic agents and/or treatment methods that can be administered in combination with an AA, and which are selected according to the condition to be treated, include surgery (e.g., surgical removal of cancerous tissue), radiation therapy, bone marrow transplantation, chemotherapeutic treatment, certain combinations of the foregoing, and the like.

(b) Use of AAs in Diseased Tissue Versus Healthy Tissue

The AAs of the present invention, when localized to a healthy tissue, show little or no activation and the AB remains in a 'masked' state, or otherwise exhibits little or no binding to the target. However, in a diseased tissue, in the presence of a disease-specific protease, for example, capable of cleaving the CM of the AA, the AB becomes 'unmasked' or can specifically bind the target.

A healthy tissue refers to a tissue that produces little or no disease-specific agent capable of specifically cleaving or otherwise modifying the CM of the AA, for example a disease-specific protease, a disease-specific enzyme, or a disease-specific reducing agent. A diseased tissue refers to a tissue that produces a disease-specific agent capable of specifically cleaving or otherwise modifying the CM of the AA, for example a disease-specific protease, a disease-specific enzyme, or a disease-specific reducing agent.

(c) Use of AAs in Diseased Tissue at Different Stages of a Disease

In some embodiments, the AAs described herein are coupled to more than one CM. Such an AA can be activated in different stages of a disease, or activated in different compartments of the diseased tissue. By way of example, an AB coupled to both a MMP-9 cleavable CM and a cathepsin D-cleavable CM can be activated in an early stage tumor and in a late stage, necrosing tumor. In the early stage tumor, the CM can be cleaved and the AA unmasked by MMP-9. In the late stage tumor, the CM can be cleaved and the AA unmasked by cathepsin D which is upregulated in the dying center of late stage tumors. In another exemplary embodiment an AB coupled to an MM and to a MMP-9-activatable CM and a caspase-activatable CM can be cleaved at both early and late stage tumors. In another plasmin at active sites of angiogenesis (early stage tumor) can cleave a plasmin-cleavable CM and legumain in disease tissues with invading macrophages can cleave a leugamain-specific CM in a late stage tumor.

(d) Use of AAs in Anti-Angiogenic Therapies

In an exemplary embodiment where the AA contains an AB that binds a mediator of angiogenesis such as EGFR, TNFalpha, CD11a, CSFR, CTLA-4, EpCAM, VEGF, CD40, CD20, Notch 1, Notch 2, Notch 3, Notch 4, Jagged 1, Jagged 2, CD52, MUC1, IGF1R, transferrin, gp130, VCAM-1, CD44, DLL4, or IL4, the AA finds use in treatment of conditions in which inhibition of angiogenesis is desired, particularly those conditions in which inhibition of VEGF is of interest. VEGF-binding AAs can include dual target binding AAs having an AB that binds to VEGF as well as an AB that binds to a second growth factor, such as a fibroblast growth factor (e.g., FGF-2), and inhibits FGF activity. Such dual target binding AAs thus can be designed to provide for inhibition of two angiogenesis-promoting factors, and which are activatable by a cleaving agent (e.g., enzyme, such as a MMP or other enzymes such as one presented in Table 3) which co-localizes at a site of aberrant angiogenesis.

Angiogenesis-inhibiting AAs find use in treatment of solid tumors in a subject (e.g., human), particularly those solid tumors that have an associated vascular bed that feeds the tumor such that inhibition of angiogenesis can provide for inhibition or tumor growth. Anti-VEGF-based anti-angiogenesis AAs also find use in other conditions having one or more symptoms amenable to therapy by inhibition of abnormal angiogenesis.

In general, abnormal angiogenesis occurs when new blood vessels either grow excessively, insufficiently or inappropriately (e.g., the location, timing or onset of the angiogenesis being undesired from a medical standpoint) in a diseased state or such that it causes a diseased state. Excessive, inappropriate or uncontrolled angiogenesis occurs when there is new blood vessel growth that contributes to the worsening of the diseased state or causes a diseased state, such as in cancer, especially vascularized solid tumors and metastatic tumors (including colon, lung cancer (especially small-cell lung cancer), or prostate cancer), diseases caused by ocular neovascularisation, especially diabetic blindness, retinopathies, primarily diabetic retinopathy or age-induced macular degeneration and rubeosis; psoriasis, psoriatic arthritis, haemangioblastoma such as haemangioma; inflammatory renal diseases, such as glomerulonephritis, especially mesangioproliferative glomerulonephritis, haemolytic uremic syndrome, diabetic nephropathy or hypertensive nephrosclerosis; various imflammatory diseases, such as arthritis, especially rheumatoid arthritis, inflammatory bowel disease, psorsasis, sarcoidosis, arterial arteriosclerosis and diseases occurring after transplants, endometriosis or chronic asthma and other conditions that will be readily recognized by the ordinarily skilled artisan. The new blood vessels can feed the diseased tissues, destroy normal tissues, and in the case of cancer, the new vessels can allow tumor cells to escape into the circulation and lodge in other organs (tumor metastases).

AA-based anti-angiogenesis therapies can also find use in treatment of graft rejection, lung inflammation, nephrotic syndrome, preeclampsia, pericardial effusion, such as that associated with pericarditis, and pleural effusion, diseases and disorders characterized by undesirable vascular permeability, e.g., edema associated with brain tumors, ascites associated with malignancies, Meigs' syndrome, lung inflammation, nephrotic syndrome, pericardial effusion, pleural effusion, permeability associated with cardiovascular diseases such as the condition following myocardial infarctions and strokes and the like.

Other angiogenesis-dependent diseases that may be treated using anti-angiogenic AAs as described herein include angiofibroma (abnormal blood of vessels which are prone to bleeding), neovascular glaucoma (growth of blood vessels in the eye), arteriovenous malformations (abnormal communication between arteries and veins), nonunion fractures (fractures that will not heal), atherosclerotic plaques (hardening of the arteries), pyogenic granuloma (common skin lesion composed of blood vessels), scleroderma (a form of connective tissue disease), hemangioma (tumor composed of blood vessels), trachoma (leading cause of blindness in the third world), hemophilic joints, vascular adhesions and hypertrophic scars (abnormal scar formation).

Amounts of an AA for administration to provide a desired therapeutic effect will vary according to a number of factors such as those discussed above. In general, in the context of cancer therapy, a therapeutically effective amount of an AA is an amount that that is effective to inhibit angiogenesis, and thereby facilitate reduction of, for example, tumor load, atherosclerosis, in a subject by at least about 5%, at least about 10%, at least about 20%, at least about 25%, at least about 50%, at least about 75%, at least about 85%, or at least about 90%, up to total eradication of the tumor, when compared to a suitable control. In an experimental animal system, a suitable control may be a genetically identical animal not treated with the agent. In non-experimental systems, a suitable control may be the tumor load present before administering the agent. Other suitable controls may be a placebo control.

Whether a tumor load has been decreased can be determined using any known method, including, but not limited to, measuring solid tumor mass; counting the number of tumor cells using cytological assays; fluorescence-activated cell sorting (e.g., using antibody specific for a tumor-associated antigen) to determine the number of cells bearing a given tumor antigen; computed tomography scanning, magnetic resonance imaging, and/or x-ray imaging of the tumor to estimate and/or monitor tumor size; measuring the amount of tumor-associated antigen in a biological sample, e.g., blood or serum; and the like.

In some embodiments, the methods are effective to reduce the growth rate of a tumor by at least about 5%, at least about 10%, at least about 20%, at least about 25%, at least about 50%, at least about 75%, at least about 85%, or at least about 90%, up to total inhibition of growth of the tumor, when compared to a suitable control. Thus, in these embodiments, effective amounts of an AA are amounts that are sufficient to reduce tumor growth rate by at least about 5%, at least about 10%, at least about 20%, at least about 25%, at least about 50%, at least about 75%, at least about 85%, or at least about 90%, up to total inhibition of tumor growth, when compared to a suitable control. In an experimental animal system, a suitable control may be tumor growth rate in a genetically identical animal not treated with the agent. In non-experimental systems, a suitable control may be the tumor load or tumor growth rate present before administering the agent. Other suitable controls may be a placebo control.

Whether growth of a tumor is inhibited can be determined using any known method, including, but not limited to, an in vivo assay for tumor growth; an in vitro proliferation assay; a $^3$H-thymidine uptake assay; and the like.

(e) Use of AAs in Anti-Inflammatory Therapies

In another exemplary embodiment where the AA contains an AB that binds mediators of inflammation such as interleukins, the AA finds use in treatment of related conditions. Interleukin-binding AAs can include dual target binding AAs having an AB that binds to for example IL12 as well as an AB that binds to IL23, or an AA where a first AB binds to IL17 and a second AB binds to IL23. Such dual target binding AAs thus can be designed to provide for mediation of inflammation, and which are activatable by a cleaving agent (e.g., enzyme, such as a MMP or other enzyme such as one presented in Table 3) which co-localizes at a site of inflammation.

Non-Therapeutic Methods of Using AAs

AAs can also be used in diagnostic and/or imaging methods. For example, AAs having an enzymatically cleavable CM can be used to detect the presence or absence of an enzyme that is capable of cleaving the CM. Such AAs can be used in diagnostics, which can include in vivo detection (e.g., qualitative or quantitative) of enzyme activity (or, in some embodiments, an environment of increased reduction potential such as that which can provide for reduction of a disulfide bond) accompanied by presence of a target of interest through measured accumulation of activated AAs in a given tissue of a given host organism.

For example, the CM can be selected to be a protease substrate for a protease found at the site of a tumor, at the site of a viral or bacterial infection at a biologically confined site (e.g., such as in an abscess, in an organ, and the like), and the like. The AB can be one that binds a target antigen. Using methods familiar to one skilled in the art, a detectable label (e.g., a fluorescent label) can be conjugated to an AB or other region of an AA. Suitable detectable labels are discussed in the context of the above screening methods and additional specific examples are provided below. Using an AB specific to a protein or peptide of the disease state, along with a protease whose activity is elevated in the disease tissue of interest, AAs will exhibit increased rate of binding to disease tissue relative to tissues where the CM specific enzyme is not present at a detectable level or is present at a lower level than in disease tissue. Since small proteins and peptides are rapidly cleared from the blood by the renal filtration system, and because the enzyme specific for the CM is not present at a detectable level (or is present at lower levels in non-diseased tissues), accumulation of activated AA in the diseased tissue is enhanced relative to non-disease tissues.

In another example, AAs can be used in to detect the presence or absence of a cleaving agent in a sample. For example, where the AA contains a CM susceptible to cleavage by an enzyme, the AA can be used to detect (either qualitatively or quantitatively) the presence of an enzyme in the sample. In another example, where the AA contains a CM susceptible to cleavage by reducing agent, the AA can be used to detect (either qualitatively or quantitatively) the presence of reducing conditions in a sample. To facilitate analysis in these methods, the AA can be detectably labeled, and can be bound to a support (e.g., a solid support, such as a slide or bead). The detectable label can be positioned on a portion of the AA that is released following cleavage. The assay can be conducted by, for example, contacting the immobilized, detectably labeled AA with a sample suspected of containing an enzyme and/or reducing agent for a time sufficient for cleavage to occur, then washing to remove excess sample and contaminants. The presence or absence of the cleaving agent (e.g., enzyme or reducing agent) in the sample is then assessed by a change in detectable signal of the AA prior to contacting with the sample (e.g., a reduction in detectable signal due to cleavage of the AA by the cleaving agent in the sample and the removal of an AA fragment to which the detectable label is attached as a result of such cleavage.

Such detection methods can be adapted to also provide for detection of the presence or absence of a target that is capable of binding the AB of the AA. Thus, the in vitro assays can be adapted to assess the presence or absence of a cleaving agent and the presence or absence of a target of interest. The presence or absence of the cleaving agent can be detected by a decrease in detectable label of the AA as described above, and the presence or absence of the target can be detected by detection of a target-AB complex, e.g., by use of a detectably labeled anti-target antibody.

As discussed above, the AAs disclosed herein can comprise a detectable label. In one embodiment, the AA comprises a detectable label which can be used as a diagnostic agent. Non-limiting examples of detectable labels that can be used as diagnostic agents include imaging agents containing radioisotopes such as indium or technetium; contrasting agents for MRI and other applications containing iodine, gadolinium or iron oxide; enzymes such as horse radish peroxidase, alkaline phosphatase, or β-galactosidase; fluorescent substances and fluorophores such as GFP, europium derivatives; luminescent substances such as N-methylacrydium derivatives or the like.

The rupture of vulnerable plaque and the subsequent formation of a blood clot are believed to cause the vast majority of heart attacks. Effective targeting of vulnerable plaques can enable the delivery of stabilizing therapeutics to reduce the likelihood of rupture.

VCAM-1 is upregulated both in regions prone to atherosclerosis as well as at the borders of established lesions. Iiyama, et al. (1999) *Circulation Research, Am Heart Assoc.* 85: 199-207. Collagenases, such as MMP-1, MMP-8 and MMP-13, are overexpressed in human atheroma which may contribute to the rupture of atheromatous plaques. Fricker, J. (2002) *Drug Discov Today* 7(2): 86-88.

In one example, AAs disclosed herein find use in diagnostic and/or imaging methods designed to detect and/or label atherosclerotic plaques, e.g., vulnerable atherosclerotic plaques. By targeting proteins associated with atherosclerotic plaques, AAs can be used to detect and/or label such plaques. For example, AAs comprising an anti-VCAM-1 AB and a detectable label find use in methods designed to detect and/or label atherosclerotic plaques. These AAs can be tested in animal models, such as ApoE mice.

Biodistribution Considerations

The therapeutic potential of the compositions described herein allow for greater biodistribution and bioavailability of the modified AB or the AA. The compositions described herein provide an antibody therapeutic having an improved bioavailability wherein the affinity of binding of the antibody therapeutic to the target is lower in a healthy tissue when compared to a diseased tissue. A pharmaceutical composition comprising an AB coupled to a MM can display greater affinity to the target in a diseased tissue than in a healthy tissue. In preferred embodiments, the affinity in the diseased tissue is 5-10,000,000 times greater than the affinity in the healthy tissue.

Generally stated, the present disclosure provides for an antibody therapeutic having an improved bioavailability wherein the affinity of binding of the antibody therapeutic to its target is lower in a first tissue when compared to the binding of the antibody therapeutic to its target in a second tissue. By way of example in various embodiments, the first tissue is a healthy tissue and the second tissue is a diseased tissue; or the first tissue is an early stage tumor and the second tissue is a late stage tumor; the first tissue is a benign tumor and the second tissue is a malignant tumor; the first tissue and second tissue are spatially separated; or in a specific example, the first tissue is epithelial tissue and the second tissue is breast, head, neck, lung, pancreatic, nervous system, liver, prostate, urogenital, or cervical tissue.

EXAMPLES

Example 1

Screening of Candidate Masking Moieties (MMs)

In order to produce compositions comprising antibodies and fragments thereof (AB) coupled to MMs with desired optimal binding and dissociation characteristics, libraries of candidate MMs are screened. MMs having different variable amino acid sequences, varying positions of the cysteine, various lengths, and the like are generated. Candidate MMs are tested for their affinity of binding to ABs of interest. Preferably, MMs not containing the native amino acid sequence of the binding partner of the AB are selected for construction of the modified antibodies.

Affinity maturation of MMs for ABs of interest to select for MMs with an affinity of about 1-10 nM is carried out.

Example 2

Screening of Modified Antibody and Activatable Antibody (AA) Libraries

In order to identify modified antibodies and AAs having desired switching characteristics (i.e., decreased target binding when in an masked and/or uncleaved conformation relative to target binding when in a masked and/or cleaved conformation), libraries of candidate modified antibodies and candidate AAs having different variable amino acid sequences in the masking moieties (MMs), varying positions of the cysteine in the MM, various linker lengths, and various points of attachment to the parent AB are generated.

A scheme for screening/sorting method to identify candidate AAs that display the switchable phenotype is provided here. The libraries are introduced via expression vectors resulting in display of the AAs on the surface of bacterial cells. After expansion of the libraries by culture, cells displaying the AA polypeptides are then treated with the appropriate enzyme or reducing agent to provide for cleavage or reduction of the CM. Treated cells are then contacted with fluorescently labeled target and the cells are sorted by FACS to isolate cells displaying AAs which bind target after cleavage/reduction. The cells that display target-binding constructs are then expanded by growth in culture. The cells are then contacted with labeled target and sorted by FACS to isolate cells displaying AAs which fail to bind labeled target in the absence of enzyme/reducing agent. These steps represent one cycle of the screening procedure. The cells can then be subjected to additional cycles by expansion by growth in culture and again subjecting the culture to all or part of the screening steps.

Library screening and sorting can also be initiated by first selecting for candidates that do not bind labeled target in the absence of enzyme/reduction agent treatment (i.e., do not bind target when not cleaved/reduced).

Example 3

In vitro Screening of Modified Antibodies to Determine Masking Efficiency of the MM In order to screen modified antibodies and AAs that exhibit optimal characteristics when masked, for example, only 10% of binding to the target when in a masked state and in the presence of target, ABs coupled to different MMs or ABs coupled to the same MMs at different points of attachment, or ABs coupled to the same MM via linkers of different lengths and/or sequences are generated.

The masking efficiency of MMs can be determined by the affinity of the MM for AB and the spatial relationship of the MM relative to the binding interface of the AB to its target. Discovery of an effective MM is based on affinity and as well optionally an empirical measure of masking efficiency. The time-dependent target displacement of the MM in the modified antibody or AA can be measured to optimize and select for MMs. A immunoabsorbant Target Displacement Assay (TDA) is described herein for the discovery and validation of efficiently masked antibodies In the TDA assay, the ability of an MM to inhibit AB binding to its target at therapeutically relevant concentrations and times is measured. The assay allows for measurement of the time-dependent target displacement of the MM.

Briefly the antibody target is adsorbed to the wells of an ELISA plate overnight a about 4° C. The plate is blocked by addition of about 150 μl 2% non-fat dry milk (NFDM) in PBS, about 0.5% (v/v) Tween20 (PBST), and incubation at room temperature for about 1 hour. The plate is then washed about three times with PBST. About 50 μl superblock is added (Thermo Scientific) and supplemented with protease inhibitors (Complete, Roche). About 50 μl of an AB coupled to a MM is dissolved in superblock with protease inhibitors (Complete, Roch) and incubated at about 37° C. for different periods of time. The plate is washed about three times with PBST. About 100 ml of anti-huIgG-HRP is added in about 2% NFDM/PBST and incubated at room temperature for about 1 hour. The plate is washed about four times with PBST and about twice with PBS. The assay is developed using TMB (Thermo Scientific) as per manufacturer's directions.

Example 4

AAs Comprising an scFv as the AB

Examples of AAs comprising an anti-Jagged1 scFv are described herein. These AAs are inactive (masked) under normal conditions due to the attached MM. When the scFv reaches the site of disease, however, a disease-specific enzyme such as ADAM17 will cleave a substrate linker connecting the peptide inhibitor to the scFv allowing it to bind to Jagged1. Bacterial cell surface display is used to find suitable MMs for the anti-Jagged1 scFv. In this example, selected MMs are combined with an enzyme substrate to be used as a trigger to create a scFv construct that becomes competent for targeted binding after protease activation.

Construction of Protease Activated Antibody

Genes encoding AAs comprising a Jagged1 antibody in single-chain form are produced by overlap extension PCR or total gene synthesis and ligated into a similarly digested expression plasmid or any other suitable bacterial, yeast, or mammalian expression vector familiar to one skilled in the art. Full length antibodies can be alternatively produced using commercially available expression vectors incorporating half-life extending moieties (e.g. the Fc region of an IgG, serum albumin, or transferrin) and methods familiar to one skilled in the art. The expression plasmid is then transformed or transfected into an appropriate expression host such as BL21 for *E. coli* or HEK293t cells. Single chain antibodies are harvested from overnight cultures using a Periplasmic fraction extraction kit (Pierce), and purified by immobilized metal ion affinity chromatography, and by size exclusion chromatography.

Assay for Antibody Switching Activity In Vitro

Aliquots of protease-activated antibodies, at a concentration of 1 pM-1 μM are incubated in a buffered aqueous solution separately with 0 and 50 nM enzyme for 3 hrs. The reaction mixtures are then assayed for binding using ELISA or surface Plasmon resonance with immobilized antigen Jagged1. An increase in binding activity for the AA after protease treatment is indicated by an increase in resonance units when using BIAcore™ SPR instrumentation. The change in apparent dissociation constant ($K_d$) as a result of cleavage can then be calculated according the instrument manufacturer's instructions (BIAcore, GE Healthcare).

Example 5

Cloning of the Anti-VEGF scFv AB

In this and following examples an AA containing a masked MMP-9 cleavable anti-VEGF scFv (target=VEGF; AB=anti-VEGF single chain Fv) was constructed. As a first step in the production of such an AA, constructs containing an anti-VEGF scFv were generated (the AB). An anti-VEGF scFv AB ($V_L$-linker L-$V_H$) was designed from the published sequence of ranibizumab (Genentech, Chen, Y., Wiesmann, C., Fuh, G., $L_1$, B., Christinger, H., McKay, P., de Vos, A. M., Lowman, H. B. (1999) Selection and Analysis of an Optimized Anti-VEGF Antibody: Crystal Structure of an Affinity-matured Fab in Complex with Antigen J. Mol. Biol. 293, 865-881) and synthesized by Codon Devices (Cambridge, Mass.).

Ranibizumab is a monoclonal antibody Fab fragment derived from the same parent murine antibody as bevacizumab (Presta L G, Chen H, O'Connor S J, et al Humanization of an anti-vascular endothelial growth factor monoclonal antibody for the therapy of solid tumors and other disorders. Cancer Res, 57: 4593-9, 1997). It is smaller than the parent molecule and has been affinity matured to provide stronger binding to VEGF-A. Ranibizumab binds to and inhibits all subtypes of vascular endothelial growth factor A (VEGF-A). A His6 tag (SEQ ID NO: 48) at the N-terminus and a TEV protease cleavage site were included in the design. The TEV protease is a protease isolated from tobacco etch virus, is very specific, and is used to separate fusion proteins following purification. The anti-VEGF scFv nucleotide and amino acid sequences are provided below in Tables 7 and 8.

TABLE 7 anti-VEGF scFv AB nucleotide sequence gatattcaactgacccagagcccttcttccctgagtgccagcgtgggtga
ccgtgttacgatcacttgctcggccagccaagatatttctaactacctga
attggtaccagcagaagccaggaaaggcaccaaaagtcctgatctacttc
acaagttcactgcattccggcgtaccgtcgcgctttagcggttctggcag
tggtaccgacttcaccctgactatctcgagtctgcaacctgaggattttg
ctacatattactgtcagcaatattcgaccgtgccgtggacgttcgggcag
ggcaccaaagtggagattaaggggggtggaggcagcggggaggtggctc
aggcggtggagggtctggcgaggtccagctggtagaaagcggggcggac
tggtccaaccgggcggatccctgcgtctgagctgcgcggcctcgggttac
gactttactcactacggaatgaactgggttcgccaagcccctggtaaagg
tctggaatgggtcggatggattaatacatacactggagaacctacttatg
ctgctgatttcaaacgtcgctttactttctctctggatacaagtaagtca
accgcctatctgcaaatgaacagcctgcgtgcagaggacacggctgtgta
ctattgtgcgaaatatccttattattatggaacttcccactggtatttcg
atgtatggggccagggtactctggttacagtgcg
(SEQ ID NO: 49)

TABLE 8 anti-VEGF scFv AB amino acid sequence

DIQLTQSPSSLSASVGDRVTITCSASQDISNYLNWYQQKPGKAPKVLIYF
TSSLHSGVPSRFSGSGSGTDFTLTISSLQPEDFATYYCQQYSTVPWTFGQ
GTKVEIKGGGGSGGGGSGGGGSGEVQLVESGGGLVQPGGSLRLSCAASGY
DFTHYGMNWVRQAPGKGLEWVGWINTYTGEPTYAADFKRRFTFSLDTSKS
TAYLQMNSLRAEDTAVYYCAKYPYYYGTSHWYFDVWGQGTLVTVS
(SEQ ID NO: 50)

Example 6

Screening and Identification of MMs for Anti-VEGF scFv

Ranibizumab was used to screen a pooled random peptide library, consisting of peptides that are $X_{15}$ ($8.3 \times 10^9$), $X_4CX_7CX_4$ ($3.6 \times 10^9$), or $X_{12}CX_3$ ($1.1 \times 10^9$), where X is any amino acid and the number represents the total diversity of the library. The total diversity of the pooled library was $1.3 \times 10^{10}$. The screening consisted of one round of MACS and two rounds of FACS sorting. In the first round MACS screen, $1 \times 10^{11}$ cells were probed with 150 nM biotinylated-ranibizumab, and $5.5 \times 10^7$ binding cells were isolated. In the first FACS screen, positive cells isolated in the MACS screen were probed with 500 nM biotinylated-ranibizumab, and visualized with neutrAvidin-PE (Molecular Probes, Eugene, Oreg.). The second and third rounds of FACS selections were done with 500 nM and then 100 nM Alexa-labeled ranibizumab in the presence of 20 uM IgG. Individual clones were sequenced and subsequently verified for their ability to bind anti-VEGF scFv by FACS analysis. Amino acid sequences of MMs for anti-VEGF scFv are provided in Table 9 below. (These sequences will hereafter be referred to as 283 MM, 292 MM, 306 MM, etc.)

TABLE 9

| \multicolumn{2}{c}{MMs for anti-VEGF scFv} | |
|---|---|
| JS283 | ATAVWNSMVKQSCYMQG (SEQ ID NO: 51) |
| JS292 | GHGMCYTILEDHCDRVR (SEQ ID NO: 52) |
| JS306 | PCSEWQSMVQPRCYYGG (SEQ ID NO: 53) |
| JS308 | NVECCQNYNLWNCCGGR (SEQ ID NO: 54) |
| JS311 | VHAWEQLVIQELYHC (SEQ ID NO: 55) |
| JS313 | GVGLCYTILEQWCEMGR (SEQ ID NO: 56) |
| JS314 | RPPCCRDYSILECCKSD (SEQ ID NO: 57) |
| JS315 | GAMACYNIFEYWCSAMK (SEQ ID NO: 58) |

Example 7

Construction of the AA: MMP-9 Cleavable, Masked-Anti-VEGF scFv Vectors

A CM (substrate for MMP-9) was fused to the masked anti-VEGF scFv construct to provide a cleavable, masked AA. An exemplary construct is provided in FIG. 4. Several exemplary AA constructs and sequences containing different CMs are described in great detail below. Primers utilized for construction of the exemplary constructs are represented in Table 10 below.

TABLE 10

| Primers utilized for construction of MMP-9 Cleavable, masked-anti-VEGF scFv |
|---|
| CX0233 5'gaattcatgggccatcaccatcaccatcacggtgggg3' (SEQ ID NO: 59) |
| CX0249 5'gtgagtaagcttttattacgacactgtaaccagagtaccctgg3' (SEQ ID NO: 60) |
| CX0270 5'gtggcatgtgcacttggccaccttggccccactcgagctggccagactggccctgaaaatacagattttccc3' (SEQ ID NO: 61) |
| CX0271 5'gagtgggccaaggtggccaagtgcacatgccactgggcttcctgggtccgggcggttctgatattcaactgacccagagcc3' (SEQ ID NO: 62) |
| CX0288 5' ttcgagctcgaacaacaacaacaataacaataacaacaac 3' (SEQ ID NO: 63) |
| CX0289 5' gctttcaccgcaggtacttccgtagctggccagtctggcc 3' (SEQ ID NO: 64) |
| CX0290 5' cgctccatgggccaccttggccgctgccaccagaaccgcc 3' (SEQ ID NO: 65) |

TABLE 10-continued

Primers utilized for construction of MMP-9 Cleavable, masked-anti-VEGF scFv

CX0308 5' gcccagccggccatggccggccagtctggccagctcgagt 3' (SEQ ID NO: 66)

CX0310 5' ccagtgccaagctttagtggtgatggtgatgatgcgaca ctgtaaccagagtaccctggcc3' (SEQ ID NO: 67)

CX0312 5'cttgtcacgaattcgggccagtctggccagctcgagt3' (SEQ ID NO: 68)

CX0314 5'cagatctaaccatggcgccgctaccgcccgacactgtaacc agagtaccctg3' (SEQ ID NO: 69)

Cloning and Expression of the AA: a MMP-9 Cleavable, Masked Anti-VEGF scFv as a MBP Fusion Cloning: A MBP:anti-VEGF scFv AB fusion was cloned. The MBP (maltose binding protein) expresses well in *E. coli*, as a fusion protein, and can be purified on a maltose column, a method well known in the art to make fusion proteins. In this example, the MBP was used to separate the masked scFv. The His6 tagged (SEQ ID NO: 48) Anti-VEGF scFv AB was cloned into the pMal-c4x vector (NEB) as a C-terminal fusion with MBP using the EcoRI and HindIII restriction sites in the multiple cloning site (MCS). The primers CX0233 and CX0249 (Table 10) were used to amplify the Anti-VEGF scFv AB and introduce the EcoRI and HindIII sites, respectively.

The accepting vector for the AA (the peptide MM, the anti-VEGF scFv AB and the MMP-9 CM) was synthesized using polymerase chain reaction (PCR) with the overlapping primers CX0271 and CX0270 which placed the cloning site for the peptide MM's, linker sequences, and MMP-9 CM protease site between the TEV protease site and the anti-VEGF scFv AB. The primers CX0271 and CX0249 (Table 10) were used to amplify the C-terminal portion of the construct, while the primers CX0270 and CX0288 (Table 10) were used to amplify the N-terminal portion. Products from both the above reactions were combined for a final PCR reaction using the outside primers, CX0249 and CX0288 (Table 10), and cloned into the pMal vector as an MBP fusion using the Sad and HindIII restriction sites.

TABLE 11

| MBP/MM accepting site/MMP-9 CM/Anti-VEGF scFv AB vector nucleotide sequence |
|---|
| atgggccatcaccatcaccatcacggtggggaaaatctgtattttcagggccagtctggccagctcgagtgggccaaggtggccaagtgca<br>catgccactgggcttcctgggtccgggcggttctgatattcaactgacccagagcccttcttccctgagtgccagcgtgggtgaccgtgttac<br>gatcacttgctcggccagccaagatatttctaactacctgaattggtaccagcagaagccaggaaaggcaccaaaagtcctgatctacttcac<br>aagttcactgcattccggcgtaccgtcgcgctttagcggttctggcagtggtaccgacttcaccctgactatctcgagtctgcaacctgaggat<br>tttgctacatattactgtcagcaatattcgaccgtgccgtggacgttcgggcagggcaccaaagtggagattaagggggtggaggcagcg<br>ggggaggtggctcaggcggtggagggtctggcgaggtccagctggtagaaagcgggggcggactggtccaaccgggcggatccctgc<br>gtctgagctgcgcggcctcgggttacgactttactcactacggaatgaactgggttcgccaagcccctggtaaaggtctggaatgggtcgg<br>atggattaatacatacactggagaacctacttatgctgctgatttcaaacgtcgctttactttctctctggatacaagtaagtcaaccgcctatc<br>tgcaaatgaacagcctgcgtgcagaggacacggctgtgtactattgtgcgaaatatccttattattatggaacttcccactggtatttcgatgta<br>tggggccagggtactctggttacagtgtcg (SEQ ID NO: 70) |

The 306 MM and 314 MM (Table 9) were amplified from the ecpX display vector using the primers CX0289 and CX0290 (Table 10), and directionally cloned into the N-terminally masked vector using the SfiI restriction sites. The corresponding nucleotide and amino acid sequences are provided in Table 12 below.

TABLE 12

| 306 or 314 MM/MMP-9 CM/Anti-VEGF scFv AB Sequences |
|---|
| MBP/306 MM/MMP-9 CM/Anti-VEGF scFv AB nucleotide sequence |
| atgggccatcaccatcaccatcacggtggggaaaatctgtattttcagggccagtctggccagccgtgttctgagtggcagtcgatggtgca<br>gccgcgttgctattatgggggcggttctggtggcagcggccaaggtggccaagtgcacatgccactgggcttcctgggtccgggcggttct<br>gatattcaactgacccagagcccttcttccctgagtgccagcgtgggtgaccgtgttacgatcacttgctcggccagccaagatatttctaact<br>acctgaattggtaccagcagaagccaggaaaggcaccaaaagtcctgatctacttcacaagttcactgcattccggcgtaccgtcgcgcttt<br>agcggttctggcagtggtaccgacttcaccctgactatctcgagtctgcaacctgaggattttgctacatattactgtcagcaatattcgaccgt<br>gccgtggacgttcgggcagggcaccaaagtggagattaagggggtggaggcagcgggggaggtggctcaggcggtggagggtctg<br>gcgaggtccagctggtagaaagcgggggcggactggtccaaccgggcggatccctgcgtctgagctgcgcggcctcgggttacgacttt |

TABLE 12-continued

306 or 314 MM/MMP-9 CM/Anti-VEGF scFv AB Sequences actcactacggaatgaactgggttcgccaagcccctggtaaaggtctggaatgggtcggatggattaatacatacactggagaacctacttat gctgctgatttcaaacgtcgctttactttctctctggatacaagtaagtcaaccgcctatctgcaaatgaacagcctgcgtgcagaggacacgg ctgtgtactattgtgcgaaatatccttattattatggaacttcccactggtatttcgatgtatggggccagggtactctggttacagtgtcg (SEQ ID NO: 71)

MBP/306 MM/MMP-9 CM/Anti-VEGF scFv AB amino acid sequence

MGHHHHHHGGENLYFQGQSGQPCSEWQSMVQPRCYYGGGSGGSGQGGQVHMPLGFL

GPGGSDIQLTQSPSSLSASVGDRVTITCSASQDISNYLNWYQQKPGKAPKVLIYFTSSLHS

GVPSRFSGSGSGTDFTLTISSLQPEDFATYYCQQYSTVPWTFGQGTKVEIKGGGGSGGGG

SGGGGSGEVQLVESGGGLVQPGGSLRLSCAASGYDFTHYGMNWVRQAPGKGLEWVG

WINTYTGEPTYAADFKRRFTFSLDTSKSTAYLQMNSLRAEDTAVYYCAKYPYYYGTSH

WYFDVWGQGTLVTVS (SEQ ID NO: 72)

MBP/314 MM/MMP-9 CM/Anti-VEGF scFv AB nucleotide sequence atgggccatcaccatcaccatcacggtggggaaaatctgtattttcagggccagtctggccagcggccgccgtgttgccgtgattatagtatt ttggagtgctgtaagagtgatggcggttctggtggcagcggccaaggtggccaagtgcacatgccactgggcttcctgggtccggcggtt ctgatattcaactgacccagagccccttcttccctgagtgccagcgtgggtgaccgtgttacgatcacttgctcggccagccaagatatttctaa ctacctgaattggtaccagcagaagccaggaaaggcaccaaaagtcctgatctacttcacaagttcactgcattccggcgtaccgtcgcgct ttagcggttctggcagtggtaccgacttcaccctgactatctcgagtctgcaacctgaggattttgctacatattactgtcagcaatattcgac cgtgccgtggacgttcgggcagggcaccaaagtgagattaaggggggtggaggcagcggggaggtggctcaggcggtggagggtctg gcgaggtccagctggtagaaagcggggcggactggtccaaccgggcggatccctgcgtctgagctgcgcggcctcgggttacgactt actcactacggaatgaactgggttcgccaagcccctggtaaaggtctggaatgggtcggatggattaatacatacactggagaacctacttat gctgctgatttcaaacgtcgctttactttctctctggatacaagtaagtcaaccgcctatctgcaaatgaacagcctgcgtgcagaggacacgg ctgtgtactattgtgcgaaatatccttattattatggaacttcccactggtatttcgatgtatggggccagggtactctggttacagtgtcg (SEQ ID NO: 73)

MBP/314 MM/MMP-9 CM/Anti-VEGF scFv AB amino acid sequence

MGHHHHHHGGENLYFQGQSGQRPPCCRDYSILECCKSDGGSGGSGQGGQVHMPLGFL

GPGGSDIQLTQSPSSLSASVGDRVTITCSASQDISNYLNWYQQKPGKAPKVLIYFTSSLHS

GVPSRFSGSGSGTDFTLTISSLQPEDFATYYCQQYSTVPWTFGQGTKVEIKGGGGSGGGG

SGGGGSGEVQLVESGGGLVQPGGSLRLSCAASGYDFTHYGMNWVRQAPGKGLEWVG

WINTYTGEPTYAADFKRRFTFSLDTSKSTAYLQMNSLRAEDTAVYYCAKYPYYYGTSH

WYFDVWGQGTLVTVS (SEQ ID NO: 74)

Expression:

Expression of the MBP:AA fusions were conducted in a K12 TB1 strain of *E. coli* An ampicillin-resistant colony containing the desired construct was used to inoculate a 5 ml overnight culture containing LB medium supplemented with 50 µg/mL Ampicillin. The entire overnight culture was used to inoculate 500 mL of fresh LB medium supplemented with 50 µg/mL ampicillin and 0.2% Glucose and allowed to grow at 37° C. shaking at 250 rpm until an O.D. of 0.5 was reached. Isopropylthio-β-D-galactosidase was then added to a final concentration of 0.3 mM and the culture was allowed to grow for a further 3 hrs under the same conditions after which the cells were harvested by centrifugation at 3000×g. Inclusion bodies were purified using standard methods. Briefly, 10 mls of BPER II cell lysis reagent (Pierce). Insoluble material was collected by centrifugation at 14,000×g and the soluble proteins were discarded. The insoluble materials were resuspended in 5 mls BPER II supplemented with 1 mg/mL lysozyme and incubated on ice for 10 minutes after which 5 mls of BPER II diluted in water 1:20 was added and the samples were spun at 14,000×g. The supernatant was removed and the pellets were wash twice in 1:20 BPERII. The purified inclusion bodies were solubilized in PBS 8 M Urea, 10 mM BME, pH 7.4.

The MBP fusion proteins were diluted to a concentration of approximately 1 mg/mL and refolded using a stepwise dialysis in PBS pH 7.4 from 8 to 0 M urea through 6, 4, 2, 0.5, and 0 M urea. At the 4, 2, and 0.5 M Urea steps 0.2 M Arginine, 2 mM reduced Glutathione, and 0.5 mM oxidized glutathione was added. The 0 M Urea dialysis included 0.2 M Arginine. After removal of the urea, the proteins were dialyzed against 0.05 M Arginine followed by and extensive dialysis against PBS pH 7.4. All dialysis were conducted at 4° C. overnight. To remove aggregates, each protein was subjected to size exclusion chromatography on a sephacryl S-200 column. Fractions containing the correctly folded proteins were concentrated using an Amicon Ultra centrifugal filter.

Cloning and Expression of the AA: a MMP-9 Cleavable, Masked Anti-VEGF scFv CHis Tag Cloning:

The primers CX0308 and CX0310 (Table 10) were used to amplify and add a NcoI restriction site to the 5' end and a HindIII restriction site and His6 tag (SEQ ID NO: 48) to the 3' end, respectively, of the (MM accepting site/MMP-9 CM/VEGFscFv AB) vector which was subsequently cloned into a vector containing the pelB signal peptide. Anti-VEGF scFv MMs were cloned as previously described. The corresponding nucleotide and amino acid sequences are provided in Table 13.

TABLE 13

306 or 314 MM/MMP-9 CM/anti-VEGF scFv CHis AB Sequences

306 MM/MMP-9 CM/anti-VEGF scFv CHis AB nucleotide sequence ggccagtctggccagccgtgttctgagtggcagtcgatggtgcagccgcgttgctattatgggggcggttctggtggcagcggccaaggt ggccaagtgcacatgccactgggcttcctgggtccggcggttctgatattcaactgacccagagcccttcttccctgagtgccagcgtggg tgaccgtgttacgatcacttgctcggccagccaagatatttctaactacctgaattggtaccagcagaagccaggaaaggcaccaaaagtcc tgatctacttcacaagttcactgcattccggcgtaccgtcgcgctttagcggttctggcagtggtaccgacttcaccctgactatctcgagtctg caacctgaggattttgctacatattactgtcagcaatattcgaccgtgccgtggacgttcgggcagggcaccaaagtggagattaaggggggg tggaggcagcggggaggtggctcaggcggtggagggtctggcgaggtccagctggtagaaagcggggcggactggtccaaccgg gcggatccctgcgtctgagctgcgcggcctcgggttacgactttactcactacggaatgaactgggttcgccaagcccctggtaaaggtctg gaatgggtcggatggattaatacatacactggagaacctacttatgctgctgatttcaaacgtcgctttactttctctctggatacaagtaagtc aaccgcctatctgcaaatgaacagcctgcgtgcagaggacacggctgtgtactattgtgcgaaatatccttattattatggaacttcccactg gtatttcgatgtatggggccagggtactctggttacagtgtcgcatcatcaccatcaccac (SEQ ID NO: 75)

306 MM/MMP-9 CM/anti-VEGF scFv CHis AB amino acid sequence

GQSGQPCSEWQSMVQPRCYYGGGSGGSGQGGQVHMPLGFLGPGGSDIQLTQSPSSLSA

SVGDRVTITCSASQDISNYLNWYQQKPGKAPKVLIYFTSSLHSGVPSRFSGSGSGTDFTL

TISSLQPEDFATYYCQQYSTVPWTFGQGTKVEIKGGGSGGGGSGGGGSGEVQLVESGG

GLVQPGGSLRLSCAASGYDFTHYGMNWVRQAPGKGLEWVGWINTYTGEPTYAADFKR

RFTFSLDTSKSTAYLQMNSLRAEDTAVYYCAKYPYYYGTSHWYFDVWGQGTLVTVSH

HHHHH (SEQ ID NO: 76)

314 MM/MMP-9 CM/anti-VEGF scFv CHis AB nucleotide sequence ggccagtctggccagcggccgccgtgttgccgtgattatagtattttggagtgctgtaagagtgatggcggttctggtggcagcggccaag gtggccaagtgcacatgccactgggcttcctgggtccggcggttctgatattcaactgacccagagcccttcttccctgagtgccagcgtg ggtgaccgtgttacgatcacttgctcggccagccaagatatttctaactacctgaattggtaccagcagaagccaggaaaggcaccaaagt cctgatctacttcacaagttcactgcattccggcgtaccgtcgcgctttagcggttctggcagtggtaccgacttcaccctgactatctcgagtc tgcaacctgaggattttgctacatattactgtcagcaatattcgaccgtgccgtggacgttcgggcagggcaccaaagtggagattaaggg ggtggaggcagcggggaggtggctcaggcggtggagggtctggcgaggtccagctggtagaaagcggggcggactggtccaacc gggcggatccctgcgtctgagctgcgcggcctcgggttacgactttactcactacggaatgaactgggttcgccaagcccctggtaaaggt ctggaatgggtcggatggattaatacatacactggagaacctacttatgctgctgatttcaaacgtcgctttactttctctctggatacaagta agtcaaccgcctatctgcaaatgaacagcctgcgtgcagaggacacggctgtgtactattgtgcgaaatatccttattattatggaacttcccac tggtatttcgatgtatggggccagggtactctggttacagtgtcgcatcatcaccatcaccactaa (SEQ ID NO: 77)

314 MM/MMP-9 CM/anti-VEGF scFv CHis AB amino acid sequence

GQSGQRPPCCRDYSILECCKSDGGSGGSGQGGQVHMPLGFLGPGGSDIQLTQSPSSLSAS

VGDRVTITCSASQDISNYLNWYQQKPGKAPKVLIYFTSSLHSGVPSRFSGSGSGTDFTLTI

TABLE 13-continued

306 or 314 MM/MMP-9 CM/anti-VEGF scFv CHis AB Sequences

SSLQPEDFATYYCQQYSTVPWTFGQGTKVEIKGGGGSGGGGSGGGGSGEVQLVESGGG

LVQPGGSLRLSCAASGYDFTHYGMNWVRQAPGKGLEWVGWINTYTGEPTYAADFKRR

FTFSLDTSKSTAYLQMNSLRAEDTAVYYCAKYPYYYGTSHWYFDVWGQGTLVTVSHH

HHHH (SEQ ID NO: 78)

Expression:

Expression of the Anti-VEGF scFv His AAs was conducted in a K12 TB1 strain of *E. coli* An ampicillin-resistant colony containing the desired construct was used to inoculate a 5 ml overnight culture containing LB medium supplemented with 50 μg/mL Ampicillin. 2.5 ml of overnight culture was used to inoculate 250 mL of fresh LB medium supplemented with 50 μg/mL ampicillin and 0.2% Glucose and allowed to grow at 37° C. shaking at 250 rpm until an O.D. of 1.0 was reached. Isopropylthio-β-D-galactosidas was then added to a final concentration of 0.3 mM and the culture was allowed to grow for a further 5 hrs at 30° C. after which the cells were harvested by centrifugation at 3000×g. The periplasmic fraction was immediately purified using the lysozyme/osmotic shock method. Briefly, the cell pellet was resuspended in 3 mLs of 50 mM Tris, 200 mM NaCl, 10 mM EDTA, 20% Sucrose, pH 7.4 and 2 uL/mL ready-use lysozyme solution was added. After a 15 min. incubation on ice, 1.5 volumes of water (4.5 mLs) was added and the cells were incubated for another 15 min. on ice. The soluble periplasmic fraction was recovered by centrifugation at 14,000× g.

The Anti-VEGF scFv His proteins were partially purified using Ni-NTA resin. Crude periplasmic extracts were loaded onto 0.5 ml of Ni-NTA resin and washed with 50 mM phosphate, 300 mM NaCl, pH 7.4. His tagged proteins were eluted with 50 mM phosphate, 300 mM NaCl, 200 mM Imidizale, pH 6.0. Proteins were concentrated to approximately 600 μl and buffer exchanged into PBS using Amicon Ultra centrifugal concentrators.

Cloning and Expression of the AA: a MMP-9 Cleavable, Masked Anti-VEGF scFv as Human Fc Fusion Cloning:

The primers CX0312 and CX0314 (Table 10) were used to amplify the sequence encoding MMP-9 CM/Anti-VEGF scFv. The primers also included sequences for a 5' EcoRI restriction site and a 3' NcoI restriction site and linker sequence. Cutting the PCR amplified sequence with EcoRI and NcoI and subsequent cloning into the pFUSE-hIgG1-Fc2 vector generated vectors for the expression of Fc fusion proteins. Anti-VEGF scFv AB MMs were inserted into these vectors as previously described. Constructs containing 306 MM, 313 MM, 314 MM, 315 MM, a non-binding MM (100 MM), as well as no MM were constructed and sequences verified. The corresponding nucleotide and amino acid sequences are provided below in Table 14.

TABLE 14

306 MM/MMP-9 CM/anti-VEGF scFv-Fc AB sequences

306 MM/MMP-9 CM/anti-VEGF scFv-Fc AB nucleotide sequence ggccagtctggccagccgtgttctgagtggcagtcgatggtgcagccgcgttgctattatgggggcggttctggtggcagcggccaaggtg gccaagtgcacatgccactgggcttcctgggtccgggcggttctgatattcaactgacccagagcccttcttccctgagtgccagcgtgggtg accgtgttacgatcacttgctcggccagccaagatatttctaactacctgaattggtaccagcagaagccaggaaaggcaccaaaagtcctga tctacttcacaagttcactgcattccggcgtaccgtcgcgctttagcggttctggcagtggtaccgacttcaccctgactatctcgagtctgcaa cctgaggattttgctacatattactgtcagcaatattcgaccgtgccgtggacgttcgggcagggcaccaaagtggagattaaggggggtgg aggcagcggggaggtggctcaggcggtggagggtctggcgaggtccagctggtagaaagcgggggcggactggtccaacgggcgga tccctgcgtctgagctgcgcggcctcgggttacgactttactcactacggaatgaactgggtcgccaagcccctggtaaaggtctggaatgg gtcggatggattaatacatacactggagaacctacttatgctgctgatttcaaacgtcgctttactttctctctggatacaagtaagtcaaccg cctatctgcaaatgaacagcctgcgtgcagaggacacggctgtgtactattgtgcgaaatatccttattattatggaacttcccactggtatttc gatgtatggggccagggtactctggttacagtgtcgggcggtagcggcgccatggttagatctgacaaaactcacacatgcccaccgtgccca gcacctgaactcctgggggaccgtcagtcttcctcttccccccaaaacccaaggacaccctcatgatctcccggacccctgaggtcacatg cgtggtggtggacgtgagccacgaagaccctgaggtcaagttcaactggtacgtggacggcgtggaggtgcataatgccaagacaaagcc gcgggaggagcagtacaacagcacgtaccgtgtggtcagcgtcctcaccgtcctgcaccaggactggctgaatggcaaggagtacaagt gcaaggtctccaacaaagccctcccagccccatcgagaaaaccatctccaaagccaaagggcagccccgagaaccacaggtgtacacc ctgcccccatcccgggaggagatgaccaagaaccaggtcagcctgacctgcctggtcaaaggcttctatcccagcgacatcgccgtggag tgggagagcaatgggcagccggagaacaactacaagaccacgcctcccgtgctggactccgacggctccttcttcctctacagcaagctca TABLE 14-continued 306 MM/MMP-9 CM/anti-VEGF scFv-Fc AB sequences ccgtggacaagagcaggtggcagcaggggaacgtcttctcatgctccgtgatgcatgagggtctgcacaaccactacacgcagaagagcc tctccctgtctccgggtaaa (SEQ ID NO: 79)

306 MM/MMP-9 CM/anti-VEGF scFv-Fc AB amino acid sequence

GQSGQPCSEWQSMVQPRCYYGGGSGGSGQGGVHMPLGFLGPGGSDIQLTQSPSSLSAS

VGDRVTITCSASQDISNYLNWYQQKPGKAPKVLIYFTSSLHSGVPSRFSGSGSGTDFTLTI

SSLQPEDFATYYCQQYSTVPWTFGQGTKVEIKGGGGSGGGGSGGGGSGEVQLVESGGG

LVQPGGSLRLSCAASGYDFTHYGMNWVRQAPGKGLEWVGWINTYTGEPTYAADFKRR

FTFSLDTSKSTAYLQMNSLRAEDTAVYYCAKYPYYYGTSHWYFDVWGQGTLVTVSGGS

GAMVRSDKTHTCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKVSNKALPAP

IEKTISKAKGQPREPQVYTLPPSREEMTKNQVSLTCLVKGFYPSDIAVEWESNGQPENNY

KTTPPVLDSDGSFFLYSKLTVDKSRWQQGNVFSCSVMHEGLHNHYTQKSLSLSPGK (SEQ ID NO: 80)

314 MM/MMP-9 CM/anti-VEGF scFv-Fc AB nucleotide sequence ggccagtctggccagcggccgccgtgttgccgtgattatagtattttggagtgctgtaagagtgatggcggttctggtggcagcggccaagg tggccaagtgcacatgccactgggcttcctgggtccggcggttctgatattcaactgacccagagcccttcttccctgagtgccagcgtggg tgaccgtgttacgatcacttgctcggccagccaagatatttctaactacctgaattggtaccagcagaagcaggaaaggcaccaaaagtcct gatctacttcacaagttcactgcattccggcgtaccgtcgcgctttagcggttctggcagtggtaccgacttcaccctgactatctcgagtctgc aacctgaggattttgctacatattactgtcagcaatattcgaccgtgccgtggacgttcgggcagggcaccaaagtggagattaagggggggt ggaggcagcggggaggtggctcaggcggtggaggtctggcgaggtccagctggtagaaagcggggggcggactggtccaacccgggcgg atccctgcgtctgagctgcgcggcctcgggttacgactttactcactacggaatgaactgggttcgccaagcccctggtaaaggtctggaat gggtcggatggattaatacatacactggagaacctacttatgctgctgatttcaaacgtcgctttactttctctctggatacaagtaagtcaac cgcctatctgcaaatgaacagcctgcgtgcagaggacacggctgtgtactattgtgcgaaatatccttattattatggaacttcccactggtatt tcgatgtatggggccagggtactctggttacagtgtcggcggtagcggcgccatggttagatctgacaaaactcacacatgcccaccgtgc ccagcacctgaactcctggggggaccgtcagtcttcctcttcccccaaaacccaaggacaccctcatgatctcccggaccctgaggtcac atgcgtggtggtggacgtgagccacgaagaccctgaggtcaagttcaactggtacgtggacggcgtggaggtgcataatgccaagacaaa gccgcgggaggagcagtacaacagcacgtaccgtgtggtcagcgtcctcaccgtcctgcaccaggactggctgaatggcaaggagtaca agtgcaaggtctccaacaaagccctcccagccccatcgagaaaccatctccaaagccaaagggcagccccgagaaccacaggtgtac accctgcccccatcccgggaggagatgaccaagaaccaggtcagcctgacctgcctggtcaaaggcttctatcccagcgacatcgccgtg gagtgggagagcaatgggcagccggagaacaactacaagaccacgcctcccgtgctggactccgacggctccttcttcctctacagcaag ctcaccgtggacaagagcaggtggcagcaggggaacgtcttctcatgctccgtgatgcatgagggtctgcacaaccactacacgcagaag agcctctccctgtctccgggtaaa (SEQ ID NO: 81)

314 MM/MMP-9 CM/anti-VEGF scFv-Fc AB amino acid sequence

GQSGQRPPCCRDYSILECCKSDGGSGGSGQGGVHMPLGFLGPGGSDIQLTQSPSSLSAS

VGDRVTITCSASQDISNYLNWYQQKPGKAPKVLIYFTSSLHSGVPSRFSGSGSGTDFTLTI

SSLQPEDFATYYCQQYSTVPWTFGQGTKVEIKGGGGSGGGGSGGGGSGEVQLVESGGG

LVQPGGSLRLSCAASGYDFTHYGMNWVRQAPGKGLEWVGWINTYTGEPTYAADFKRR

FTFSLDTSKSTAYLQMNSLRAEDTAVYYCAKYPYYYGTSHWYFDVWGQGTLVTVSGGS

GAMVRSDKTHTCPPCPAPELLGGPSVFLFPPKPKDTLMISRTPEVTCVVVDVSHEDPEVK

TABLE 14-continued

306 MM/MMP-9 CM/anti-VEGF scFv-Fc AB sequences

FNWYVDGVEVHNAKTKPREEQYNSTYRVVSVLTVLHQDWLNGKEYKCKVSNKALPAP

IEKTISKAKGQPREPQVYTLPPSREEMTKNQVSLTCLVKGFYPSDIAVEWESNGQPENNY

KTTPPVLDSDGSFFLYSKLTVDKSRWQQGNVFSCSVMHEGLHNHYTQKSLSLSPGK (SEQ ID NO: 82)

Expression:

10 µg of expression vectors for 306 MM/MMP-9 CM/anti-VEGFscFv-Fc, 314 MM/MMP-9 CM/anti-VEGFscFv-Fc or anti-VEGFscFv-Fc were introduced into $10^7$ HEK-293 freestyle cells (Invitrogen, CA) by transfection using transfectamine 2000 as per manufacturer's protocol (Invitrogen, CA). The transfected cells were incubated for an additional 72 hours. After incubation, the conditioned media was harvested and cleared of cells and debris by centrifugation. The conditioned media was assayed for activity by ELISA.

Example 8

Measurement of the Activation of a Masked MMP-9 Cleavable AA

To measure the activation of the masked MMP-9 cleavable anti-VEGF AAs by MMP-9, 100 ul of a 2 µg/ml PBS solution of VEGF was added to microwells (96 Well Easy Wash; Corning) and incubated overnight at 4° C. Wells were then blocked for 3×15 minute with 300 uL Superblock (Pierce). One hundred microliters of an AA (see below for details pertaining to each construct), treated or untreated with MMP-9, were then added to wells in PBST, 10% Superblock and incubated at room temperature (RT) for 1 hr. All wash steps were done three times and performed with 300 ul PBST. One hundred microliters of secondary detection reagent were then added and allowed to incubate at RT for 1 hr. Detection of HRP was completed using 100 ul of TMB one (Pierce) solution. The reaction was stopped with 100 µl of 1N HCL and the absorbance was measured at 450 nM.

ELISA Assay of an AA Construct Containing: MBP/MM/MMP-9 CM/Anti-VEGF scFv AB

Figure 5:
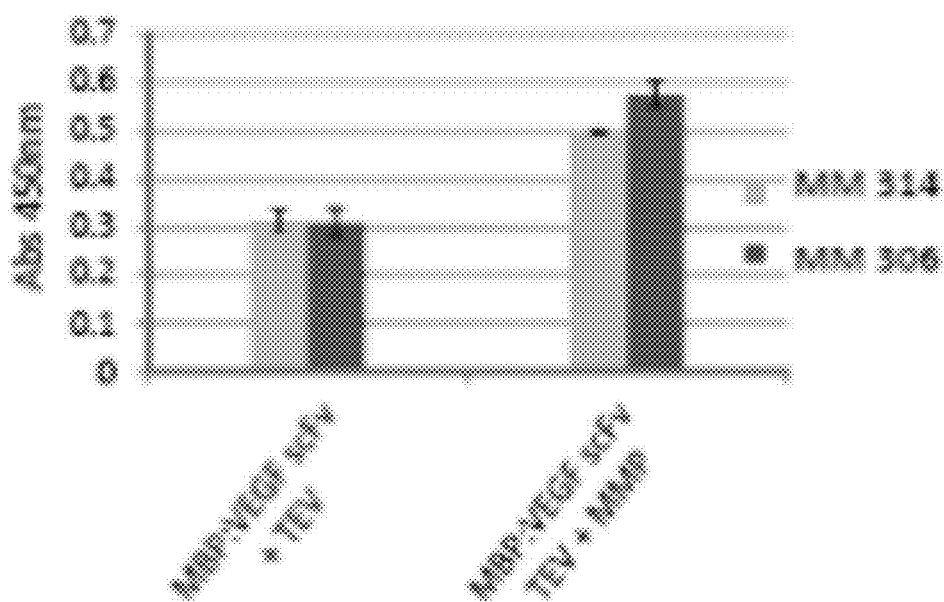
FIG. 5 provides ELISA data showing the MMP-9 activation of the MBP:anti-VEGFscFv AAs with the MMs 306 and 314. Samples were treated with TEV to remove the MBP fusion partner and subsequently activated by MMP-9 digestion.

Two hundred microliters of biotinylated AA in MMP-9 digestion buffer (50 mM Tris, 2 mM $CaCl_2$, 20 mM NaCl, 100 µM $ZnCl_2$, pH 6.8) at a concentration of 200 nM was digested with 20 U TEV protease overnight at 4° C. to remove the MBP fusion partner. Samples were then incubated for 3 hrs with or without ~3 U of MMP-9 at 37° C., diluted 1:1 to a final concentration of 100 nM in PBST, 10% Superblock, and added to the ELISA wells. Detection of the AA was achieved with an Avidin-HRP conjugate at a dilution of 1:7500. MMP-9 activation of MMP-9 cleavable masked MBP:anti-VEGF scFv AA is presented in FIG. 5.

ELISA Assay of an AA Construct Containing: MM/MMP-9 CM/Anti-VEGF scFv His

Figure 6:
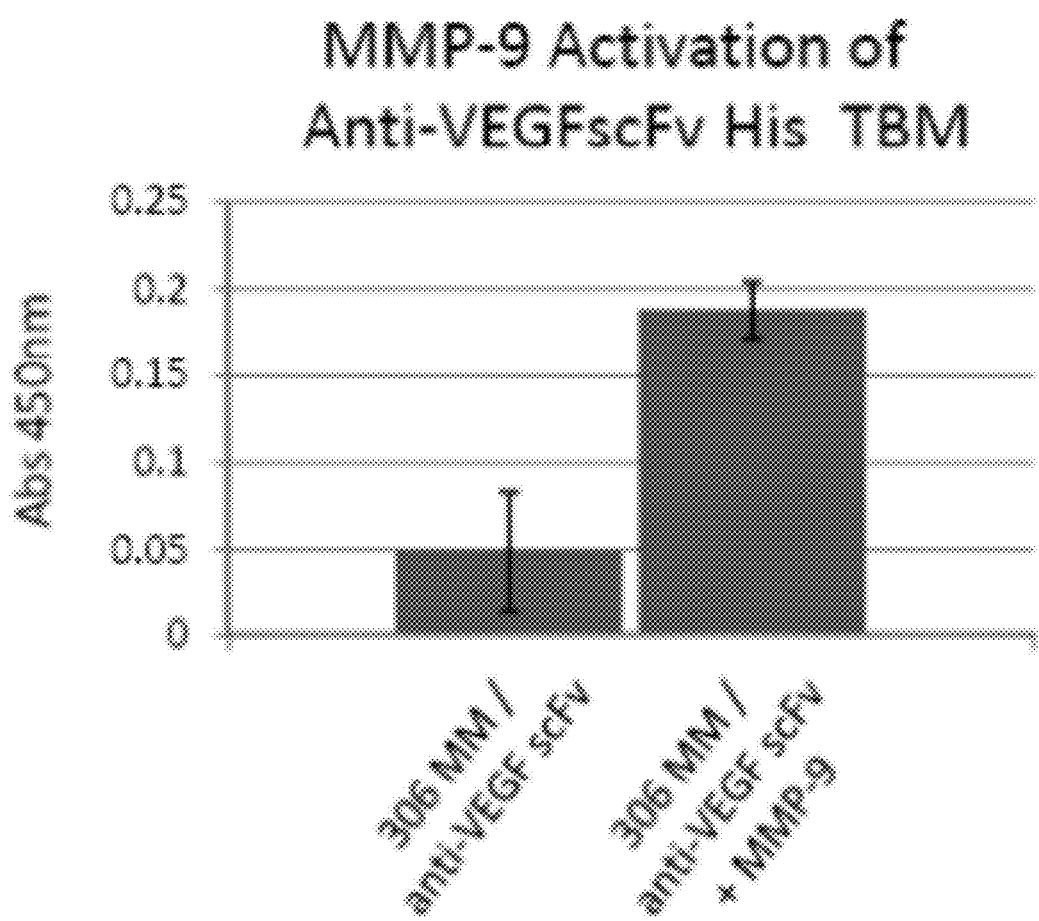
FIG. 6 provides ELISA data demonstrating the MMP-9-dependent VEGF binding of the anti-VEGFscFv His construct with the 306 MM.

Crude periplasmic extracts dialyzed in MMP-9 digestion buffer (150 µL) were incubated with or without ~3 U of MMP-9 for 3 hrs at 37° C. Samples were then diluted to 400 µL with PBST, 10% Superblock and added to the ELISA wells. Detection of the AA was achieved using an Anti-His6 (SEQ ID NO: 48)-HRP conjugate at a dilution of 1:5000. MMP-9 activation of MMP-9 cleavable masked anti-VEGF scFv His AA is presented in FIG. 6.

ELISA Assay of an AA Construct Containing: MM/MMP-9 CM/Anti-VEGF scFv-Fc

Figure 7:
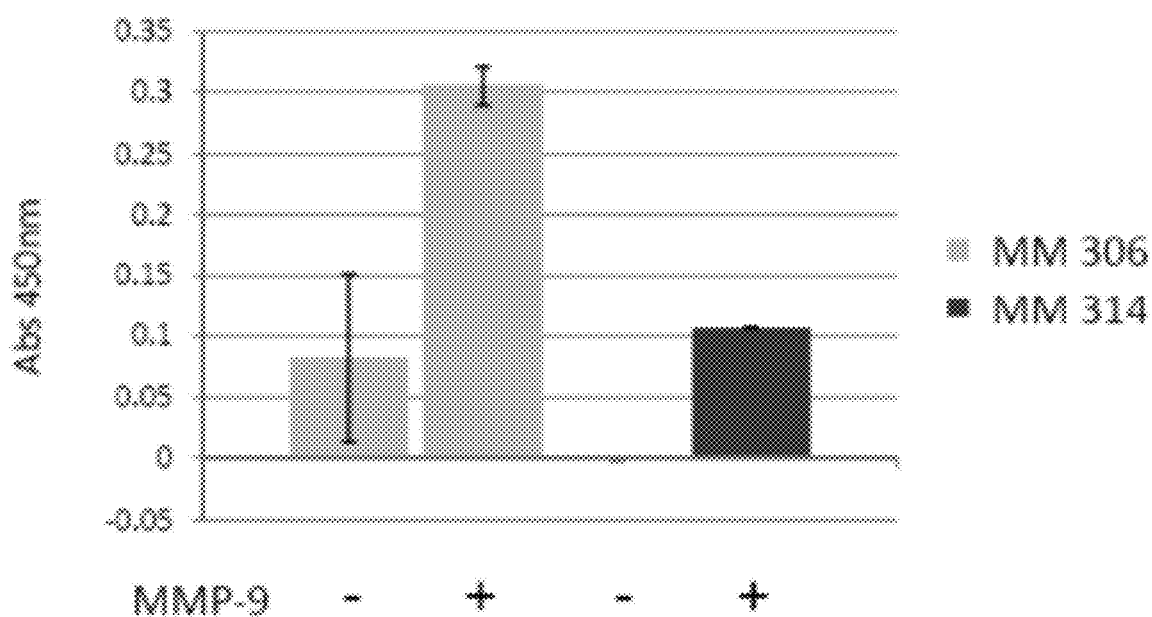
FIG. 7 provides ELISA data demonstrating the MMP-9-dependent VEGF binding of anti-VEGFscFv-Fc AAs with the MMs 306 and 314 from HEK cell supernatants.

Fifty microliters of HEK cell supernatant was added to 200 µL MMP-9 digestion buffer and incubated with or without ~19 U MMP-9 for 2 hrs at 37° C. Samples were then diluted 1:1 in PBST, 10% Superblock and 100 µL were added to the ELISA wells. Detection of the AA was achieved using Anti-human Fc-HRP conjugate at a dilution of 1:2500. MMP-9 activation of MMP-9 cleavable masked anti-VEGF scFv-Fc is presented in FIG. 7.

Figure 8:
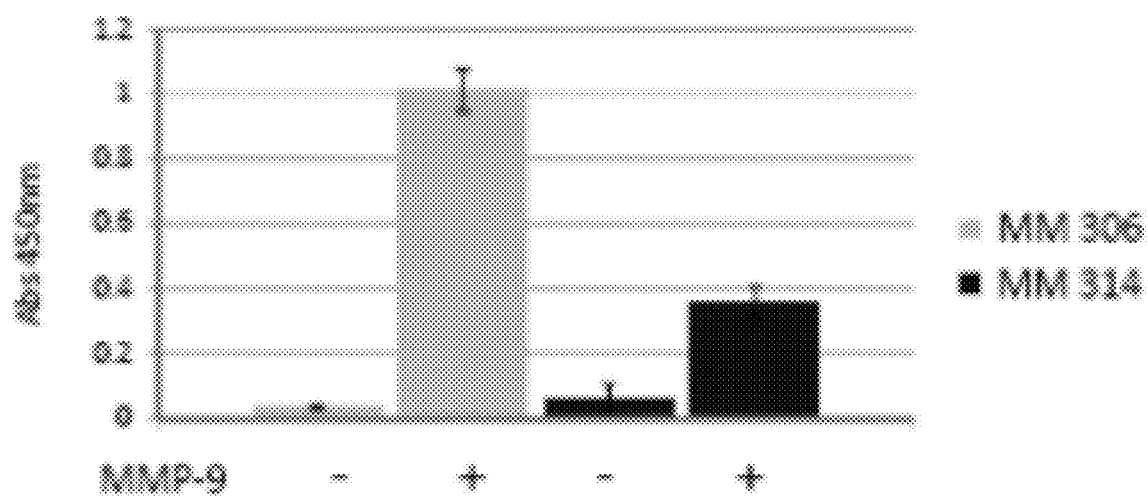
FIG. 8 provides ELISA data showing the MMP-9-dependent VEGF binding of anti-VEGF scFv-Fc AA constructs with the MMs 306 and 314 that were purified using a Protein A column.
Figure 9:
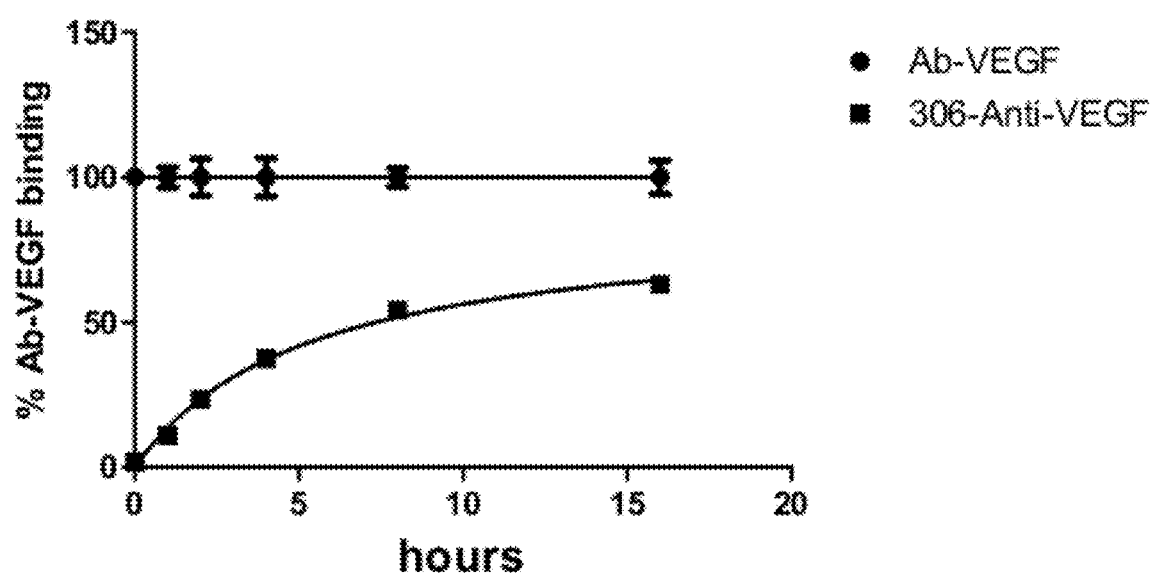
FIG. 9 shows that the 306 MM, which binds to an anti-VEGF antibody with an affinity of >600 nM, does not efficiently preclude binding to VEGF.

Purification and Assay of an AA Construct Containing: MM/MMP-9 CM/Anti-VEGF scFv-Fc Anti-VEGF scFv Fc AAs were purified using a Protein A column chromatography. Briefly, 10 mLs of HEK cell supernatants were diluted 1:1 with PBS and added to 0.5 mL Protein A resin pre-equilibrated in PBS. Columns were washed with 10 column volumes of PBS before eluting bound protein with 170 mM acetate, 300 mL NaCl pH. 2.5 and immediately neutralized 1 mL fractions with 200 µL of 2 M Tris pH 8.0. Fractions containing protein were then concentrated using Amicon Ultra centrifugal concentrators. ELISA was conducted as with HEK cell supernatants. ELISA data showing the MMP-9 dependent VEGF binding of Anti-VEGFscFv Fc AA constructs with the MMs 306 and 314 that were purified using a Protein A column are presented in FIG. 8.

Example 9

Target Displacement Assay for the Discovery and Validation of Efficiently Masked Therapeutic Proteins VEGF was adsorbed to the wells of a 96-well micro-titer plate, washed and blocked with milk protein. 25 ml of culture media containing anti-VEGF antibody or anti-VEGF AA's containing the MM JS306, was added to the coated wells and incubated for 1, 2, 4, 8 or 24 hours. Following incubation, the wells were washed and the extent of bound AA's was measured by anti-huIgG immunodetection. FIG. 9 shows mask 306 can completely inhibit binding to VEGF at one hour; however, at 16 hours, >50% of the 306-antiVEGF AA is bound to its antigen, VEGF. The 306 mask, which binds to anti-VEGF antibody with an affinity of >600 nM, does not efficiently preclude binding to VEGF.

Example 10

Library Screening and Isolation of anti-CTLA4 MMs

CTLA4 antibody masking moieties (MMs) were isolated from a combinatorial library of $10^{10}$ random 15mer peptides displayed on the surface of *E. coli* according to the method of Bessette et al (Bessette, P. H., Rice, J. J and Daugherty, P.S. Rapid isolation of high-affinity protein binding peptides using bacterial display. Protein Eng. Design & Selection. 17:10,731-739, 2004). Biotinylated mouse anti-CTLA4 antibody (clone UC4 F10-11, 25 nM) was incubated with the library and antibody-bound bacteria expressing putative binding peptides were magnetically sorted from non-binders using streptavidin-coated magnetic nanobeads. Subsequent rounds of enrichment were carried out using FACS. For the initial round of FACS, bacteria were sorted using biotinylated target (5 nM) and secondary labeling step with streptavidiin phycoerythrin. In subsequent rounds of FACS, sorting was performed with Dylight labeled antibody and the concentration of target was reduced (1 nM, then 0.1 nM) to avoid the avidity effects of the secondary labeling step and select for the highest affinity binders. One round of MACS and three rounds of FACS resulted in a pool of binders from which individual clones were sequenced. Relative affinity and off-rate screening of individual clones were performed using a ficin digested Dylight-labeled Fab antibody fragment to reduce avidity effects of the bivalent antibody due to the expression of multiple peptides on the bacterial surface. As an additional test of target specificity, individual clones were screened for binding in the presence of 20 uM *E. Coli* depleted IgG as a competitor. Amino acid and nucleotide sequences of the 4 clones chosen for MM optimization are shown in Table 15. These sequences will interchangeably referred to as 115 MM, 184 MM, 182 MM, and 175 MM. MM candidates with a range of off-rates were chosen, to determine the effects of off-rates on MM dissociation after cleavage. An MM that did not bind anti-CTLA4 was used as a negative control.

to the method of Gilliland et al. (Gilliland L. K., N. A. Norris, H. Marquardt, T. T. Tsu, M. S. Hayden, M. G. Neubauer, D. E. Yelton, R. S. Mittler, and J. A. Ledbetter. Rapid and reliable cloning of antibody variable regions and generation of recombinant single chain antibody fragments. Tissue Antigens 47:1, 1-20, 1996). A detailed version of this protocol can be found at the Institute of Biomedical Sciences (IBMS) at Academia Sinica in Taipei, Taiwan website. In brief, total RNA was isolated from hybridomas using the RNeasy total RNA isolation kit (Qiagen). The primers IgK1 (gtyttrtgngtnacytcrca (SEQ ID NO: 93)) and IgH1 (acdatyttyttrtcnacyttngt (SEQ ID NO: 94)) (Gilliland et al. referenced above) were used for first strand synthesis of the variable light and heavy chains, respectively. A poly G tail was added with terminal transferase, followed by PCR using the 5' ANCTAIL primer (Gilliland et al. referenced above) (cgtcgatgagctctagaattcgcatgtgcaagtccgatggtcccccccccccccc (SEQ ID NO: 95)) containing EcoRI, SacI and XbaI sites for both light and heavy chains (poly G tail specific) and the 3' HBS-hIgK (cgtcatgtcgacggatccaagcttacyttccayttnacrttdatrtc (SEQ ID NO: 96)) and HBS-hIgH (cgtcatgtcgacggatccaagettrcangcnggngcnarnggrtanac (SEQ ID NO: 97)) derived from mouse antibody constant region sequences and containing HindIII, BamHI and SalI sites for light and heavy chain amplification, respectively (Gilliland et al. referenced above). Constructs and vector were digested with HindIII and SacI, ligated and transformed into *E. Coli*. Individual colonies were sequenced and the correct sequences for $V_L$ and $V_H$ (Tables 16 and 17 respectively) were confirmed by comparison with existing mouse and hamster antibodies. The leader

TABLE 15

| Amino acid and nucleotide sequences for MMs that mask anti-CTLA4 |
|---|
| KK115 MM |
| M I L L C A A G R T W V E A C A N G R (SEQ ID NO: 84) |
| ATGATTTTGTTGTGCGCGGCGGGTCGGACGTGGGTGGAGGCTTGCGCTAA TGGTAGG (SEQ ID NO: 83) |
| KK184 MM |
| A E R L C A W A G R F C G S (SEQ ID NO: 86) |
| GCTGAGCGGTTGTGCGCGTGGGCGGGGCGGTTCTGTGGCAGC (SEQ ID NO: 85) |
| KK182 MM |
| W A D V M P G S G V L P W T S (SEQ ID NO: 88) |
| TGGGCGGATGTTATGCCTGGGTCGGGTGTGTTGCCGTGGACGTCG (SEQ ID NO: 87) |
| KK175 MM |
| S D G R M G S L E L C A L W G R F C G S (SEQ ID NO: 90) |
| AGTGATGGTCGTATGGGGAGTTTGGAGCTTTGTGCGTTGTGGGGGCGGTTCTGTGGCAGC (SEQ ID NO: 89) |
| Negative control (does not bind anti-CTLA4) |
| P C S E W Q S M V Q P R C Y Y (SEQ ID NO: 92) |
| CCGTGTTCTGAGTGGCAGTCGATGGTGCAGCCGCGTTGCTATTAT (SEQ ID NO: 91) |

Example 11

Cloning of Anti-CTLA4 scFv

Anti-CTLA4 ScFv was cloned from the HB304 hybridoma cell line (American Type Culture Collection) secreting UC4F10-11 hamster anti-mouse CTLA4 antibody according sequences, as described for anti-CTLA4 in the presented sequence is also commonly called a signal sequence or secretion leader sequence and is the amino acid sequence that directs secretion of the antibody. This sequence is cleaved off, by the cell, during secretion and is not included in the mature protein. Additionally, the same scFv cloned by Tuve et al (Tuve, S. Chen, B. M., Liu, Y., Cheng, T-L., Toure, P., Sow, P.S., Feng, Q., Kiviat, N., Strauss, R., Ni, S., Li, Z., Roffler, S. R. and Lieber, A. Combination of Tumor Site—Located CTL-Associated Antigen-4 Blockade and Systemic Regulatory T-Cell Depletion Induces Tumor Destructive Immune Responses. Cancer Res. 67:12, 5929-5939, 2007) was identical to sequences presented here.

with half of a (GGGS)$_3$ linker (SEQ ID NO: 102) at either the N- or C-terminus for a subsequent 'splicing by overlapping extension' PCR (SOE-PCR; Horton, R. M., Hunt, H. D., Ho, S. N., Pullen, J. K. and Pease, L. R. (1989) Engineering hybrid genes without the use of restriction enzymes: gene splicing by overlap extension. Gene 77, 61-68) with either $V_H$ or $V_L$ at the

TABLE 16

Hamster anti-mouse CTLA4 $V_L$

Leader

M E S H I H V F M S L F L W V S G S C A D I M M T Q S
P S S L S V S A G E K A T I S C K S S Q S L F N S N A
K T N Y L N W Y L Q K P G Q S P K L L I Y Y A S T
R H T G V P D R F R G S G T D F T L T I S S V Q D E
D L A F Y Y C Q Q W Y D Y P Y T F G A G T K V E I K (SEQ ID NO: 98)

atggaatcacatatccatgtcttcatgtccttgttcctttgggtgtctggttcctgtgcagacatcatgatgacccagtctccttcatccctga gtgtgtcagcgggagagaaagccactatcagctgcaagtccagtcagagtcttttcaacagtaacgccaaaacgaactacttgaactgg tatttgcagaaaccagggcagtctcctaaactgctgatctattatgcatccactaggcatactggggtccctgatcgcttcagaggcagtg gatctgggacggatttcactctcaccatcagcagtgtccaggatgaagacctggcattttattactgtcagcagtggtatgactacccata cacgttcggagctgggaccaaggtggaaatcaaa (SEQ ID NO: 99)

TABLE 17

Hamster anti mouse CTLA4 $V_H$

Leader

K M R L L G L L Y L V T A L P G V L S Q I Q L Q E S
G P G L V N P S Q S L S L S C S V T G Y S I T S G Y G
W N W I R Q F P G Q K V E W M G F I Y Y E G S T Y
Y N P S I K S R I S I T R D T S K N Q F F L Q V N S V
T T E D T A T Y Y C A R Q T G Y F D Y W G Q G T M V
T V S S (SEQ ID NO: 100)

aagatgagactgttgggtcttctgtacctggtgacagcccttcctggtgtcctgtcccagatccagcttcaggagtcaggacctggcctggt gaacccctcacaatcactgtccctctcttgctctgtcactggttactccatcaccagtggttatggatggaactggatcaggcagttcccag ggcagaaggtggagtggatgggattcatatattatgagggtagcacctactacaaccccttccatcaagagccgcatctccatcaccagag acacatcgaagaaccagttcttcctgcaggtgaattctgtgaccactgaggacacagccacatattactgtgcgagacaaactgggtact ttgattactggggccaaggaaccatggtcaccgtctcctca (SEQ ID NO: 101)

Example 12

Construction of the Anti-CTLA4 scFv with MMs and CMs

Figure 10:
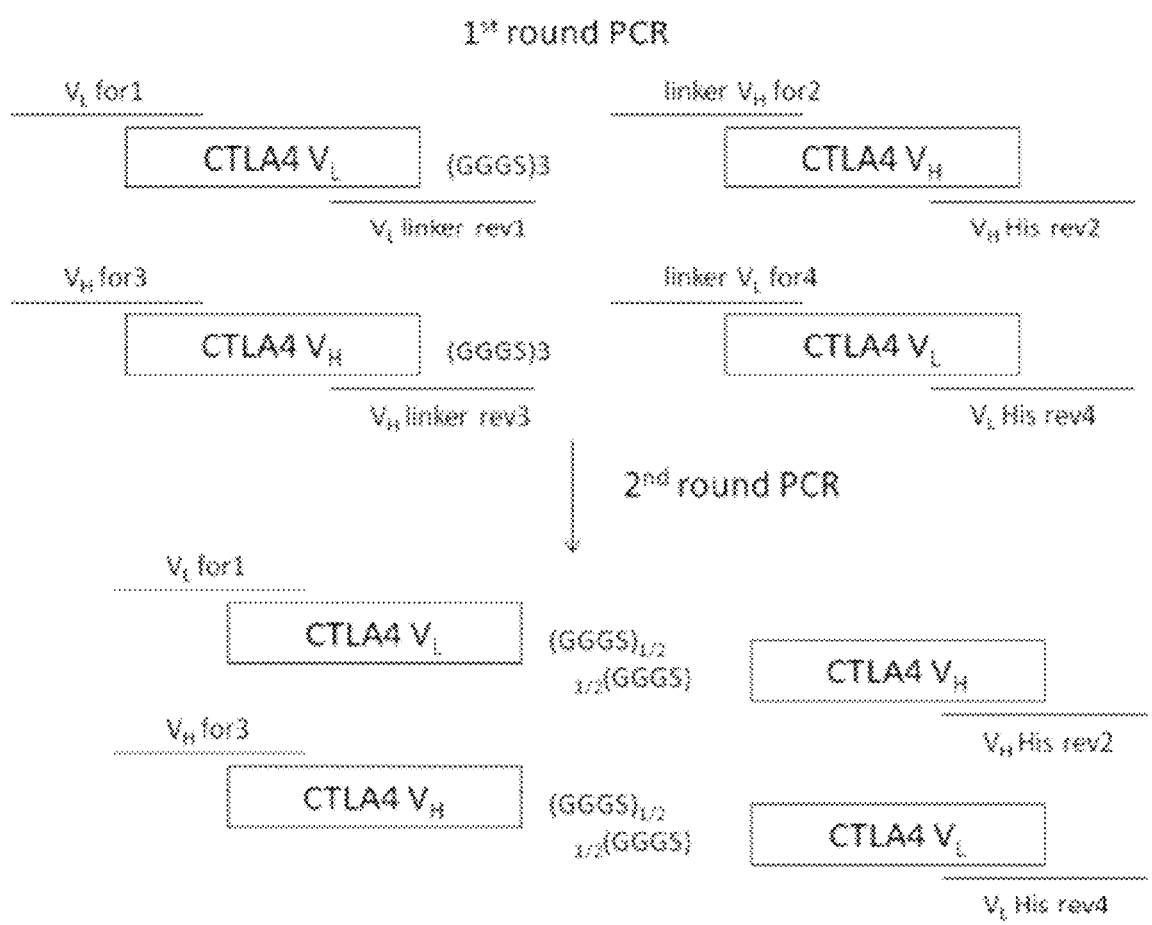
FIG. 10 shows light and heavy chains of anti-CTLA4 joined via SOE-PCR to generate scFv constructs in both orientations, $V_HV_L$ and $V_LV_H$. '(GGGS)3' disclosed as SEQ ID NO: 102, '(GGGS)$_{1/2}$' disclosed as SEQ ID NO: 35 land '$_{1/2}$(GGGS)' disclosed as SEQ ID NO: 235.
Figure 12:
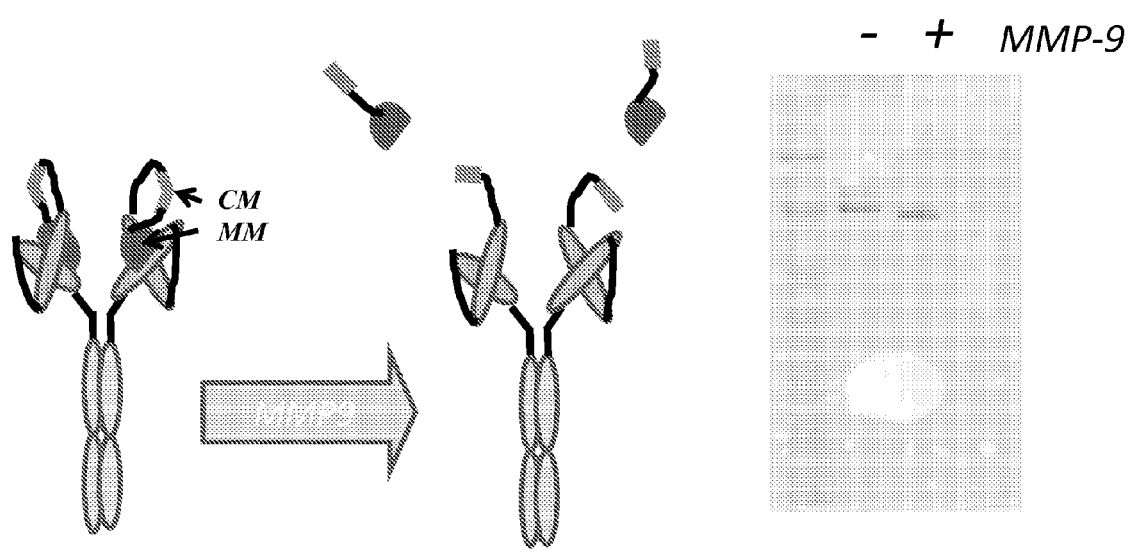
FIG. 12 shows the activation of an AA by MMP-9.
Figure 13:
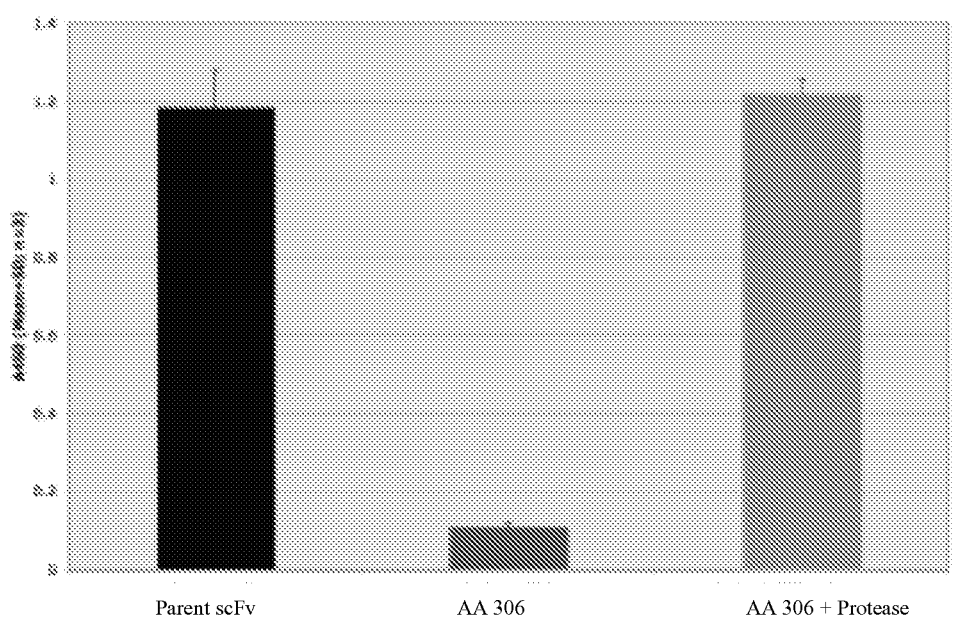
FIG. 13 shows that when the CM is cleaved to remove the MM, the binding of the AB is restored.
Figure 14:
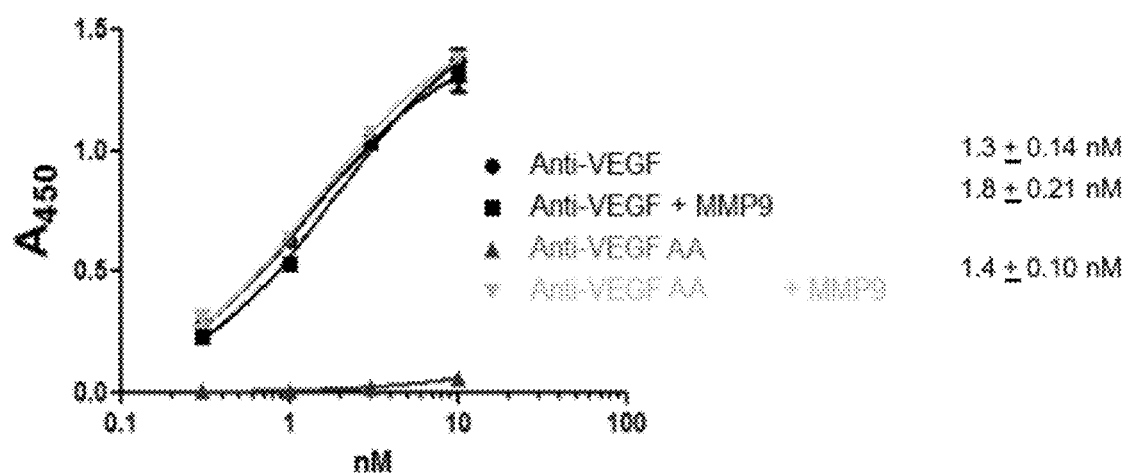
FIG. 14 shows the activation of an AA by a protease that leads to antibody binding indistinguishable from unmodified antibodies.
Figure 15:
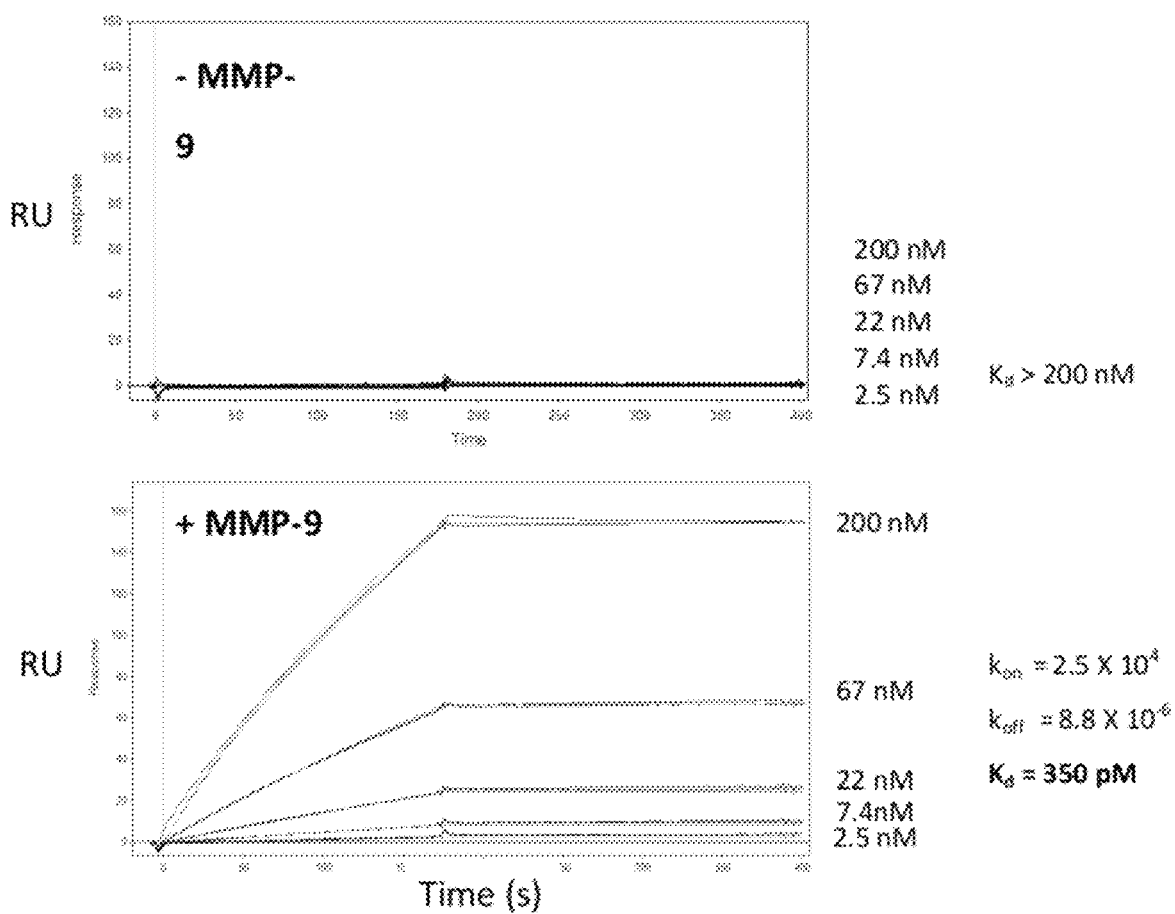
FIG. 15 illustrates that an AA comprising an AB with specific binding affinity to VEGF is inhibited; the activated AA binds VEGF with picomolar affinity.
Figure 16:
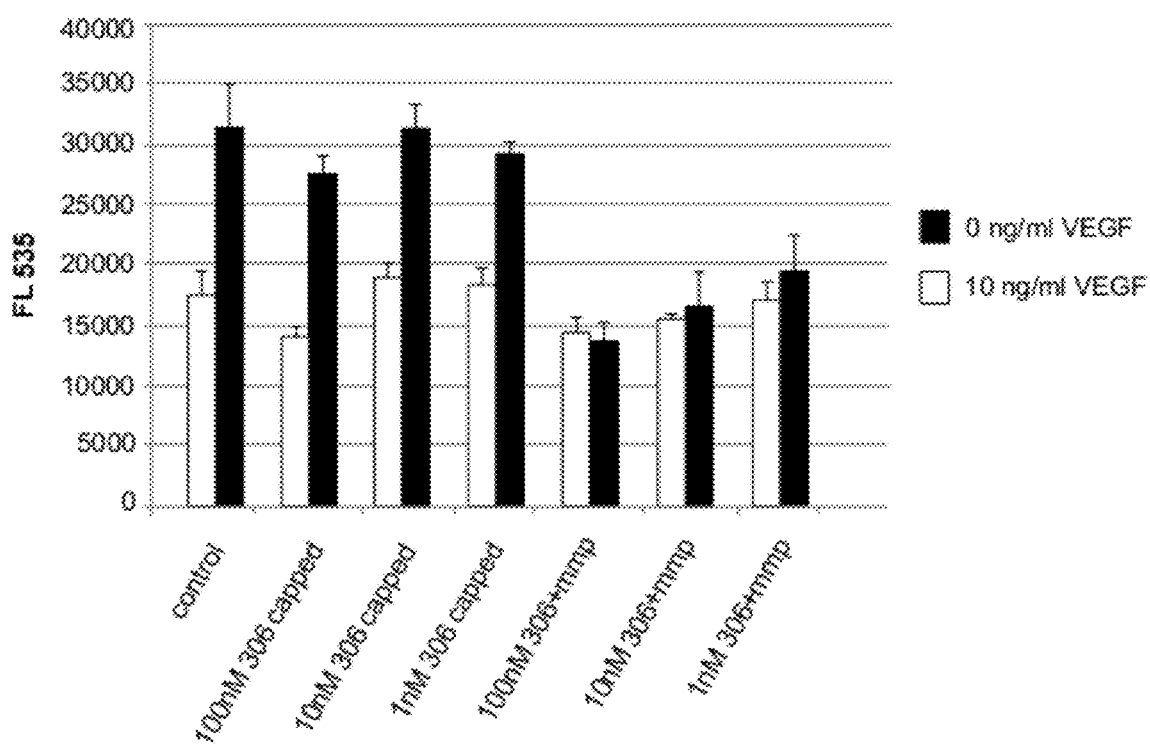
FIG. 16 depicts that an AA comprising an AB with specific binding affinity to VEGF inhibits HUVEC proliferation.
Figure 17:
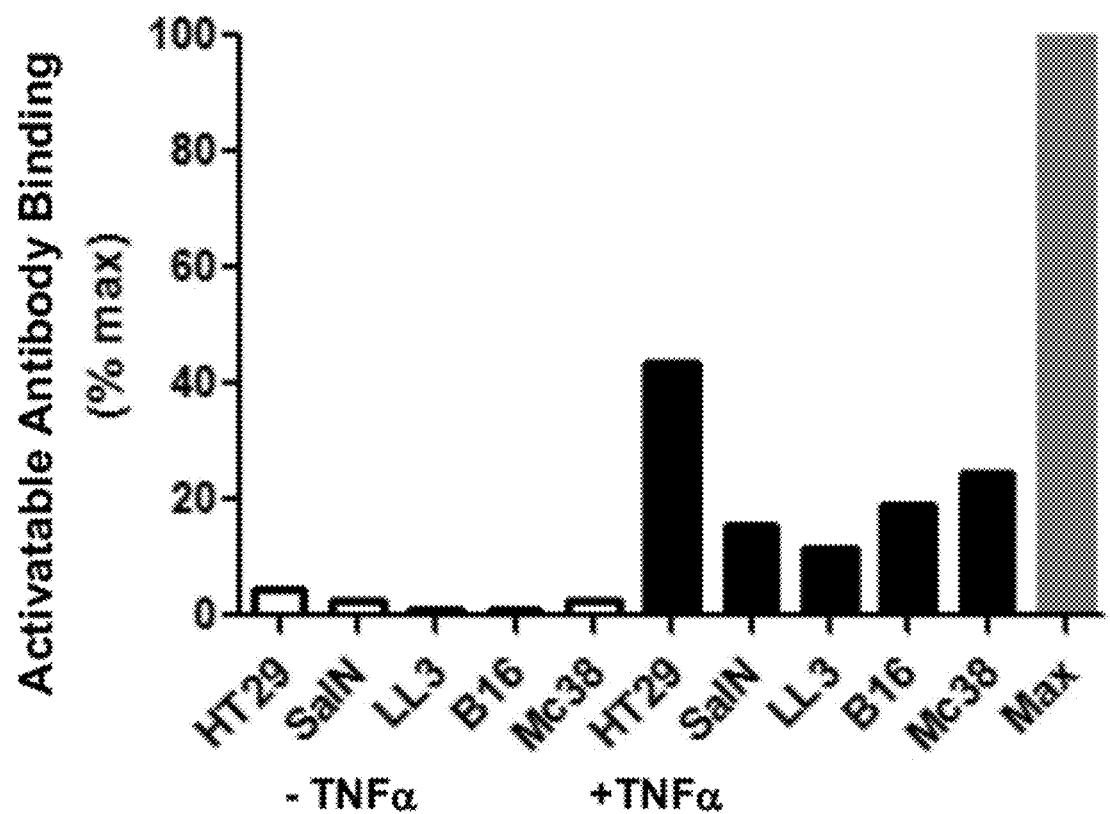
FIG. 17 illustrates that cultured tumor cells demonstrate robust in situ activation of an AA comprising an AB with specific binding affinity to VEGF.
Figure 18:
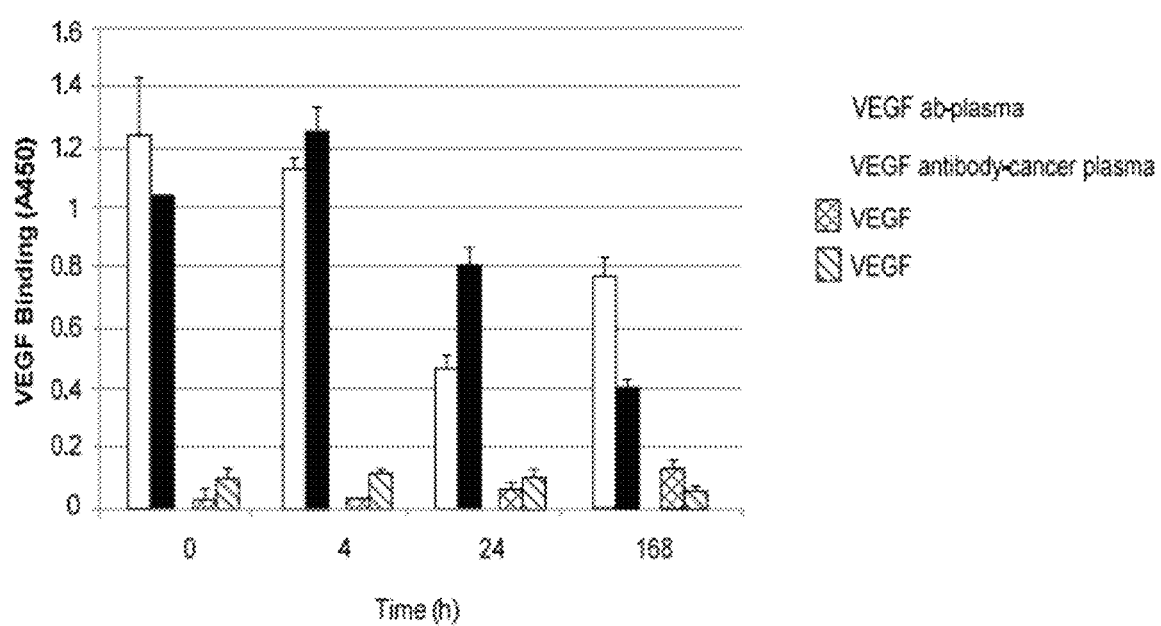
FIG. 18 illustrates that an AA is inactive in normal and cancer patient plasma

To determine the optimal orientation of the anti-CTLA4 scFv for expression and function, primers were designed to PCR amplify the variable light and heavy chains individually, N-terminus. An NdeI restriction site was engineered at the N-terminus to generate a start codon in frame at the beginning of the nucleotide sequence and a His tag and stop codon were added to the C-terminus. Light and heavy chains were then joined via sewing PCR using the outer primers to generate ScFvs in both $V_HV_L$ and $V_LV_H$ (FIG. 10). Primers are shown below in Table 18.

TABLE 18

Primers to generate scFvs V$_H$V$_L$ and V$_L$V$_H$

| | |
|---|---|
| VL for1 | caaggaccatagcatatggacatcatgatgacccagtct (SEQ ID NO: 103) |
| VL linker rev1 | acttccgcctccacctgatccaccaccacctttgatttccaccttggtcc (SEQ ID NO: 104) |
| linker VH for2 | ggatcaggtggaggcggaagtggaggtggcggttcccagatccagcttcaggagtcagga (SEQ ID NO: 105) |
| VH his rev2 | ggccggatccaagcttttagtggtgatggtgatgatgtgaggagacggtgaccatggttcc (SEQ ID NO: 106) |
| VH for3 | acaaggaccatagcatatgcagatccagcttcaggagtca (SEQ ID NO: 107) |
| VH linker rev3 | acttccgcctccacctgatccaccaccacctgaggagacggtgaccatggttcc (SEQ ID NO: 108) |
| linker VL for4 | ggtggatcaggtggaggcggaagtggaggtggcggttccgacatcatgatgacccagtctcct (SEQ ID NO: 109) |
| VL his rev4 | cggccggatccaagcttttagtggtgatggtgatgatgtttgatttccaccttggtcccagc (SEQ ID NO: 110) |

Next, a set of overlapping primers were designed to add sfi and xho1 sites for MM cloning followed by the MMP-9 cleavage sequence and (GGS)$_2$ linker (SEQ ID NO: 111) on the N-terminus of the ScFv constructs. These primers are presented in Table 19 and shown schematically in FIG. 10.

TABLE 19

Primers MM and CM cloning

| | |
|---|---|
| for 1c linker | gccagtctggccggtagggctcgagcggccaagtgcacatgccactgggcttcctgggtc (SEQ ID NO: 112) |
| for 1d linker VL | gccactgggcttcctgggtccgggtggaagcggcggctcagacatcatgatgacccagtc (SEQ ID NO: 113) |
| for 1e linker VH | gccactgggcttcctgggtccgggtggaagcggcggctcacagatccagcttcaggagtca (SEQ ID NO: 114) |
| for 1a | ttcaccaacaaggaccatagcatatgggccagtctggccggtagggc (SEQ ID NO: 115) |
| VH his rev2 | ggccggatccaagcttttagtggtgatggtgatgatgtgaggagacggtgaccatggttcc (SEQ ID NO: 116) |
| VH linker rev3 | acttccgcctccacctgatccaccaccacctgaggagacggtgaccatggttcc (SEQ ID NO: 117) |

Linker containing ScFvs were PCR amplified, digested with Nde1 and EcoR1 (an internal restriction site in V$_H$) and gel purified. The PCR fragments were ligated into the vectors and transformed into E. coli The nucleotide and amino acid sequences are presented in Table 20.

TABLE 20

Sequence of MM linker-CM-anti-CTLA4 scFv linker

Amino acid sequence:

(---MM Linker---) (----------CM-----------) (scFv Linker)

G G S G G S G G S S G Q V H M P L G F L G P G G S G G S (SEQ ID NO: 118)

Nucleotide sequence:

GGCGGTTCTGGTGGCAGCGGTGGCTCGAGCGGCCAAGTGCACATGCCACTGGGCTT

CCTGGGTCCGGGTGGAAGCGGCGGCTCA (SEQ ID NO: 119)

MM sequences were PCR amplified, digested at sfi1 and xho1 sites, ligated into linker anti-CTLA4 scFv constructs, transformed into E. Coli and sequenced. The complete nucleotide and amino acid sequences of the MM115-CM-AB are shown below in Tables 21 and 22 respectively.

TABLE 21

Amino acid sequence of MM115-anti-CTLA4 ScFv AB

M I L L C A A G R T W V E A C A N G R G G S G G S G G S S G Q
V H M P L G F L G P G G S G G S Q I Q L Q E S G P G L V N P S Q
S L S L S C S V T G Y S I T S G Y G W N W I R Q F P G Q K V E W
M G F I Y Y E G S T Y Y N P S I K S R I S I T R D T S K N Q F F L
Q V N S V T T E D T A T Y Y C A R Q T G Y F D Y W G Q G T M V
T V S S G G G G S G G G G S G G G G S D I M M T Q S P S S L S V
S A G E K A T I S C K S S Q S L F N S N A K T N Y L N W Y L Q K
P G Q S P K L L I Y Y A S T R H T G V P D R F R G S G S G T D F
T L T I S S V Q D E D L A F Y Y C Q Q W Y D Y P Y T F G A G T K
V E I K (SEQ ID NO: 120)

TABLE 22

Nucleotide sequence of MM115-anti-CTLA4 ScFv AB atgattttgttgtgcgcggcgggtcggacgtgggtggaggcttgcgctaatggtaggggcggttctggtggcagcggtggctcgagcggc caagtgcacatgccactgggcttcctgggtccgggtggaagcggcggctcacagatccagcttcaggagtcaggacctggcctggtgaa cccctcacaatcactgtccctctcttgctctgtcactggttactccatcaccagtggttatggatggaactggatcaggcagttcccagggcag aaggtggagtggatgggattcatatattatgagggtagcacctactacaacccttccatcaagagccgcatctccatcaccagagacacatc gaagaaccagttcttcctgcaggtgaattctgtgaccactgaggacacagccacatattactgtgcgagacaaactgggtactttgattactg gggccaaggaaccatggtcaccgtctcctcaggtggtggtggatcaggtggaggcggaagtggaggtggcggttccgacatcatgatga cccagtctccttcatccctgagtgtgtcagcgggagagaaagccactatcagctgcaagtccagtcagagtcttttcaacagtaacgccaaa acgaactacttgaactggtatttgcagaaaccagggcagtctcctaaactgctgatctattatgcatccactaggcatactggggtccctgatc gcttcagaggcagtggatctgggacggatttcactctcaccatcagcagtgtccaggatgaagacctggcattttattactgtcagcagtggt atgactacccatacacgttcggagctgggaccaaggtggaaatcaaacatcatcaccatcaccactaa (SEQ ID NO: 121)

To generate MM-CM-anti-CTLA4 scFv-Fc fusions, the following primers listed in Table 23 were designed to PCR amplify the constructs for cloning into the pfuse Fc vector via the in fusion system (Clontech). Plasmids were transformed into E. coli, and the sequence of individual clones was verified.

TABLE 23

Primers to generate MM-CM-anti-CTLA4 scFv-Fc fusions

| | |
|---|---|
| HLCTLA4ScFv pFuse reverse | tcagatctaaccatggctttgatttccaccttggtcc (SEQ ID NO: 122) |
| LHCTLA4ScFv pFuse reverse | tcagatctaaccatggctgaggagacggtgaccatgg (SEQ ID NO: 123) |
| p115CTLA4 pfuse forward | cacttgtcacgaattcgatgattttgttgtgcgcggc (SEQ ID NO: 124) |
| p182CTLA4 pfuse forward | cacttgtcacgaattcgtgggcggatgttatgcctg (SEQ ID NO: 125) |
| p184CTLA4 pfuse forward | cacttgtcacgaattcggctgagcggttgtgcgcgtg (SEQ ID NO: 126) |

TABLE 23-continued

Primers to generate MM-CM-anti-CTLA4 scFv-Fc fusions

| | |
|---|---|
| p175CTLA4 pfuse forward | cacttgtcacgaattcgagtgatggtcgtatggggag (SEQ ID NO: 127) |
| pnegCTLA4 pfuse forward | cacttgtcacgaattcgccgtgttctgagtggcagtcg (SEQ ID NO: 128) |

Example 13

Expression and Assay of masked/MMP-9/anti-CTLA4 scFv-Fc in HEK-293 Cells 10 ug of expression vectors for p175CTLA4pfuse, p182CTLA4pfuse, p184CTLA4pfuse, p115CTLA4pfuse, or pnegCTLA4pfuse were introduced into $10^7$ HEK-293 freestyle cells (Invitrogen) by transfection using transfectamine 2000 as per manufacturer's protocol (Invitrogen). The transfected cells were incubated for an additional 72 hours. After incubation the conditioned media was harvested and cleared of cells and debris by centrifugation. The conditioned media was assayed for activity by ELISA as described below.

Fifty microliters of conditioned media from HEK-293 expressing MM175-anti-CTLA4 scFv, MM182-anti-CTLA4 scFv, MM184-anti-CTLA4 scFv, MM115-anti-CTLA4 scFv, or MMneg-anti-CTLA4 scFv was added to 200 µL MMP-9 digestion buffer and incubated with or without ~19 U MMP-9 for 2 hrs at 37° C. Samples were then diluted 1:1 in PBS, 4% non fat dry milk (NFDM) and assayed for binding activity by competition ELISA.

100 ul of 0.5 mg/ml solution of murine CTLA4-Fc fusion protein (R & D systems) in PBS was added to wells of 96 well Easy Wash plate (Corning) and incubated overnight at 4° C. Wells were then blocked for one hour at room temperature (RT) with 100 ul of 2% non-fat dry milk (NFDM) in PBS and then washed 3× with PBS; 0.05% Tween-20 (PBST). 50 ul of conditioned media from cultures of transfected HEK-293 cells expressing MM175-anti-CTLA4 scFv, MM182-anti-CTLA4 scFv, MM184-anti-CTLA4 scFv, MM115-anti-CTLA4 scFv, or MMneg-anti-CTLA4 scFv that had previously been untreated or treated with MMP-9, were added to wells and incubated RT for 15 minutes. Following incubation, 50 ul of PBS containing 0.5 ug/ml biotinylated murine B71-Fc (R & D systems) was added to each well. Following a further incubation at RT of 30 minutes the wells were washed 5× with 150 ul PBST. 100 ul of PBS containing 1:3000 dilution of avidin-HRP was added and the plate incubated at RT for 45 minutes and then washed 7× with 150 ul PBST. The ELISA was developed with 100 ul of TMB (Pierce), stopped with 100 uL of 1N HCL and the absorbance was measured at 450 nM.

Example 14

Construction of an Anti-CTLA4

Tables 24 and 25 display nucleotide and amino acid sequences for anti-human CTLA-4 scFv, respectively. M13 bacteriophage capable of binding human CTLA were supplied (under contract, by Creative Biolabs, 21 Brookhaven Blvd., Port Jefferson Station, N.Y. 11776). Phage were produced in *E. coli* TG-1 and purified by PEG; NaCl precipitation.

TABLE 24 anti-human CTLA4 scFv AB nucleotide sequence gaaattgtgttgacacagtctccaggcaccctgtctttgtctccaggggaaagagccaccctctcctgcagggccagtcagagtgttagcag cagctacttagcctggtaccagcagaaacctggccaggctcccaggctcctcatctatggtgcatccagcagggccactggcatcccagac aggttcagtggcagtgggtctgggacagacttcactctcaccatcagcagactggagcctgaagatttgcagtgtattactgtcagcagtat ggtagctcaccgctcactttcggcggagggaccaaggtggaaatcaaacgttccggaggtcgaccataacttcgtataatgtatactatac gaagttatcctcgagcggtacccaggtgcagctggtgcagactgggggaggcgtggtccagcctggaggtccctgagactctcctgtgc agcctctggatccaccttagcagctatgccatgagctgggtccgccaggctccagggaaggggctggagtgggtctcagctattagtggt agtggtggtagcacatactacgcagactccgtgaagggccggttcaccatctccagagacaattccaagaacacgctgtatctgcaaatga acagcctgagagccgaggacacggccgtatattactgtgcgacaaactccctttactggtacttcgatctctggggccgtggcaccctggtc actgtctcttcagctagc (SEQ ID NO: 129)

TABLE 25 anti-human CTLA4 scFv AB amino acid sequence

EIVLTQSPGTLSLSPGERATLSCRASQSVSSSYLAWYQQKPGQAPRLLIY

GASSRATGIPDRFSGSGSGTDFTLTISRLEPEDFAVYYCQQYGSSPLTFG

GGGTKVEIKRSGGSTITSYNVYYTKLSSSGTQVQLVQTGGGVVQPGRSL

RLSCAASGSTFSSYAMSWVRQAPGKGLEWVSAIAGSGGSTYYADSVKG

RFTISRDNSKNTLYLQMNSLRAEDTAVYYCATNSLYWYFDLWGRGTLVT

VSSAS (SEQ ID NO: 130)

Figure 19:
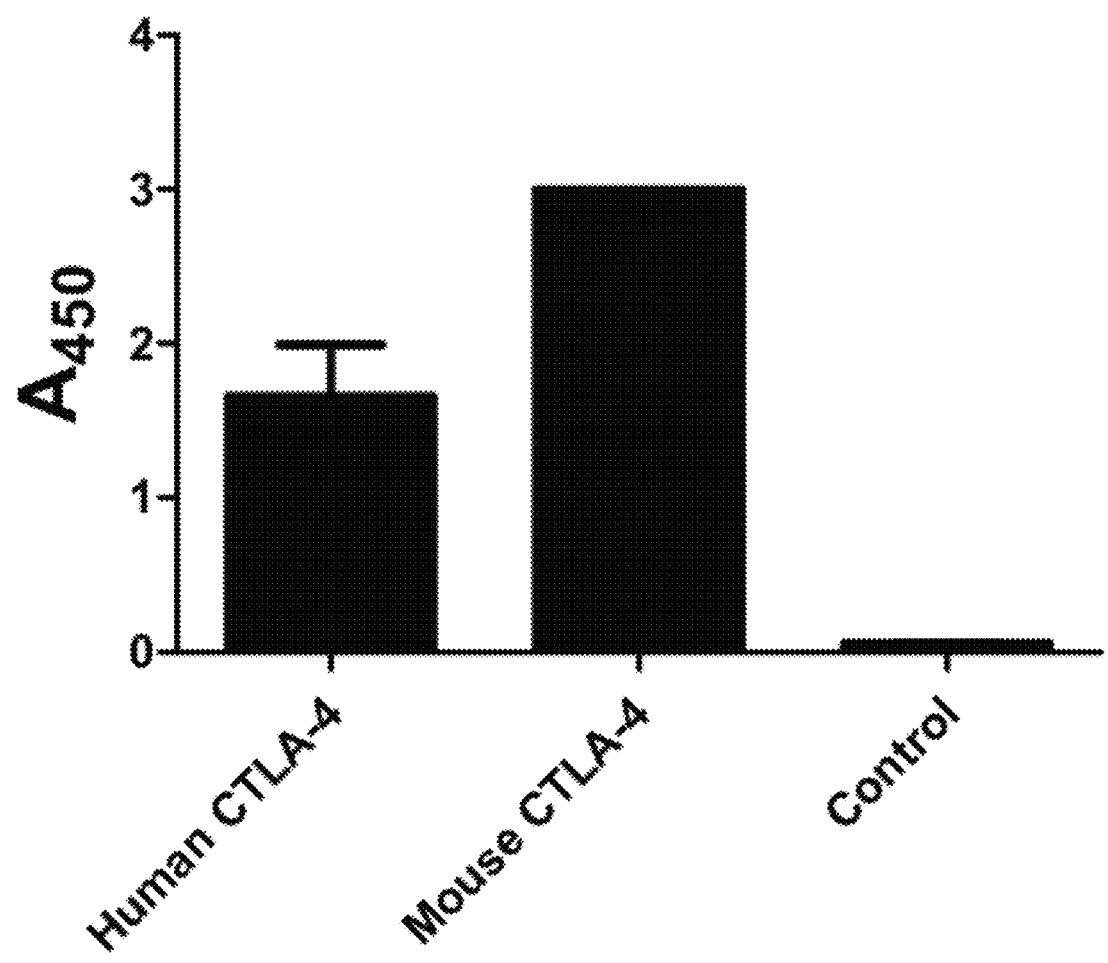
FIG. 19 illustrates the binding of anti-CTLA4 scFv to both murine and human CTLA4.
Figure 20:
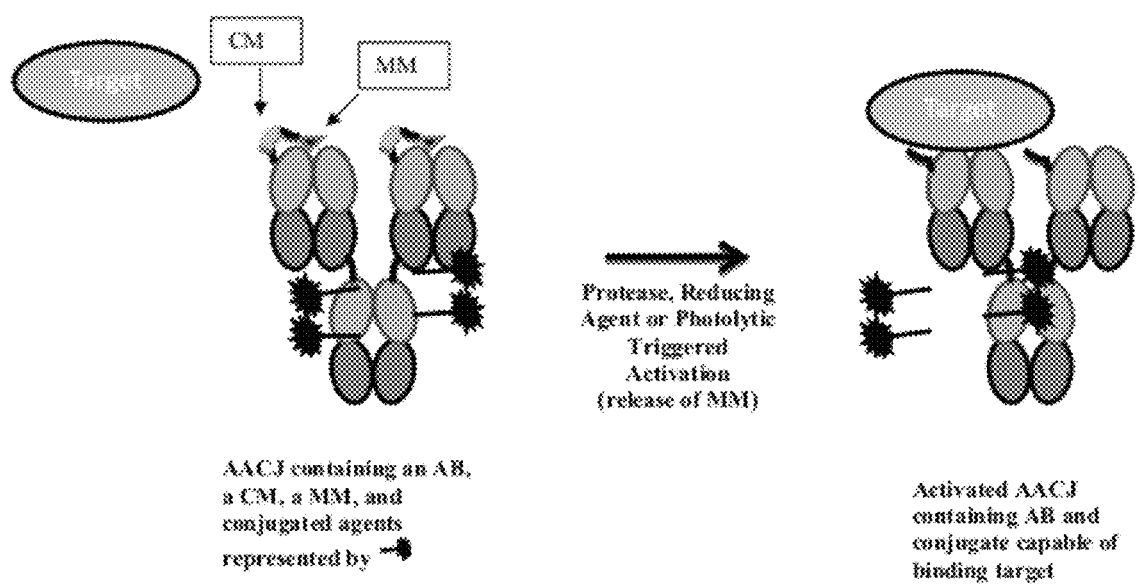
FIG. 20 shows a protease-activated AACJ-containing an antibody (containing an AB), a masking moiety (MM), a cleavable moiety (CM), and a conjugated agent. Upon cleavage of the CM and unmasking, the conjugated AB is released.

Phage ELISA Measurement of CTLA-4 Binding:

To measure the binding of anti-CTLA-4 scFv-C2, 100 ul of a 0.5 ug/ml Human CTLA-4-IgG or murine CTLA-4-IgG (R&D Systems) in PBS was added to microwells (96 Well Easy Wash; Corning) and incubated overnight at 4° C. Wells were then blocked for 1 hour at room temperature (RT) with 150 ul of 2% non-fat dry milk (NFDM) in PBST (PBS, pH 7.4, 0.5% Tween-20). The wells were then washed 3× with 300 ul PBST. Following washing 100 ul of purified anti-CTLA-4 scFv phage in PBST were added to triplicate wells and incubated RT for 1 hr. The wells were then washed 3× with 300 ul PBST. One hundred microliters of anti-M13 HRP-conjugated antibody was then added and incubated at RT for 1 hr. Detection of HRP was completed using 100 ul of TMB one (Pierce) solution. The reaction was stopped 100 ul of 1N HCL and the absorbance was measured at 450 nM. FIG. 19 shows the binding of anti-CTLA4 scFv to both murine and human CTLA4.

AAs Comprising an IgG as the AB

Examples of AAs comprising an anti-EGFR and anti-VEGF in the human IgG are described in the following sections. These AAs are masked and inactive under normal conditions. When the AAs reach the diseased tissue, they are cleaved by a disease-specific protease and can then bind their target. Bacterial display is used to discover suitable MMs for the anti-EGFR and anti-VEGF antibodies. In, these examples, selected MMs are combined with an enzyme substrate to be used as a trigger to create AAs that become competent for specific binding to target following protease activation. Furthermore, bacterial display is used to alter the discovered peptides to increase affinity for the ABs and enhance the inhibition of targeted binding in the un-cleaved state. The, increased MM affinity and enhanced inhibition is important for appropriate AA function.

Example 15

Construction of an Anti-VEGF IgG AA

Construction of the Anti-VEGF IgG Antibody

The anti-VEGF light chain variable region was PCR amplified with primers CX0311 and CX0702 using the anti-VEGF mmp-9 306 scFv (described above) as template and then cloned into the pFIL2-CL-hk vector using the EcoRI and BsiWI restriction sites (pFIL2-VEGF-Lc). The 306 mmp-9 light chain was PCR amplified with primers CX0325 and CX0702 using the anti-VEGF mmp-9 scFv as template and cloned as above (pFIL2-306 mVEGF-Lc). The anti-VEGF heavy chain variable regions were PCR amplified using primers CX0700 and CX0701 using the 306 MM/MMP-9 CM/anti-VEGFscFv (described above) as template and cloned into the pFIL-CHIg-hG1 vector using the EcoRI and NheI restriction sites (pFIL-VEGF-Hc). The primers are provided below in Table 26.

TABLE 26

| Primers for Construction of an anti-VEGF IgG antibody | |
|---|---|
| CX0311 | cttgtcacgaattcggatattcaactgacccagagc (SEQ ID NO: 131) |
| CX0702 | gtgcagccaccgtacgcttaatctccactttggtg (SEQ ID NO: 132) |
| CX0325 | tgcttgctcaactctacgtc (SEQ ID NO: 133) |
| CX0289 | gctttcaccgcaggtacttccgtagctggccagtctggcc (SEQ ID NO: 134) |
| CX0687 | cgctccatgggccaccttggccgctgccaccgctcgagcc (SEQ ID NO: 135) |
| CX0700 | cacttgtcacgaattcggaggtccagctggtagaaag (SEQ ID NO: 136) |
| CX0701 | ggcccttggtgctagcgctcgacactgtaaccagagtac (SEQ ID NO: 137) |

TABLE 27

| Sequences for heavy and light chain anti-VEGF antibody |
|---|
| pFIL2-CL-hk anti-VEGF Lc (pFIL2-VEGF-Lc) |
| gatattcaactgacccagagcccttcttccctgagtgccagcgtgggtgaccgtgttacgatcacttgctcggccagccaagatatttctaact<br>acctgaattggtaccagcagaagccaggaaaggcaccaaaagtcctgatctacttcacaagttcactgcattccggcgtaccgtcgcgcttt<br>agcggttctggcagtggtaccgacttcaccctgactatctcgagtctgcaacctgaggattttgctacatattactgtcagcaatattcgaccgt<br>gccgtggacgttcgggcagggcaccaaagtggagattaagcgtacggtggctgcaccatctgtcttcatcttcccgccatctgatgagcagt<br>tgaaatctggaactgcctctgttgtgtgcctgctgaataacttctatcccagagaggccaaagtacagtggaaggtggataacgccctccaat<br>cgggtaactcccaggagagtgtcacagagcaggacagcaaggacagcacctacagcctcagcagcaccctgacgctgagcaaagcag<br>actacgagaaacacaaagtctacgcctgcgaagtcacccatcagggcctgagctcgcccgtcacaaagagcttcaacaggggagagtgtt<br>ag (SEQ ID NO: 138) |
| DIQLTQSPSSLSASVGDRVTITCSASQDISNYLNWYQQKPGKAPKVLIYFTSSLHSGVPSR<br>FSGSGSGTDFTLTISSLQPEDFATYYCQQYSTVPWTFGQGTKVEIKRTVAAPSVFIFPPSD<br>EQLKSGTASVVCLLNNFYPREAKVQWKVDNALQSGNSQESVTEQDSKDSTYSLSSTLTL<br>SKADYEKHKVYACEVTHQGLSSPVTKSFNRGEC (SEQ ID NO: 139) |

As described above, the mask 306, used for anti-VEGF AA development did not efficiently mask the target binding over long exposure to target, due to low affinity of the MM for the AB. One approach to increasing the affinity of the MM is to subject the peptide to affinity maturation as described below.

Library Construction for Affinity Maturation The 306 anti-VEGF MM was affinity matured by using a soft randomization approach. An ecpX cell display library was constructed in with the nucleotide ratios shown in Table 28. The final library diversity (306 SR) was approximately $2.45 \times 10^8$.

TABLE 28

| Original Base | Ratio of Bases |
|---|---|
| G | G = 70%; T = 8%; A = 11%; C = 11% |
| T | T = 70%; G = 8%; A = 11%; C = 11% |
| A | A = 80%; G = 5%; T = 6%; C = 9% |
| C | C = 80%; G = 5%; T = 6%; A = 9% |

306 SR Library Screening

An initial MACS round was performed with protein-A labeled magnetic beads and a number of cells that provided greater than 100× oversampling of the library. Prior to magnetic selection the cells were incubated with 100 nM anti-VEGF IgG and 10 μM 306 peptide (306P, PCSEWQSMVQPRCYYG (SEQ ID NO: 140)), to reduce the binding of variants with equal or lower affinity than the original 306 sequence. Magnetic selection resulted in the isolation of $2 \times 10^7$ cells.

The first round of FACS sorting was performed on cells labeled with 1 nM DyLight (fluor 530 nM)-anti-VEGF. To apply selective pressure to the population, the second and third round of FACS was performed on cells labeled with 1 nM DyLight-anti-VEGF in the presence of 100 nM 306P. Selection gates were set so that only 5% of cells with the strongest binding were collected. The population of cells sorted in the third round were first incubated with 10 nM DyLight-anti-VEGF followed by addition of 306P to a final concentration of 100 nM and incubated at 37° C. for 20 minutes. The brightest 2% of the positive population was collected, representing binding that was not competed by 306P. FACS rounds 5 through 7 were done as follows; the populations were labeled with 10 nM DyLight labeled anti-VEGF and then competed off with unlabeled VEGF (100 nM) at 37° C. for 7, 10, and 15 minutes, respectively. The brightest 1% were sorted in FACS rounds 5 through 7.

TABLE 29

| 306SR M1F7 peptide sequences | | |
|---|---|---|
| JS306 | PCSEWQSMVQPRCYYG (SEQ ID NO: 141) | |
| JS1825 | SCTAWQSMVEQRCYFG (SEQ ID NO: 142) | 3X |
| JS1826 | PCSKWESMVEQRCYFA (SEQ ID NO: 143) | |
| JS1827 | PCSAWQSMVEQRCYFG (SEQ ID NO: 144) | 2X |
| JS1829 | PCSKWESMVLQSCYFG (SEQ ID NO: 145) | 4X |
| JS1830 | TCSAWQSMVEQRCYFG (SEQ ID NO: 146) | 2X |
| JS1837 | TCSQWESMVEPRCYFG (SEQ ID NO: 147) | |

306SR Affinity Matured Peptide Analysis

Figure 21:
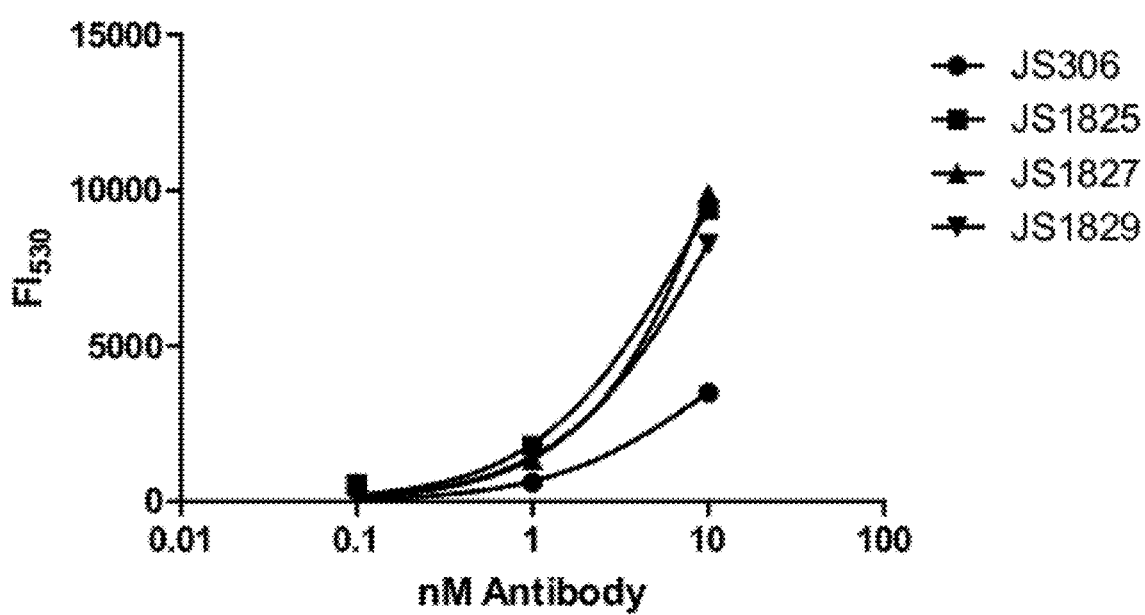
FIG. 21 shows that binding of the eCPX3.0 clones JS306, JS1825, JS1827, and JS1829 were analyzed on FACS at 3 different concentrations of DyLight labeled anti-VEGF. All three of the affinity matured peptides displayed at least 10 fold higher affinity than the JS306.

Binding of the eCPX3.0 clones 306, JS1825, JS1827, and JS1829 were analyzed on FACS at 3 different concentrations of DyLight labeled anti-VEGF. The binding curves are shown in FIG. 21. All three of the affinity matured peptides displayed at least 10 fold higher affinity than 306P.

Construction of Anti-VEGF AAs

Affinity matured ecpX3.0 clones (JS1825, JS1827, and JS1829) were PCR amplified using primers CX0289 and CX0687 and cloned into pFIL2-306 mVEGF-Lc using the SfiI restriction sites to produce the vectors pFIL2-1825 mVEGF-Lc, pFIL2-1827 mVEGF-Lc, and pFIL2-1829 mVEGF-Lc. The nucleotide and amino acid sequences are provided in the tables following. Parentheses delineate the demarcations between the various sequence domains: (Linker)(MM)(Linker)(CM)(Linker)(AB).

TABLE 30

| Sequences of anti-VEGF AA: pFIL2-CL-hk anti-VEGF mmp-9 306 Lc (pFIL2-306mVEGF-Lc) |
|---|
| ggccagtctggccagccgtgttctgagtggcagtcgatggtgcagccgcgttgctattatgggggcggttctggtggcagcggccaaggt |
| ggccaagtgcacatgccactgggcttcctgggtccgggcggttctgatattcaactgacccagagcccttcttccctgagtgccagcgtggg |
| tgaccgtgttacgatcacttgctcggccagccaagatatttctaactacctgaattggtaccagcagaagccaggaaaggcaccaaaagtcc |
| tgatctacttcacaagttcactgcattccggcgtaccgtcgcgctttagcggttctggcagtggtaccgacttcaccctgactatctcgagtctg |
| caacctgaggattttgctacatattactgtcagcaatattcgaccgtgccgtggacgttcgggcagggcaccaaagtggagattaagcgtac |
| ggtggctgcaccatctgtcttcatcttcccgccatctgatgagcagttgaaatctggaactgcctctgttgtgtgcctgctgaataacttctatc |
| ccagagaggccaaagtacagtggaaggtggataacgccctccaatcgggtaactcccaggagagtgtcacagagcaggacagcaaggac |
| agcacctacagcctcagcagcaccctgacgctgagcaaagcagactacgagaaacacaaagtctacgcctgcgaagtcacccatcaggg |
| cctgagctcgcccgtcacaaagagcttcaacaggggagagtgttag (SEQ ID NO: 148) |
| Linker MM Linker CM Linker AB<br>(GQSGQ)(PCSEWQSMVQPRCYYG)(GGSGGSGQGG)(QVHMPLGFLGP)(GGS)(DIQLTQS |
| PSSLSASVGDRVTITCSASQDISNYLNWYQQKPGKAPKVLIYFTSSLHSGVPSRFSGSGSG |
| TDFTLTISSLQPEDFATYYCQQYSTVPWTFGQGTKVEIKRTVAAPSVFIFPPSDEQLKSGT |
| ASVVCLLNNFYPREAKVQWKVDNALQSGNSQESVTEQDSKDSTYSLSSTLTLSKADYE |
| KHKVYACEVTHQGLSSPVTKSFNRGEC) (SEQ ID NO: 149) |

TABLE 31

Sequences of anti-VEGF AA: pFIL2-CL-hk anti-VEGF mmp-9 1825 Lc (pFIL2-1825mVEGF-Lc)

ggccagtctggccagtcgtgtacggcgtggcagtcgatggtggagcagcgttgctatttggggctcgagcggtggcagcggccaaggt
ggccaagtgcacatgccactgggcttcctgggtccgggcggttctgatattcaactgacccagagcccttcttccctgagtgccagcgtggg
tgaccgtgttacgatcacttgctcggccagccaagatatttctaactacctgaattggtaccagcagaagccaggaaaggcaccaaaagtcc
tgatctacttcacaagttcactgcattccggcgtaccgtcgcgctttagcggttctggcagtggtaccgacttcaccctgactatctcgagtctg
caacctgaggattttgctacatattactgtcagcaatattcgaccgtgccgtggacgttcgggcagggcaccaaagtggagattaagcgtac
ggtggctgcaccatctgtcttcatcttcccgccatctgatgagcagttgaaatctggaactgcctctgttgtgtgcctgctgaataacttctatc
ccagagaggccaaagtacagtggaaggtggataacgcccctccaatcgggtaactcccaggagagtgtcacagagcaggacagcaaggac
agcacctacagcctcagcagcaccctgacgctgagcaaagcagactacgagaaacacaaagtctacgcctgcgaagtcacccatcaggg
cctgagctcgcccgtcacaaagagcttcaacaggggagagtgttag (SEQ ID NO: 150)

Linker    MM           Linker      CM      Linker     AB
(GQSGQ)(SCTAWQSMVEQRCYFG)(GSSGGSGQGGQ)(VHMPLGFLGP)(GGS)(DIQLTQS

PSSLSASVGDRVTITCSASQDISNYLNWYQQKPGKAPKVLIYFTSSLHSGVPSRFSGSGSG

TDFTLTISSLQPEDFATYYCQQYSTVPWTFGQGTKVEIKRTVAAPSVFIFPPSDEQLKSGT

ASVVCLLNNFYPREAKVQWKVDNALQSGNSQESVTEQDSKDSTYSLSSTLTLSKADYE

KHKVYACEVTHQGLSSPVTKSFNRGEC) (SEQ ID NO: 151)

TABLE 32

Sequences of anti-VEGF AA: pFIL2-CL-hk anti-VEGF mmp-9 1827 Lc (pFIL2-1827mVEGF-Lc)

ggccagtctggccagccgtgttctgcgtggcagtctatggtggagcagcgttgctatttggggggctcgagcggtggcagcggccaaggt
ggccaagtgcacatgccactgggcttcctgggtccgggcggttctgatattcaactgacccagagcccttcttccctgagtgccagcgtggg
tgaccgtgttacgatcacttgctcggccagccaagatatttctaactacctgaattggtaccagcagaagccaggaaaggcaccaaaagtcc
tgatctacttcacaagttcactgcattccggcgtaccgtcgcgctttagcggttctggcagtggtaccgacttcaccctgactatctcgagtctg
caacctgaggattttgctacatattactgtcagcaatattcgaccgtgccgtggacgttcgggcagggcaccaaagtggagattaagcgtac
ggtggctgcaccatctgtcttcatcttcccgccatctgatgagcagttgaaatctggaactgcctctgttgtgtgcctgctgaataacttctatc
ccagagaggccaaagtacagtggaaggtggataacgcccctccaatcgggtaactcccaggagagtgtcacagagcaggacagcaaggac
agcacctacagcctcagcagcaccctgacgctgagcaaagcagactacgagaaacacaaagtctacgcctgcgaagtcacccatcaggg
cctgagctcgcccgtcacaaagagcttcaacaggggagagtgttag (SEQ ID NO: 152)

Linker    MM           Linker      CM     Linker     AB
(GQSGQ)(PCSAWQSMVEQRCYFG)(GSSGGSGQGG)(QVHMPLGFLGP)(GGS)(DIQLTQS

PSSLSASVGDRVTITCSASQDISNYLNWYQQKPGKAPKVLIYFTSSLHSGVPSRFSGSGSG

TDFTLTISSLQPEDFATYYCQQYSTVPWTFGQGTKVEIKRTVAAPSVFIFPPSDEQLKSGT

ASVVCLLNNFYPREAKVQWKVDNALQSGNSQESVTEQDSKDSTYSLSSTLTLSKADYE

KHKVYACEVTHQGLSSPVTKSFNRGEC) (SEQ ID NO: 153)

TABLE 33

Sequences of anti-VEGF AA: pFIL-CL-hk anti-VEGF mmp-9 1829 Lc (pFIL2-1829mVEGF-Lc)

ggccagtctggccagccgtgttctaagtgggaatcgatggtgctgcagagttgctattttggcggctcgagcggtggcagcggccaaggtg
gccaagtgcacatgccactgggcttcctgggtccgggcggttctgatattcaactgacccagagcccttcttccctgagtgccagcgtgggt
gaccgtgttacgatcacttgctcggccagccaagatatttctaactacctgaattggtaccagcagaagccaggaaaggcaccaaaagtcct
gatctacttcacaagttcactgcattccggcgtaccgtcgcgctttagcggttctggcagtggtaccgacttcaccctgactatctcgagtctgc TABLE 33-continued Sequences of anti-VEGF AA: pFIL-CL-hk anti-VEGF mmp-9 1829 Lc (pFIL2-1829mVEGF-Lc)

```
aacctgaggattttgctacatattactgtcagcaatattcgaccgtgccgtggacgttcgggcagggcaccaaagtggagattaagcgtacg gtggctgcaccatctgtcttcatcttcccgccatctgatgagcagttgaaatctggaactgcctctgttgtgtgcctgctgaataacttctatcc cagagaggccaaagtacagtggaaggtggataacgccctccaatcgggtaactcccaggagagtgtcacagagcaggacagcaaggaca gcacctacagcctcagcagcaccctgacgctgagcaaagcagactacgagaaacacaaagtctacgcctgcgaagtcacccatcagggc ctgagctcgcccgtcacaaagagcttcaacaggggagagtgttag (SEQ ID NO: 154)

Linker       MM               Linker        CM          Linker       AB
(GQSGQ) (PCSKWESMVLQSCYFG) (GSSGGSGQGG) (QVHMPLGFLGP) (GGS) (DIQLTQSP

SSLSASVGDRVTITCSASQDISNYLNWYQQKPGKAPKVLIYFTSSLHSGVPSRFSGSGSGT

DFTLTISSLQPEDFATYYCQQYSTVPWTFGQGTKVEIKRTVAAPSVFIFPPSDEQLKSGTA

SVVCLLNNFYPREAKVQWKVDNALQSGNSQESVTEQDSKDSTYSLSSTLTLSKADYEK

HKVYACEVTHQGLSSPVTKSFNRGEC) (SEQ ID NO: 155)
```

Expression and Purification of Anti-VEGF Antibody and AA

3 μg of pFIL-VEGF-Hc and 3 μg pFIL2-VEGF-Lc were co-transfected into CHO—S cells (Invitrogen) using Lipofectamine 200 (Invitrogen) according to manufacturers protocol. Transfected cells were cultured in Freestyle CHO media (Invitrogen) and selected for resistance to zeocin and blasticidin. Individual clones were isolated by limiting dilution and selected for expression of human IgG capable of binding EGFR by ELISA. All antibodies and AAs are purified by Protein-A chromatography using standard techniques.

Likewise, 3 μg of each expression vector for AA light chains pFIL2-306 mVEGF-Lc, pFIL2-1825 mVEGF-Lc, pFIL2-1827 mVEGF-Lc, or pFIL2-1829 mVEGF-Lc was co-transfected into CHO—S cells with 3 μg pFIL-VEGF-Hc. Transfected cells were cultured in Freestyle CHO media (Invitrogen) and selected for resistance to zeiocin and blasticiidin Inkdivideual clones were isolated by limiting dilution and selected for expression of human IgG capable of binding EGFR by ELISA.

Target Displacement Assay of Anti-VEGF Antibody and AA

VEGF is adsorbed to the wells of a 96 well micro-titer plate, washed and blocked with milk protein. About 25 ml of culture media containing anti-VEGF antibody or anti-VEGF AA's containing the MM's JS306, JS1825, JS1827 and JS1829 is added to the coated wells and incubated for about 1, 2, 4, 8 or 24 hours. Following incubation the wells are washed and the extent of bound AA's measured by anti-huIgG immunodetection.

Example 16

Construction of an Anti-EGFR IgG AA

Construction of an Anti-EGFR IgG Antibody

The C225 light chain variable region gene was synthesized by assembly PCR using oligos CX638-CX655 as in Bessette et al., Methods in Molecular Biology, vol. 231. The resulting product was digested with BamHI/NotI and ligated to the large fragment of pXMal digested with BamHI/NotI to create plasmid pX-scFv225-Vk. Similarly, the C225 heavy chain variable region gene was synthesized by assembly PCR using oligos CX656-CX677, digested with BglII/NotI and ligated to pXMal BamHI/NotI to create plasmid pX-scFv225-Vh. The variable light chain gene was then cloned from pX-scFv225-Vk as a BamHI/NotI fragment into the pX-scFv225-Vh plasmid at BamHI/Not to create the plasmid pX-scFv225m-HL, containing the scFv gene based on C225.

The IL2 signal sequence was moved from pINFUSE-hIgG1-Fc2 (InvivoGen) as a KasI/NcoI fragment to pFUSE2-CLIg-hk (InvivoGen) digested with KasI/NcoI, resulting in plasmid pFIL2-CL-hk. The IL2 signal sequence was also moved from pINFUSE-hIgG1-Fc2 as a KasI/EcoRI fragment to pFUSE-CHIg-hG1 (InvivoGen) digested with KasI/EcoRI (large and medium fragments) in a three-way ligation, resulting in plasmid pFIL-CHIg-hG1.

The human IgG light chain constant region was site specifically mutated by amplification from plasmid pFIL2-CL-hk with oligos CX325/CX688, digestion with BsiWI/NheI, and cloning into pFIL2-CL-hk at BsiWI/NheI, resulting in plasmid pFIL2-$CL_{225}$.

The human IgG heavy chain constant region was site specifically mutated by amplification from plasmid pFIL-CHIg-hG1 in three segments with oligos CX325/CX689, CX690/CX692, and CX693/CX694, followed by overlap PCR of all three products using outside primers CX325/CX694. The resulting product was digested with EroRI/AvrII and cloned into pINFUSE-hIgG1-Fc2 at EcoRI/NheI, resulting in plasmid pFIL-$CH_{225}$.

The variable light chain gene segment was amplified from pX-scFv225m-HL with oligos CX695/CX696, digested with BsaI, and cloned into pFIL2-$CL_{225}$ at EcoRI/BsiWI, resulting in the C225 light chain expression vector pFIL2-C225-light.

The variable heavy chain gene segment was amplified from pX-scFv225m-HL with oligos CX697/CX698, digested with BsaI, and cloned into pFIL-$CH_{225}$ at EcoRI/NheI, resulting in the C225 heavy chain expression vector pFIL-C225-heavy.

TABLE 33

Primers Used in the Construction of anti-EGFR IgG antibody

CX268  ccgcaggtacctcgagcgctagccagtctggccag (SEQ ID NO: 156)

CX325  tgcttgctcaactctacgtc (SEQ ID NO: 157)

CX370  aacttgtttattgcagctt (SEQ ID NO: 158)

CX448  gagttttgtcggatccaccagagccaccgctgccaccgctcgagcc (SEQ ID NO: 159)

CX638  gcgtatgcaggatccggcggcgatattctgctgacccaga (SEQ ID NO: 160)

CX639  cacgctcagaatcaccgggctctgggtcagcagaatatcg (SEQ ID NO: 161)

CX640  gcccggtgattctgagcgtgagcccgggcgaacgtgtgag (SEQ ID NO: 162)

CX641  ggctcgcgcggcagctaaagctcacacgttcgcccgggct (SEQ ID NO: 163)

CX642  ctttagctgccgcgcgagccagagcattggcaccaacatt (SEQ ID NO: 164)

CX643  gtgcgctgctgataccaatgaatgttggtgccaatgctct (SEQ ID NO: 165)

CX644  cattggtatcagcagcgcaccaacggcagcccgcgcctgc (SEQ ID NO: 166)

CX645  ttcgctcgcatatttaatcagcaggcgcgggctgccgttg (SEQ ID NO: 167)

CX646  tgattaaatatgcgagcgaaagcattagcggcattccgag (SEQ ID NO: 168)

CX647  tgccgctgccgctaaagcggctcggaatgccgctaatgct (SEQ ID NO: 169)

CX648  ccgctttagcggcagcggcagcggcaccgattttaccctg (SEQ ID NO: 170)

CX649  cttccacgctgttaatgctcagggtaaaatcggtgccgc (SEQ ID NO: 171)

CX650  agcattaacagcgtggaaagcgaagatattgcggattatt (SEQ ID NO: 172)

CX651  gttgttgttctgctggcaataataatccgcaatatcttcg (SEQ ID NO: 173)

CX652  attgccagcagaacaacaactggccgaccacctttggcgc (SEQ ID NO: 174)

CX653  tcagttccagtttggtgcccgcgccaaaggtggtcggcca (SEQ ID NO: 175)

CX654  gggcaccaaactggaactgaaacgcggccgccatcaccat (SEQ ID NO: 176)

CX655  ctcccacgcgtatggtgatgatggtgatggcggccgcgtt (SEQ ID NO: 177)

CX656  cgtatgcaagatctggtagcggtacccaggtgcagctgaa (SEQ ID NO: 178)

CX657  ccaggcccgggccgctctgtttcagctgcacctgggtacc (SEQ ID NO: 179)

CX658  acagagcggcccgggcctggtgcagccgagccagagcctg (SEQ ID NO: 180)

CX659  ctcacggtgcaggtaatgctcaggctctggctcggctgca (SEQ ID NO: 181)

CX660  agcattacctgcaccgtgagcggctttagcctgaccaact (SEQ ID NO: 182)

CX661  gcgcacccaatgcacgccatagttggtcaggctaaagccg (SEQ ID NO: 183)

CX662  atggcgtgcattgggtgcgccagagcccgggcaaaggcct (SEQ ID NO: 184)

CX663  aaatcacgcccagccattccaggcctttgcccgggctctg (SEQ ID NO: 185)

CX664  ggaatggctgggcgtgatttggagcggcggcaacaccgat (SEQ ID NO: 186)

CX665  ctggtaaacggggtgttataatcggtgttgccgccgctcc (SEQ ID NO: 187)

CX666  tataacacccgtttaccagccgcctgagcattaacaaag (SEQ ID NO: 188)

CX667  cacctggcttttgctgttatctttgttaatgctcaggcgg (SEQ ID NO: 189)

CX668  ataacagcaaaagccaggtgttttttaaaatgaacagcct (SEQ ID NO: 190)

CX669  tcgcggtatcgttgctttgcaggctgttcatttttaaaaaa (SEQ ID NO: 191)

CX670  gcaaagcaacgataccgcgatttattattgcgcgcgcgcg (SEQ ID NO: 192)

CX671  tcataatcataataggtcagcgcgcgcgcgcaataataaa (SEQ ID NO: 193)

CX672  ctgacctattatgattatgaatttgcgtattggggccagg (SEQ ID NO: 194)

TABLE 33-continued

Primers Used in the Construction of anti-EGFR IgG antibody

| | | |
|---|---|---|
| CX673 | gctcacggtcaccagggtgccctggccccaatacgcaaat | (SEQ ID NO: 195) |
| CX674 | gcaccctggtgaccgtgagcgcgggtggtagcggtagcgg | (SEQ ID NO: 196) |
| CX675 | taccgccgcctccagatcctccgctaccgctaccacccgc | (SEQ ID NO: 197) |
| CX676 | aggatctggaggcggcggtagtagtggtggaggatccggt | (SEQ ID NO: 198) |
| CX677 | tggtgatggcggccgcggccaccggatcctccaccactac | (SEQ ID NO: 199) |
| CX688 | cgagctagctccctctacgctccctgttgaagctctttg | (SEQ ID NO: 200) |
| CX690 | acaagcgcgttgagcccaaatcttgtg | (SEQ ID NO: 201) |
| CX692 | cagttcatcccgggatgggggcagggtg | (SEQ ID NO: 202) |
| CX693 | ccccatcccgggatgaactgaccaagaaccaggtcagc | (SEQ ID NO: 203) |
| CX694 | ctggccacctaggactcatttaccc | (SEQ ID NO: 204) |
| CX695 | gcactggtctcgaattcggatattctgctgacccagag | (SEQ ID NO: 205) |
| CX696 | ggtgcggtctccgtacgtttcagttccagtttggtg | (SEQ ID NO: 206) |
| CX697 | gcactggtctcgaattcgcaggtgcagctgaaacagag | (SEQ ID NO: 207) |
| CX698 | gagacggtctcgctagccgcgctcacggtcaccag | (SEQ ID NO: 208) |
| CX730 | tgcgtatgcaagatctggtagcggtaccgatattctgctgacccagag | (SEQ ID NO: 209) |
| CX731 | actactaccgccgcctccagatcctccgctaccgctaccacctttcagttccagtttggtg | (SEQ ID NO: 210) |
| CX732 | tctggaggcggcggtagtagtggtggaggctcaggcggccaggtgcagctgaaacagag | (SEQ ID NO: 211) |
| CX733 | gatggtgatggcggccgcgcgcgctcacggtcaccag | (SEQ ID NO: 212) |
| CX735 | tgtcggatccaccgctaccgcccgcgctcacggtcaccag | (SEQ ID NO: 213) |
| CX740 | tcacgaattcgcaaggccagtctggccagggctcgagcggtggcagcggtggctctggtggatccggcggtggca (SEQ ID NO: 214) | |
| CX741 | tggtggatccggcggtggcagcggtggtggctccggcggtaccggcggtagcggtagatctgacaaaactcacac (SEQ ID NO: 215) | |
| CX747 | gatccccgtctccgccagtcaaaatgatgccggaaggcggtac | (SEQ ID NO: 216) |
| CX748 | cgccttccggcatcattttgactggcggagacggg | (SEQ ID NO: 217) |

Construction of Expression Vectors for Anti-EGFR AAs

Plasmid pX-scFv225m-HL was PCR amplified in separate reactions with primers CX730/CX731 and CX732/CX733, and the resulting products were amplified by overlap PCR with outside primers CX730/CX733, digested with BglII/NotI, and cloned into pXMal at BamHI/NotI, resulting in plasmid pX-scFv225m-LH.

Linker sequence was added to the N-terminal side of the human IgG Fc fragment gene by PCR amplification of pFUSE-hIgG-Fc2 in a reaction with overlapping forward primers CX740,CX741 and reverse primer CX370. The resulting product was digested with EcoRI/BglII, and the ~115 bp fragment was cloned into pFUSE-hIgG-Fc2 at EcoRI/BglII. The resulting plasmid was digested with KpnI/BglII, and the large fragment was ligated to the KpnI/BamHI-digested PCR product of amplifying pX-scFv225m-LH with oligos CX736/CX735, resulting in plasmid pPHB3734.

The resulting plasmid was digested with SfiI/XhoI, and masking peptide 3690 was cloned in as an SfiI/XhoI fragment of pPHB3690, resulting in plasmid pPHB3783.

The protease substrate SM984 was added by digesting the resulting plasmid with BamHI/KpnI and ligating the product of annealing the phosphorylated oligos CX747/CX748, resulting in plasmid pPHB3822.

The tandem peptide mask was constructed by digesting the resulting plasmid with XhoI, dephosphorylating the 5' ends, and cloning in the XhoI-digested PCR product of amplifying pPHB3579 with primers CX268/CX448, resulting in plasmid pPHB3889.

The masking region, linker, substrate, and light chain variable region of pPHB3783, pPHB3822, and pPHB3889 were amplified by PCR with primers CX325/CX696, digested with EcoRI/BsiWI, and cloned into pFIL2-CL$_{225}$ at EcoRI/BsiWI, resulting in the AA light chain expression vectors pPHB4007, pPHB3902, and pPHB3913 respectively.

Affinity matured masking peptides were swapped into the AA light chain expression vectors by cloning as SfiI/XhoI fragments. Protease substrates were swapped in as BamHI/KpnI compatible fragments.

Expression and Purification of the Anti-EGFR Antibody and AAs

3 μg of pFIL-CH$_{225}$-HL and 3 μg pFIL2-CH$_{225}$-light were co-transfected into CHO—S cells (Invitrogen) using Lipofectamine 200 (Invitrogen) according to manufacturers protocol. Transfected cells were cultured in Freestyle CHO media (Invitrogen) and selected for resistance to zeocin and blasticidin. Individual clones were isolated by limiting dilution and selected for expression of human IgG capable of binding EGFR by ELISA. All antibodies and AAs are purified by Protein-A chromatography using standard techniques.

Likewise, 3 µg of each expression vector for AA light chains was co-transfected into CHO—S cells with 3 µg pFIL-CH$_{225}$-HL. Transfected cells were cultured in Freestyle CHO media (Invitrogen) and selected for resistance to zeiocin and blasticiidin Inkdivideual clones were isolated by limiting dilution and selected for expression of human IgG capable of binding EGFR by ELISA.

Screening of the Affinity Matured Anti-EGFR MM Library.

Figure 22:
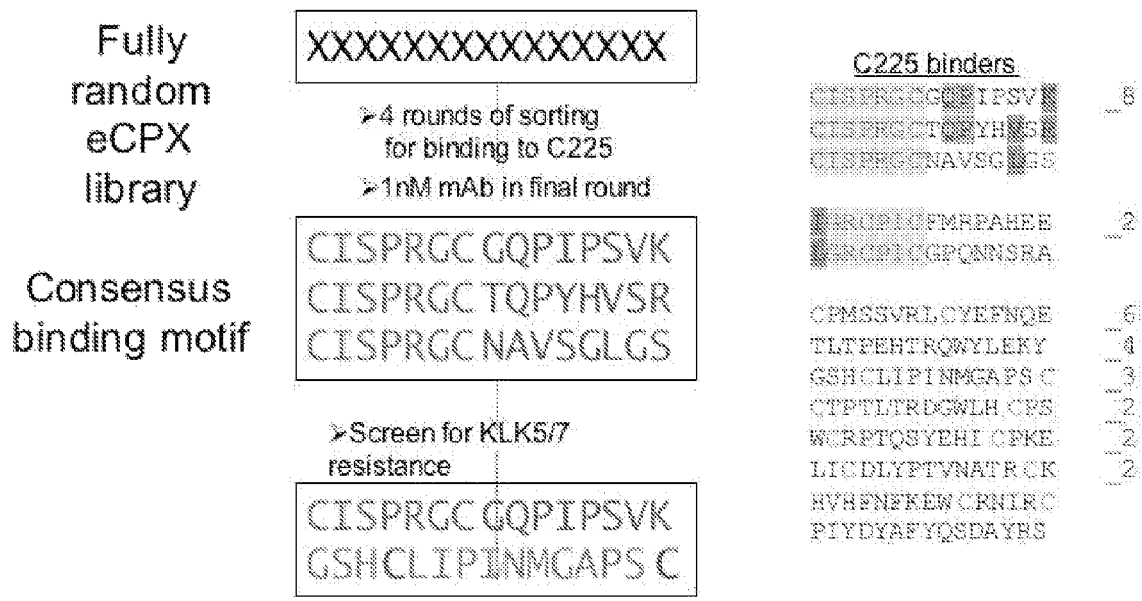
FIG. 22 shows the process for affinity maturation of some of the EGFR MM's. Consensus binding motifs disclosed as SEQ ID NOS 264-266, 264 and 236, respectively, in order of appearance, and C225 binders disclosed as SEQ ID NOS 264-266, 352-355, 236, 356-360, respectively, in order of appearance.

An initial MACS round was performed with SA dynabeads and 1.4×10$^8$ cells from the ecpX3-755 library. Prior to magnetic selection the cells were incubated with 3 nM biotin labeled C225Mab. Magnetic selection resulted in the isolation of 6×10$^6$ cells. The first round of FACS sorting was performed on 2×10$^7$ cells labeled with 0.1 nM DyLight (fluor 530 nM)-C225Mab and resulted in isolation of 1.5×10$^5$ cells with positive binding. To apply increased selective pressure to the population, the second round of FACS was performed on cells labeled with 10 nM DyLight-C225Mab in the presence of 100 uM 3690 peptide (CISPRGC (SEQ ID NO: 1)) at 37° C. To further increase the selection pressure the 3$^{rd}$ and 4$^{th}$ rounds were performed on cells labeled with 100 nM DyLight-C225Fab in the presence of 100 uM3690 peptide (CISPRGC (SEQ ID NO: 1)) at 37° C. The brightest 1% of the positive population were collected, representing binding that was not competed by 3690 peptide. On cell affinity measurements of individual clones isolated from the above screen revealed three peptides, 3954(CISPRGCPDGPYVM (SEQ ID NO: 218)), 3957(CISPRGCEPGTYVPT (SEQ ID NO: 219)) and 3958(CISPRGCPGQIWHPP (SEQ ID NO: 220)) with affinities for C225 at least 100 fold greater than 3690 (CISPRGC (SEQ ID NO: 1)). These three MMs were incorporated into anti-EGFR AAs. FIG. 22 shows the process for affinity maturation of some of the EGFR MM's.

Affinity Measurement for C225 MMs

Figure 23:
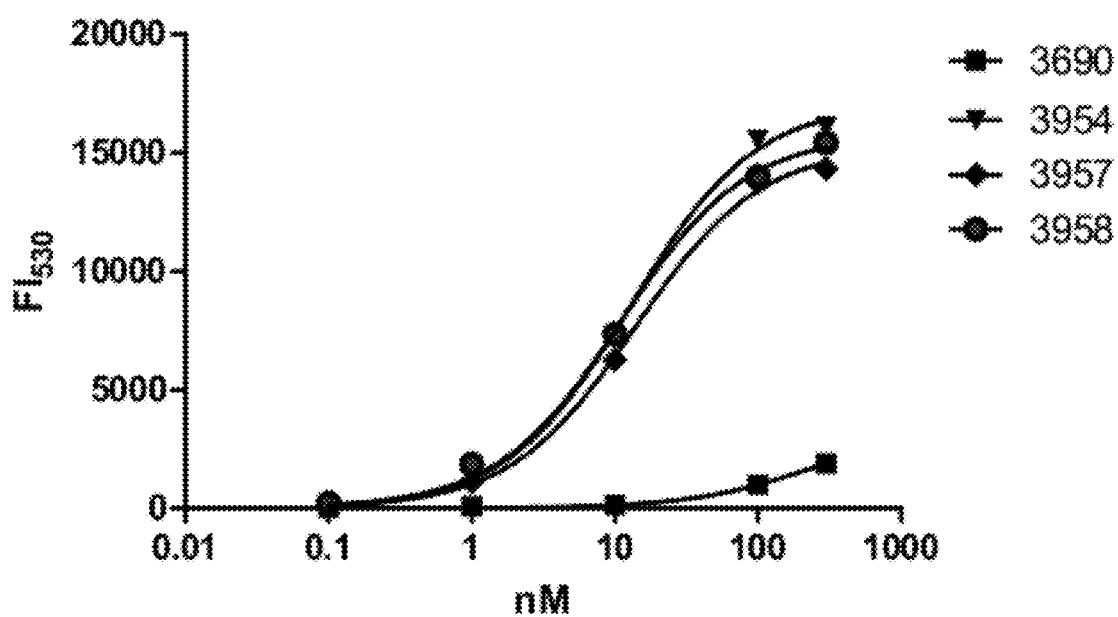
FIG. 23 shows the binding curves for the on-cell affinity measurement of C225 Fab binding to MM's 3690, 3954 and 3957. MMs 3954 and 3957 displayed at least 100 fold higher affinity than 3690.

On-cell affinity measurement of C225 Fab binding to MM's 3690, 3954 and 3957. Binding of the eCPX3.0 clones 3690, 3954 and 3957 were analyzed on FACS at 3 different concentrations of DyLight labeled anti-EGFR Fab. The binding curves are shown in FIG. 23. MMs 3954 and 3957 displayed at least 100 fold higher affinity than 3690.

Target Displacement Assay for Anti-EGFR AAs

Figure 24:
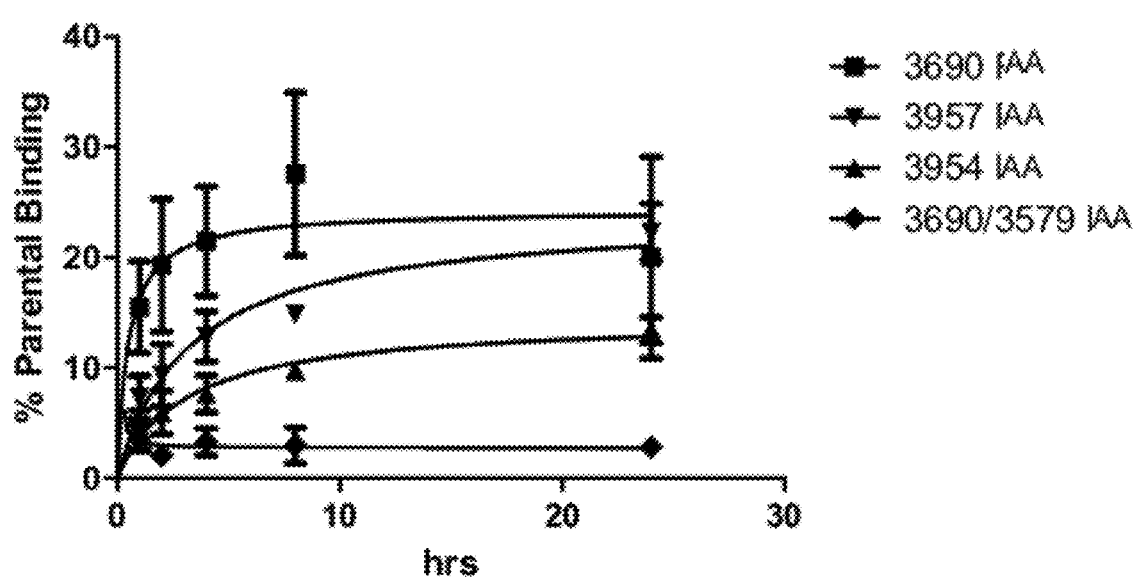
FIG. 24 displays the Target Displacement Assay and extent of equilibrium binding as a percent of parental antibody binding.

EGFR was adsorbed to the wells of a 96 well micro-titer plate, washed and blocked with milk protein. 25 ml of culture media containing 2 nM anti-EGFR antibody or anti-EGFR AA's containing the MM's 3690, 3957, 3954 and 3960/3579 was added to the coated wells and incubated for 1, 2, 4, 8 or 24 hours. Following incubation the wells were washed and the extent of bound AA's measured by anti-huIgG immunodetection. Anti-EGFR AA binding was normalized to anti-EGFR antibody binding (100%) for direct comparison of the masking efficiency in the AA context. The extents of equilibrium binding as a percent of parental or unmodified antibody binding are shown in Table 34 and FIG. 24. Whereas MMs 3954 and 3957 display the same affinity, 100 times higher than 3609, 3954 is at least 2 times more efficient at inhibiting target binding. The sequences of the C225 heavy and light chains, MMs, and AAs are provided in the tables following. Nucleotide and amino acid sequences provided in the tables following. Parentheses delineate the demarcations between the various sequence domains: (Linker)(MM)(Linker)(CM)(Linker)(AB).

TABLE 34

C225 TDA: Percent of parental antibody binding ± SEM at each time point

| Time (hours) | 3690 AA | 3954 AA | 3975 AA | 3690/3579 AA |
|---|---|---|---|---|
| 1 | 15.5 ± 4.2 | 4.4 ± 1.8 | 7.3 ± 2.0 | 3.6 ± 1.2 |
| 2 | 19.3 ± 6.0 | 6.0 ± 2.0 | 9.3 ± 2.8 | 2.1 ± 0.6 |
| 4 | 21.5 ± 5.0 | 7.6 ± 1.7 | 12.8 ± 2.3 | 3.3 ± 1.2 |
| 8 | 27.6 ± 7.4 | 9.7 ± 0.4 | 14.9 ± 0.03 | 3.0 ± 1.6 |
| 24 | 20.0 ± 9.1 | 13.4 ± 1.2 | 22.3 ± 2.6 | 2.8 ± 0.1 |

TABLE 35

C225 Heavy Chain caggtgcagctgaaacagagcggcccgggcctggtgcagccgagccagagcctgagcattacctgcaccgtgagcggctttagcctga ccaactatggcgtgcattgggtgcgccagagcccgggcaaaggcctggaatggctgggcgtgatttggagcggcggcaacaccgattat aacacccgtttaccagccgcctgagcattaacaaagataacagcaaaagccaggtgttttttaaaatgaacagcctgcaaagcaacgatac cgcgatttattattgcgcgcgcgcgctgacctattatgattatgaatttgcgtattggggccagggcaccctggtgaccgtgagcgcggctag caccaagggcccatcggtcttccccctggcaccctcctccaagagcacctctgggggcacagcggccctgggctgcctggtcaaggact acttccccgaaccggtgacggtgtcgtggaactcaggcgccctgaccagcggcgtgcacaccttcccggctgtcctacagtcctcaggact ctactccctcagcagcgtggtgaccgtgccctccagcagcttgggcacccagacctacatctgcaacgtgaatcacaagcccagcaacac caaggtggacaagcgcgttgagcccaaatcttgtgacaaaactcacacatgcccaccgtgcccagcacctgaactcctgggggaccgtc agtcttcctcttccccccaaaacccaaggacaccctcatgatctcccggacccctgaggtcacatgcgtggtggtggacgtgagccacgaa gaccctgaggtcaagttcaactggtacgtggacggcgtggaggtgcataatgccaagacaaagccgcgggaggagcagtacaacagca cgtaccgtgtggtcagcgtcctcaccgtcctgcaccaggactggctgaatggcaaggagtacaagtgcaaggtctccaacaaagccctcc cagcccccatcgagaaaaccatctccaaagccaaagggcagccccgagaaccacaggtgtacaccctgccccatcccgggatgaact gaccaagaaccaggtcagcctgacctgcctggtcaaaggcttctatcccagcgacatcgccgtggagtgggagagcaatgggcagccgg agaacaactacaagaccacgcctcccgtgctggactccgacggctccttcttcctctacagcaagctcaccgtggacaagagcaggtggc

TABLE 35-continued

C225 Heavy Chain agcaggggaacgtcttctcatgctccgtgatgcatgaggctctgcacaaccactacacgcagaagagcctctccctgtctccgggtaaa (SEQ ID NO: 221)

QVQLKQSGPGLVQPSQSLSITCTVSGFSLTNYGVHWVRQSPGKGLEWLGVIWSGGNTD
YNTPFTSRLSINKDNSKSQVFFKMNSLQSNDTAIYYCARALTYYDYEFAYWGQGTLVT
VSAASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSCDKTHTCPPCPAPE
LLGGPSVFLFPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQPREPQVYTL
PPSRDELTKNQVSLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 222)

TABLE 36

Sequence of 3690-SM984-C225 Light Chain

Caaggccagtctggccagtgcatctcgccccgtggttgtggaggctcgagcggtggcagcggtggctctggtggatcccgtctccgcc
agtcaaaatgatgccggaaggcggtacccagatcttgctgacccagagcccggtgattctgagcgtgagcccgggcgaacgtgtgagctt
tagctgccgcgcgagccagagcattggcaccaacattcattggtatcagcagcgcaccaacggcagcccgcgcctgctgattaaatatgc
gagcgaaagcattagcggcattccgagccgctttagcggcagcggcagcggcaccgattttaccctgagcattaacagcgtggaaagcg
aagatattgcggattattattgccagcagaacaacaactggccgaccacctttggcgcgggcaccaaactggaactgaaacgtacggtggc
tgcaccatctgtcttcatcttcccgccatctgatgagcagttgaaatctggaactgcctctgttgtgtgcctgctgaataacttctatcccagag
aggccaaagtacagtggaaggtggataacgcccctccaatcgggtaactcccaggagagtgtcacagagcaggacagcaaggacagcacc
tacagcctcagcagcaccctgacgctgagcaaagcagactacgagaaacacaaagtctacgcctgcgaagtcacccatcagggcctgag
ctcgcccgtcacaaagagcttcaacaggggagcg (SEQ ID NO: 223)

Linker MM Linker CM Linker AB
(QGQSGQ)(CISPRGC)(GGSSGGSGGSGGS)(PSPPVKMMPE)(GG)(TQILLTQSPVILSVSPG
ERVSFSCRASQSIGTNIHWYQQRTNGSPRLLIKYASESISGIPSRFSGSGSGTDFTLSINSVE
SEDIADYYCQQNNNWPTTFGAGTKLELKRTVAAPSVFIFPPSDEQLKSGTASVVCLLNN
FYPREAKVQWKVDNALQSGNSQESVTEQDSKDSTYSLSSTLTLSKADYEKHKVYACEV
THQGLSSPVTKSFNRGA) (SEQ ID NO: 224)

TABLE 37

Sequence of 3579-NSUB-C225 Light Chain caaggccagtctggccagggttcacattgtctcattcctattaacatgggcgcgccgtcatgcggctcgagcggtggcagcggtggctctg
gtggatccggcggtggcagcggtggtggctccggcggtacccagatcttgctgacccagagcccggtgattctgagcgtgagcccgggc
gaacgtgtgagctttagctgccgcgcgagccagagcattggcaccaacattcattggtatcagcagcgcaccaacggcagcccgcgcctg
ctgattaaatatgcgagcgaaagcattagcggcattccgagccgctttagcggcagcggcagcggcaccgattttaccctgagcattaaca
gcgtggaaagcgaagatattgcggattattattgccagcagaacaacaactggccgaccacctttggcgcgggcaccaaactggaactga
aacgtacggtggctgcaccatctgtcttcatcttcccgccatctgatgagcagttgaaatctggaactgcctctgttgtgtgcctgctgaataac TABLE 37-continued Sequence of 3579-NSUB-C225 Light Chain ttctatcccagagaggccaaagtacagtggaaggtggataacgccctccaatcgggtaactcccaggagagtgtcacagagcaggacag caaggacagcacctacagcctcagcagcaccctgacgctgagcaaagcagactacgagaaacacaaagtctacgcctgcgaagtcacc catcagggcctgagctcgcccgtcacaaagagcttcaacaggggagcg (SEQ ID NO: 225)

Linker MM Linker AB
(QGQSGQ)(GSHCLIPINMGAPSC)(GSSGGSGGSGGSGGGSGGGSGG)(TQILLTQSPVILSV

SPGERVSFSCRASQSIGTNIHWYQQRTNGSPRLLIKYASESISGIPSRFSGSGSGTDFTLSIN

SVESEDIADYYCQQNNNWPTTFGAGTKLELKRTVAAPSVFIFPPSDEQLKSGTASVVCLL

NNFYPREAKVQWKVDNALQSGNSQESVTEQDSKDSTYSLSSTLTLSKADYEKHKVYAC

EVTHQGLSSPVTKSFNRGA) (SEQ ID NO: 226)

TABLE 38

Sequence of 3690-3579-SM984-C225 Light Chain caaggccagtctggccagtgcatctcgccccgtggttgtggaggctcgagcgctagccagtctggccagggttcacattgtctcattcctatt aacatgggcgcgccgtcatgcggctcgagcggtggcagcggtggctctggtggatccccgtctccgccagtcaaaatgatgccggaagg cggtacccagatcttgctgacccagagcccggtgattctgagcgtgagcccgggcgaacgtgtgagctttagctgccgcgcgagccaga gcattggcaccaacattcattggtatcagcagcgcaccaacggcagcccgcgcctgctgattaaatatgcgagcgaaagcattagcggcat tccgagccgctttagcggcagcggcagcggcaccgattttaccctgagcattaacagcgtggaaagcgaagatattgcggattattattgcc agcagaacaacaactggccgaccacctttggcgcgggcaccaaactggaactgaaacgtacggtggctgcaccatctgtcttcatcttccc gccatctgatgagcagttgaaatctggaactgcctctgttgtgtgcctgctgaataacttctatcccagagaggccaaagtacagtggaaggt ggataacgccctccaatcgggtaactcccaggagagtgtcacagagcaggacagcaaggacagcacctacagcctcagcagcaccctg acgctgagcaaagcagactacgagaaacacaaagtctacgcctgcgaagtcacccatcagggcctgagctcgcccgtcacaaagagctt caacaggggagcg (SEQ ID NO: 227)

Linker MM Linker CM
(QGQSGQ)(CISPRGCGGSSASQSGQGSHCLIPINMGAPSC)(GSSGGSGGSGGS)(PSPPVKM

MPE)

Linker AB
(GG)(TQILLTQSPVILSVSPGERVSFSCRASQSIGTNIHWYQQRTNGSPRLLIKYASESISGI

PSRFSGSGSGTDFTLSINSVESEDIADYYCQQNNNWPTTFGAGTKLELKRTVAAPSVFIFP

PSDEQLKSGTASVVCLLNNFYPREAKVQWKVDNALQSGNSQESVTEQDSKDSTYSLSST

LTLSKADYEKHKVYACEVTHQGLSSPVTKSFNRGA) (SEQ ID NO: 228)

TABLE 39

Sequence of 3954-NSUB-C225 Light Chain caaggccagtctggccagtgcatctcacctcgtggttgtccggacggcccatacgtcatgtacggctcgagcggtggcagcggtggctctg gtggatccggcggtggcagcggtggtggctccggcggtacccagatcttgctgacccagagcccggtgattctgagcgtgagcccgggc gaacgtgtgagctttagctgccgcgcgagccagagcattggcaccaacattcattggtatcagcagcgcaccaacggcagcccgcgcctg ctgattaaatatgcgagcgaaagcattagcggcattccgagccgctttagcggcagcggcagcggcaccgattttaccctgagcattaaca gcgtggaaagcgaagatattgcggattattattgccagcagaacaacaactggccgaccacctttggcgcgggcaccaaactggaactga

TABLE 39-continued

Sequence of 3954-NSUB-C225 Light Chain aacgtacggtggctgcaccatctgtcttcatcttcccgccatctgatgagcagttgaaatctggaactgcctctgttgtgtgcctgctgaataac ttctatcccagagaggccaaagtacagtggaaggtggataacgcccctccaatcgggtaactcccaggagagtgtcacagagcaggacag caaggacagcacctacagcctcagcagcaccctgacgctgagcaaagcagactacgagaaacacaaagtctacgcctgcgaagtcacc catcagggcctgagctcgcccgtcacaaagagcttcaacaggggagcg (SEQ ID NO: 229)

Linker MM Linker AB
(QGQSGQ)(CISPRGCPDGPYVMY)(GSSGGSGGSGGSGGGSGGGSGG)(TQILLTQSPVILS

VSPGERVSFSCRASQSIGTNIHWYQQRTNGSPRLLIKYASESISGIPSRFSGSGSGTDFTLSI

NSVESEDIADYYCQQNNNWPTTFGAGTKLELKRTVAAPSVFIFPPSDEQLKSGTASVVC

LLNNFYPREAKVQWKVDNALQSGNSQESVTEQDSKDSTYSLSSTLTLSKADYEKHKVY

ACEVTHQGLSSPVTKSFNRGA) (SEQ ID NO: 230)

20

TABLE 40

Sequence of 3957-NSUB-C225 Light Chain caaggccagtctggccagtgcatctcacctcgtggttgtgagcctggcacctatgttccaacaggctcgagcggtggcagcggtggctctg gtggatccggcggtggcagcggtggtggctccggcggtacccagatcttgctgacccagagcccggtgattctgagcgtgagcccgggc gaacgtgtgagctttagctgccgcgcgagccagagcattggcaccaacattcattggtatcagcagcgcaccaacggcagcccgcgcctg ctgattaaatatgcgagcgaaagcattagcggcattccgagccgctttagcggcagcggcagcggcaccgattttaccctgagcattaaca gcgtggaaagcgaagatattgcggattattattgccagcagaacaacaactggccgaccacctttggcgcgggcaccaaactggaactga aacgtacggtggctgcaccatctgtcttcatcttcccgccatctgatgagcagttgaaatctggaactgcctctgttgtgtgcctgctgaataac ttctatcccagagaggccaaagtacagtggaaggtggataacgcccctccaatcgggtaactcccaggagagtgtcacagagcaggacag caaggacagcacctacagcctcagcagcaccctgacgctgagcaaagcagactacgagaaacacaaagtctacgcctgcgaagtcacc catcagggcctgagctcgcccgtcacaaagagcttcaacaggggagcg (SEQ ID NO: 231)

Linker MM Linker AB
(QGQSGQ)(CISPRGCEPGTYVPT)(GSSGGSGGSGGSGGGSGGGSGG)(TQILLTQSPVILSV

SPGERVSFSCRASQSIGTNIHWYQQRTNGSPRLLIKYASESISGIPSRFSGSGSGTDFTLSIN

SVESEDIADYYCQQNNNWPTTFGAGTKLELKRTVAAPSVFIFPPSDEQLKSGTASVVCLL

NNFYPREAKVQWKVDNALQSGNSQESVTEQDSKDSTYSLSSTLTLSKADYEKHKVYAC

EVTHQGLSSPVTKSFNRGA) (SEQ ID NO: 232)

TABLE 41

Sequence of 3958-NSUB-C225 Light Chain caaggccagtctggccagtgcatctcacctcgtggttgtccgggccaaatttggcatccacctggctcgagcggtggcagcggtggctctg gtggatccggcggtggcagcggtggtggctccggcggtacccagatcttgctgacccagagcccggtgattctgagcgtgagcccgggc gaacgtgtgagctttagctgccgcgcgagccagagcattggcaccaacattcattggtatcagcagcgcaccaacggcagcccgcgcctg ctgattaaatatgcgagcgaaagcattagcggcattccgagccgctttagcggcagcggcagcggcaccgattttaccctgagcattaaca gcgtggaaagcgaagatattgcggattattattgccagcagaacaacaactggccgaccacctttggcgcgggcaccaaactggaactga aacgtacggtggctgcaccatctgtcttcatcttcccgccatctgatgagcagttgaaatctggaactgcctctgttgtgtgcctgctgaataac ttctatcccagagaggccaaagtacagtggaaggtggataacgcccctccaatcgggtaactcccaggagagtgtcacagagcaggacag TABLE 41-continued Sequence of 3958-NSUB-C225 Light Chain caaggacagcacctacagcctcagcagcaccctgacgctgagcaaagcagactacgagaaacacaaagtctacgcctgcgaagtcacc catcagggcctgagctcgcccgtcacaaagagcttcaacaggggagcg (SEQ ID NO: 233)

Linker        MM                Linker              AB
(QGQSGQ) (CISPRGCPGQIWHPP) (GSSGGSGGSGGSGGGSGGGSGG) (TQILLTQSPVILSV

SPGERVSFSCRASQSIGTNIHWYQQRTNGSPRLLIKYASESISGIPSRFSGSGSGTDFTLSIN

SVESEDIADYYCQQNNNWPTTFGAGTKLELKRTVAAPSVFIFPPSDEQLKSGTASVVCLL

NNFYPREAKVQWKVDNALQSGNSQESVTEQDSKDSTYSLSSTLTLSKADYEKHKVYAC

EVTHQGLSSPVTKSFNRGA) (SEQ ID NO: 234)

TABLE 42

Sequences of C225 MMs:

| | | |
|---|---|---|
| 3690 | CISPRGC | (SEQ ID NO: 1) |
| 3579 | GSHCLIPINMGAPSC | (SEQ ID NO: 236) |
| 3690-3579 | CISPRGCGGSSASQSGQGSHCLIPINMGAPSC | (SEQ ID NO: 237) |
| 3954 | CISPRGCPDGPYVMY | (SEQ ID NO: 238) |
| 3957 | CISPRGCEPGTYVPT | (SEQ ID NO: 239) |
| 3958 | CISPRGCPGQIWHPP | (SEQ ID NO: 240) |
| 4124 | CNHHYFYTCGCISPRGCPG | (SEQ ID NO: 241) |
| 4125 | ADHVFWGSYGCISPRGCPG | (SEQ ID NO: 242) |
| 4127 | CHHVYWGHCGCISPRGCPG | (SEQ ID NO: 243) |
| 4133 | CPHFTTTSCGCISPRGCPG | (SEQ ID NO: 244) |
| 4137 | CNHHYHYYCGCISPRGCPG | (SEQ ID NO: 245) |
| 4138 | CPHVSFGSCGCISPRGCPG | (SEQ ID NO: 246) |
| 4140 | CPYYTLSYCGCISPRGCPG | (SEQ ID NO: 247) |
| 4141 | CNHVYFGTCGCISPRGCPG | (SEQ ID NO: 248) |
| 4143 | CNHFTLTTCGCISPRGCPG | (SEQ ID NO: 249) |
| 4148 | CHHFTLTTCGCISPRGCPG | (SEQ ID NO: 250) |
| 4157 | YNPCATPMCCISPRGCPG | (SEQ ID NO: 251) |

EGFR MM Consensus Sequences

The consensus sequences for the EGFR MMs are provided below. The 3690 MM consensus (CISPRGC (SEQ ID NO: 111 is one major consensus sequence.

TABLE 43

C225 EGFR MM Consensus Sequences

| | | |
|---|---|---|
| PHB4124 | CNHHYFYTCGCISPRGCG | (SEQ ID NO: 252) |
| PHB4137 | CNHHYHYYCGCISPRGCG | (SEQ ID NO: 253) |
| PHB4141 | CNHVYFGTCGCISPRGCG | (SEQ ID NO: 254) |
| PHB4127 | CHHVYWGHCGCISPRGCG | (SEQ ID NO: 255) |

TABLE 43-continued

C225 EGFR MM Consensus Sequences

| | | |
|---|---|---|
| PHB4133 | CPHFTTTSCGCISPRGCG | (SEQ ID NO: 256) |
| PHB4143 | CNHFTLTTCGCISPRGCG | (SEQ ID NO: 257) |
| PHB4148 | CHHFTLTTCGCISPRGCG | (SEQ ID NO: 258) |
| PHB4140 | CPYYTLSYCGCISPRGCG | (SEQ ID NO: 259) |
| PHB4138 | CPHVSFGSCGCISPRGCG | (SEQ ID NO: 260) |
| PHB4125 | ADHVFWGSYGCISPRGCG | (SEQ ID NO: 261) |
| PHB4157 | YNPCATPMCCISPRGCG | (SEQ ID NO: 262) |
| PHB4127 | CHHVYWGHCGCISPRGCG | (SEQ ID NO: 263) |

EGFR consensus Sequences from the 2$^{nd}$ round of screening for higher affinity masks

| | |
|---|---|
| C(N/P)H(H/V/F) (X/T)(F/W/T/L)(Y/G/T/S) | (SEQ ID NO: 2) |
| (T/S/Y/H)CGCISPRGCG | |
| CISPRGCGQRIPSVK | (SEQ ID NO: 264) |
| CISPRGCTQRYHVSR | (SEQ ID NO: 265) |
| CISPRGCNAVSGLGS | (SEQ ID NO: 266) |

Example 17

Selective Substrate/CM Discovery and Testing

Figure 25:
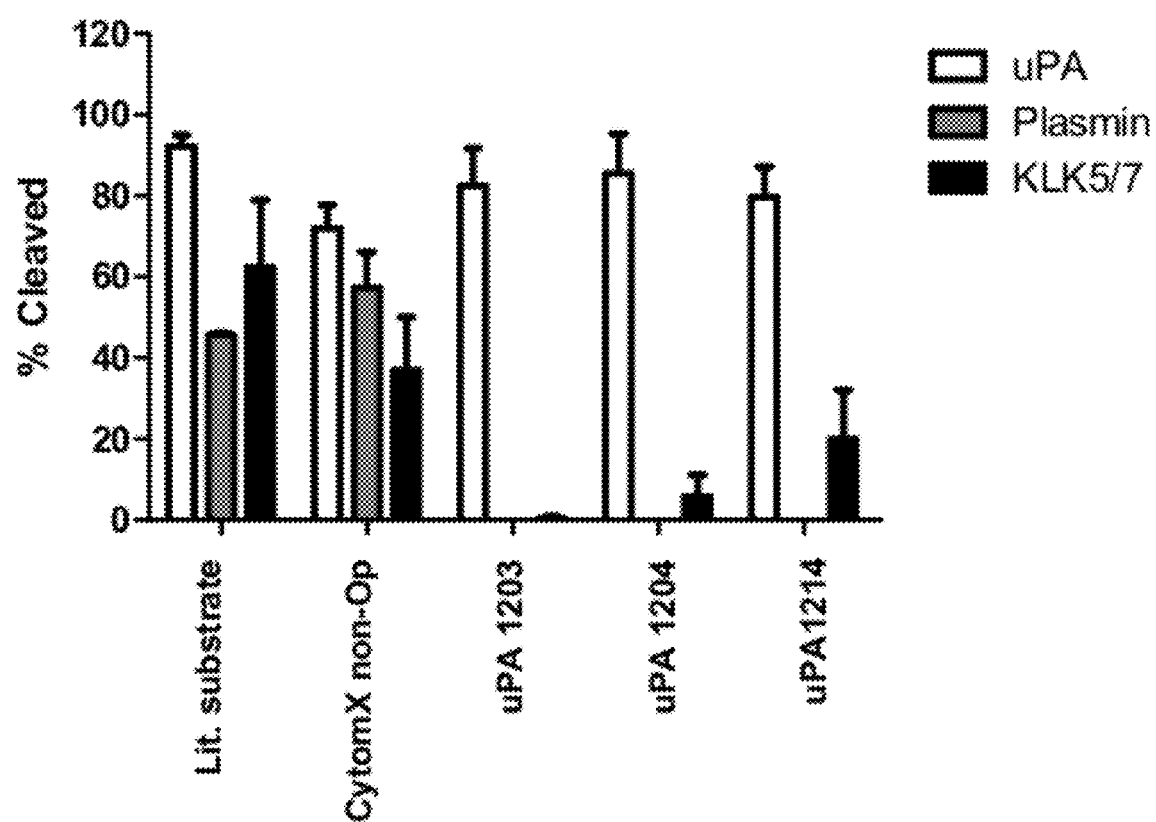
FIG. 25 shows that unlike the uPA control and substrate SM16, KK1203, 1204 and 1214 show resistance to cleavage by KLK5, KLK7 and Plasmin.

The section below the process for selective substrate discovery and testing for a number of exemplary enzymes.

uPA Selective Substrate Discovery uPA-selective substrates were isolated from an 8eCLiPS bacterial library consisting of ~10$^8$ random 8-mer substrates expressed as N-terminal fusions on the surface of E. coli. Alternating rounds of positive and negative selections by FACS were used to enrich for substrates optimized for cleavage by uPA and resistant to cleavage by the off-target serine proteases klk5 and 7. The naive library was incubated with 8 ug/ml uPA for 1 h at 37° C. followed by labeling with SAPE (red) and yPET mona (green). Cleavage by uPA results in loss of the SAPE tag and allows for sorting of bacteria expressing uPA substrates (green only, positive selection) from bacteria expressing uncleaved peptides (red+green). uPA substrates were sorted by FACS and the enriched pool was amplified and then incubated with 5 ng/ml KLK5 and 7 for 1 h at 37° C., labeled with SAPE and yPET mona, and sorted for lack of cleavage by these off-target proteases (red+green, negative selection). The pool was amplified and sorted with 4 additional alternating rounds of positive and negative FACS using decreasing concentrations of uPA (4 ug/ml, 2 ug/ml) and increasing concentrations of klk5 and 7 (5 ng/ml, 10 ng/ml). Individual clones from the last 3 rounds of FACS were sequenced and grouped into several consensuses (Table 44). Clones from each consensus were then analyzed individually for cleavage by a range of concentrations of uPA, klk5 and 7 and plasmin for specificity of cleavage by on versus off-target proteases in Table 44. FIG. 25 shows that unlike the uPA control and substrate SM16, KK1203, 1204 and 1214 show resistance to cleavage by KLK5, KLK7 and Plasmin.

TABLE 44 uPA Consensus sequences (SEQ ID NOS 267-280, respectively, in order of appearance)

```
            (1) 1         9
kk1203(1)      TGRGPS-WV
kk1206(1)      SARGPSRW-
kk1216(1)      TARGPSFK-
Consensus(1)   TARGPS W (1) 1           11
kk1204(1)      ---LSGRSDNH
kk1208(1)      GGWHTGRN---
kk1211(1)      ---HTGRSGAL
kk1214(1)      --PLTGRSGG-
Consensus(1)      LTGRSGA (1) 1        10
kk1217(1)      AARGPAIH--
kk1219(1)      --RGPAFNPM kk1196(1)      SSRGPAYL--
kk1201(1)      --RGPATPIM
Consensus(1)     RGPA
```

Plasmin Selective Substrate Discovery

Plasmin-selective substrates were isolated from a second generation plasmin 10eCLiPS bacterial library consisting of ~$10^8$ random 10-mer substrates expressed as N-terminal fusions on the surface of E. coli (ref). Alternating rounds of positive and negative selections by FACS were used to enrich for substrates optimized for cleavage by plasmin and resistant to cleavage by the off-target matrix metalloproteinases (represented by MMP-9) and serine proteases (represented by klk5 and klk7).

The second generation plasmin 10eCLiPS library was based on a consensus sequence identified in-house by selecting the naïve 8eCLiPS for rapidly cleaved plasmin substrates using concentrations as low as 30 pM plasmin for selection. Individual residues within the 10mer were either random (n=20), restricted (1<n>20) or fixed (n=1) to bias the peptide toward the consensus sequence while allowing flexibility to down-select away from unfavorable off-target sequences.

Figure 26:
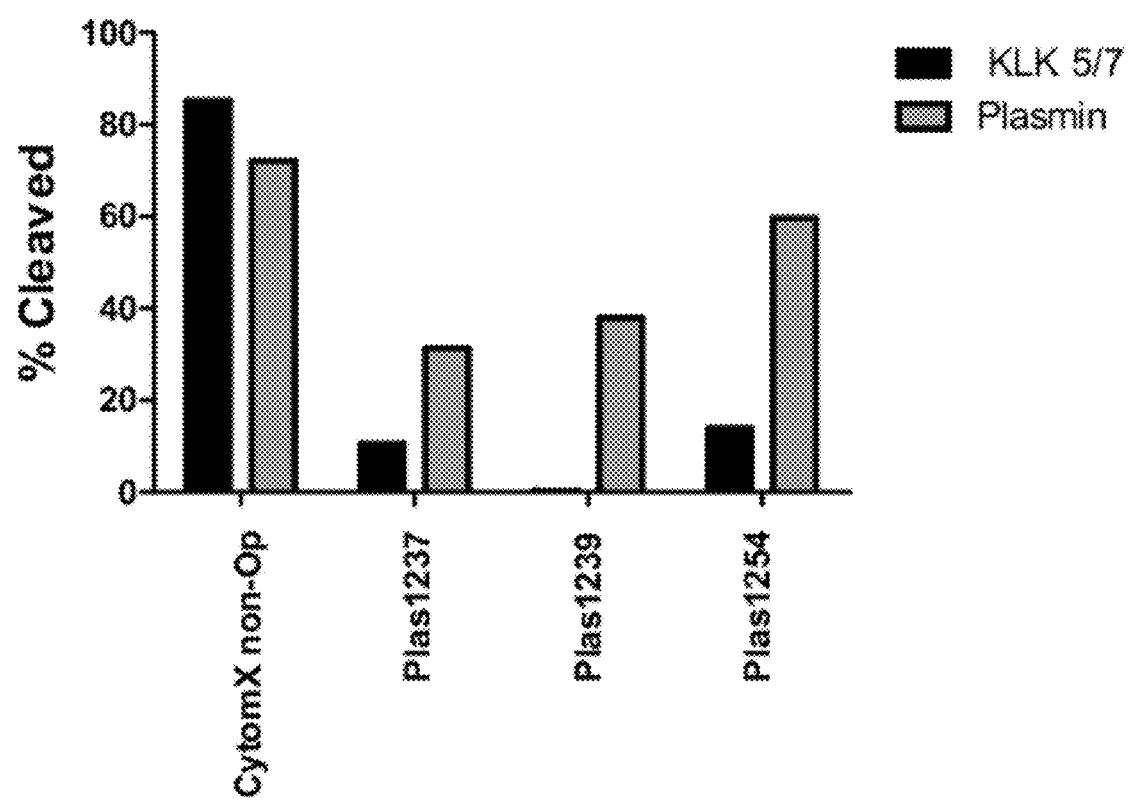
FIG. 26 shows that unlike a non-optimized substrate, the optimized substrates Plas1237, Plas129 and Plas 1254 show resistance to cleavage by KLK5, KLK7.

The second generation plasmin 10eCLiPS library was incubated with 300 pM plasmin for 1 h at 37° C. followed by labeling with SAPE (red) and yPET mona (green). Cleavage by plasmin results in loss of the SAPE tag and allows for sorting of bacteria expressing plasmin substrates (green only, positive selection) from bacteria expressing uncleaved peptides (red+green). plasmin substrates were sorted by FACS and the enriched pool was amplified and then incubated with 80 U/ml MMP-9 2 h at 37° C., labeled with SAPE and yPET mona, and sorted for lack of cleavage by these off-target proteases (red+green, negative selection). The pool was amplified and sorted with 4 additional alternating rounds of positive and negative FACS using plasmin (round three at 100 pM or 300 pM, round five at 100 pM or 300 pM) and klk5 and 7 (Round four at 100 ng/ml, round six at 200 ng/ml). Individual clones from each the last 2 rounds of FACS were sequenced (Table 45). Clones from each consensus were then analyzed individually for cleavage by plasmin, MMP-9, klk5 and klk7 for specificity of cleavage by on versus off-target proteases. Representative data showing increased specificity towards Plasmin cleavage is shown in FIG. 26. FIG. 26 shows that unlike a non-optimized substrate, the optimized substrates Plas1237, Plas129 and Plas 1254 show resistance to cleavage by KLK5, KLK7.

TABLE 45

Peptide sequences derived from three rounds of Positive selection for Plasmin cleavage and negative selection for MMP9, KLK5 and KLK7

| | | |
|---|---|---|
| SM1191 | EHPRVKVVSE | (SEQ ID NO: 281) |
| SM1197 | PPPDMKLFPG | (SEQ ID NO: 282) |
| SM1200 | PPPVLKLLEW | (SEQ ID NO: 283) |
| SM1203 | VLPELRSVFS | (SEQ ID NO: 284) |
| SM1206 | APPSFKLVNA | (SEQ ID NO: 285) |
| SM1212 | PPPEVRSFSV | (SEQ ID NO: 286) |
| SM1214 | ALPSVKMVSE | (SEQ ID NO: 287) |
| SM1215 | ETPSVKTMGR | (SEQ ID NO: 288) |
| SM1219 | AIPRVRLFDV | (SEQ ID NO: 289) |
| SM1224 | GLGTPRGLFA | (SEQ ID NO: 290) |
| SM1276 | DRPKVKTMDF | (SEQ ID NO: 291) |
| SM1275 | RVPKVKVMLD | (SEQ ID NO: 292) |
| SM1274 | APPLVKSMVV | (SEQ ID NO: 293) |
| SM1272 | REPFMKSLPW | (SEQ ID NO: 294) |
| SM1270 | PVPRLKLIKD | (SEQ ID NO: 295) |
| SM1269 | KGPKVKVVTL | (SEQ ID NO: 296) |
| SM1268 | ERPGVKSLVL | (SEQ ID NO: 297) |
| SM1267 | NZPRVRLVLP | (SEQ ID NO: 298) |
| SM1265 | PRPFVKSVDQ | (SEQ ID NO: 299) |
| SM1263 | RFPSLKSFPL | (SEQ ID NO: 300) |
| SM1261 | ESPVMKSMAL | (SEQ ID NO: 301) |
| SM1260 | VAPQLKSLVP | (SEQ ID NO: 302) |
| SM1255 | APPLVKSMVV | (SEQ ID NO: 303) |
| SM1254 | NMPSFKLVTG | (SEQ ID NO: 304) |
| SM1245 | DRPEMKSLSG | (SEQ ID NO: 305) |
| SM1244 | EQPEVKMVKG | (SEQ ID NO: 306) |
| SM1243 | AVPKVRVVPE | (SEQ ID NO: 307) |
| SM1241 | DLPLVKSLPS | (SEQ ID NO: 308) |

TABLE 45-continued

Peptide sequences derived from three rounds of Positive selection for Plasmin cleavage and negative selection for MMP9, KLK5 and KLK7

| | | |
|---|---|---|
| SM1240 | EAPKVKALPK | (SEQ ID NO: 309) |
| SM1239 | GFPHMKTFQH | (SEQ ID NO: 310) |
| SM1238 | YDPZVKVVLA | (SEQ ID NO: 311) |
| SM1237 | ASPTMKTVGL | (SEQ ID NO: 312) |
| SM1236 | DVPPMKTLRP | (SEQ ID NO: 313) |
| SM1235 | AFPDMRSVRS | (SEQ ID NO: 314) |
| SM1234 | SAPYFRMMDM | (SEQ ID NO: 315) |
| SM1233 | EKPRMKLFQG | (SEQ ID NO: 316) |
| SM1231 | YVPRVKALEM | (SEQ ID NO: 317) | uPA Enzyme Activated AA Sequences

Nucleotide and amino acid sequences of uPA enzyme-activated anti VEGF light chain AAs are provided in the tables below. Parentheses delineate the demarcations between the various sequence domains: (Linker)(MM)(Linker)(CM)(Linker)(AB).

TABLE 46

PFIL2-CLIg-HK-anti-VegF 306 KK1203 LC

Ggccagtctggccagccgtgttctgagtggcagtcgatggtgcagccgcgttgctattatgggggcggttctggtggcagcggccaaggt
ggccaaggtactggccgtggtccaagctgggttggcagtagcggcggttctgatattcaactgacccagagcccttcttccctgagtgccag
cgtgggtgaccgtgttacgatcacttgctcggccagccaagatatttctaactacctgaattggtaccagcagaagccaggaaaggcaccaa
aagtcctgatctacttcacaagttcactgcattccggcgtaccgtcgcgctttagcggttctggcagtggtaccgacttcaccctgactatctcg
agtctgcaacctgaggattttgctacatattactgtcagcaatattcgaccgtgccgtggacgttcgggcagggcaccaaagtggagattaag
cgtacggtggctgcaccatctgtcttcatcttcccgccatctgatgagcagttgaaatctggaactgcctctgttgtgtgcctgctgaataactt
ctatcccagagaggccaaagtacagtggaaggtggataacgccctccaatcgggtaactcccaggagagtgtcacagagcaggacagcaa
ggacagcacctacagcctcagcagcaccctgacgctgagcaaagcagactacgagaaacacaaagtctacgcctgcgaagtcacccatc
agggcctgagctcgcccgtcacaaagagcttcaacaggggagagtgttag (SEQ ID NO: 318)

Linker     MM               Linker        CM           Linker         AB
(GQSGQ)(PCSEWQSMVQPRCYYG)(GGSGGSGQGGQ)(GTGRGPSWVSS)(GGS)(DIQLT
QSPSSLSASVGDRVTITCSASQDISNYLNWYQQKPGKAPKVLIYFTSSLHSGVPSRFSGSG
SGTDFTLTISSLQPEDFATYYCQQYSTVPWTFGQGTKVEIKRTVAAPSVFIFPPSDEQLKS
GTASVVCLLNNFYPREAKVQWKVDNALQSGNSQESVTEQDSKDSTYSLSSTLTLSKAD
YEKHKVYACEVTHQGLSSPVTKSFNRGEC) (SEQ ID NO: 319)

45

TABLE 47

PFIL2-CLIg-HK-antiVegF 306 KK1204 LC ggccagtctggccagccgtgttctgagtggcagtcgatggtgcagccgcgttgctattatgggggcggttctggtggcagcggccaaggt
ggccaaggtctgagcggccgttccgataatcatggcagtagcggcggttctgatattcaactgacccagagcccttcttccctgagtgccag
cgtgggtgaccgtgttacgatcacttgctcggccagccaagatatttctaactacctgaattggtaccagcagaagccaggaaaggcaccaa
aagtcctgatctacttcacaagttcactgcattccggcgtaccgtcgcgctttagcggttctggcagtggtaccgacttcaccctgactatctcg
agtctgcaacctgaggattttgctacatattactgtcagcaatattcgaccgtgccgtggacgttcgggcagggcaccaaagtggagattaag
cgtacggtggctgcaccatctgtcttcatcttcccgccatctgatgagcagttgaaatctggaactgcctctgttgtgtgcctgctgaataactt
ctatcccagagaggccaaagtacagtggaaggtggataacgccctccaatcgggtaactcccaggagagtgtcacagagcaggacagcaa
ggacagcacctacagcctcagcagcaccctgacgctgagcaaagcagactacgagaaacacaaagtctacgcctgcgaagtcacccatc
agggcctgagctcgcccgtcacaaagagcttcaacaggggagagtgttag (SEQ ID NO: 320)

Linker      MM             Linker        CM           Linker         AB

TABLE 47-continued

PFIL2-CLIg-HK-antiVegF 306 KK1204 LC (GQSGQ)(PCSEWQSMVQPRCYYG)(GGSGGSGQGGQ)(GLSGRSDNHGSS)(GGS)(DIQLT
QSPSSLSASVGDRVTITCSASQDISNYLNWYQQKPGKAPKVLIYFTSSLHSGVPSRFSGSG
SGTDFTLTISSLQPEDFATYYCQQYSTVPWTFGQGTKVEIKRTVAAPSVFIFPPSDEQLKS
GTASVVCLLNNFYPREAKVQWKVDNALQSGNSQESVTEQDSKDSTYSLSSTLTLSKAD
YEKHKVYACEVTHQGLSSPVTKSFNRGEC) (SEQ ID NO: 321)

TABLE 48

PFIL2-CLIg-HK-antiVegF 306 KK1214 LC ggccagtctggccagccgtgttctgagtggcagtcgatggtgcagccgcgttgctattatggggcggttctggtggcagcggccaaggt
ggccaaccactgactggtcgtagcggtggtggaggaagtagcggcggttctgatattcaactgacccagagcccttcttccctgagtgcca
gcgtgggtgaccgtgttacgatcacttgctcggccagccaagatatttctaactacctgaattggtaccagcagaagccaggaaaggcacc
aaaagtcctgatctacttcacaagttcactgcattccggcgtaccgtcgcgctttagcggttctggcagtggtaccgacttcaccctgactatct
cgagtctgcaacctgaggattttgctacatattactgtcagcaatattcgaccgtgccgtggacgttcgggcagggcaccaaagtggagatta
agcgtacggtggctgcaccatctgtcttcatcttcccgccatctgatgagcagttgaaatctggaactgcctctgttgtgtgcctgctgaataac
ttctatcccagagaggccaaagtacagtggaaggtggataacgccctccaatcgggtaactcccaggagagtgtcacagagcaggacag
caaggacagcacctacagcctcagcagcaccctgacgctgagcaaagcagactacgagaaacacaaagtctacgcctgcgaagtcacc
catcagggcctgagctcgcccgtcacaaagagcttcaacaggggagagtgttag (SEQ ID NO: 322)

Linker    MM    Linker    CM    Linker    AB
(GQSGQ)(PCSEWQSMVQPRCYYG)(GGSGGSGQGGQ)(PLTGRSGGGGSS)(GGS)(DIQLT
QSPSSLSASVGDRVTITCSASQDISNYLNWYQQKPGKAPKVLIYFTSSLHSGVPSRFSGSG
SGTDFTLTISSLQPEDFATYYCQQYSTVPWTFGQGTKVEIKRTVAAPSVFIFPPSDEQLKS
GTASVVCLLNNFYPREAKVQWKVDNALQSGNSQESVTEQDSKDSTYSLSSTLTLSKAD
YEKHKVYACEVTHQGLSSPVTKSFNRGEC) (SEQ ID NO: 323)

TABLE 49

PFIL2-CLIg-HK-antiVegF 306 SM1215 LC ggccagtctggccagccgtgttctgagtggcagtcgatggtgcagccgcgttgctattatggggcggttctggtggcagcggccaaggt
ggccaagaaactccatctgtaaagactatgggccgtagtagcggcggttctgatattcaactgacccagagcccttcttccctgagtgccag
cgtgggtgaccgtgttacgatcacttgctcggccagccaagatatttctaactacctgaattggtaccagcagaagccaggaaaggcaccaa
aagtcctgatctacttcacaagttcactgcattccggcgtaccgtcgcgctttagcggttctggcagtggtaccgacttcaccctgactatctcg
agtctgcaacctgaggattttgctacatattactgtcagcaatattcgaccgtgccgtggacgttcgggcagggcaccaaagtggagattaag
cgtacggtggctgcaccatctgtcttcatcttcccgccatctgatgagcagttgaaatctggaactgcctctgttgtgtgcctgctgaataactt
ctatcccagagaggccaaagtacagtggaaggtggataacgccctccaatcgggtaactcccaggagagtgtcacagagcaggacagcaa
ggacagcacctacagcctcagcagcaccctgacgctgagcaaagcagactacgagaaacacaaagtctacgcctgcgaagtcacccatc
agggcctgagctcgcccgtcacaaagagcttcaacaggggagagtgttag (SEQ ID NO: 324)

Linker    MM    Linker    CM    Linker    AB
GQSGQ)(PCSEWQSMVQPRCYYG)(GGSGGSGQGGQ)(ETPSVKTMGRSS)(GGS)(DIQLTQ
SPSSLSASVGDRVTITCSASQDISNYLNWYQQKPGKAPKVLIYFTSSLHSGVPSRFSGSGS

TABLE 49-continued

PFIL2-CLIg-HK-antiVegF 306 SM1215 LC

GTDFTLTISSLQPEDFATYYCQQYSTVPWTFGQGTKVEIKRTVAAPSVFIFPPSDEQLKSG

TASVVCLLNNFYPREAKVQWKVDNALQSGNSQESVTEQDSKDSTYSLSSTLTLSKADY

EKHKVYACEVTHQGLSSPVTKSFNRGEC) (SEQ ID NO: 325)

Plasmin-Activated AA Sequences

Nucleotide and amino acid sequences of plasmin enzyme-activated antiVEGF light chain AAs are provided in the tables below. Parentheses delineate the demarcations between the various sequence domains: (Linker)(MM)(Linker)(CM)(Linker)(AB).

TABLE 50

PFIL2-CLIg-HK-antiVegF 306 SM1239 LC ggccagtctggccagccgtgttctgagtggcagtcgatggtgcagccgcgttgctattatgggggcggttctggtggcagcggccaaggt ggccaaggtttcccacatatgaaaactttccagcatagtagcggcggttctgatattcaactgacccagagcccttcttccctgagtgccagc gtgggtgaccgtgttacgatcacttgctcggccagccaagatatttctaactacctgaattggtaccagcagaagccaggaaaggcaccaaa agtcctgatctacttcacaagttcactgcattccggcgtaccgtcgcgctttagcggttctggcagtggtaccgacttcaccctgactatctcga gtctgcaacctgaggattttgctacatattactgtcagcaatattcgaccgtgccgtggacgttcgggcagggcaccaaagtggagattaagc gtacggtggctgcaccatctgtcttcatcttcccgccatctgatgagcagttgaaatctggaactgcctctgttgtgtgcctgctgaataacttc tatcccagagaggccaaagtacagtggaaggtggataacgccctccaatcgggtaactcccaggagagtgtcacagagcaggacagcaa ggacagcacctacagcctcagcagcaccctgacgctgagcaaagcagactacgagaaacacaaagtctacgcctgcgaagtcacccatc agggcctgagctcgcccgtcacaaagagcttcaacaggggagagtgttag (SEQ ID NO: 326)

Linker      MM      Linker    CM    Linker    AB
(GQSGQ)(PCSEWQSMVQPRCYYG)(GGSGGSGQGGQ)(GFPHMKTFQHSS)(GGS)(DIQLT

QSPSSLSASVGDRVTITCSASQDISNYLNWYQQKPGKAPKVLIYFTSSLHSGVPSRFSGSG

SGTDFTLTISSLQPEDFATYYCQQYSTVPWTFGQGTKVEIKRTVAAPSVFIFPPSDEQLKS

GTASVVCLLNNFYPREAKVQWKVDNALQSGNSQESVTEQDSKDSTYSLSSTLTLSKAD

YEKHKVYACEVTHQGLSSPVTKSFNRGEC) (SEQ ID NO: 327)

Legumain-Activated AAs

The sequences for the legumain substrates AANL (SEQ ID NO: 361) and PTNL (SEQ ID NO: 362) are known in the art (Liu, et al. 2003. Cancer Research 63, 2957-2964; Mathieu, et al 2002. Molecular and Biochemical Parisitology 121, 99-105). Nucleotide and amino acid sequences of legumain enzyme-activated anti VEGF light chain AAs are provided in the tables below. Parentheses delineate the demarcations between the various sequence domains: (Linker)(MM)(Linker)(CM)(Linker)(AB).

TABLE 51

PFIL2-CLIg-HK-antiVEGF 306 AANL (SEQ ID NO: 361) Light Chain ggccagtctggccagccgtgttctgagtggcagtcgatggtgcagccgcgttgctattatgggggcggttctggtggcagcggccaaggt ggccaagcagctaatctgggcagcggaggaagtagcggcggttctgatattcaactgacccagagcccttcttccctgagtgccagcgtg ggtgaccgtgttacgatcacttgctcggccagccaagatatttctaactacctgaattggtaccagcagaagccaggaaaggcaccaaaagt cctgatctacttcacaagttcactgcattccggcgtaccgtcgcgctttagcggttctggcagtggtaccgacttcaccctgactatctcgagtc tgcaacctgaggattttgctacatattactgtcagcaatattcgaccgtgccgtggacgttcgggcagggcaccaaagtggagattaagcgta

TABLE 51-continued

PFIL2-CLIg-HK-antiVEGF 306 AANL (SEQ ID NO: 361) Light Chain cggtggctgcaccatctgtcttcatcttcccgccatctgatgagcagttgaaatctggaactgcctctgttgtgtgcctgctgaataacttctat cccagagaggccaaagtacagtggaaggtggataacgccctccaatcgggtaactcccaggagagtgtcacagagcaggacagcaagga cagcacctacagcctcagcagcaccctgacgctgagcaaagcagactacgagaaacacaaagtctacgcctgcgaagtcacccatcagg gcctgagctcgcccgtcacaaagagcttcaacaggggagagtgttag (SEQ ID NO: 328)

Linker     MM         Linker       CM        Linker      AB
(GQSGQ)(PCSEWQSMVQPRCYYG)(GGSGGSGQGGQ)(AANLGSGGSS)(GGS)(DIQLTQS

PSSLSASVGDRVTITCSASQDISNYLNWYQQKPGKAPKVLIYFTSSLHSGVPSRFSGSGSG

TDFTLTISSLQPEDFATYYCQQYSTVPWTFGQGTKVEIKRTVAAPSVFIFPPSDEQLKSGT

ASVVCLLNNFYPREAKVQWKVDNALQSGNSQESVTEQDSKDSTYSLSSTLTLSKADYE

KHKVYACEVTHQGLSSPVTKSFNRGEC) (SEQ ID NO: 329)

TABLE 52

PFIL2-CLIg-HK-antiVEGF 306 PTNL (SEQ ID NO: 362) Light Chain ggccagtctggccagccgtgttctgagtggcagtcgatggtgcagccgcgttgctattatggggggcggttctggtggcagcggccaaggt ggccaaccgactaatctgggcagcggaggaagtagcggcggttctgatattcaactgacccagagcccttcttcccctgagtgccagcgtgg gtgaccgtgttacgatcacttgctcggccagccaagatatttctaactacctgaattggtaccagcagaagccaggaaaggcaccaaaagtc ctgatctacttcacaagttcactgcattccggcgtaccgtcgcgctttagcggttctggcagtggtaccgacttcaccctgactatctcgagtct gcaacctgaggattttgctacatattactgtcagcaatattcgaccgtgccgtggacgttcgggcagggcaccaaagtggagattaagcgta cggtggctgcaccatctgtcttcatcttcccgccatctgatgagcagttgaaatctggaactgcctctgttgtgtgcctgctgaataacttctat cccagagaggccaaagtacagtggaaggtggataacgccctccaatcgggtaactcccaggagagtgtcacagagcaggacagcaagga cagcacctacagcctcagcagcaccctgacgctgagcaaagcagactacgagaaacacaaagtctacgcctgcgaagtcacccatcagg gcctgagctcgcccgtcacaaagagcttcaacaggggagagtgttag (SEQ ID NO: 330)

Linker     MM         Linker       CM        Linker      AB
(GQSGQ)(PCSEWQSMVQPRCYYG)(GGSGGSGQGGQ)(PTNLGSGGSS)(GGS)(DIQLTQSP

SSLSASVGDRVTITCSASQDISNYLNWYQQKPGKAPKVLIYFTSSLHSGVPSRFSGSGSGT

DFTLTISSLQPEDFATYYCQQYSTVPWTFGQGTKVEIKRTVAAPSVFIFPPSDEQLKSGTA

SVVCLLNNFYPREAKVQWKVDNALQSGNSQESVTEQDSKDSTYSLSSTLTLSKADYEK

HKVYACEVTHQGLSSPVTKSFNRGEC) (SEQ ID NO: 331)

TABLE 53

PFIL2-CLIg-HK-antiVEGF 306 PTN Light Chain ggccagtctggccagccgtgttctgagtggcagtcgatggtgcagccgcgttgctattatggggggcggttctggtggcagcggccaaggt ggccaaccgactaatggtggcagcggaggaagtagcggcggttctgatattcaactgacccagagcccttcttcccctgagtgccagcgtg ggtgaccgtgttacgatcacttgctcggccagccaagatatttctaactacctgaattggtaccagcagaagccaggaaaggcaccaaaagt cctgatctacttcacaagttcactgcattccggcgtaccgtcgcgctttagcggttctggcagtggtaccgacttcaccctgactatctcgagtc tgcaacctgaggattttgctacatattactgtcagcaatattcgaccgtgccgtggacgttcgggcagggcaccaaagtggagattaagcgta cggtggctgcaccatctgtcttcatcttcccgccatctgatgagcagttgaaatctggaactgcctctgttgtgtgcctgctgaataacttctat

TABLE 53-continued

PFIL2-CLIg-HK-antiVEGF 306 PTN Light Chain cccagagaggccaaagtacagtggaaggtggataacgccctccaatcgggtaactcccaggagagtgtcacagagcaggacagcaagga cagcacctacagcctcagcagcaccctgacgctgagcaaagcagactacgagaaacacaaagtctacgcctgcgaagtcacccatcagg gcctgagctcgcccgtcacaaagagcttcaacaggggagagtgttag (SEQ ID NO: 332)

Linker        MM        Linker      CM    Linker      AB
(GQSGQ)(PCSEWQSMVQPRCYYG)(GGSGGSGQGGQ)(PTNGGSGGSS)(GGS)(DIQLTQS

PSSLSASVGDRVTITCSASQDISNYLNWYQQKPGKAPKVLIYFTSSLHSGVPSRFSGSGSG

TDFTLTISSLQPEDFATYYCQQYSTVPWTFGQGTKVEIKRTVAAPSVFIFPPSDEQLKSGT

ASVVCLLNNFYPREAKVQWKVDNALQSGNSQESVTEQDSKDSTYSLSSTLTLSKADYE

KHKVYACEVTHQGLSSPVTKSFNRGEC) (SEQ ID NO: 333)

Caspase Activated AAs

Nucleotide and amino acid sequences of caspase enzyme-activated antiVEGF light chain AAs are provided in the tables below. Parentheses delineate the demarcations between the various sequence domains: (Linker)(MM)(Linker)(CM)(Linker)(AB). The caspase substrate, sequence DEVD (SEQ ID NO: 334), is known in the art.

TABLE 54

PFIL2-CLIg-HK-antiVegF 306 DEVD (SEQ ID NO: 334) LC ggccagtctggccagccgtgttctgagtggcagtcgatggtgcagccgcgttgctattatggggcggttctggtggcagcggccaaggt ggccaagacgaagtcgatggcagcggaggaagtagcggcggttctgatattcaactgacccagagcccttcttccctgagtgccagcgtg ggtgaccgtgttacgatcacttgctcggccagccaagatatttctaactacctgaattggtaccagcagaagccaggaaaggcaccaaaagt cctgatctacttcacaagttcactgcattccggcgtaccgtcgcgctttagcggttctggcagtggtaccgacttcaccctgactatctcgagtc tgcaacctgaggattttgctacatattactgtcagcaatattcgaccgtgccgtggacgttcgggcagggcaccaaagtggagattaagcgta cggtggctgcaccatctgtcttcatcttcccgccatctgatgagcagttgaaatctggaactgcctctgttgtgtgcctgctgaataacttctat cccagagaggccaaagtacagtggaaggtggataacgccctccaatcgggtaactcccaggagagtgtcacagagcaggacagcaagga cagcacctacagcctcagcagcaccctgacgctgagcaaagcagactacgagaaacacaaagtctacgcctgcgaagtcacccatcagg gcctgagctcgcccgtcacaaagagcttcaacaggggagagtgttag (SEQ ID NO: 335)

Linker        MM        Linker      CM    Linker      AB
(GQSGQ)(PCSEWQSMVQPRCYYG)(GGSGGSGQGGQ)(DEVDGSGGSS)(GGS)(DIQLTQS

PSSLSASVGDRVTITCSASQDISNYLNWYQQKPGKAPKVLIYFTSSLHSGVPSRFSGSGSG

TDFTLTISSLQPEDFATYYCQQYSTVPWTFGQGTKVEIKRTVAAPSVFIFPPSDEQLKSGT

ASVVCLLNNFYPREAKVQWKVDNALQSGNSQESVTEQDSKDSTYSLSSTLTLSKADYE

KHKVYACEVTHQGLSSPVTKSFNRGEC) (SEQ ID NO: 336)

Construction of Legumain and Caspase Activated AA Expression Vectors

Substrates were constructed in a two step process. First, two products were PCR amplified using the CX0325 forward primer with a substrate specific reverse primer (CX0720 AANL (SEQ ID NO: 361), CX0722 PTNL (SEQ ID NO: 362), CX0724 PTN, and CX0758 DEVD (SEQ ID NO: 334)), the other PCR amplified using the CX0564 reverse primer with a substrate specific forward primer (CX0721 AANL (SEQ ID NO:361), CX0723 PTNL (SEQ ID NO: 362), CX0725 PTN, and CX0754 DEVD (SEQ ID NO: 334). In both cases the substrate for the PCR was the anti-VEGF mmp-9 306 scFv. Second, the two products were combined and PCR amplified using the outside primers CX0325 and CX0564. The final products were cloned into the pFIL2-CL-anti-VEGF Lc using the EcoRI and XhoI restriction sites.

TABLE 55

Primers for Construction of Legumain and Caspase Activated AA expression Vectors CX0564 aggttgcagactcgagatagtcagggtgaagtc (SEQ ID NO: 337)

CX0720 tcctccgctgcccagattagctgcttggccaccttggccgctg ccac (SEQ ID NO: 338)

CX0721 gcagctaatctgggcagcggaggaagtagcggcggttctgata ttcaactg (SEQ ID NO: 339)

CX0722 tcctccgctgcccagattagtcggttggccaccttggccgctg ccac (SEQ ID NO: 340)

CX0723 ccgactaatctgggcagcggaggaagtagcggcggttctgata ttcaactg (SEQ ID NO: 341)

CX0724 tcctccgctgccaccattagtcggttggccaccttggccgctg ccac (SEQ ID NO: 342)

CX0725 ccgactaatggtggcagcggaggaagtagcggcggttctgata ttcaactg (SEQ ID NO: 343)

CX0754 gacgaagtcgatggcagcggaggaagtagcggcggttctgata ttcaactg (SEQ ID NO: 344)

CX0758 tcctccgctgccatcgacttcgtcttggccaccttggccgctgc cac (SEQ ID NO: 345)

Expression and Purification of Legumain Activated AAs

3 µg of pFIL-VEGF-HL and 3 µg pFIL2-306-substrate-VEGF-light were co-transfected into CHO—S cells (Invitrogen) using Lipofectamine 200 (Invitrogen) according to manufacturers protocol. Transfected cells were cultured in Freestyle CHO media (Invitrogen) and selected for resistance to zeocin and blasticidin. Individual clones were isolated by limiting dilution and selected for expression of human IgG capable of binding EGFR by ELISA. All antibodies and AAs are purified by Protein-A chromatography using standard techniques.

Assay Description for the scFv AA Digest

Figure 27A:
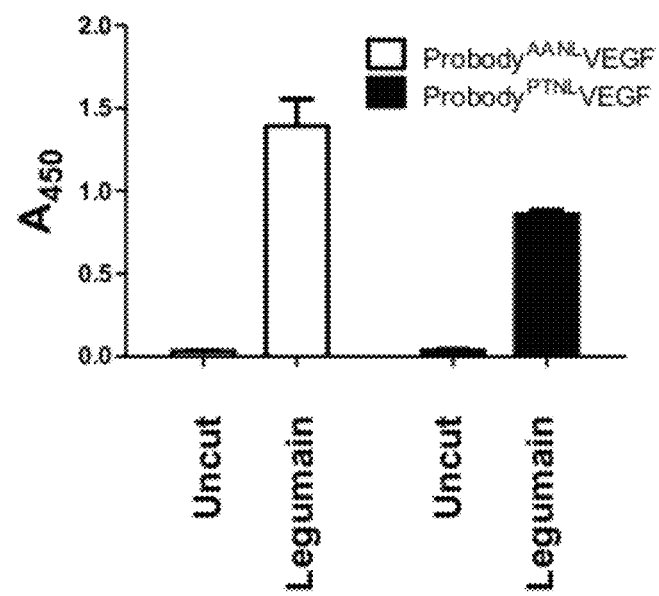
FIG. 27 Panel A shows activation of ScFv AAs containing legumain substrates AANL (SEQ ID NO: 361) and PTNL (SEQ ID NO: 362) following treatment with 5 mg/mL legumain. Panel B shows activation of an anti-VEGF IgG AA containing the legumain substrate PTNL (SEQ ID NO: 362).
Figure 27:
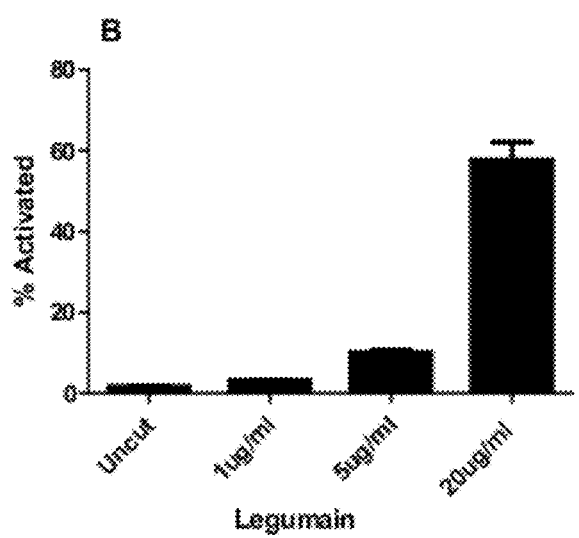

ScFv AAs were diluted to 200 nM in assay buffer and combined with rhLegumain diluted in assay buffer at 2 ug/ml. Digests were incubated overnight at room temperature. IgG AAs were diluted to 200 nM in assay buffer and combined with rhLegumain diluted in assay buffer at concentrations form 2-40 mg/mL (final rhLegumain concentrations 1 ug/ml, 5 ug/ml, 20 ug/ml. Digests were incubated overnight a 37° C. Following digestion, the extent of activation was measured by the extent of AA binding to VEGF on ELISA plates, visualized with anti-human-Fc. FIG. 27 Panel A shows activation of ScFv AAs containing legumain substrates AANL (SEQ ID NO: 361) and PTNL (SEQ ID NO: 362) following treatment with 5 mg/mL legumain. Panel B shows activation of an anti-VEGF IgG AA containing the legumain substrate PNTL.

In Vivo Stability of Legumain Activated AAs

Figure 28:
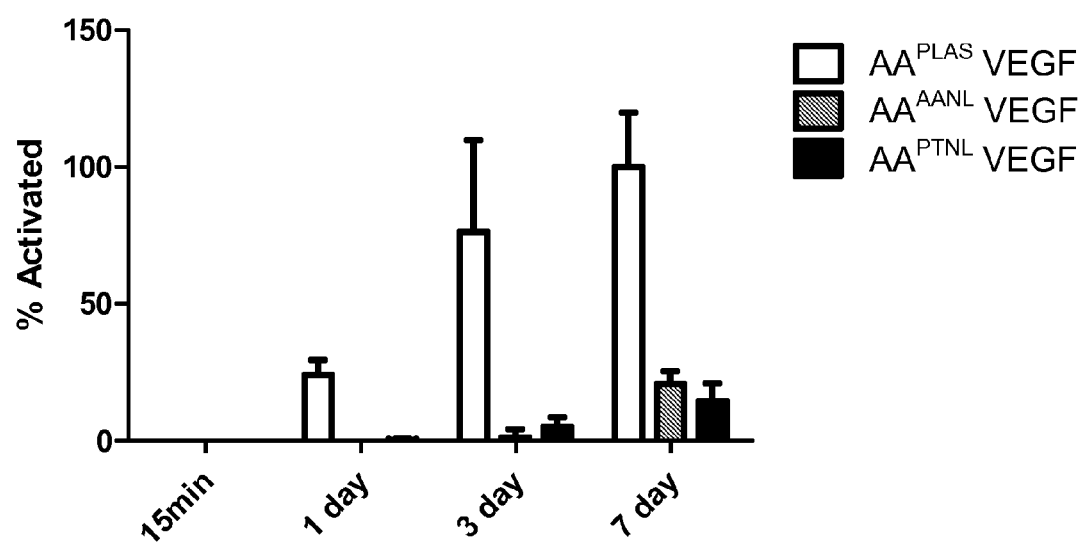
FIG. 28 shows the ratio of activated AA to total AA at each time point in a legumain-activated AA. While the plasmin-activated AA is nearly completely activated at 7 days, both legumain-activatable AAs are only minimally activated. Legumain-activatable AAs isolated from serum up to 7 days following injection remain masked. (n=4). 'AANL' disclosed as SEQ ID NO: 361 and 'PTNL' disclosed as SEQ ID NO: 362.

Four 12 week old Balb/C mice were each given a single bolus injection of 100 µg of a plasmin activated AA, $AA^{PLAS}$ VEGF, or one of the legumain activated AAs, $AA^{AANL\ (SEQ\ ID\ NO:\ 361)}$VEGF or $AA^{PTNL\ (SEQ\ ID\ NO:\ 362)}$VEGF. At 15 minutes, 1 day, 3 days, and 7 days following injection, serum was collected. Total AA concentration was calculated from ELISA measurement of total human Fc in the serum. The concentration of activated antibody was calculated from a human VEGF binding ELISA measurement and is shown in FIG. 28. Legumain activated AAs isolated from serum up to 7 days following injection remain masked. (n=4). The ratio of activated AA to total AA at each time point is shown in FIG. 28 as the average of measurements from individual animals and is expressed as percent activated. While the plasmin activated AA is nearly completely activated at 7 days both legumain activated AAs are only minimally activated.

Example 18

Serum Half Lives of AAs

Figure 29:
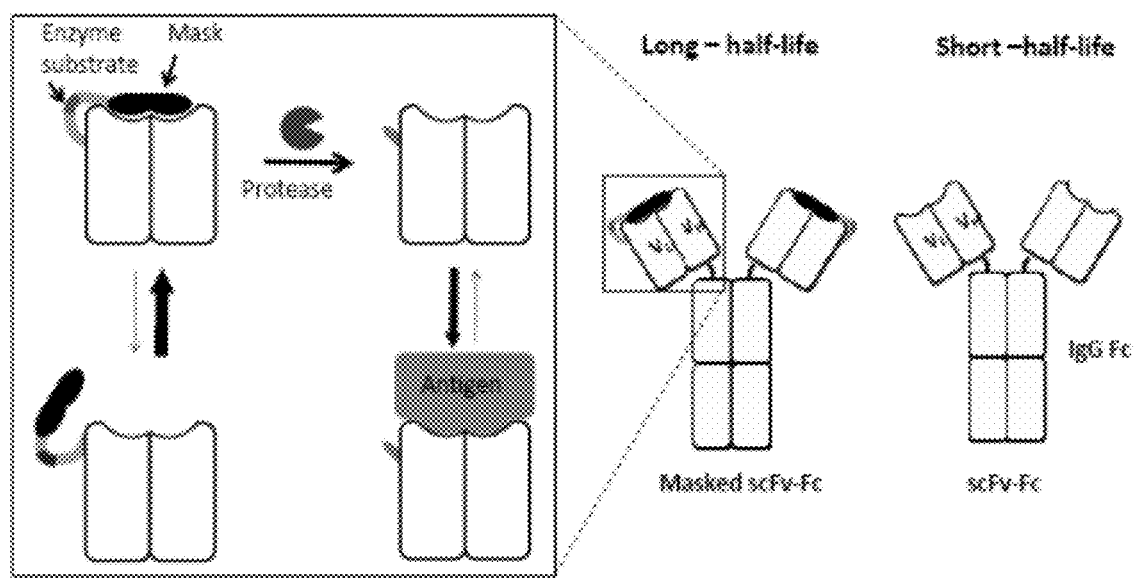
FIG. 29 shows that masked single-chain Fv-Fc fusion pro-antibodies exhibit increased serum half-life.

FIG. 29 shows that a masked single-chain Fv-Fc fusion pro-antibodies exhibit increased serum half-life. A masking polypeptide is appended to an antibody N-terminus such that the mask can interact with the antibody combining site to increase thermodynamic stability or block neutralizing antibodies. A protease substrate can be used to enable removal of the mask at different rates in serum or specific tissues.

Figure 30:
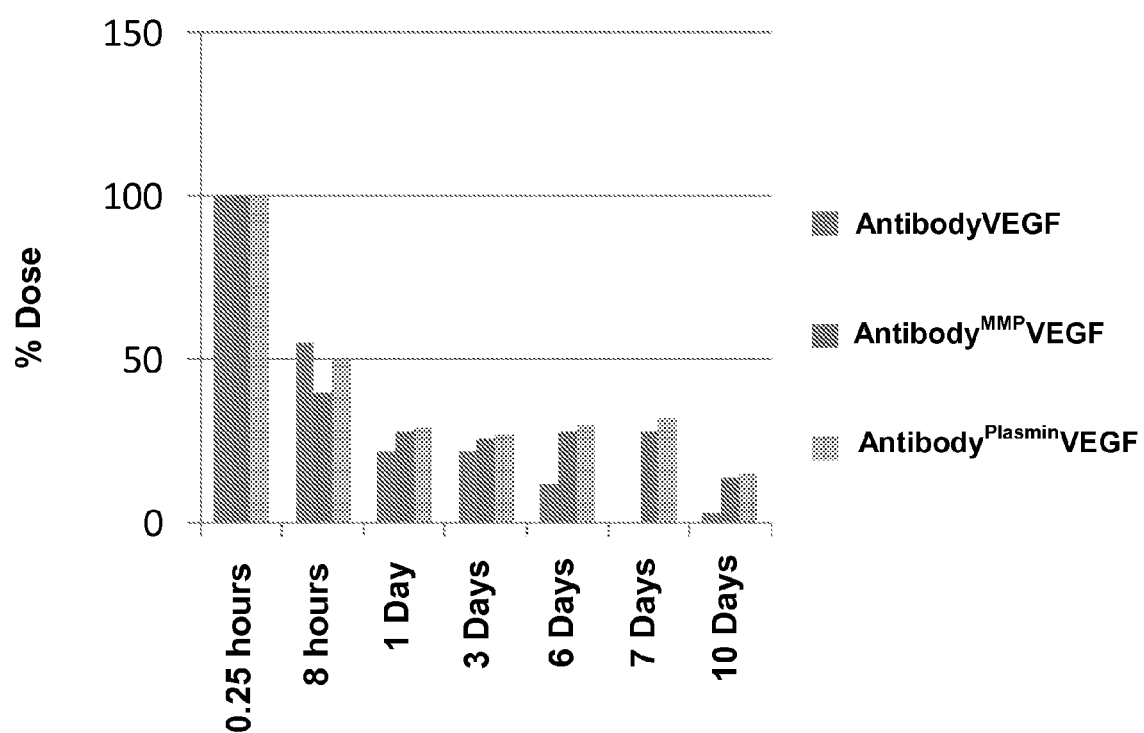
FIG. 30 shows that the scFv-Fc serum concentration in healthy mice over 10 days. The AA concentration remained stable 7 days post dose, whereas the parent scFv-Fc concentration decreased after 3 days and was almost undetectable at 10 days.

FIG. 30 shows that the scFv-Fc serum concentration in healthy mice over 10 days. C57Bl/6 mice (n=3 per time point) were given a single dose (150 ug) of anti-VEGF scFv-Fc, AA $^{MMP}$VEGF (AA 1) or AA $^{Plasmin}$VEGF (AA 2). Serum was collected at the indicated times and the concentration of total scFv-Fc was measured by ELISA. The AA concentration remained stable 7 days post does, whereas the parent scFv-Fc concentration decreased after 3 days and was almost undetectable at 10 days.

Figure 31:
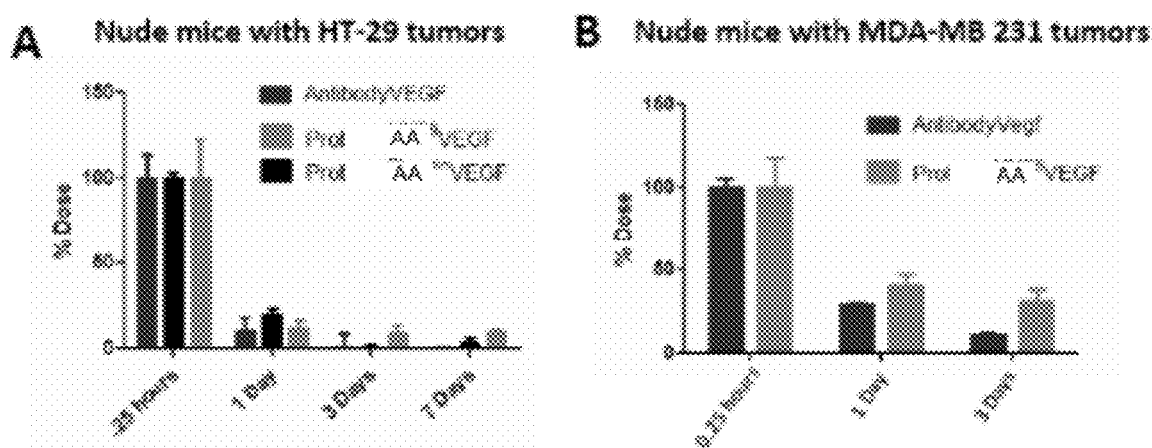
FIG. 31 shows that AA scFv-Fc concentrations are elevated and persist longer in serum compared with parent scFv-Fc in tumor-bearing mice. A higher percentage of the initial AA dose was detected in the serum at 3 days (B) and 3 and 7 days (A).

FIG. 31 shows that AA scFv-Fc concentrations are elevated and persist longer in serum compared with parent scFv-Fc in tumor-bearing mice: An equivalent single dose of anti-VEGF scFv-Fc, AA $^{MMP}$VEGF (AA 1) or AA $^{Plasmin}$VEGF (AA 2) was given Nude mice bearing HT29 xenografts (A) or MDA-MB-231 xenografts (B). Serum was collected at the indicated times and the concentration of total scFv-Fc was measured by ELISA. In both studies a higher percentage of the initial AA dose was detected in the serum at 3 days (B) and 3 and 7 days (A).

Figure 32:
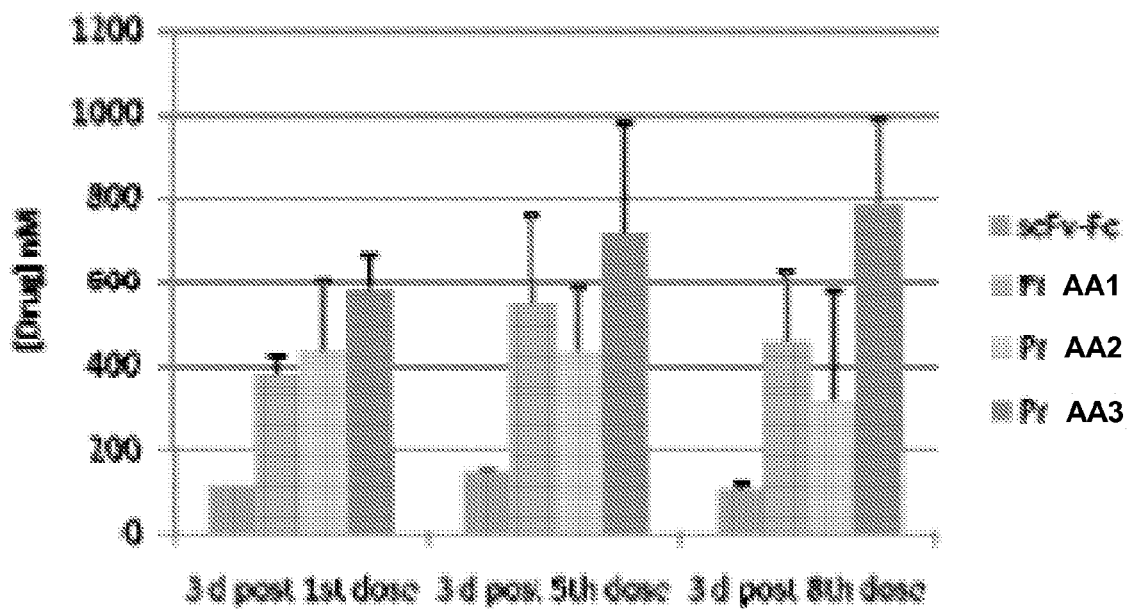
FIG. 32 shows that AA scFv-Fcs persist at higher concentrations in a multidose study in Tumor-bearing mice. AAs maintained significantly higher serum concentrations than the parent throughout the study.

FIG. 32 shows that AAs persist at higher concentrations in a multidose study: Tumor-bearing Balb/c nu/nu mice were injected with 5 mg/kg of parental VEGF scFv-Fc, AA1, 2 or 3 every 3 days. Serum was collected at the indicated times and the concentration of AA or parent scFv-Fc was measured by ELISA. All three AAs maintained significantly higher serum concentrations than the parent throughout the study.

Amino Acid Sequences of VEGF scFv-Fcs AAs

TABLE 56

The amino acid sequence of Anti-VEGF scFv-Fc from which AA scFvs were derived

DIQLTQSPSSLSASVGDRVTITCSASQDISNYLNWYQQKPGKAPKVLIYF

TSSLHSGVPSRFSGSGSGTDFTLTISSLQPEDFATYYCQQYSTVPWTFGQ

TABLE 56-continued

The amino acid sequence of Anti-VEGF scFv-Fc from which AA scFvs were derived

GTKVEIKGGGSGGGSGGGSGGGGSGGGGSGGGGSGEVQLVESGGGLVQPG
GSLRLSCAASGYDFTHYGMNWVRQAPGKGLEWVGWINTYTGEPTYAADFK
RRFTFSLDTSKSTAYLQMNSLRAEDTAVYYCAKYPYYYGTSHWYFDVWGQ
GTLVTVSGGSGAMVRSDKTHTCPPCPAPELLGGPSVFLFPPKPKDTLMIS
RTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSF
FLYSKLTVDKSRWQQGNVFSCSVMHEGLHNHYTQKSLSLSPGK (SEQ ID NO: 346)

TABLE 57

AA$^{MMP}$VEGF: AAs contain a masking peptide and MMP substrate attached by a short linker as shown masking peptide                    substrate
GQSGQPCSEWQSMVQPRCYYGGGSGGSGQGGQVHMPLGFLGPGGSDIQLTQSPSSLSA
SVGDRVTITCS
ASQDISNYLNWYQQKPGKAPKVLIYFTSSLHSGVPSRFSGSGSGTDFTLTISSLQPEDFAT
YYCQQYSTVPWTFGQGTKVEIKGGGSGGGSGGGSGGGGSGGGGSGGGGSGEVQLVES
GGGLVQPGGSLRLSCAASGYDFTHYGMNWVRQAPGKGLEWVGWINTYTGEPTYAADF
KRRFTFSLDTSKSTAYLQMNSLRAEDTAVYYCAKYPYYYGTSHWYFDVWGQGTLVTV
SGGSGAMVRSDKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYKCKVSNK
ALPAPIEKTISKAKGQPREPQVYTLPPSREEMTKNQVSLTCLVKGFYPSDIAVEWESNGQ
PENNYKTTPPVLDSDGSFFLYSKLTVDKSRWQQGNVFSCSVMHEGLHNHYTQKSLSLSP
GK (SEQ ID NO: 347)

TABLE 58

AA$^{PLASMIN}$VEGF: AAs contain a masking peptide and Plasmin substrate attached by a short linker as shown masking peptide                    substrate
GQSGQPCSEWQSMVQPRCYYGGGSGGSGQGGQQGPMFKSLWDGGSDIQLTQSPSSLSA
SVGDRVTITCSASQDISNYLNWYQQKPGKAPKVLIYFTSSLHSGVPSRFSGSGSGTDFTL
TISSLQPEDFATYYCQQYSTVPWTFGQGTKVEIKGGGSGGGSGGGSGGGGSGEVQLVESGG
GLVQPGGSLRLSCAASGYDFTHYGMNWVRQAPGKGLEWVGWINTYTGEPTYAADFKR
RFTFSLDTSKSTAYLQMNSLRAEDTAVYYCAKYPYYYGTSHWYFDVWGQGTLVTVSG
GSGAMVRSDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCKVSNKAL
PAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEGLHNHYTQKSLSLSPGK
(SEQ ID NO: 348)

TABLE 59

AA$^{NoSubstrate}$VEGF AAs contain a masking peptide,
Gly Ser (GS) linkers and VEGF but no substrate
attached by a short linker as shown masking peptide                          substrate
PCSEWQSMVQPRCYYGGSGGGSGQSGQGGSGGSGQGGQGSDIQLTQSPSS

LSASVGDRVTITCSASQDISNYLNWYQQKPGKAPKVLIYFTSSLHSGVPS

RFSGSGSGTDFTLTISSLQPEDFATYYCQQYSTVPWTFGQGTKVEIKGGG

SGGGSGGGSGGGGSGGGGSGGGGSGEVQLVESGGGLVQPGGSLRLSCAAS

GYDFTHYGMNWVRQAPGKGLEWVGWINTYTGEPTYAADFKRRFTFSLDTS

KSTAYLQMNSLRAEDTAVYYCAKYPYYYGTSHWYFDVWGQGTLVTVSGGS

GAMVRSDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDWL

NGKEYKCKVSNKALPAPIEKTISKAKGQPREPQVYTLPPSREEMTKNQVS

LTCLVKGFYPSDIAVEWESNGQPENNYKTTPPVLDSDGSFFLYSKLTVDK

SRWQQGNVFSCSVMHEGLHNHYTQKSLSLSPGK (SEQ ID NO: 349)

AAs Exhibit Increased Serum Half-Life as Compared to the Parental Antibody

Figure 33:
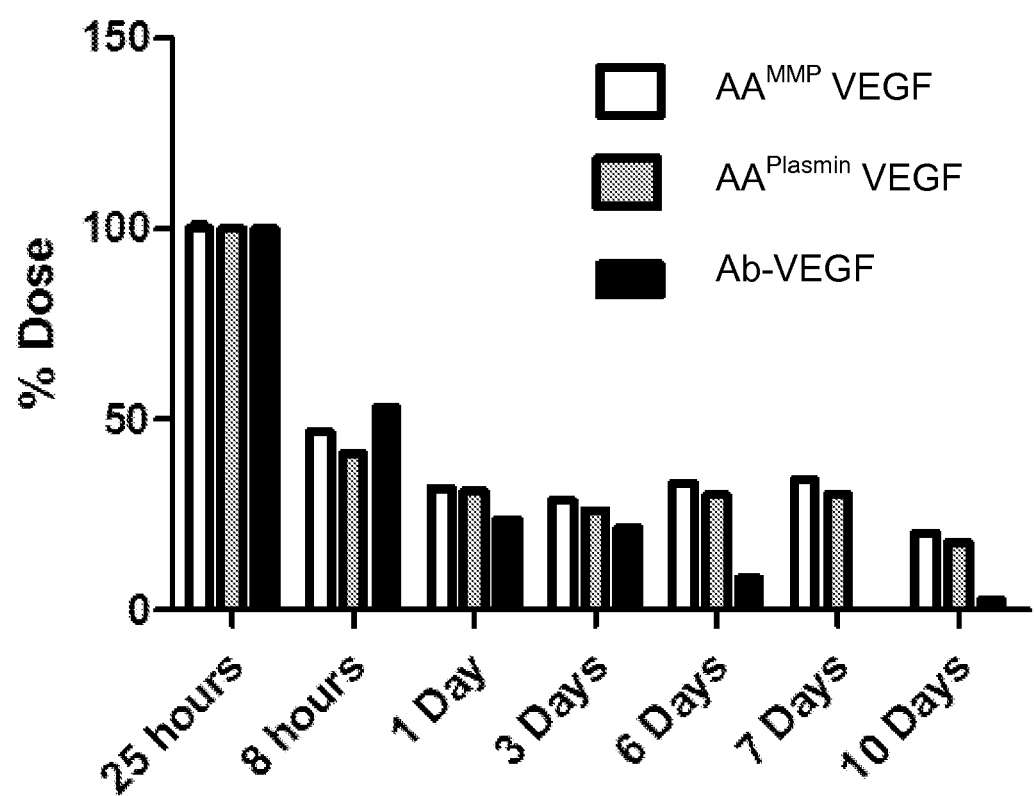
FIG. 33 shows that AAs persist at high levels in serum of normal mice as compared to the parental antibody not modified with a MM.

Eight 12 week old Balb/C mice were each given a single bolus injection of 100 μg of a MMP activated AA, AA$^{M}_{MP}$VEGF, a Plasmin activated AA, AA$^{PLAS}$VEGF or parental anti-VEGF antibody Ab-VEGF. At 15 minutes, 8 hours, 1 day, 3 days, 7 days and 10 days following injection, serum was collected. Total AA concentration was calculated from ELISA measurement of total human Fc in the serum. The concentration of total AA at each time point is shown in FIG. 33 as the average of measurements from individual animals and is expressed as percent of initial dose. The AAs and parental antibody distribute similarly and as expected. Reaching a high and equal concentration at 15 minutes and distributing into the tissues over the first day. In contrast to the parental antibody which is nearly completely eliminated over 10 days, both AAs persist at higher levels in the serum for the duration of the experiment.

Example 19

Reduction in Side Effects Upon Administration of an AA

Greater than 80% of the patients typically administered a conventional EGFR antibody therapeutic exhibit toxicity of the skin, the largest organ of the body. When patients are administered AAs directed against EGFR it is expected that there will be little or no toxicity of the skin, as the AA will not be activated in the skin, due to lack of disease specific CM. As such, it is expected that the anti-EGFR AB of the AA will not be able to specifically bind the EGFR target. Additionally it is expected that in such patients, because the AA will not be active in the skin, the AA will not be sequestered and it is expected that the serum levels of the AA will remain high, thereby increasing the concentration of the AA in the diseased tissue, effectively raising the effective dose. Hydrolysis of the CM in the diseased tissue based on the disease environment will lead to an activated AA allowing for unmasking and specific binding of the AB to the EGFR target, and will lead to the desired therapeutic effect.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of manufacturing an activatable antibody, the method comprising:
(a) culturing a cell comprising a nucleic acid construct that encodes the activatable antibody under conditions that lead to expression of the activatable antibody, wherein the activatable antibody comprises a masking moiety (MM) comprising an amino acid sequence selected from the group consisting of SEQ ID NO: 1, 218-220, 236-265 and 266, a first peptide linker (LP1), a cleavable moiety (CM), a second peptide linker (LP2), and an antibody or an antigen binding fragment thereof (AB) that specifically binds Epidermal Growth Factor Receptor (EGFR),
(i) wherein:
the MM has an equilibrium dissociation constant for binding to the AB which is greater than the equilibrium dissociation constant of the AB for binding to EGFR;
(ii) wherein the CM is a polypeptide that functions as a substrate for a protease selected from the group consisting of urokinase type plasminogen activator (uPA), legumain and matriptase (MT-SP1), and wherein the protease cleaves the CM in the activatable antibody when the activatable antibody is exposed to the protease;
(iii) wherein the AB has an equilibrium dissociation constant of at most 100 nM for binding to EGFR;
(iv) wherein each of LP1 and LP2 is a peptide, and wherein the two LPs need not be identical to each other;
(v) wherein the activatable antibody in an uncleaved state has the structural arrangement from N-terminus to C-terminus as follows: MM-LP1-CM-LP2-AB or AB-LP2-CM-LP1-MM;
(vi) wherein the MM of the activatable antibody in an uncleaved state interferes with specific binding of the AB to EGFR and wherein the MM of the activatable antibody in a cleaved state does not interfere or compete with specific binding of the AB to EGFR; and
(vii) wherein the MM of the activatable antibody in an uncleaved state inhibits the binding of the AB to EGFR such that the dissociation constant ($K_d$) of the AB of the activatable antibody in an uncleaved state towards EGFR is at least 100 times greater than the $K_d$ of the AB of the activatable antibody in a cleaved state towards EGFR;
and
(b) recovering the activatable antibody.

2. The method of claim 1, wherein the CM is a polypeptide of up to 15 amino acids in length.

3. The method of claim 1, wherein each of LP1 and LP2 is a peptide of about 1 to 20 amino acids in length.

4. The method of claim 1, wherein the AB is or is from cetuximab or panitumumab.

5. The method of claim 1, wherein the AB is or is from cetuximab.

6. The method of claim 1, wherein the CM is a substrate for a protease selected from the group consisting of uPA, legumain and MT-SP1 and is a substrate for at least one additional protease that is co-localized in a tissue with EGFR, wherein the additional protease is an enzyme selected from the group consisting of the enzymes in Table 3.

7. The method of claim 1, wherein the CM is a substrate for uPA and at least one additional protease that is co-localized in a tissue with EGFR, wherein the additional protease is legumain, plasmin, TMPRSS-3/4, MMP-9, MT1-MMP, cathepsin, caspase, human neutrophil elastase, beta-secretase, MT-SP1 or PSA.

8. The method of claim 1, wherein the antigen binding fragment is selected from the group consisting of a Fab' fragment, a F(ab')$_2$ fragment, a scFv, a scAB, a dAb, a single domain heavy chain antibody, and a single domain light chain antibody.

9. The method of claim 1, wherein the activatable antibody comprises at least a first CM that functions as a substrate for a protease-selected from the group consisting of uPA, legumain and matriptase MT-SP1 and a second CM.

10. The method of claim 9, wherein the first CM is cleavable by a first cleaving agent in a target tissue and wherein the second CM is cleavable by a second cleaving agent in a target tissue.

11. The method of claim 10, wherein the first cleaving agent and the second cleaving agent are the same enzyme, and where the first CM and the second CM are different substrates for the enzyme.

12. The method of claim 10, wherein the first cleaving agent and the second cleaving agent are different enzymes.

13. The method of claim 10, wherein the first cleaving agent and the second cleaving agent are co-localized in the tissue.

14. The method of claim 9, wherein the first CM and the second CM are cleavable by at least one cleaving agent in the tissue.

15. The method of claim 1, wherein the MM is a polypeptide of no more than 40 amino acids in length.

16. The method of claim 1, wherein at least one of LP1 or LP2 comprises an amino acid sequence selected from the group consisting of $(GS)_n$, $(GSGGS)_n$ (SEQ ID NO: 12) and $(GGGS)_n$ (SEQ ID NO: 13), where n is an integer of at least one.

17. The method of claim 1, wherein at least one of LP1 or LP2 comprises an amino acid sequence selected from the group consisting of GGSG (SEQ ID NO: 14), GGSGG (SEQ ID NO: 15), GSGSG (SEQ ID NO: 16), GSGGG (SEQ ID NO: 17), GGGSG (SEQ ID NO: 18), and GSSSG (SEQ ID NO: 19).

18. The method of claim 1, wherein the CM is a substrate for uPA and at least one additional protease, wherein the additional protease is legumain, MT-SP1 or both legumain and MT-SP1.

19. The method of claim 1, wherein the CM comprises an amino acid sequence selected from the group consisting of SEQ ID NO: 267-279 and 280.

20. The method of claim 9, wherein at least one of the first CM and the second CM comprises an amino acid sequence selected from the group consisting of SEQ ID NO: 267-279 and 280.

21. A method of manufacturing an activatable antibody, the method comprising:
(a) culturing a cell comprising a nucleic acid construct that encodes the activatable antibody under conditions that lead to expression of the activatable antibody, wherein the activatable antibody comprises a masking moiety (MM) comprising an amino acid sequence selected from the group consisting of SEQ ID NO: 1, 218-220, 236-265 and 266, a first peptide linker (LP1), a cleavable moiety (CM) comprising an amino acid sequence selected from the group consisting of SEQ ID NO: 267-279 and 280, a second peptide linker (LP2), and an antibody or an antigen binding fragment thereof (AB) that specifically binds Epidermal Growth Factor Receptor (EGFR), (i) wherein:
  the MM has an equilibrium dissociation constant for binding to the AB which is greater than the equilibrium dissociation constant of the AB for binding to EGFR;
(ii) wherein the CM is a polypeptide that functions as a substrate for urokinase type plasminogen activator (uPA), and wherein the protease cleaves the CM in the activatable antibody when the activatable antibody is exposed to the protease;
(iii) wherein the AB has an equilibrium dissociation constant of at most 100 nM for binding to EGFR;
(iv) wherein each of LP1 and LP2 is a peptide, and wherein the two LPs need not be identical to each other;
(v) wherein the activatable antibody in an uncleaved state has the structural arrangement from N-terminus to C-terminus as follows: MM-LP1-CM-LP2-AB or AB-LP2-CM-LP1-MM;
(vi) wherein the MM of the activatable antibody in an uncleaved state interferes with specific binding of the AB to EGFR and wherein the MM of the activatable antibody in a cleaved state does not interfere or compete with specific binding of the AB to EGFR; and
(vii) wherein the MM of the activatable antibody in an uncleaved state inhibits the binding of the AB to EGFR such that the dissociation constant ($K_d$) of the AB of the activatable antibody in an uncleaved state towards EGFR is at least 100 times greater than the $K_d$ of the AB of the activatable antibody in a cleaved state towards EGFR;

and (b) recovering the activatable antibody.

22. The method of claim 21, wherein the CM is a polypeptide of up to 15 amino acids in length.

23. The method of claim 21, wherein each of LP1 and LP2 is a peptide of about 1 to 20 amino acids in length.

24. The method of claim 21, wherein the MM is a polypeptide of no more than 40 amino acids in length.

25. The method of claim 21, wherein the AB is or is derived from cetuximab or panitumumab.

26. The method of claim 21, wherein the AB is or is derived from cetuximab.

27. The method of claim 21, wherein the CM is a substrate for uPA and at least one additional protease that is co-localized in a tissue with EGFR, wherein the additional protease is an enzyme selected from the group consisting of the enzymes in Table 3.

28. The method of claim 21, wherein the CM is a substrate for uPA and at least one additional protease that is co-localized in a tissue with EGFR, wherein the additional protease is legumain, plasmin, TMPRSS-3/4, MMP-9, MT1-MMP, cathepsin, caspase, human neutrophil elastase, beta-secretase, MT-SP1 or PSA.

29. The method of claim 21, wherein the CM is a substrate for uPA and at least one additional protease, wherein the additional protease is legumain, MT-SP1 or both legumain and MT-SP1.

30. The method of claim 21, wherein the antigen binding fragment is selected from the group consisting of a Fab' fragment, a F(ab')$_2$ fragment, a scFv, a scAB, a dAb, a single domain heavy chain antibody, and a single domain light chain antibody.

31. The method of claim 21, wherein the CM comprises an amino acid sequence selected from the group consisting of SEQ ID NO: 267-279 and 280 and a second CM.

32. The method of claim 31, wherein the first CM is cleavable by uPA in a target tissue and wherein the second CM is cleavable by a second cleaving agent in a target tissue.

33. The method of claim 32, wherein the first cleaving agent and the second cleaving agent are uPA, and where the first CM and the second CM are different substrates for uPA.

34. The method of claim 32, wherein the first cleaving agent and the second cleaving agent are different enzymes.

35. The method of claim 32, wherein uPA and the second cleaving agent are co-localized in the tissue.

36. The method of claim 31, wherein the first CM and the second CM are cleavable by at least one cleaving agent in the tissue.

37. The method of claim 20, wherein at least one of LP1 or LP2 comprises an amino acid sequence selected from the group consisting of (GS)$_n$, (GSGGS)$_n$ (SEQ ID NO: 12) and (GGGS)$_n$ (SEQ ID NO: 13), where n is an integer of at least one.

38. The method of claim 20, wherein at least one of LP1 or LP2 comprises an amino acid sequence selected from the group consisting of GGSG (SEQ ID NO: 14), GGSGG (SEQ ID NO: 15), GSGSG (SEQ ID NO: 16), GSGGG (SEQ ID NO: 17), GGGSG (SEQ ID NO: 18), and GSSSG (SEQ ID NO: 19).

* * * * *